US006342610B2

(12) United States Patent
Chan et al.

(10) Patent No.: US 6,342,610 B2
(45) Date of Patent: *Jan. 29, 2002

(54) N-ARYL THIENYL-, FURYL-, AND PYRROLYL-SULFONAMIDES AND DERIVATIVES THEREOF THAT MODULATE THE ACTIVITY OF ENDOTHELIN

(75) Inventors: Ming Fai Chan, San Diego, CA (US); Chengde Wu, Houston, TX (US); Bore Gowda Raju; Timothy Kogan, both of Sugar Land, TX (US); Erik Joel Verner, Foster City, CA (US); Rosario Silvestre Castillo, San Diego, CA (US); Venkatachalapathi Yalamoori, San Diego, CA (US); Adam Kois, San Diego, CA (US); Vitukudi Narayanaiyengar Balaji, Encinitas, CA (US)

(73) Assignee: Texas Biotechnology Corp., Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/913,331

(22) PCT Filed: Apr. 4, 1996

(86) PCT No.: PCT/US96/04759

§ 371 Date: Nov. 7, 1997

§ 102(e) Date: Nov. 7, 1997

(87) PCT Pub. No.: WO96/31492

PCT Pub. Date: Oct. 10, 1996

(Under 37 CFR 1.47)

Related U.S. Application Data

(63) Continuation-in-part of application No. 08/477,223, filed on Jun. 6, 1995, now Pat. No. 5,594,021, which is a continuation-in-part of application No. 08/417,075, filed on Apr. 4, 1995, now abandoned, which is a continuation-in-part of application No. 08/416,199, filed on Apr. 4, 1995, now abandoned, which is a continuation-in-part of application No. 08/247,072, filed on May 20, 1994, now Pat. No. 5,571,821, which is a continuation-in-part of application No. 08/222,287, filed on Apr. 5, 1994, now Pat. No. 5,591,761, which is a continuation-in-part of application No. 08/142,552, filed on Oct. 21, 1993, now Pat. No. 5,514,691, which is a continuation-in-part of application No. 08/142,159, filed on Oct. 21, 1993, now Pat. No. 5,464,853, which is a continuation-in-part of application No. 08/142,631, filed on Oct. 21, 1993, now abandoned, which is a continuation-in-part of application No. 08/100,565, filed on Jul. 30, 1993, now abandoned, which is a continuation-in-part of application No. 08/100,125, filed on Jul. 30, 1993, now abandoned, which is a continuation-in-part of application No. 08/065,202, filed on May 20, 1993, now abandoned.

(51) Int. Cl.[7] .............. C07D 207/36; C07D 333/34; C07D 307/38

(52) U.S. Cl. ............ 548/543; 514/421; 514/441; 514/470; 548/550; 549/65; 549/470

(58) Field of Search .................... 514/380, 311, 514/312, 313, 384, 378, 379, 421, 470, 441; 548/244, 245, 247, 543, 550; 549/65, 470

(56) References Cited

U.S. PATENT DOCUMENTS

| 2,888,456 A | 5/1959 | Kano et al. ............. 260/239.9 |
|---|---|---|
| 3,300,488 A | 1/1967 | Onoue et al. ........... 260/239.9 |
| 3,660,383 A | 5/1972 | Sumimoto et al. ...... 260/239.9 |
| 3,710,795 A | 1/1973 | Higuchi et al. ............ 128/260 |
| RE28,819 E | 5/1976 | Thompson ................ 424/243 |
| 4,044,126 A | 8/1977 | Cook et al. ................ 424/243 |
| 4,328,245 A | 5/1982 | Yu et al. .................... 424/305 |
| 4,358,603 A | 11/1982 | Yu .............................. 560/2 |
| 4,364,923 A | 12/1982 | Cook et al. .................. 424/46 |
| 4,409,239 A | 10/1983 | Yu ............................ 424/305 |
| 4,410,545 A | 10/1983 | Yu et al. .................... 424/305 |
| 4,414,209 A | 11/1983 | Cook et al. ................ 424/243 |
| 4,485,108 A | 11/1984 | Jozic ......................... 424/267 |
| 4,659,369 A | 4/1987 | Levitt .......................... 239/69 |
| 4,752,613 A | 6/1988 | Floyd et al. ............... 514/438 |
| 4,753,672 A | 6/1988 | Levitt ........................... 71/92 |

(List continued on next page.)

FOREIGN PATENT DOCUMENTS

| AU | 5461286 | 3/1985 |
|---|---|---|
| CA | 2067288 | 10/1992 |
| CA | 2071193 | 12/1992 |

(List continued on next page.)

OTHER PUBLICATIONS

Fujimoto and Sakai, "Synthesis and Structure of N1–Acylated Sulfiodizole and its homologues", *Chem. Pharm. Bull.* 14(3):280–284 (1996). Published in French.
Certified Translation of Japanese Patent 63238006 (item E), "Agent protecting against rice blase disease".

(List continued on next page.)

*Primary Examiner*—Floyd D. Higel
(74) *Attorney, Agent, or Firm*—Stephanie L. Seidman; Dale L. Rieger; Heller Ehrman White & McAuliffe LLP

(57) ABSTRACT

Thienyl-, furyl- and pyrrolyl-sulfonamides and methods for modulating or altering the activity of the endothelin family of peptides are provided. In particular, N-(isoxazolyl)thienylsulfonamides, N-(isoxazolyl)furylsulfonamides and N-(isoxazolyl)pyrrolylsulfonamides and methods using these sulfonamides for inhibiting the binding of an endothelin peptide to an endothelin receptor by contacting the receptor with the sulfonamide are provided. Methods for treating endothelin-mediated disorders by administering effective amounts of one or more of these sulfonamides or prodrugs thereof that inhibit or increase the activity of endothelin are also provided.

52 Claims, No Drawings

U.S. PATENT DOCUMENTS

| | | | |
|---|---|---|---|
| 4,861,366 A | 8/1989 | Levitt | 71/90 |
| 4,997,836 A | 3/1991 | Sugihara et al. | 514/253 |
| 5,082,838 A | 1/1992 | Naka et al. | 514/211 |
| 5,114,918 A | 5/1992 | Ishikawa et al. | 514/11 |
| 5,187,195 A | 2/1993 | Oohata et al. | 514/610 |
| 5,198,548 A | 3/1993 | Beylin et al. | 546/136 |
| 5,208,243 A | 5/1993 | Peglion et al. | 514/309 |
| 5,230,999 A | 7/1993 | Suzuki et al. | 435/71 |
| 5,240,910 A | 8/1993 | Lam et al. | 514/11 |
| 5,248,807 A | 9/1993 | Fujimoto et al. | 560/75 |
| 5,262,437 A | 11/1993 | Chan | 514/530 |
| 5,270,313 A | 12/1993 | Burri et al. | |
| 5,292,740 A | 3/1994 | Burri et al. | 514/256 |
| 5,312,842 A | 5/1994 | Chan | 514/708 |
| 5,334,598 A | 8/1994 | Bagley et al. | 514/303 |
| 5,352,659 A | 10/1994 | Wakimasu et al. | 514/9 |
| 5,352,800 A | 10/1994 | Bills et al. | 548/539 |
| 5,378,715 A | 1/1995 | Stein et al. | 514/329 |
| 5,382,569 A | 1/1995 | Cody et al. | 517/17 |
| 5,389,620 A | 2/1995 | Ishikawa et al. | 514/80 |
| 5,389,633 A | 2/1995 | Miyake et al. | 514/233.2 |
| 5,407,941 A | 4/1995 | Carceller et al. | 514/290 |
| 5,420,123 A | 5/1995 | Murugesan | 514/220 |
| 5,420,129 A | 5/1995 | Breu et al. | 514/252 |
| 5,420,131 A | 5/1995 | Carceller et al. | 514/253 |
| 5,420,133 A | 5/1995 | Dhanoa et al. | 514/256 |
| 5,420,138 A | 5/1995 | Corbier et al. | 514/300 |
| 5,420,275 A | 5/1995 | Masuya et al. | 544/236 |
| 5,464,853 A | 11/1995 | Chan et al. | 514/378 |
| 5,476,872 A | 12/1995 | Garst et al. | 514/530 |
| 5,514,691 A | 5/1996 | Chan et al. | 514/312 |
| 5,514,696 A | 5/1996 | Murugesan et al. | 514/380 |
| 5,543,521 A | 8/1996 | Chan et al. | 544/349 |
| 5,565,485 A | 10/1996 | Bagley et al. | 514/452 |
| 5,571,821 A | 11/1996 | Chan et al. | 514/312 |
| 5,574,066 A | 11/1996 | Chan et al. | 514/548 |
| 5,585,397 A | 12/1996 | Tung et al. | 514/473 |
| 5,589,478 A | 12/1996 | Yamada et al. | 514/269 |
| 5,591,728 A | 1/1997 | de Nanteuil et al. | 514/80 |
| 5,591,761 A | 1/1997 | Chan et al. | 514/380 |
| 5,594,021 A | 1/1997 | Chan et al. | 514/378 |
| 5,599,811 A | 2/1997 | Berryman et al. | 514/226.5 |
| 5,612,359 A | 3/1997 | Murugesan | 514/365 |
| 5,641,793 A | 6/1997 | Bradbury | 514/352 |
| 5,656,635 A | 8/1997 | Chan et al. | 514/530 |
| 5,661,152 A | 8/1997 | Bishop et al. | 514/254 |
| 5,668,137 A | 9/1997 | Phillips et al. | 514/255 |
| 5,668,176 A | 9/1997 | Bagley et al. | 514/569 |
| 5,726,194 A | 3/1998 | Osswald et al. | 514/362 |
| 5,736,509 A | 4/1998 | Balaji et al. | 514/9 |
| 5,783,701 A | 7/1998 | Tung et al. | 546/169 |
| 5,783,705 A | 7/1998 | Blok et al. | 548/247 |
| 5,804,585 A | 9/1998 | Verner | 514/301 |
| 5,827,869 A | 10/1998 | Murugesan | 514/374 |
| 5,962,490 A | 10/1999 | Chan et al. | 514/380 |
| 5,977,117 A | 11/1999 | Chan et al. | 514/256 |
| 6,013,655 A | 1/2000 | Verner | 514/301 |
| 6,017,916 A | 1/2000 | Berryman et al. | 514/233.8 |
| 6,017,951 A | 1/2000 | Patt et al. | 514/464 |
| 6,030,991 A | 2/2000 | Chan et al. | 514/380 |
| 6,043,241 A | 3/2000 | Cheng et al. | 514/233.8 |
| 6,043,265 A | 3/2000 | Murugesan et al. | 514/374 |
| 6,060,475 A | 5/2000 | Bradbury et al. | 514/255 |
| 6,063,911 A | 5/2000 | Vournakis et al. | 536/200 |
| 6,080,774 A | 6/2000 | Murugesan et al. | 514/380 |
| 6,083,951 A | 7/2000 | Bradbury | 514/256 |
| 6,083,955 A | 7/2000 | Harada et al. | 514/269 |
| 6,107,320 A | 8/2000 | Murugesan et al. | 514/379 |
| 6,133,263 A | 10/2000 | Cheng et al. | 514/223.8 |
| 6,133,442 A | 10/2000 | Breu et al. | 544/123 |

FOREIGN PATENT DOCUMENTS

| | | |
|---|---|---|
| EP | 0248399 | 12/1987 |
| EP | 0404525 | 12/1990 |
| EP | 0405421 | 1/1991 |
| EP | 0411150 | 2/1991 |
| EP | 0436189 | 7/1991 |
| EP | 0457195 | 11/1991 |
| EP | 0460679 | 12/1991 |
| EP | 0496452 | 7/1992 |
| EP | 0558258 | 9/1993 |
| EP | 0569193 | 11/1993 |
| EP | 0626174 | 11/1994 |
| EP | 0640596 | 3/1995 |
| EP | 0682016 | 11/1995 |
| EP | 0702012 | 3/1996 |
| EP | 0725067 | 8/1996 |
| EP | 0768305 | 4/1997 |
| EP | 0870764 | 10/1998 |
| GB | 0804036 | 11/1958 |
| GB | 1473433 | 5/1977 |
| GB | 2259450 | 3/1993 |
| JP | 60188084 | 9/1985 |
| JP | 63238006 | 4/1990 |
| JP | 4134084 | 5/1992 |
| WO | 9115479 | 10/1991 |
| WO | 93-08799 | 5/1993 |
| WO | 94-27979 | 12/1994 |
| WO | 95-24385 | 9/1995 |
| WO | 96-04759 | 4/1996 |
| WO | 96-31492 | 10/1996 |
| WO | 98-49162 | 11/1998 |

OTHER PUBLICATIONS

Certified Translation of French Publication (item F) "Synthesis and Structure of N1–Acylated Sulfiodizole and its homologues".

Allen et al., The Cambridge crystallographic data centre: Computer–based search, retrieval, analysis and display of information, *Acta Crystallogr. B35*:2331–2339 (1979).

Anagnostou et al., Erythropoietin has mitogenic and positive chemotactic effects on endothelial cells, *P.N.A.S.* 87:5978–5982 (1990).

Ansel, *Introduction to Pharmaceutical Dosage Forms*, 4th Edition, pp. 126–163 (1985).

Arai et al., Cloning and expression of a cDNA encoding an endothelin receptor, *Nature* 348:730–732 (1990).

Aumelas et al., Determination of the structure of [Nle$^7$] endothelin by $^1$H NMR, *Int. J. Peptide Protein Res.* 37:315–324 (1991).

Balasubramanian, New type of representation for mapping chain folding in protein molecules, *Nature* 266:856–857 (1977).

Benigni et al., A specific endothelin subtype A receptor antagonist protects against injury in renal disease progression, *Kidney International* 44:440–444 (1993).

Berge et al., Pharmaceutical salts, *J. Pharmaceut. Sci.* 66(1):1–19 (1977).

Bolger et al., Vascular reactivity, tissue levels, and binding sites for endothelin: a comparison in the spontaneously hypertensive and Wistar–Kyoto rats, *Can. J. Physiol. Pharmacol* 69:406–413.

Bolger et al., Characterization of binding of the Ca$^{++}$ channel antagonist [$^3$H] nitrendipine, to guinea–pig ileal smooth muscle, *J. Pharmacol. Exptl. Ther.* 225:291–309 (1983).

Bolger et al., Interactions between endothelin and atrial natruiretic factor in the rat aortic ring preparation, *Can J. Physiol Pharmacol* 69(8):1155–62 (1991).

Borges et al., Tissue selectivity of endothelin, *Eur. J. Pharmacol.* 165:223–230 (1989).

Brint et al., Upperbound procedures for the identification of similar three–dimensional chemical structures, *J. Comput.–Aided Mol. Design* 2:311–310 (1988).

Brooks et al., Effect of nifedipine on cyclosporine A–induced nephrotoxicity, urinary endothelin excretion and renal endothelin receptor number, *Eur. J. Pharmacology* 194:115–117 (1991).

Buemi et al., Influence of recombinant erythropoietin on the production of endothelin–1 from human umbilical artery, *Nephron* 64(1):165–166 (1993).

Cardell et al., Two functional endothelin receptors in guinea–pig pulmonary arteries, *Neurochem. Int.* 18(4):571–574 (1991).

Carlini et al., Intravenous erythropoietin (rHuEPO) administration increases plasma endothelin and blood pressure in hemodialysis patients, *Am. J. Hyper.* 6:103–107 (1993).

Castiglione et al., Alanine scan of endothelin, Peptides: Chemistry and Biology, Proc. Amer. Rept. Symp. (12th), J.A. Smith and J.E. Rivier, Eds., ESCOM, Leiden, 1992, pp. 402–403.

Chan et al., Identification of a new class of ETA selective endothelin antagonists by pharmacophore directed screening, *Biochem Biophys Res Commun* 201(1):228–34 (1994).

Chan et al., The discovery and structure–activity relationships of nonpeptide, low molecular weight antagonists selective for the endothelin ET(B) receptor, *Bioorg Med Chem* 6(12):2301–16 (1998).

Clarke et al., Endothelin is a potent long–lasting vasoconstrictor in men, *Am J. Physiol.* 257(6 pt 2):H2033–H2035 (1989).

Clozel et al., Pathophysiological role of endothelin revealed by the first orally active endothelin receptor antagonist, *Nature* 365:759–761, (1993).

Cody et al., The rational design of a highly potent combined $ET_A$ and $ET_B$ receptor antagonist (PD145065) and related analogues, *Med. Chem. Res.* 3:154–162 (1993).

Cooper et al., A novel approach to molecular similarity, *J. Comput.–Aided Mol. Design* 3:253–259 (1989).

De Nucci et al., Pressor effects of circulating endothelin are limited by its removal in the pulmonary circulation and by the release of prostacyclin and endothelium–derived relaxing factor, *Proc. Natl. Acad. Sci.* 85:9797 (1988).

DiCarlo et al., $ET_A$–recpetor antagonist prevents and reverses chronic hypoxia–induced pulmonary hypertension, *Am. J. Physiol.* 269:L690–L697 (1995).

Doherty, Endothelin: a new challenge, *J. Medicinal Chem.* 35(9):1493–1508 (1992).

Endothelin, Receptor Antagonist (TBC 11251), Research and Development—Compounds Under Development, (available at http://www.tbc.com/clinical.html on Jan. 27, 1999).

Eschbach et al., Recombinant human erythropoietin in anemic patients with end stage renal disease; results of a phase III multicenter clinical trial, *Ann. Intern. Med.* 111:992–1000 (1989).

Filep et al., Endothelin–1 induces prostacyclin release from bovine aortic endothelial cells, *Biochem. and Biophys. Research Comm.* 177(1):171–176 (1991).

Fujimoto et al., A novel non–peptide endothelin antagonist isolated from bayberry, *FEBS* 305(1):41–44 (1992).

Fujimoto et al., Isoxazole derivatives. II. Synthesis and structure of N–acylsufodiazoles and their homologs, *Chemical Abstracts:* 65(2), Abstract No. 2241eq. Jul. 18, 1996.

Furchgott et al., The obligatory role of endothelial cells in the relaxation of arterial smooth muscle by acetylcholine, *Nature* 288:373–376, (1980).

Galantino et al., D–Amino acid scan of endothelin, Peptides: Chemistry & Biology, Proc. Amer. Report. Symp. (12th), J.A. Smith and J.E. Rivier, Eds., ESCOM, Leiden, 1992, pp. 404–405.

Gibaldi, Chapter 8: Bioavailability, *Biopharmaceutics and Pharmacology*, 4th ed., Lea and Sediger, pp. 146–175 (1991).

Gu et al., The inhibitory effect of [D–$Arg^1$, D–Phe, D–$Try^{7,9}$, $Leu^{11}$] substance P on endothelin–1 binding sites in rat cardiac membranes, *Biochem. and Biophys. Research Commun.* 179(1):130–133 (1991).

Heidenreich et al., Erythropoietin induces contraction of isolated renal small resistance vessels, *Nephrol. Dial. Transplant* 5:739–740 (1990).

Hiley et al., Functional studies on endothelin catch up with molecular biology, *Trends Pharmacol. Sci.* 10:47–49 (1989).

Hirata et al., Receptor binding activity and cytosolic free calcium response by synthetic endothelin analogs in culture rat vascular smooth muscle cells, *Biochem. and Biophys. Research Commun.* 160:228–234 (1989).

Hori et al., Hemodynamics and volume changes by recombinant human erythropoietin (rHuEPO) in the treatment of anemic hemodialysis patients, *Clin. Nephrol.* 33:293–298 (1990).

Ihara et al., An endothelin receptor ($ET_A$) antagonist isolated from *Streptomyces misakiensis*, *Biochem. and Biophys. Research Commun.* 178(1):132–137 (1991).

Ihara et al., Biological profiles of highly potent novel endothelin antagonists selective for the $ET_A$ receptor, *Life Sciences* 50:247–255 (1991).

Inoue et al., The human endothelin family: Three structurally and pharmacologically distinct isopeptides predicted by three separate genes, *Proc. Natl. Acad. Sci. USA*, 86:2863–2867 (1989).

Ishida et al., Differential activities of two distinct endothelin family peptides on ileum and coronary artery, *FEBS Lett* 247(2):337–40 (1989).

Ishikawa et al., Cyclic pentapeptide endothelin antagonists with high $ET_A$ selectivity. Potency– and solubility–enhancing modifications, *J. Med. Chem.* 35:2139–2142 (1992).

IUPAC–IUB Commission on Biochemical Nomenclature, *Biochem.* 11:942–944, (1972).

Kaltenbronn et al., Renin inhibitors containing isosteric replacements of the amide bond connecting the $P_3$ and $P_2$ sites, *J. Med. Chem.* 33:838–845 (1990).

Kanno et al., Endothelin–1 and Vasculitis, *J. Amer. Med. Assoc.* 264:2868, (1990).

Karplus, Molecular Dynamics: Applications to Proteins, Computer Simulation of Chemical and Biomolecular Systems, (Bevendge and Jorfensen, Eds.) *Ann. New York Acad. Sci.*:482:255–266 (1986).

Kashiwabara et al., Putative precursors of endothelin have less vasoconstrictor activity in vitro but a potent pressor effect in vivo, *FEBS Letters* 247(1):73–76 (1989).

Kemp, Peptidomimetics and the template approach to nucleation of β–sheets and α–helices in peptides, *Trends in Biotech.* 8:249–255 (1990).

Kloog et al., Similarities in mode and sites of action of sarafotoxins and endothelins, *Trends Pharmacol. Sci.* 10:212–214 (1989).

Koyama et al., Plasma endothelin levels in patients with uremia, *Lancet* 1(8645):991–992 (1989).

Kurihara et al., The possible role of endothelin–1 in the pathogenesis of coronary vasospasm, *J. Cardiovas. Pharmacol.* 13:Suppl. 5, S132–S142, (1989).

Lerman et al., Circulating and tissue endothelin immunoreactivity in advanced atherosclerosis, *New Engl. J. Med.* 325:997–1001, (1991).

Maggi et al., Potent contractile effect of endothelin in isolated guinea–pig airways, *Eur. J. Pharmacol.* 160:179–182 (1989).

Martin et al., Identification and characterization of endothelin binding sites in rat renal papillary and glomerular membranes, *Biochem. Biophys. Res. Commun.* 162:130–137 (1989).

Miyata et al., WS–7338, new endothelin receptor antagonists isolated from Streptomyces sp. No. 7338, *J. Antibiotics* 45(1):74–82 (1992).

Miyata et al., WS009 A and B, new endothelin receptor antagonists isolated from Streptomyces sp. No. 89009, *J. Antibiotics* 45(7):1029–1040 (1992).

Miyata et al., WS009 A and B, new endothelin receptor antagonists isolated from Streptomyces sp. No. 89009. II. Biological characterization and pharmacological characterization of WS009 A and B, *J. Antibiot* 45(7):1041–6 (1992).

Miyata et al., WS–7338, new endothelin receptor antagonists isolated from Streptomyces sp. No. 7338. II. Biological characterization and pharmacological characterization of WS–7338 B., *J. Antibiot* 45(1):83–7 (1992).

Miyata et al., WS–7338, new endothelin receptor antagonists isolated from Streptomyces sp. No. 7338. III. Structures of WS–7338 A, B, C and D and total synthesis if WS–7338B., *J. Antibiot* 45(5):788–91 (1992).

Miyauchi et al., Increase of the function of intra–cardiac autonomic nerves in isolated atria of swim–trained rats: study by the intra–cardiac nerve stimulation, *Jpn. J. Pharmacol.* 58:279, (1992).

Morel et al., Increased plasma and pulmonary lymph levels of endothelin during endotoxin shock, *Eur. J. Pharm.* 167:427–428 (1989).

Nakajima et al., Endothelin–binding inhibitors, BE–18257A and BE–18257B II. Structure determination, *J. Antibiotics* 44(12):1348–1356 (1991).

Nakajima et al., Synthesis of endothelin–1 analogues, endothelin–3, and sarafotoxin S6b: structure–activity relationships, *J. Cardiovascular Pharm.* 13(Suppl. 5):S8–S12 (1989).

Nirei et al., An endotheline $ET_A$ receptor antagonist, FR139317, Amerliorates cerebral vasospasm in dogs, *Life Sciences* 52:1869–1874, (1993).

Nishikibe et al., Antihypertensive effect of a newly synthesized endothelin antagonist, BQ–123, in a genetic hypertensive model, *Life Sci.* 52:717–724 (1993).

Nishikori et al., Receptor binding affinity and biological activity of C–terminal elongated forms of endothelin–1, *Neurochem. Int.* 18(4):535–539 (1991).

Nogrady et al., 4–pro–drugs and soft drugs, *Medicinal Chemistry A Biochemical Approach*:388–392, (1985).

Nonnast–Daniel et al., Atrial natriuretic peptide and central hemodynamics during correction of renal anemia by recombinant human erythropoietin treatment in regular dialysis treatment patients, *Nephrol Dial Transplant* 4:478 (1989).

Ogawa et al., Molecular cloning of a non–isopeptide–selective human endothelin receptor, *Biochem. and Biophys. Research Comm.* 7, 18(1):248–255 (1991).

Ohashi et al., Asterric acid, a new endothelin binding inhibitor, *J. Antibiotics*, 45(10):1684–1685 (1992).

Ormsbee et al., Production of hypertension with desoxycorticosterone acetate–impregnated silicone rubber implants, *J. Pharm. Sci.* 255–257 (1973).

Palmer et al., Nitric oxide release accounts for the biological activity of endothelium–derived relaxing factor, *Nature* 327:524–526 (1987).

Panek et al., Endothelin and structurally related analogs distinguish between endothelin receptor subtypes, *Biochem. and Biophys. Research Commun.* 183(2):566–571 (1992).

Perkins et al., Proposed solution structure of endothelin, *Int. J. Peptide Protein Res.* 36:128–133 (1990).

Rachele, The methyl esterificaton of amino acids with 2,2–dimethoxypropane and aqueous hydrogen, *J. of Org Chemistry* 28:2898 (1963).

Raine et al., Effect of erythropoietin on blood pressure, *Am. J. Kid. Dis.* 18(suppl):76–83 (1991).

Raju et al., Thiophenesulfonamides as endothelin receptor antagonists, *Bioorganic Medicinal Chem. Lett.* 6(22):2651–2656 (1996).

Raju et al., Search for surrogates: a study of endothelin receptor antagonist structure activity relationships, *Bioorganic Medicinal Chem. Lett.* 7(7): 933–938 (1997).

Raju et al., Amide bond surrogates: a study in thiophenesulfonamide based endothelin receptor antagonists, *Bioorganic Medicinal Chem. Lett.* 7(7):939–944 (1997).

Ramachandran et al., Conformation of polypeptides and proteins, *Adv. Prot. Chem.*, 23:283–437 (1968).

Ray et al., Circulating endothelin in acute ischaemic syndromes, *Br. Heart J.* 67:383–386 (1992).

Saeki et al., [Ala$^{1,3,11,15}$] endothelin–1 analogs with $ET_B$ agonistic activity, *Biochem. Biophys. Research Commun.* 179(1):286–292 (1991).

Saida et al., A novel peptide, vasoactive intestinal contractor, of a new (endothelin) peptide family, *J. Biol. Chem.* 264(25):14613–14616 (1989).

Saito et al., Application of monoclonal antibodies for endothelin to hypertensive research, *Hypertension* 15:734–738 (1990).

Sakurai et al., Cloning of a cDNA encoding a non–isopeptide–selective subtype of the endothelin receptor, *Nature* 348:732–735 (1990).

Samtleben et al., Blood pressure change during treatment with recombinant human erythropoietin, *Contrib. Nephrol.* 66:114–122 (1988).

Sanjay et al., Does PTCA increase circulating endothelin level in Man?, *Circulation* 84:(Suppl. 4):726, (1991).

Saudek et al., $^1$H–NMR study of endothelin, sequence–specific assignment of the spectrum and a solution structure, *FEBS Letters* 257(1):145–148 (1989).

Saudek et al., Solution conformation of endothelin–1 by $^1$H NMR, CD, and molecular modeling, *Int. J. Peptide Protein Res.* 37:174–179 (1991).

Schafer et al., Treatment of renal anemia with recombinant human erythropoietin, *Am. J. Nephrol.* 8:352–362 (1989).

Schvartz et al., Bovine cerebellum endothelin receptor: Solubilization and identification, *Endocrinology* 126(6):3218–3222 (1990).

Shimazaki et al., Piperazine derivatives, *Chem. Abstracts* 106:558 (abst. No. 33114a) (1987).

Simonson et al., Endothelin–1 stimulates contraction of rat glomerfular mesangial cells and potentiates β–adrenergic––mediated cyclic adenosine monophosphate accumulation, *J. Clin. Invest.* 85:790–797, (1990).

Spinella et al., Design and synthesis of a specific endothelin 1 antagonist: Effects on pulmonary vasoconstriction, *Proc. Natl. Acad. Sci. USA* 88p:7443–7446 (1991).

Spinella et al., A proposed structural model of endothelin, *Peptide Research* 2(4):286–291 (1989).

Spokes et al., Studies with endothelin–3 and endothelin–1 on rat blood pressure and isolated tissues: Evidence for multiple endothelin receptor subtypes, *J. Cardiovasc. Pharmacol.* 13(Suppl. 5):S191–S192 (1989).

Stein et al., The Discovery of Sulfonamide Endothelin Antagonists and the Development of the Orally Active $ET_A$–Antagonist 5–(Dimethylamino)–N–(3, 4–dimethyl–5–isoxazolyl)–1–naphthalenesulfonamide, *J. Med. Chem.* 37(3):329–331 (1994).

Stewart et al., Increased plasma endothelin–1 in pulmonary hypertension: marker or mediator of disease? *Annals of Internal Med.* 114:464–469, (1991).

Sundal et al., Correction of anemia of chronic renal failure with recombinant human erythropoietin: safety and efficacy of one year's treatment in a European multicenter study of 150 hemodialysis–dependent patients, *Nephrol. Dial. Transplant* 4:979–987 (1989).

Szelke et al., Novel transition–state analogue inhibitors of renin, In *Peptides: Structure and Function, Proceedings of the Eighth American peptide symposium*, (Hurby and Rich, Eds.), pp. 579–582, Pierce Chemical Co., Rockford, Illinois (1983).

Tahara et al., Circulating immunoreactive endothelin in patients undergoing percutaneous transluminal coronary angioplasty, *Metab. Clin. Exp.* 40:1235–1237, (1991).

Takayanagi et al., Multiple subtypes of endothelin receptors in porcine tissues: characerization by ligand binding, affinity labeling and regional distribution, *Reg. Pep.* 32:23–37 (1991).

Takayanagi et al., Presence of non–selective type of endothelin receptor on vascular endothelium and its linkage to vasodilation, *FEBS Letters*, 282(1):103–106 (1991).

Texas Biotechnology Receives First Patent Issued For New Class of Cardiovascular Drugs, Houston, TX, Dec. 6, 1995, For Immediate Release (available at http://www.tbc.com/press/pr120695.html on Jan. 27, 1999).

Texas Biotechnology Reports Endothelin A Receptor Antagonist and VCAM/VLA–4 Inhibitor Patents, Houston, TX, May 16, 1996, For Immediate Release, (available at http://www.tbc.com/press/pr051696.html on Jan. 27, 1999).

Texas Biotechnology Announces Initiation of Phase 1 Clinical Trial For TBC 1269 To Treat Asthma, Houston, TX, Jan. 21, 1997, For Immediate Release, (available at http://www.tbc.com/press/pr012197.html on Jan. 27, 1999).

Texas Biotechnology Announces Initiation of Phase 1 Clinical Trail For TBC 11251 To Treat Congestive Heart Failure, Houston, TX, Nov. 13, 1996, For Immediate Release, (available at http://www.tbc.com/press/pr111396.html on Jan. 27, 1999).

Texas Biotechnology Receives U.S. Patents For New Class of Cardiovascular Therapeutics, Endothelin A Receptor Antagonists, Houston, TX, Jan. 22, 1977, For Immediate Release, (available to http://www.tbc.com/press/pr012297.html on Jan. 28, 1999).

Texas Biotechnology Completes Phase I Safety Trial for Oral Endothelin Antagonist, Houston, TX, Dec. 11, 1997 (http://www.tbc.com/press/pr121197.html).

Texas Biotechnology Reports Positive Phase IIA Trial Results of Endothelin Receptor Antagonist in CHF, Houston, TX, Feb. 11, 1998, pp. 1–2 (available at http://www.tbc.com/press/pr021198.html) on Jan. 28, 1999).

Texas Biotechnology Updates Stockholders at 1998 Annual Meeting, Houston, TX, Jun. 9, 1998, pp. 1–2, (abailable at http://www.tbc.com/press/pr060998.html).

Texas Biotechnology Reports Additional Positive Phase IIA Trial Results in Congestive Heart Failure, Houston, TX, Jul. 21, 1998, pp. 1–2 (available at http://www.tbc.com/press/pr072298.html).

Texas Biotechnology Presents Clinical Results on its Endothelin A Receptor Antagonist, TBC11251, at AHA Sessions, Houston, TX, Nov. 10, 1998, pp. 1–2 (available at http://www.tbc.com/press/pr111098.html).

Tkayama et al., Effects of recombinant human eryghropoietin on blood coagulation, fibrinolysis and endothelium in hemodialysis patients, *Blood Purif.* 1:53–54 (1991).

Tomita et al., Plasma endothelin levels in patients with acute renal failure, *N. Engl. J. Med.* 321:1127 (1989).

Vanhoutte et al., Modulation of vascular smooth muscle contraction by the endothelium, *Ann. Rev. Physiol.* 48:307–320, (1986).

von Geldern et al., A fluorogenic assay for endothelin–converting enzyme, *Peptide Research* 4(1):32–35 (1991).

Weiner et al., An all atom force field for simulations of proteins and nucleic acids, *J. Comput. Chem.* 7(2):230–252 (1986).

Weiner et al., A new force field for melecular mechanical simulation of nucleic acids and proteins, *J. Am. Chem. Soc.* 106(3):765–784 (Eng.) (1984).

Williams et al., Sarafotoxin S6c: An agonist which distinguished between endothelin receptor subytpes, *Biochem. and Biophys. Research Commun.* 175(2):556–561 (1991).

Wu et al., Discovery of TBC11251, a potent, long acting, orally active endothelin receptor–A selective antagonist, *J. Medicinal Chem.* 40(11):1690–1697 (1997).

Wu et al., Structure–activity relationships of N–2–aryl–3–(isoxazolylsulfamoyl)–2–thiophenecarbox amides as selective endothelin receptor–A antagonists, *J. Medicinal Chem.* 40(11):1682–1689 (1997).

Yamashita et al., Recombinant human erythropoietin (rHuEPO) induces high plasma endothelin (ET) levels in hemodialysis patients, *J. Am. Soc. Nephrol.* 1:409 (1990).

Yanagisawa et al., A novel potent vasoconstrictor peptide produced by vascular endothelial cells, *Nature* 332:411–415 (1988).

Yasuda et al., Circulating immunoreactive endothelin in ischemic heart disease, *Amer. Heart J.* 119:801–806, (1990).

Zamora et al., Serum endothilin–1 concentrations and cold provocation in primary Raynaud's phenomenon, *Lancet* 336:1144–1147, (1990).

Database Crossfire Beilstein Registry No. 1021364 and 1086426, citing Saito et al., *Yakugaku Zasshi* 88:1289, 1292 (1968).

Chemical Abstracts vol. 65, abstract No. 14649g, citing Uno et al., *Chem. Pharm. Bull.* 14:756–762 (1966).

N-ARYL THIENYL-, FURYL-, AND PYRROLYL-SULFONAMIDES AND DERIVATIVES THEREOF THAT MODULATE THE ACTIVITY OF ENDOTHELIN

RELATED APPLICATIONS

For purposes of the U.S. national stage of this application, this application is a continuation-in-part of U.S. application Ser. No. 08/477,223, filed Jun. 6, 1995, entitled, THIENYL-, FURYL- AND PYRROLYL SULFONAMIDES AND DERIVATIVES THEREOF THAT MODULATE THE ACTIVITY OF ENDOTHELIN; issued Jan. 14, 1997 as U.S. Pat. No. 5,594,021 is also a continuation-in-part of U.S. application Ser. No. 08/417,075, filed Apr. 4, 1995, entitled, THIENYL-, FURYL- AND PYRROLYL SULFONAMIDES AND DERIVATIVES THEREOF THAT MODULATE THE ACTIVITY OF ENDOTHELIN, now abandoned and is also a continuation-in-part of U.S. application Ser. No. 08/416,199, filed Apr. 4, 1995, entitled, BENZENESULFONAMIDES AND THE USE THEREOF TO MODULATE THE ACTIVITY OF ENDOTHELIN, now abandoned. Priority is claimed to these applications.

U.S. application Ser. No. 08/477,223 is a continuation-in-part of U.S. application Ser. No. 08/417,075. Each of U.S. application Ser. Nos. 08/477,223, 417,075 and 08/416,199 is in turn a continuation-in-part of U.S. application Ser. No. 08/247,072 to Chan et al., filed May 20, 1994, entitled "SULFONAMIDES AND DERIVATIVES THEREOF THAT MODULATE THE ACTIVITY OF ENDOTHELIN"; issued Jan. 7, 1 997 as U.S. Pat. No. 5,571,821 U.S. application Ser. No. 08/222,287 to Chan et al., filed Apr. 5, 1994, U.S. Pat. No. 5,891,761 entitled "THIOPHENYL-, FURYL- AND PYRROLYL-SULFONAMIDES AND DERIVATIVES THEREOF THAT MODULATE THE ACTIVITY OF ENDOTHELIN"; U.S. application Ser. No. 08/142,552 to Chan et al., filed Oct. 21, 1993, entitled "N-(4-HALO-ISOXAZOLYL)-SULFONAMIDES AND DERIVATIVES THEREOF THAT MODULATE THE ACTIVITY OF ENDOTHELIN", issued May 7, 1996 as U.S. Pat. No. 5,514,691 U.S. application Ser. No. 08/142,159 to Chan et al., filed Oct. 21, 1993, entitled "N-(5-ISOXAZOLYL)BIPHENYLSULFONAMIDES, N-(3-ISOXAZOLYL)BIPHENYLSULFONAMIDES AND DERIVATIVES THEREOF THAT MODULATE THE ACTIVITY OF ENDOTHELIN", now U.S. Pat. No. 5,464,853; U.S. application Ser. No. 08/142,631 to Chan et al., filed Oct. 21, 1993, "N-(5-ISOXAZOLYL)-BENZENESULFONAMIDES, N-(3-ISOXAZOLYL)-BENZENESULFONAMIDES AND DERIVATIVES THEREOF THAT MODULATE THE ACTIVITY OF ENDOTHELIN", now abandoned; U.S. application Ser. No. 08/100,565 to Chan et al., filed Jul. 30, 1993, entitled "N-(5-ISOXAZOLYL)-SULFONAMIDES AND DERIVATIVES THEREOF THAT MODULATE THE ACTIVITY OF ENDOTHELIN", now abandoned; U.S. application Ser. No. 08/100,125 to Chan et al., filed Jul. 30, 1993, entitled "N-(3-ISOXAZOLYL)-SULFONAMIDES AND DERIVATIVES THEREOF THAT MODULATE THE ACTIVITY OF ENDOTHELIN", now abandoned; and U.S. application Ser. No. 08/065,202, to Chan, filed May 20, 1993, entitled "SULFONAMIDES AND DERIVATIVES THEREOF THAT MODULATE THE ACTIVITY OF ENDOTHELIN", now abandoned.

U.S. application Ser. No. 08/417,075 is a continuation-in-part of U.S. application Ser. No. 08/247,072, which is a continuation-in -part of U.S. application Ser. Nos. 08/222,287, 08/416,199, 08/247,072 and 08/222,287 are each a continuation-in-part of the following applications: U.S. application Ser. No. 08/142,552 to Chan et al., filed Oct. 21, 1993, entitled "N-(4-HALO-ISOXAZOLYL)-SULFONAMIDES AND DERIVATIVES THEREOF THAT MODULATE THE ACTIVITY OF ENDOTHELIN", U.S. application Ser. No. 08/142,159 to Chan et al., filed Oct. 21, 1993, entitled "N-(5-ISOXAZOLYL)BIPHENYLSULFONAMIDES, N-(3-ISOXAZOLYL)BIPHENYLSULFONAMIDES AND DERIVATIVES THEREOF THAT MODULATE THE ACTIVITY OF ENDOTHELIN"; U.S. application Ser. No. 08/142,631 to Chan et al., filed Oct. 21, 1993, "N-(5-ISOXAZOLYL)-BENZENESULFONAMIDES, N-(3-ISOXAZOLYL)-BENZENESULFONAMIDES AND DERIVATIVES THEREOF THAT MODULATE THE ACTIVITY OF ENDOTHELIN"; U.S. application Ser. No. 08/100,565 to Chan et al., filed Jul. 30, 1993, entitled "N-(5-ISOXAZOLYL)-SULFONAMIDES AND DERIVATIVES THEREOF THAT MODULATE THE ACTIVITY OF ENDOTHELIN"; U.S. application Ser. No. 08/100,125 to Chan et al., filed Jul. 30, 1993, entitled "N-(3-ISOXAZOLYL)-SULFONAMIDES AND DERIVATIVES THEREOF THAT MODULATE THE ACTIVITY OF ENDOTHELIN", and U.S. application Ser. No. 08/065,202, to Chan, filed May 20, 1993, entitled "SULFONAMIDES AND DERIVATIVES THEREOF THAT MODULATE THE ACTIVITY OF ENDOTHELIN".

U.S. application Ser. No. 08/416,199 is a continuation-in-part of U.S. application Ser. No. 08/247,072 to Chan et al., filed May 20, 1994, entitled "SULFONAMIDES AND DERIVATIVES THEREOF THAT MODULATE THE ACTIVITY OF ENDOTHELIN"; U.S. application Ser. No. 08/222,287 to Chan et al., filed Apr. 5, 1994, entitled "THIOPHENYL-, FURYL- AND PYRROLYL-SULFONAMIDES AND DERIVATIVES THEREOF THAT MODULATE THE ACTIVITY OF ENDOTHELIN"; U.S. application Ser. No. 08/142,159 to Chan et al., filed Oct. 21, 1993, entitled "N-(5-ISOXAZOLYL) BIPHENYLSULFONAMIDES, N-(3-ISOXAZOLYL) BIPHENYLSULFONAMIDES AND DERIVATIVES THEREOF THAT MODULATE THE ACTIVITY OF ENDOTHELIN"; U.S. application Ser. No. 08/142,552 to Chan et al., filed Oct. 21, 1993, entitled "N-(4-HALO-ISOXAZOLYL)-SULFONAMIDES AND DERIVATIVES THEREOF THAT MODULATE THE ACTIVITY OF ENDOTHELIN"; U.S. application Ser. No. 08/100,565 to Chan et al., filed Jul. 30, 1993, entitled "N-(5-ISOXAZOLYL)-SULFONAMIDES AND DERIVATIVES THEREOF THAT MODULATE THE ACTIVITY OF ENDOTHELIN", now abandoned; U.S. application Ser. No. 08/100,125 to Chan et al., filed Jul. 30, 1993, entitled "N-(3-ISOXAZOLYL)-SULFONAMIDES AND DERIVATIVES THEREOF THAT MODULATE THE ACTIVITY OF ENDOTHELIN", now abandoned; and U.S. application Ser. No. 08/065,202, to Chan, filed May 20, 1993, entitled "SULFONAMIDES AND DERIVATIVES THEREOF THAT MODULATE THE ACTIVITY OF ENDOTHELIN", now abandoned.

U.S. application Ser. Nos. 08/142,159, 08/142,559, 08/142,631 are continuation-in-part applications of U.S. application Ser. Nos. 08/100,565, 08/100,125 and 08/065,202, and 08/100,565 and 08/100,125 are continuation-in-part applications of U.S. application Ser. No. 08/065,202.

The subject matter of each of U.S. application Ser. Nos. 08/477,223, 8/416,199, 08/247,072, 08/222,287, 08/142,159, 08/142,559, 08/142,631, 08/100,565, 08/100,125 and 08/065,202 is incorporated herein in its entirety.

FIELD OF THE INVENTION

The present invention relates to the compounds that modulate the activity of the endothelin family of peptides. In particular, the invention relates to the use of sulfonamides and sulfonamide pro-drugs as endothelin agonists and antagonists.

BACKGROUND OF THE INVENTION

The vascular endothelium releases a variety of vasoactive substances, including the endothelium-derived vasoconstrictor peptide, endothelin (ET) (see, e.g., Vanhoutte et al. (1986) *Annual Rev. Physiol.* 48: 307–320; Furchgott and Zawadski (1980) *Nature* 288: 373–376). Endothelin, which was originally identified in the culture supernatant of porcine aortic endothelial cells (see, Yanagisawa et al. (1988) *Nature* 332: 411–415), is a potent twenty-one amino acid peptide vasoconstrictor. It is the most potent vasopressor known and is produced by numerous cell types, including the cells of the endothelium, trachea, kidney and brain. Endothelin is synthesized as a two hundred and three amino acid precursor preproendothelin that contains a signal sequence which is cleaved by an endogenous protease to produce a thirty-eight (human) or thirty-nine (porcine) amino acid peptide. This intermediate, referred to as big endothelin, is processed in vivo to the mature biologically active form by a putative endothelin-converting enzyme (ECE) that appears to be a metal-dependent neutral protease (see, e.g., Kashiwabara et al. (1989) *FEBS Lttrs.* 247: 337–340). Cleavage is required for induction of physiological responses (see, e.g., von Geldern et al. (1991) *Peptide Res.* 4: 32–35). In porcine aortic endothelial cells, the thirty-nine amino acid intermediate, big endothelin, is hydrolyzed at the $Trp^{21}$-$Val^{22}$ bond to generate endothelin-1 and a C-terminal fragment. A similar cleavage occurs in human cells from a thirty-eight amino acid intermediate. Three distinct endothelin isopeptides, endothelin-1, endothelin-2 and endothelin-3, that exhibit potent vasoconstrictor activity have been identified.

The family of three isopeptides endothelin-1, endothelin-2 and endothelin-3 are encoded by a family of three genes (see, Inoue et al. (1989) *Proc. Natl. Acad. Sci. USA* 86: 2863–2867; see, also Saida et al. (1989)*J. Biol. Chem.* 264: 14613–14616). The nucleotide sequences of the three human genes are highly conserved within the region encoding the mature 21 amino acid peptides and the C-terminal portions of the peptides are identical. Endothelin-2 is ($Trp^6$,$Leu^7$) endothelin-1 and endothelin-3 is ($Thr^2$,$Phe^4$,$Thr^5$,$Tyr^6$,$Lys^7$,$Tyr^{14}$) endothelin-1. These peptides are, thus, highly conserved at the C-terminal ends.

Release of endothelins from cultured endothelial cells is modulated by a variety of chemical and physical stimuli and appears to be regulated at the level of transcription and/or translation. Expression of the gene encoding endothelin-1 is increased by chemical stimuli, including adrenaline, thrombin and $Ca^{2+}$ ionophore. The production and release of endothelin from the endothelium is stimulated by angiotensin II, vasopressin, endotoxin, cyclosporine and other factors (see, Brooks et al. (1991) *Eur. J. Pharm.* 194:115–117), and is inhibited by nitric oxide. Endothelial cells appear to secrete short-lived endothelium-derived relaxing factors (EDRF), including nitric oxide or a related substance (Palmer et al. (1987) *Nature* 327: 524–526), when stimulated by vasoactive agents, such as acetylcholine and bradykinin. Endothelin-induced vasoconstriction is also attenuated by atrial natriuretic peptide (ANP).

The endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively (see, e.g., Bolger et al. (1991) *Can. J. Physiol. Pharmacol.* 69: 406–413). In isolated vascular strips, for example, endothelin-1 is a potent ($EC_{50}$=$4 \times 10^{-10}$ M), slow acting, but persistent, contractile agent. In vivo, a single dose elevates blood pressure in about twenty to thirty minutes. Endothelin-induced vasoconstriction is not affected by antagonists to known neurotransmitters or hormonal factors, but is abolished by calcium channel antagonists. The effect of calcium channel antagonists, however, is most likely the result of inhibition of calcium influx, since calcium influx appears to be required for the long-lasting contractile response to endothelin.

Endothelin also mediates renin release, stimulates ANP release and induces a positive inotropic action in guinea pig atria. In the lung, endothelin-1 acts as a potent bronchoconstrictor (Maggi et al. (1989) *Eur. J. Pharmacol.* 160: 179–182). Endothelin increases renal vascular resistance, decreases renal blood flow, and decreases glomerular filtrate rate. It is a potent mitogen for glomerular mesangial cells and invokes the phosphoinoside cascade in such cells (Simonson et al. (1990) *J. Clin. Invest.* 85: 790–797).

There are specific high affinity binding sites (dissociation constants in the range of $2-6 \times 10^{-10}$ M) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides. The sarafotoxins, a group of peptide toxins from the venom of the snake *Atractaspis eingadensis* that cause severe coronary vasospasm in snake bite victims, have structural and functional homology to endothelin-1 and bind competitively to the same cardiac membrane receptors (Kloog et al. (1989) *Trends Pharmacol. Sci.* 10: 212–214).

Two distinct endothelin receptors, designated $ET_A$ and $ET_B$, have been identified and DNA clones encoding each receptor have been isolated (Arai et al. (1990) *Nature* 348: 730–732; Sakurai et al. (1990) *Nature* 348: 732–735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain. The distribution of receptor subtypes is tissue specific (Martin et al. (1989) *Biochem. Biophys. Res. Commun.* 162: 130–137). $ET_A$ receptors appear to be selective for endothelin-1 and are predominant in cardiovascular tissues. $ET_B$ receptors are predominant in noncardiovascular tissues, including the central nervous system and kidney, and interact with the three endothelin isopeptides (Sakurai et al. (1990) *Nature* 348: 732–734). In addition, $ET_A$ receptors occur on vascular smooth muscle, are linked to vasoconstriction and have been associated with cardiovascular, renal and central nervous system diseases; whereas $ET_B$ receptors are located on the vascular endothelium, linked to vasodilation (Takayanagi et al. (1991) *FEBS Lttrs.* 282: 103–106) and have been associated with bronchoconstrictive disorders.

By virtue of the distribution of receptor types and the differential affinity of each isopeptide for each receptor type, the activity of the endothelin isopeptides varies in different tissues. For example, endothelin-1 inhibits $^{125}$I-labelled endothelin-1 binding in cardiovascular tissues forty to seven hundred times more potently than endothelin-3. $^{125}$I-labelled endothelin-1 binding in non-cardiovascular tissues, such as kidney, adrenal gland, and cerebellum, is inhibited to the same extent by endothelin-1 and endothelin-3, which indicates that $ET_A$ receptors predominate in cardiovascular tissues and $ET_B$ receptors predominate in non-cardiovascular tissues.

Endothelin plasma levels are elevated in certain disease states (see, e.g., International PCT Application WO 94/27979, and U.S. Pat. No. 5,382,569, which disclosures are herein incorporated in their entirety by reference). Endothelin-1 plasma levels in healthy individuals, as measured by radioimmunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels as high as 35 pg/ml have been observed (see, Stewart et al. (1991) *Annals Internal Med.* 114: 464–469). Because endothelin is likely to be a local, rather than a systemic, regulating factor, it is probable that the levels of endothelin at the endothelium/smooth muscle interface are much higher than circulating levels.

Elevated levels of endothelin have also been measured in patients suffering from ischemic heart disease (Yasuda et al. (1990) *Amer. Heart J.* 119:801–806, Ray et al. (1992) *Br. Heart J.* 67:383–386). Circulating and tissue endothelin immunoreactivity is increased more than twofold in patients with advanced atherosclerosis (Lerman et al. (1991) *New Engl. J. Med.* 325:997–1001). Increased endothelin immunoreactivity has also been associated with Buerger's disease (Kanno et al. (1990) *J. Amer. Med. Assoc.* 264:2868) and Raynaud's phenomenon (Zamora et al. (1990) Lancet 336 1144–1147). Increased circulating endothelin levels were observed in patients who underwent percutaneous transluminal coronary angioplasty (PTCA) (Tahara et al. (1991) *Metab. Clin. Exp.* 40:1235–1237; Sanjay et al. (1991) *Circulation* 84(*Suppl.* 4):726), and in individuals (Miyauchi et al. (1992) *Jpn. J. Pharmacol.*58:279P; Stewart et al. (1991) *Ann.Internal Medicine* 114:464–469) with pulmonary hypertension. Thus, there is clinical human data supporting the correlation between increased endothelin levels and numerous disease states.

Endothelin agonists and antagonists

Because endothelin is associated with certain disease states and is implicated in numerous physiological effects, compounds that can interfere with or potentiate endothelin-associated activities, such as endothelin-receptor interaction and vasoconstrictor activity, are of interest. Compounds that exhibit endothelin antagonistic activity have been identified. For example, a fermentation product of *Streptomyces misakiensis,* designated BE-18257B, has been identified as an $ET_A$ receptor antagonist. BE-18257B is a cyclic pentapeptide, cyclo(D-Glu-L-Ala-allo-D-Ile-L-Leu-D-Trp), which inhibits $^{125}$I-labelled endothelin-1 binding in cardiovascular tissues in a concentration-dependent manner ($IC_{50}$ 1.4 µM in aortic smooth muscle, 0.8 µM in ventricle membranes and 0.5 µM in cultured aortic smooth muscle cells), but fails to inhibit binding to receptors in tissues in which $ET_B$ receptors predominate at concentrations up to 100 µM. Cyclic pentapeptides related to BE-18257B, such as cyclo(D-Asp-Pro-D-Val-Leu-D-Trp) (BQ-123), have been synthesized and shown to exhibit activity as ETA receptor antagonists (see, U.S. Pat. No. 5,114,918 to Ishikawa et al.; see, also, EP A1 0 436 189 to BANYU PHARMACEUTICAL CO., LTD (Oct. 7, 1991)). Studies that measure the inhibition by these cyclic peptides of endothelin-1 binding to endothelin-specific receptors indicate that these cyclic peptides bind preferentially to $ET_A$ receptors. Other peptide and non-peptidic $ET_A$ antagonists have been identified (see, e.g., U.S. Pat. Nos. 5,352,800, 5,334,598, 5,352,659, 5,248,807, 5,240,910, 5,198,548, 5,187,195, 5,082,838). These include other cyclic pentapeptides, acyltripeptides, hexapeptide analogs, certain anthraquinone derivatives, indanecarboxylic acids, certain N-pyrimidinylbenzenesulfonamides, certain benzenesulfonamides, and certain naphthalenesulfonamides (Nakajima et al. (1991) *J. Antibiot.* 44:1348–1356; Miyata et al. (1992) *J. Antibiot.* 45:74–8; Ishikawa et al. (1992) *J.Med. Chem.* 35:2139–2142; U.S. Pat. No. 5,114,918 to Ishikawa et al.; EP A1 0 569 193; EP A1 0 558 258; EP A1 0 436 189 to BANYU PHARMACEUTICAL CO., LTD (Oct. 7, 1991); Canadian Patent Application 2,067,288; Canadian Patent Application 2,071,193; U.S. Pat. Nos. 5,208,243; 5,270,313; 5,464,853 to Chan et al.; Cody et al. (1993) *Med. Chem. Res.* 3:154–162; Miyata et al. (1992) *J. Antibiot* 45:1041–1046; Miyata et al. (1992) *J. Antibiot* 45:1029–1040, Fujimoto et al. (1992) *FEBS Lett.* 305:41–44; Oshashi et al. (1002) *J. Antibiot* 45:1684–1685; EP A1 0 496 452; Clozel et al. (1993) *Nature* 365:759–761; International Patent Application WO093/08799; Nishikibe et al. (1993) *Life Sci.* 52:717–724; and Benigni et al. (1993) *Kidney Int.* 44:440–444). In general, the identified compounds have activities in in vitro assays as $ET_A$ antagonists at concentrations on the order of about 50–100 µM or less. A number of such compounds have also been shown to possess activity in in vivo animal models. Very few selective $ET_B$ antagonists have been identified.

Endothelin antagonists and agonists as therapeutic agents

It has been recognized that compounds that exhibit activity at $IC_{50}$ or $EC_{50}$ concentrations on the order of $10^{-4}$ or lower in standard in vitro assays that assess endothelin antagonist or agonist activity have pharmacological utility (see, e.g., U.S. Pat. Nos. 5,352,800, 5,334,598, 5,352,659, 5,248,807, 5,240,910, 5,198,548, 5,187,195, 5,082,838). By virtue of this activity, such compounds are considered to be useful for the treatment of hypertension such as peripheral circulatory failure, heart disease such as angina pectoris, cardiomyopathy, arteriosclerosis, myocardial infarction, pulmonary hypertension, vasospasm, vascular restenosis, Raynaud's disease, cerebral stroke such as cerebral arterial spasm, cerebral ischemia, late phase cerebral spasm after subarachnoid hemorrhage, asthma, bronchoconstriction, renal failure, particularly post-ischemic renal failure, cyclosporine nephrotoxicity such as acute renal failure, colitis, as well as other inflammatory diseases, endotoxic shock caused by or associated with endothelin, and other diseases in which endothelin has been implicated.

In view of the numerous physiological effects of endothelin and its association with certain diseases, endothelin is believed to play a critical role in these pathophysiological conditions (see, e.g., Saito et al. (1990) *Hypertension* 15: 734–738; Tomita et al. (1989) *N. Engl. J. Med.* 321: 1127; Kurihara et al. (1989) *J. Cardiovasc. Pharmacol.* 13(*Suppl.*

5): S13–S17; Doherty (1992) *J. Med. Chem.* 35: 1493–1508; Morel et al. (1989) *Eur. J. Pharmacol.* 167: 427–428). More detailed knowledge of the function and structure of the endothelin peptide family should provide insight in the progression and treatment of such conditions.

To aid in gaining further understanding of and to develop treatments for endothelin-mediated or related disorders, there is a need to identify compounds that modulate or alter endothelin activity. Identification of compounds that modulate endothelin activity, such as those that act as specific antagonists or agonists, may not only aid in elucidating the function of endothelin, but may yield in therapeutically useful compounds. In particular, compounds that specifically interfere with the interaction of endothelin peptides with the $ET_A$ or $ET_B$ receptors should be useful in identifying essential characteristics of endothelin peptides, should aid in the design of therapeutic agents, and may be useful as disease specific therapeutic agents.

Therefore, it is an object herein to provide compounds that have the ability to modulate the biological activity of one or more of the endothelin isopeptides. It is another object to provide compounds that have use as specific endothelin antagonists. It is also an object to use compounds that specifically interact with or inhibit the interaction of endothelin peptides with $ET_A$ or $ET_B$ receptors. Such compounds should be useful as therapeutic agents for the treatment of endothelin-mediated diseases and disorders and also for the identification of endothelin receptor subtypes.

SUMMARY OF THE INVENTION

Sulfonamides and methods for modulating the interaction of an endothelin peptide with $ET_A$ and/or $ET_B$ receptors are provided. In particular, sulfonamides and methods for inhibiting the binding of an endothelin peptide to $ET_A$ or $ET_B$ receptors are provided. The methods are effected by contacting the receptors with one or more sulfonamides prior to, simultaneously with, or subsequent to contacting the receptors with an endothelin peptide. The sulfonamides are substituted or unsubstituted mohocyclic or polycyclic aromatic or heteroaromatic sulfonamides, such as benzene sulfonamides, naphthalene sulfonamides and thiophene sulfonamides. Particularly preferred sulfonamides are N-isoxazolyl sulfonamides. More particularly preferred among such sulfonamides are those in which $Ar^2$ is a heterocycle that contains one ring, multiple rings or fused rings, typically two or three rings and one or two heteroatoms in the ring or rings.

The sulfonamides have formula I:

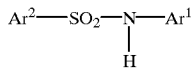

(I)

in which $Ar^1$ is a substituted or unsubstituted aryl group with one or more substituents, including an alkyl group, an aryl group, a substituted aryl group, a nitro group, an amino group or a halide or is an alkyl group. In particular, $Ar^1$ is alkyl or is a five or six membered substituted or unsubstituted aromatic or heteroaromatic ring, particularly 3- or 5-isoxazolyl and pyridazinyl, and also including thiazolyl, including 2-thiazolyl, pyrimidinyl, including 2-pyrimidinyl, or substituted benzene groups, including aryloxy substituted benzene groups or is a bicyclic or tricyclic carbon or heterocyclic ring.

$Ar^1$ is, in certain embodiments, selected from groups such as:

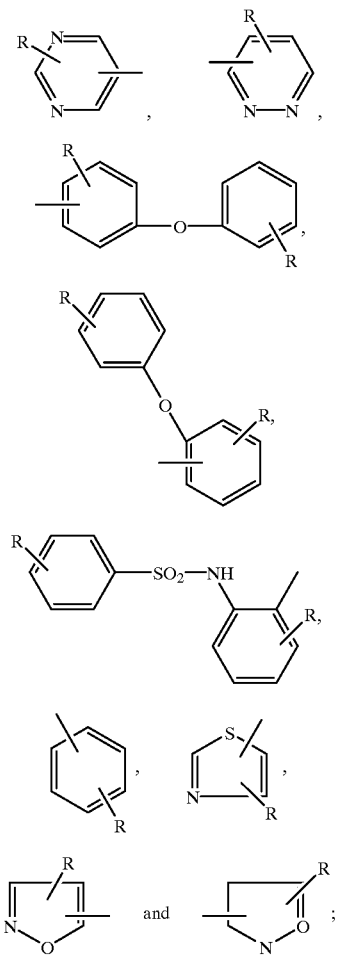

and R is selected from H, $NH_2$, halide, pseudohalide, alkyl, alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted with any of the preceding groups, and straight or branched chains of from about 1 up to about 10–12 carbons, preferably, 1 to about 5 or 6 carbons. R is preferably H, $NH_2$, halide, $CH_3$, $CH_3O$ or another aromatic group. $Ar^2$ is any group such that the resulting sulfonamide inhibits binding by 50%, compared to binding in the absence of the sulfonamide, of an endothelin peptide to an endothelin receptor at a concentration of less than about 100 μM, except that $Ar^2$ is not phenyl or naphthyl when $Ar^1$ is N-(5-isoxazolyl) or N-(3-isoxazolyl) unless the isoxazole is a 4-halo-isoxazole, a 4-higher alkyl ($C_8$ to $C_{15}$)-isoxazole, or the compound is a 4-biphenyl that is unsubstituted at the 2 or 6 position on the sulfonamide-linked phenyl group.

In the embodiments described in detail herein, $Ar^1$ is an isoxazole and compounds are represented by the formulae II:

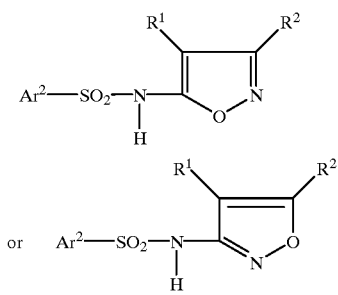

(II)

in which $R^1$ and $R^2$ are either (i), (ii) or (iii) as follows:

(i) $R^1$ and $R^2$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, except that $R^2$ is not halide or pseudohalide; or, (ii) $R^1$ and $R^2$ together form $—(CH_2)_n—$, where n is 3 to 6; or, (iii) $R^1$ and $R^2$ together form 1,3-butadienyl, and with the above proviso that $Ar^2$ is not phenyl or naphthyl when $Ar^1$ is N-(5-isoxazolyl) or N-(3-isoxazolyl) unless the isoxazole is a 4-halo-isoxazole, a 4-higher alkyl ($C_8$ to $C_{15}$)-isoxazole, or the compound is a 4-biphenylsulfonamide that is unsubstituted at the 2 or 6 position on the sulfonamide-linked phenyl group.

In preferred embodiments herein, $R^1$ and $R^2$ are each selected independently from among alkyl, lower alkenyl, lower alkynyl, lower haloalkyl, halide, pseudohalide or H, except that $R^2$ is not halide;

$Ar^2$ is any group such that the resulting sulfonamide inhibits binding by 50%, compared to binding in the absence of the sulfonamide, of an endothelin peptide to an endothelin receptor at a concentration of less than about 100 μM, with the above proviso. In particular, $Ar^2$ is a substituted or unsubstituted group selected from among groups including, but not limited to, the following: naphthyl, phenyl, biphenyl, quinolyl, styryl, thienyl, furyl, isoquinolyl, pyrrolyl, benzofuranyl, pyridinyl, thionaphthalyl, indolyl, alkyl, and alkenyl. It is understood that the positions indicated for substituents, including the sulfonamide groups, may be varied. Thus, for example, compounds herein encompass groups that include thiophene-3-sulfonamides and thiophene-2-sulfonamides.

In certain embodiments described in detail herein, $Ar^2$ is a 4-biphenyl or is a single ring heterocycle, particularly a 5-membered ring, or is a fused bicyclic or tricyclic heterocycle that contains one or more, particularly one, heteroatom selected from S, O and $NR^{42}$, in the ring, where $R^{42}$ contains up to about 30 carbon atoms, preferably 1 to 10, more preferably 1 to 6 and is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{42}$ and $R^{15}$ are unsubstituted or are substituted with one or more substituents each selected independently from Z, which is hydrogen, halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{42}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{42}$, $R^{12}$, $R^{15}$ and $R^{16}$ may be further substituted with the any of the groups set forth for Z.

In preferred embodiments herein, $R^{42}$ is aryl, such as phenyl or alkyl phenyl, hydrogen or loweralkyl.

Thus, in the compounds provided herein $Ar^2$ includes thienyl, furyl and pyrrolyl, benzofuryl, benzopyrolyl, benzothienyl, benzo[b]furyl, benzo[b]thienyl, and indolyl (benzo[b]pyrrolyl) and 4-biphenyl, and $Ar^1$ is preferably N-(5-isoxazolyl) or N-(3-isoxazolyl). The sulfonamides are N-isoxazolyl sulfonamides and the compounds have either have formula III:

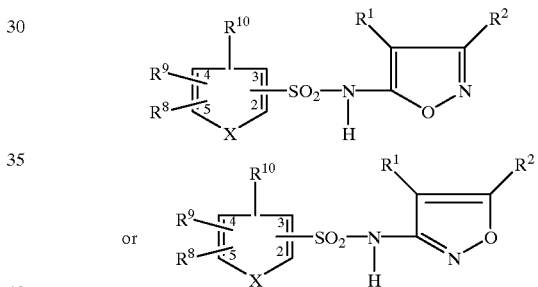

in which X is S, O or $NR^{11}$ in which $R^{11}$ contains up to about 30 carbon atoms, preferably 1 to 10, more preferably 1 to 6 and is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z, which is hydrogen, halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{11}$, $R^{12}$, $R^{15}$ and $R^{16}$ may be further substituted with the any of the groups set forth for Z, and $R^{11}$ is preferably hydrogen, aryl, such as phenyl or alkyl phenyl, loweralkyl; or the compounds are 4-biphenylsulfonamides in which $Ar^1$ is preferably N-(5-isoxazolyl) or N-(3-isoxazolyl).

Among the embodiments described in detail herein, $Ar^2$ is thienyl, furyl, pyrrolyl or a group that is a derivative or analog, as described below, of a thienyl, furyl or pyrrolyl group, including benzo[b] derivatives such as a benzo[b]thienyl, $Ar^1$ is N-(5-isoxazolyl) or N-(3-isoxazolyl). $Ar^2$ has the formula IV:

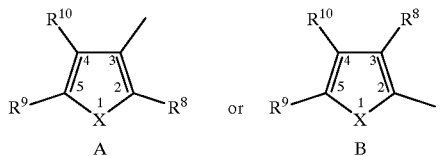

in which X is O, S or $NR^{11}$, where $R^{11}$ is as defined above; that can be substituted at any or all positions or is an analog or derivative of the groups of formula (IV) in which the substituents form fused aromatic, aliphatic or heterocyclic rings; and $R^8$, $R^9$ and $R^{10}$ are each independently selected as follows from (i) or (ii):

(i) $R^8$, $R^9$ and $R^{10}$, which each contain hydrogen or up to about 50 carbon atoms, generally up to about 30, more generally 20 or fewer, are each independently selected from hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, AcO-C=$CHR^{18}$—, $CO_2R^{18}$, SH, $(CH_2)_rC(O)(CH_2)_nR^{18}$, $(CH_2)_r(CH=CH)_s(CH_2)_nR^{18}$, $(CH_2)_rC(O)(CH=CH)_s(CH_2)_nR^{18}$, $(CH_2)_r(CH=CH)_sC(O)(CH_2)_nR^{18}$, $(CH_2)_rNH(CH=CH)_s(CH_2)_nR^{18}$, C=N(OH)$(CH_2)_nR^{18}$ $(CH_2)_r(CH=CH)_sNH(CH_2)_nR^{18}$, $(CH_2)_rC(O)NH(CH_2)_nR^{18}$, $C(O)(CH_2)_rNH(CH_2)_nR^{18}$, $(CH_2)_rNH(CH_2)_nR^{18}$, $(CH_2)_rR^{18}$, $S(O)_mR^{18}$ in which m is 0–2, s, n and r are each independently 0 to 6, preferably 0–3, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$, $S(O)_nR^{20}$ in which n is 0–2; and $R^{18}$ and $R^{20}$ are independently selected from hydrogen, alkyl, alkenyl, alkynyl, aryl, heteroaryl, alkylaryl, heterocycle, alkoxy, aryloxy, aralkyl, aralkoxy, cycloalkyl, cycloalkenyl or cycloalkynyl; and any of the groups set forth for $R^8$, $R^9$ and $R^{10}$ are unsubstituted or substituted with any substituents set forth for Z, which is hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{21}$, $CO_2R^{21}$, SH, $S(O)_nR^{21}$ in which n is 0–2, NHOH, $NR^{22}R^{21}$, $NO_2$, $N_3$, $OR^{21}$, $R^{22}NCOR^{21}$ and $CONR^{22}R^{21}$; $R^{22}$ is selected from hydrogen, alkyl, alkenyl, alkynyl, aryl, alkylaryl, heterocycle, aralkyl, alkoxy, aralkoxy, cycloalkyl, cycloalkenyl, cycloalkynyl, $C(O)R^{23}$ and $S(O)_nR^{23}$ in which n is 0–2; and $R^{21}$ and $R^{23}$ are independently selected from hydrogen, alkyl, alkenyl, alkynyl, aryl, alkylaryl, heterocycle, aralkyl, aralkoxy, cycloalkyl, cycloalkenyl or cycloalkynyl, with the proviso that if $R^8$ is $NR^{18}R^{19}$, $OR^{18}$, $R^{19}NCOR^{18}$ and $CONR^{19}R^{18}$ $CO_2R^{18}$, $(CH_2)_rNH(CH=CH)_s(CH_2)_nR^{18}$, $(CH_2)_r(CH=CH)_sNH(CH_2)_nR^{18}$, $(CH_2)_rC(O)NH(CH_2)_nR^{18}$, $C(O)(CH_2)_rNH(CH_2)_nR^{18}$, $(CH_2)_rNH(CH_2)_nR^{18}$ or $(CH_2)_rR^{18}$ and $R^{18}$ is an aryl group containing 5 or 6 members, then the aryl group has at least two substituents, and preferably one substituent at the 2-position relative to the linkage to the thienyl, furyl or pyrrolyl;

(ii) any two of $R^8$, $R^9$ and $R^{10}$ with the carbon to which each is attached form an aryl, aromatic ring, heteroaromatic ring, carbocyclic or heterocyclic ring, which is saturated or unsaturated, containing from about 3 to about 16 members, preferably 3 to about 10 members, more preferably 5 to 7 members that is substituted with one or more substituents, each substituent is independently selected from Z; the other of $R^8$, $R^9$ and $R^{10}$ is selected as in (i); and the heteroatoms are $NR^{11}$, O, or S, with the proviso that $Ar^2$ is not 5-halo-3-loweralkylbenzo[b]thienyl, 5-halo-3-loweralkylbenzo[b]furyl, 5-halo-3-loweralkylbenzo[b]pyrrolyl.

In the embodiments provided herein, the alkyl, alkynyl and alkenyl portions of each listed substituent are straight or branched chains, acyclic or cyclic, and preferably have from about 1 up to about 10 carbons; in more preferred embodiments they have from 1–6 carbons. The aryl, alicyclic, aromatic rings and heterocyclic groups can have from 3 to 16, generally, 3–7, more often 5–7 members in the rings, and may be single or fused rings. The ring size and carbon chain length are selected up to an amount that the resulting molecule binds and retains activity as an endothelin antagonist or agonist, such that the resulting compound inhibits binding by 50%, compared to binding in the absence of the sulfonamide, of an endothelin peptide to an endothelin receptor at a concentration of less than about 100 $\mu$M.

In preferred embodiments of interest herein, $R^9$ and $R^{10}$ are hydrogen, halide or methyl, more preferably hydrogen or halide, and $R^8$ is selected from $CO_2R^{18}$, $(CH_2)_rC(O)(CH_2)_nR^{18}$, $(CH_2)_r(CH=CH)_s(CH_2)_nR^{18}$, C=N(OH)$(CH_2)_nR^{18}$, $(CH_2)_rC(O)(CH=CH)_s(CH_2)_nR^{18}$, $(CH_2)_r(CH=CH)_sC(O)(CH_2)_nR^{18}$, $(CH_2)_rNH(CH=CH)_s(CH_2)_nR^{18}$, $(CH_2)_r(CH=CH)_sNH(CH_2)_nR^{18}$, $(CH_2)_rC(O)NH(CH_2)_nR^{18}$, $C(O)(CH_2)_rNH(CH_2)_nR^{18}$, $(CH_2)_rNH(CH_2)_nR^{18}$, $(CH_2)_rR^{18}$, with the proviso that if $R^8$ is $CO_2R^{18}$, $(CH_2)_rC(O)NH(CH_2)_nR^{18}$, $C(O)(CH_2)_rNH(CH_2)_nR^{18}$, $(CH_2)_rC(O)NH(CH_2)_nR^{18}$ or $(CH_2)_rR^{18}$ and $R^{18}$ is phenyl, the phenyl group is substituted at at least two positions, and preferably, at least one of those positions is ortho.

In the preferred compounds, $R^{18}$ is aryl or heteroaryl, preferably having 5 or 6 members in the ring, more preferably phenyl or pyrimidinyl, most preferably phenyl.

In the most preferred compounds herein, $R^{18}$ is phenyl, which is substituted at more than one position, and most preferably at least one substituent is at the ortho position, $R^9$ and $R^{10}$ are each hydrogen, halide or loweralkyl, preferably hydrogen, and $R^8$ is $C(O)NHR^{18}$, $C(O)CH_2R^{18}$, $(CH_2)_rR^{18}$, whith the proviso that if $R^8$ is $C(O)NHR^{18}$, then the phenyl group must have at least two substituents, preferably one of the substituents is in the ortho position.

In other preferred embodiments, $Ar^2$ is a benzo[b]thienyl, benzo[b]furyl, or indolyl (benzo[b]pyrrolyl), with the proviso that the benzene ring is substituted and the substituents are other than 5 halo, 3-loweralkyl. Preferred substituents on the benzene ring, include, but are not limited to, one or more selected from alkylenedioxy, particularly methylenedioxy, preferably 3,4-methylenedioxy, ethylenedioxy, aryl, particularly phenyl, dimethylamino, diethylamino, benzyl, alkoxy, particularly lower alkoxy, such as methoxy and ethoxy, halide, and alkyl, preferably loweralkyl.

In the preferred compounds herein, $R^2$ is preferably selected from among alkyl, lower alkenyl, lower alkynyl, lower haloalkyl or H; and $R^1$ is halide or loweralkyl, and more preferably, $R^1$ is bromide or chloride, methyl or ethyl.

In the most active compounds provided herein, as evidenced by in vitro binding assays, $R^1$ is bromide or chloride. For use in vivo $R^1$ is preferably chloride.

Of the compounds described herein, those that inhibit or increase an endothelin-mediated activity by about 50% at concentrations of less than about 10 $\mu$M are preferred. More preferred are those that inhibit or increase an endothelin-mediated activity by about 50% at concentrations of less than about 1 $\mu$M, more preferably less than about 0.1 $\mu$M, even more preferably less than about 0.01 $\mu$M, and most preferably less than about 0.001 $\mu$M. It is noted that, as described below, the $IC_{50}$ concentration determined in the in vitro assays is a non-linear function of incubation temperature. The preferred values recited herein refer to the assays that are performed at 4° C. When the assays are performed at 24° C., somewhat higher (see, Table 1) $IC_{50}$ concentrations are observed. Accordingly, the preferred $IC_{50}$ concentrations are about 10-fold higher.

Also among the most preferred compounds for use in methods provided herein, are those that are $ET_A$ selective, i.e., they interact with $ET_A$ receptors at substantially lower concentrations (at an $IC_{50}$ at least about 10-fold lower, preferably 100-fold lower) than they interact with $ET_B$ receptors. In particular, compounds that interact with $ET_A$ with an $IC_{50}$ of less than about 10 $\mu$M, preferably less than 1 $\mu$M, more preferably less than 0.1 $\mu$M, but with $ET_B$ with an $IC_{50}$ of greater than about 10 $\mu$M or compounds that interact with $ET_B$ with an $IC_{50}$ of less than about 10 $\mu$M, preferably less than 1 $\mu$M, more preferably less than 0.1 $\mu$M, but with $ET_A$ with an $IC_{50}$ of greater than about 10 $\mu$M are preferred.

Preferred compounds also include compounds that are $ET_B$ receptor selective or that bind to $ET_B$ receptors with an $IC_{50}$ of less than about 1 $\mu$M. $ET_B$ selective compounds interact with $ET_B$ receptors at $IC_{50}$ concentrations that are at least about 10-fold lower than the concentrations at which they interact with $ET_A$ receptors. In these compounds, $R^2$ is selected from among alkyl, lower alkenyl, lower alkynyl, lower haloalkyl, halide or H; and $R^1$ is halide or loweralkyl, and in preferred embodiments, $R^1$ is bromide or chloride, preferably chloride; $R^9$ and $R^{10}$ are selected independently from hydrogen, loweralkyl, preferably methyl or ethyl, or halide, and $R^8$, which is the substituent at the 5-position (see, e.g., formulae III and IV), is aryl or a heterocycle, particularly phenyl and isoxazolyl, which are unsubstituted or substituted with Z, which is preferably loweralkyl or halide.

Pharmaceutical compositions formulated for administration by an appropriate route and means containing effective concentrations of one or more of the compounds provided herein or pharmaceutically acceptable salts or acids thereof that deliver amounts effective for the treatment of hypertension, stroke, asthma, shock, ocular hypertension, glaucoma, renal failure, inadequate retinal perfusion and other conditions that are in some manner mediated by an endothelin peptide or that involve vasoconstriction or whose symptoms can be ameliorated by administration of an endothelin antagonist or agonist, are also provided. Particularly preferred compositions are those that deliver amounts effective for the treatment of hypertension or renal failure. The effective amounts and concentrations are effective for ameliorating any of the symptoms of any of the disorders.

Methods for inhibiting binding of an endothelin peptide to an endothelin receptor are provided. These methods are practiced by contacting the receptor with one or more of the compounds provided herein simultaneously, prior to, or subsequent to contacting the receptor with an endothelin peptide.

Methods for treatment of endothelin-mediated disorders, including but not limited to, hypertension, asthma, shock, ocular hypertension, glaucoma, inadequate retinal perfusion and other conditions that are in some manner mediated by an endothelin peptide, or for treatment of disorder that involve vasoconstriction or that are ameliorated by administration of an endothelin antagonist or agonist are provided.

In particular, methods of treating endothelin-mediated disorders by administering effective amounts of the sulfonamides, prodrugs or other suitable derivatives of the sulfonamides are provided. In particular, methods for treating endothelin-mediated disorders, including hypertension, cardiovascular diseases, cardiac diseases including myocardial infarction, pulmonary hypertension, erythropoietin-mediated hypertension, respiratory diseases and inflammatory diseases, including asthma, bronchoconstriction, ophthalmologic diseases, gastroenteric diseases, renal failure, endotoxin shock, menstrual disorders, obstetric conditions, wounds, anaphylactic shock, hemorrhagic shock, and other diseases in which endothelin mediated physiological responses are implicated, by administering effective amounts of one or more of the compounds provided herein in pharmaceutically acceptable carriers are provided. Preferred methods of treatment are methods for treatment of hypertension and renal failure.

More preferred methods of treatment are those in which the compositions contain at least one compound that inhibits the interaction of endothelin-1 with $ET_A$ receptors at an $IC_{50}$ of less than about 10 $\mu$M, and preferably less than about 5 $\mu$M, more preferably less than about 1 $\mu$M, even more preferably less than 0.1 $\mu$M, and most preferably less than 0.05 $\mu$M Other preferred methods are those in which the compositions contain one or more compounds that is (are) $ET_A$ selective or one or more compounds that is (are) $ET_B$ selective. Methods in which the compounds are $ET_A$ selective are for treatment of disorders, such as hypertension; and methods in which the compounds are $ET_B$ selective are for treatment of disorders, such as asthma, that require bronchodilation.

In practicing the methods, effective amounts of compositions containing therapeutically effective concentrations of the compounds formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, immunosuppressant-mediated renal vasoconstriction, erythropoietin-mediated vasoconstriction, endotoxin shock, anaphylactic shock, hemorrhagic shock, pulmonary hypertension, and other diseases in which endothelin mediated physiological responses are implicated are administered to an individual exhibiting the symptoms of one or more of these disorders. The amounts are effective to ameliorate or eliminate one or more symptoms of the disorders.

Methods for the identification and isolation of endothelin receptor subtypes are also provided. In particular, methods for detecting, distinguishing and isolating endothelin receptors using the disclosed compounds are provided. In particular, methods are provided for detecting, distinguishing and isolating endothelin receptors using the compounds provided herein.

In addition, methods for identifying compounds that are suitable for use in treating particular diseases based on their preferential affinity for a particular endothelin receptor subtype are also provided.

Articles of manufacture containing packaging material, a compound provided herein, which is effective for ameliorating the symptoms of an endothelin-mediated disorder, antagonizing the effects of endothelin or inhibiting binding of an endothelin peptide to an ET receptor with an $IC_{50}$ of less than about 10 μM, within the packaging material, and a label that indicates that the compound or salt thereof is used for antagonizing the effects of endothelin, treating an endothelin-mediated disorder, or inhibiting the binding of an endothelin peptide to an ET receptor are provided.

Also provided herein are substituted biphenyl sulfonamides that have $ET_B$ activity.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, endothelin (ET) peptides include peptides that have substantially the amino acid sequence of endothelin-1, endothelin-2 or endothelin-3 and that act as potent endogenous vasoconstrictor peptides.

As used herein, an endothelin-mediated condition is a condition that is caused by abnormal endothelin activity or one in which compounds that inhibit endothelin activity have therapeutic use. Such diseases include, but are not limited to hypertension, cardiovascular disease, asthma, inflammatory diseases, ophthalmologic disease, menstrual disorders, obstetric conditions, gastroenteric disease, renal failure, pulmonary hypertension, endotoxin shock, anaphylactic shock, or hemorrhagic shock. Endothelin-mediated conditions also include conditions that result from therapy with agents, such as erythropoietin and immunosuppressants, that elevate endothelin levels.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, an endothelin agonist is a compound that potentiates or exhibits a biological activity associated with or possessed by an endothelin peptide.

As used herein, an endothelin antagonist is a compound, such as a drug or an antibody, that inhibits endothelin-stimulated vasoconstriction and contraction and other endothelin-mediated physiological responses. The antagonist may act by interfering with the interaction of the endothelin with an endothelin-specific receptor or by interfering with the physiological response to or bioactivity of an endothelin isopeptide, such as vasoconstriction. Thus, as used herein, an endothelin antagonist interferes with endothelin-stimulated vasoconstriction or other response or interferes with the interaction of an endothelin with an endothelin-specific receptor, such as $ET_A$ receptors, as assessed by assays known to those of skill in the art.

The effectiveness of potential agonists and antagonists can be assessed using methods known to those of skill in the art. For example, endothelin agonist activity can be identified by its ability to stimulate vasoconstriction of isolated rat thoracic aorta or portal vein ring segments (Borges et al. (1989) "Tissue selectivity of endothelin" *Eur. J. Pharmacol.* 165: 223–230). Endothelin antagonist activity can be assessed by the ability to interfere with endothelin-induced vasoconstriction. Exemplary assays are set forth in the EXAMPLES. As noted above, the preferred $IC_{50}$ concentration ranges are set forth with reference to assays in which the test compound is incubated with the ET receptor-bearing cells at 4° C. Data presented for assays in which the incubation step is performed at the less preferred 24° C. are identified. It is understood that for purposes of comparison, these concentrations are somewhat higher than the concentrations determined at 4° C.

As used herein, the biological activity or bioactivity of endothelin includes any activity induced, potentiated or influenced by endothelin in vivo. It also includes the ability to bind to particular receptors and to induce a functional response, such as vasoconstriction. It may be assessed by in vivo assays or by in vitro assays, such as those exemplified herein. The relevant activities include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction. Any assay known to those of skill in the art to measure or detect such activity may be used to assess such activity (see, e.g., Spokes et al. (1989) *J. Cardiovasc. Pharmacol.* 13(Suppl. 5):S191–S192; Spinella et al. (1991) *Proc. Natl. Acad. Sci. USA* 88: 7443–7446; Cardell et al. (1991) *Neurochem. Int.* 18:571–574); and the Examples herein).

As used herein, the $IC_{50}$ refers to an amount, concentration or dosage of a particular test compound that achieves a 50% inhibition of a maximal response, such as binding of endothelin to tissue receptors, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein a sulfonamide that is $ET_A$ selective refers to sulfonamides that exhibit an $IC_{50}$ that is at least about 10-fold lower with respect to $ET_A$ receptors than $ET_B$ receptors.

As used herein, a sulfonamide that is $ET_B$ selective refers to sulfonamides that exhibit an $IC_{50}$ that is at least about 10-fold lower with respect to $ET_B$ receptors than $ET_A$ receptors.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, treatment means any manner in which the symptoms of a conditions, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392). For example, succinylsulfathiazole is a prodrug of 4-amino-N-(2-thiazoyl) benzenesulfonamide (sulfathiazole) that exhibits altered transport characteristics.

As used herein, acid isostere means a group that is significantly ionized at physiological pH. Examples of suitable acid isosteres include sulfo, phosphono, alkylsulfonylcarbamoyl, tetrazolyl, arylsulfonylcarbamoyl or heteroarylsulfonylcarbamoyl.

As used herein, halo or halide refers to the halogen atoms; F, Cl, Br and I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to, cyanide, cyanate, thiocyanate, selenocyanate and azide.

As used herein, haloalkyl refers to a loweralkyl radical in which one or more of the hydrogen atoms are replaced by halogen including, but not limited to, chloromethyl, trifluoromethyl, 1-chloro-2-fluoroethyl and the like.

As used herein, alkyl means an aliphatic hydrocarbon group that is a straight or branched chain preferably having about 1 to 12 carbon atoms in the chain. Preferred alkyl groups are loweralkyl groups which are alkyls containing 1 to about 6 carbon atoms in the chain. Branched means that one or more loweralkyl groups such as methyl, ethyl or propyl are attached to a linear alkyl chain. The alkyl group may be unsubstituted or independently substituted by one or more groups, such as, but not limited to: halo, carboxy, formyl, sulfo, sulfino, carbamoyl, amino and imino. Exemplary alkyl groups include methyl, ethyl, propyl, methanoic acid, ethanoic acid, propanoic acid, ethanesulfinic acid and ethane sulfonic acid.

As used herein the term lower describes alkyl, alkenyl and alkynyl groups containing about 6 carbon atoms or fewer. It is also used to describe aryl groups or heteroaryl groups that contain 6 or fewer atoms in the ring. Loweralkyl, lower alkenyl, and lower alkynyl refer to carbon chains having less than about 6 carbons. In preferred embodiments of the compounds provided herein that include alkyl, alkenyl, or alkynyl portions include loweralkyl, lower alkenyl, and lower alkynyl portions.

As used herein, alkenyl means an aliphatic hydrocarbon group containing a carbon-carbon double bond and which may be straight or branched chained having from about 2 to about 10 carbon atoms in the chain. Preferred alkenyl groups have 2 to about 4 carbon atoms in the chain. Branched means that one or more loweralkyl or lower alkenyl groups are attached to a linear alkenyl chain. The alkenyl group may be unsubstituted or independently substituted by one or more groups, such as halo, carboxy, formyl, sulfo, sulfino, carbamoyl, amino and imino. Exemplary alkenyl groups include ethenyl, propenyl, carboxyethenyl, carboxypropenyl, sulfinoethenyl and sulfonoethenyl.

As used herein, alkynyl means an aliphatic hydrocarbon group containing a carbon-carbon triple bond and which may be straight or branched having about 2 to 10 carbon atoms in the chain. Branched means that one or more loweralkyl, alkenyl or alkynyl groups are attached to a linear alkynyl chain. An exemplary alkynyl group is ethynyl.

As used herein, aryl means an aromatic monocyclic or multicyclic hydrocarbon ring system containing from 3 to 15 or 16 carbon atoms, preferably from 5 to 10. Aryl groups include, but are not limited to, groups, such as phenyl, substituted phenyl, naphthyl, substituted naphthyl, in which the substituent is loweralkyl, halogen, or lower alkoxy. Preferred aryl groups are lower aryl groups that contain less than 7 carbons in the ring structure.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

As used herein, cycloalkyl refers to saturated cyclic carbon chains; cycloalkyenyl and cycloalkynyl refer to cyclic carbon chains that include at least one unsaturated double or triple bond, respectively. The cyclic portions of the carbon chains may include one ring or two or more fused rings.

As used herein, cycloalkenyl means a non-aromatic monocyclic or multicyclic ring system containing a carbon-carbon double bond and having about 3 to about 10 carbon atoms. Exemplary monocyclic cycloalkenyl rings include cyclopentenyl or cyclohexenyl; preferred is cyclohexenyl. An exemplary multicyclic cycloalkenyl ring is norbornylenyl. The cycloalkenyl group may be independently substituted by one or more halo or alkyl.

As used herein, "haloalkyl" refers to a loweralkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "carboxamide" refers to groups of formula $R_pCONH_2$ in which R is selected from alkyl or aryl, preferably loweralkyl or lower aryl and p is 0 or 1.

As used herein, "alkylaminocarbonyl" refers to —C(O)NHR in which R is hydrogen, alkyl, preferably loweralkyl or aryl, preferably lower aryl.

As used herein "dialkylaminocarbonyl" as used herein refers to —C(O)NR'R in which R' and R are independently selected from alkyl or aryl, preferably loweralkyl or loweraryl; "carboxamide" refers to groups of formula NR'COR.

As used herein, "alkoxycarbonyl" as used herein refers to —C(O)OR in which R is alkyl, preferably loweralkyl or aryl, preferably lower aryl.

As used herein, "alkoxy" and "thioalkoxy" refer to RO— and RS—, in which R is alkyl, preferably loweralkyl or aryl, preferably lower aryl.

As used herein, "haloalkoxy" refers to RO— in which R is a haloalkyl group.

As used herein, "aminocarbonyl" refers to —C(O)NH$_2$.

As used herein, "alkylaminocarbonyl" refers to —C(O)NHR in which R is alkyl, preferably loweralkyl or aryl, preferably lower aryl.

As used herein, "alkoxycarbonyl" refers to —C(O)OR in which R is alkyl, preferably loweralkyl.

As used herein, cycloalkyl refers to saturated cyclic carbon chains; cycloalkenyl and cycloalkynyl refer to cyclic carbon chains that include at least one unsaturated double or triple bond. The cyclic portions of the carbon chains may include one ring or two or more fused rings.

As used herein, alkylenedioxy means an —O-alkyl-O— group in which the alkyl group is as previously described. A replacement analog of alkylenedioxy means an alkylenedioxy in which one or both of the oxygen atoms is replaced by a similar behaving atom or group of atoms such as, S, N, NH, Se. An exemplary replacement alkylenedioxy group is ethylenebis(sulfandiyl). Alkylenethioxyoxy is —S-alkyl-O—, —O-alkyl-S— and alkylenedithioxy is —S-alkyl-S—.

As used herein, heteroaryl means an aromatic monocyclic or fused ring system in which one or more of the carbon atoms in the ring system is(are) replaced by an element(s) other than carbon, for example nitrogen, oxygen or sulfur. Preferred cyclic groups contain one or two fused rings and include from about 3 to about 7 members in each ring. Similar to "aryl groups", the heteroaryl groups may be unsubstituted or substituted by one or more substituents. Exemplary heteroaryl groups include pyrazinyl, pyrazolyl, tetrazolyl, furanyl, (2- or 3-)thienyl, (2-,3- or 4-)pyridyl, imidazoyl, pyrimidinyl, isoxazolyl, thiazolyl, isothiazolyl, quinolinyl, indolyl, isoquinolinyl, oxazolyl and 1,2,4-oxadiazolyl. Preferred heteroaryl groups include 5 to 6-membered nitrogen-containing rings, such as pyrmidinyl.

As used herein, alkoxycarbonyl means an alkyl-O—CO— group. Exemplary alkoxycarbonyl groups include methoxy- and ethoxycarbonyl.

As used herein, carbamoyl means —CONH$_2$. As with all groups described herein, these groups may be unsubstituted or substituted. Substituted carbamoyl includes groups such as —CONY$^2$Y$^3$ in which Y$^2$ and Y$^3$ are independently hydrogen, alkyl, cyano(loweralkyl), aryalkyl, heteroaralkyl, carboxy(loweralkyl), carboxy(aryl substituted loweralkyl), carboxy(carboxy substituted loweralkyl), carboxy(hydroxy substituted loweralkyl), carboxy(heteroaryl substituted loweralkyl), carbamoyl(loweralkyl), alkoxycarbonyl(loweralkyl) or alkoxycarbonyl(aryl substituted loweralkyl), provided that only one of Y$^2$ and Y$^3$ may be hydrogen and when one of Y$^2$ and Y$^3$ is carboxy(loweralkyl), carboxy(aryl substituted loweralkyl), carbamoyl(loweralkyl), alkoxycarbonyl(loweralkyl) or alkoxycarbonyl(aryl substituted loweralkyl) then the other of Y$^2$ and Y$^3$ is hydrogen or alkyl. Preferred for Y$^2$ and Y$^3$ are independently hydrogen, alkyl, cyano(loweralkyl), aryalkyl, heteroaralkyl, carboxy(loweralkyl), carboxy(aryl substituted loweralkyl) and carbamoyl(loweralkyl).

As used herein, any corresponding N-(4-halo-3-methyl-5-isoxazolyl), N-(4-halo-5-methyl-3-isoxazolyl), N-(3,4-dimethyl-5-isoxazolyl), N-(4-halo-5-methyl-3-isoxazolyl), N-(4-halo-3-methyl-5-isoxazolyl), N-(4,5-dimethyl-3-isoxazolyl) derivative thereof refers to compounds in which Ar$^2$ is the same as the compound specifically set forth, but Ar$^1$ is N-(4-halo-3-methyl-5-isoxazolyl), N-(4-halo-5-methyl-3-isoxazolyl), N-(3,4-dimethyl-5-isoxazolyl), N-(4-halo-5-methyl-3-isoxazolyl), N-(4-halo-3-methyl-5-isoxazolyl), or N-(4,5-dimethyl-3-isoxazolyl) in which halo is any halide, preferably Cl or Br.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942–944).

A. Compounds for Use in Treating Endothelin-mediated Diseases

Compounds and methods for treating endothelin-mediated diseases using the compounds of formulae I and II are provided. In particular, in the compounds provided herein, Ar$^2$ is thienyl, furyl, pyrrolyl or a group, such as benzofuryl, thionaphthyl or indolyl, that is a derivative or analog, as described below, of a thienyl, furyl or pyrrolyl group or a 4-biphenyl group, Ar$^1$ is preferably N-(5-isoxazolyl) or N-(3-isoxazolyl).

1. Ar$^2$ is a thiophene, pyrrole, furan, benzo[b]thiophene, indolyl (benzo[b]pyrrole), or benzo[b]furan Among the compounds provided herein are those represented by the formula V:

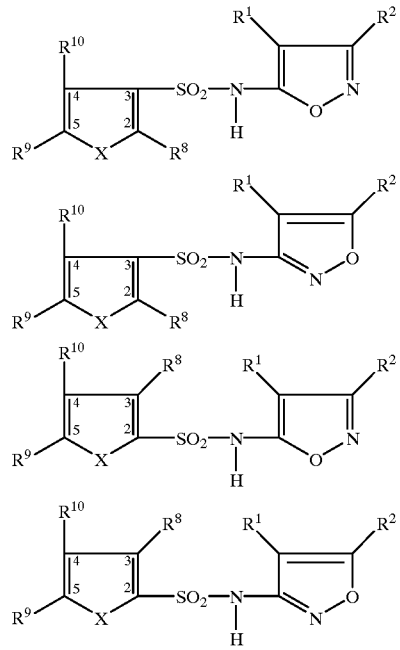

in which
R$^1$ and R$^2$ are either (i), (ii) or (iii) as follows:
(i) R$^1$ and R$^2$ are each independently selected from H, NH$_2$, NO$_2$, halide, pseudohalide, alkyl, alkenyl, alkynyl, aryl, arylalkyl, heterolaryl, alkoxy, alkylamino, alkylthio, haloalkoxy, haloalkyl, alkylsufinyl, alkylsulfonyl, aryloxy, arylamino, arylthio, arylsufinyl, arylsulfonyl, aminocarbonyl, arylaminocarbonyl, haloalkyl, haloaryl, alkoxycarbonyl, alkylcarbonyl, arylcarbonyl, formyl, substituted or unsubstituted amido, substituted or unsubstituted ureido, in which the alkyl, alkenyl and alkynyl portions are either straight or branched chains that contain from 1 up to about 10 carbon atoms, and the aryl portions contain from about 4 to about 14 carbons, except the $R^2$ is not halide, pseudohalide or higher alkyl; or, (ii) $R^1$ and $R^2$ together form —$(CH_2)_n$, where n is 3 to 6; or, (iii) $R^1$ and $R^2$ together form 1,3-butadienyl; and X is S, O or $NR^{11}$ in which $R^{11}$ contains up to about 30 carbon atoms, preferably 1 to 10, more preferably 1 to 6 and is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z, which is hydrogen, halide, pseudohalide, alkyl, alkoxy, alkenyl, alkynyl, aryl, heterocycle, aralkyl, aralkoxy, cycloalkyl, cycloalkenyl, cycloalkynyl, OH, CN, C(O)$R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkyl; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{11}$, $R^{12}$, $R^{15}$ and $R^{16}$ may be further substituted with the any of the groups set forth for Z, and $R^{11}$ is preferably hydrogen, aryl, such as phenyl or alkyl phenyl, loweralkyl; and $R^8$, $R^9$ and $R^{10}$, which each contain hydrogen or up to about 50 carbon atoms, generally up to about 30, more generally 20 or fewer, are each independently selected as described above, and more preferably from (i) or (ii) as follows:

(i) $R^9$ and $R^{10}$ are selected from hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, AcO-C=CHR$^{18}$, $CO_2R^{18}$, SH, $(CH_2)_rC(O)(CH_2)_nR^{18}$, $(CH_2)_r(CH=CH)_s(CH_2)_nR^{18}$, $(CH_2)_rC(CH=CH)_s(CH_2)_nR^{18}$, $(CH_2)_r(CH=CH)_sC(O)(CH_2)_nR^{18}$, $(CH_2)_rNH(CH=CH)_s(CH_2)_nR^{18}$, C=N(OH)$(CH_2)_rR^{18}$, $(CH_2)_r(CH=CH)_sNH(CH_2)_nR^{18}$, $(CH_2)_rC(O)NH(CH_2)_nR^{18}$, $C(O)(CH_2)_rNH(CH_2)_nR^{18}$, $(CH_2)_rNH(CH_2)_nR^{18}$, $(CH_2)_rR^{18}$, $S(O)_nR^{18}$ in which m is 0–2, s, n and r are each independently 0 to 6, preferably 0–3, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$, $S(O)_nR^{20}$ in which n is 0–2; and $R^{18}$ and $R^{20}$ are independently selected from hydrogen, alkyl, alkenyl, alkynyl, aryl, heteroaryl, alkylaryl, heterocycle, alkoxy, aryloxy, aralkyl, aralkoxy, cycloalkyl, cycloalkenyl or cycloalkynyl;

$R^8$ is selected from $C(O)R^{18}$, AcO-C=CHR$^{18}$, $CO_2R^{18}$, $(CH_2)_rC(O)(CH_2)_nR^{18}$, $(CH_2)_r(CH=CH)_s(CH_2)_nR^{18}$, $(CH_2)_rC(O)(CH=CH)_s(CH_2)_nR^{18}$, $(CH_2)_r(CH=CH)_sC(O)(CH_2)_nR^{18}$, $(CH_2)_rNH(CH=CH)_s(CH_2)_nR^{18}$, C=N(OH)$(CH_2)_rR^{18}$, $(CH_2)_r(CH=CH)_sNH(CH_2)_nR^{18}$, $(CH_2)_rC(O)NH(CH_2)_nR^{18}$, $C(O)(CH_2)_rNH(NH_2)_nR^{18}$, $(CH_2)_rNH(CH_2)_nR^{18}$, $(CH_2)_rR^{18}$, in which m is 0–2, s, n and r are each independently 0 to 6, preferably 0–3, in which $R^{18}$ is aryl, preferably phenyl, with the proviso that, if $R^8$ is $(CH_2)_rC(O)NH(CH_2)_nR^{18}$, $C(O)(CH_2)_rNH(CH_2)_nR^{18}$, $(CH_2)_rNH(CH_2)_nR^{18}$, $(CH_2)_rR^{18}$, particularly if r is 0 and/or n is 0, and $R^{18}$ is aryl, particularly phenyl, then $R^{18}$ must have two or more substituents, with preferably at least one ortho substituent;

where any of the groups set forth for $R^8$, $R^9$ and $R^{10}$ are unsubstituted or substituted with any substituents set forth for Z, which is hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{21}$, $CO_2R^{21}$, SH, $S(O)_nR^{21}$ in which n is 0–2, NHOH, $NR^{22}R^{21}$, $NO_2$, $N_3$, $OR^{21}$, $R^{22}NCOR^{21}$ and $CONR^{22}R^{21}$; $R^{22}$ is selected from hydrogen, alkyl, alkenyl, alkynyl, aryl, alkylaryl, heterocycle, aralkyl, alkoxy, aralkoxy, cycloalkyl, cycloalkenyl, cycloalkynyl, $C(O)R^{23}$ and $S(O)_nR^{23}$ in which n is 0–2; and $R^{21}$ and $R^{23}$ are independently selected from hydrogen, alkyl, alkenyl, alkynyl, aryl, alkylaryl, heterocycle, aralkyl, aralkoxy, cycloalkyl, cycloalkenyl or cycloalkynyl; or (ii) any two of $R^8$, $R^9$ and $R^{10}$ form an aryl, aromatic ring, heteroaromatic ring, carbocyclic or heterocyclic ring, which is saturated or unsaturated, containing from about 3 to about 16 members, preferably 3 to about 10 members, more preferably 5 to 7 members that is substituted with one or more substituents, each substituent being independently selected from Z; the other of $R^8$, $R^9$ and $R^{10}$ is selected as from the groups set forth for $R^9$ and $R^{10}$ in (i); and the heteroatoms are $NR^{11}$, O, or S, with the proviso that $Ar^2$ is not 5-halo-3-loweralkylbenzo[b]thienyl, 5-halo-3-loweralkylbenzo[b]furyl, 5-halo-3-loweralkylbenzo[b]pyrrolyl.

In these embodiments, $Ar^2$ is, thus, represented by the formulae (IVA and IVB):

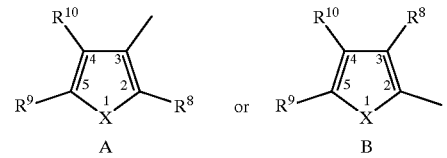

that can be substituted at any or all positions or is an analog of compounds of formula (IV) in which the substituents form fused aromatic, aliphatic or heterocyclic rings; and in which X is $NR^{11}$, O, or S, and $R^{11}$, which is hydrogen or contains up to about 30 carbon atoms, preferably 1 to 10, more preferably 1 to 6, and is selected as defined above. $R^8$, $R^9$, $R^{10}$ are selected as described above.

In the embodiments provided herein, when $R^8$, $R^9$ and $R^{10}$ are selected as in (i), above, $R^8$ is preferably selected from among $(CH_2)_rC(O)(CH_2)_nR^{18}$, $(CH_2)_rNH(CH_2)_nR^{18}$, $(CH_2)_rNH(CH_2)_nR^{18}$, $(CH_2)_r(CH=CH)_s(CH_2)_nR^{18}$, $(CH_2)_rC(O)(CH=CH)_s(CH_2)_nR^{18}$, $(CH_2)_r(CH=CH)_sC(O)(CH_2)_nR^{18}$, $(CH_2)_r(CH=CH)_sNH(CH_2)_nR^{18}$, $C=N(OH)(CH_2)_rR^{18}$, $(CH_2)_rC(O)NH(CH_2)_nR^{18}$, $C(O)(CH_2)_rNH(CH_2)_nR^{18}$, $(CH_2)_rNH(CH=CH)_s(CH_2)_nR^{18}$, $(CH_2)_rC(O)NH(CH_2)_nR^{18}$, $(CH_2)_rNH(CH_2)_nR^{18}$, $(CH_2)_rR^{18}$, with the proviso that if $R^8$ is $(CH_2)_rC(O)NH(CH_2)_nR^{18}$, $(CH_2)_rC(O)NH(CH_2)_nR^{18}$, or $(CH_2)_rR^{18}$, and $R^{18}$ is phenyl, the phenyl group is substituted at least two positions, and preferably, at least one of those positions is ortho.

In preferred of these compounds, $R^{18}$ is aryl or heteroaryl, preferably having 5 or 6 members in the ring, more preferably phenyl or pyrimidinyl, most preferably phenyl. $R^9$ and $R^{10}$ are preferably hydrogen, halide, loweralkyl, or halo loweralkyl.

The more preferred compounds provided herein are compounds in which the alkyl, alkynyl and alkenyl portions are straight or branched chains, acyclic or cyclic, and have from about 1 up to about 10 carbons; in certain of the more preferred embodiments they have from 1–6 carbons, and they can have fewer than 6 carbons. The aryl, homocyclic and heterocyclic groups can have from 3 to 16, generally, 3–7, more often 5–7 members in the rings, and may be single or fused rings. The ring size and carbon chain length are selected such that the resulting molecule exhibits activity as an endothelin antagonist or agonist as evidenced by in vitro or in vivo tests, particularly the tests exemplified herein.

In any of the above preferred embodiments: $R^1$ and $R^2$ are preferably selected independently from alkyl, lower alkenyl, lower alkynyl, lower haloalkyl, halide, pseudohalide and H, except that $R^2$ is not halide or pseudohalide, and in preferred embodiments is also not higher alkyl.

In preferred embodiments: X is S, O, $NR^{11}$ in which $R^{11}$ is aryl, hydrogen, or loweralkyl, preferably, a substituted or unsubstituted aryl, particularly phenyl, preferably unsubstituted or substituted with loweralkyl or halogen hydrogen or loweralkyl; $R^1$ is hydrogen, halide, pseudohalide, loweralkyl or lower haloalkyl, most preferably halide; $R^2$ is hydrogen, loweralkyl or lower haloalkyl.

The aryl groups are unsubstituted or is substituted with groups such as alkyl, alkoxy, alkoxyalkyl, halogen, alkylenedioxy, particularly methylene dioxy, amino, nitro and other such groups. The alkyl substituents are preferably loweralkyl, more preferably containing 1–3 carbons.

In more preferred embodiments, two of $R^9$ and $R^{10}$ are hydrogen, halide or loweralkyl and $R^8$ is $C(O)NHR^{18}$ or $C(O)CH_2R^{18}$ in which $R^{18}$ is a phenyl group that is substituted at at least two positions, most preferably at least one substituent at the ortho position and also 3,4 or 4,5 alkylenedioxy substituents. In more preferred of these embodiments X is S.

In all embodiments, $R^1$ is preferably halide, H, $CH_3$ or $C_2H_5$, and $R^2$ is H, $CH_3$, $C_2H_5$, $C_2F_5$ or $CF_3$. In yet more preferred embodiments, $R^1$ preferably Br, Cl or $CH_3$; $R^2$ is H, $CH_3$, $C_2H_5$, or $CF_3$.

In other embodiments two of $R^8$, $R^9$ and $R^{10}$ form a ring so that $Ar^2$ is benzo[b]thienyl, benzo[b]furyl, or indolyl, with the proviso that there is one or more substituents and they are other than 5-halo and 3-loweralkyl, and the other of $R^8$, $R^9$ and $R^{10}$ is selected from aryl, $(CH_2)_rR^{18}$, $C(O)R^{18}$, $C_2R^{18}$, $NR^{18}R^{19}$, SH, $S(O)_nR^{18}$ in which n is 0–2, HNOH, $NO_2$, $N_3$, $OR^{18}$, $R^{19}NCOR^{18}$ and $CONR^{19}R^{18}$. $Ar^2$ may be further substituted with any of the groups set forth for $R^8$, $R^9$ and $R^{10}$, and are preferably selected from among alkyl, alkoxy, alkoxyalkyl, aryl, alkylaryl, aminoalkyl, arylamino, aryl-substituted amino, and $NR^{11}$.

In embodiments in which $ET_B$ antagonists are desired, it is preferred that $R^8$ and $R^{10}$ are H or loweralkyl and $R^9$ includes heterocyclic or aromatic ring of preferably from 3 to 14, more preferably, 5 to 7, members in the ring. In particular, if X is S, $R^8$ and $R^{10}$ are H or loweralkyl, and $R^9$, includes an aryl group, particularly a substituted phenyl, such as a 2-loweralkyl substituent. The aryl portion is substituted with groups such as alkyl, alkoxy, alkoxyalkyl, halogen, alkylenedioxy, particularly methylenedioxy, amino, nitro and other such groups. The alkyl substituents are preferably loweralkyl, more preferably containing 1–3 carbons.

If X is $NR^{11}$, then $R^{11}$ is aryl, particularly unsubstituted phenyl or substituted phenyl, such as isopropylphenyl.

Other preferred compounds, which are $ET_B$ active, are those in which $Ar^2$ has formula IVB in which $R^9$ is aryl or Z-substituted aryl, particularly phenyl, and Z is loweralkyl or loweralkoxy.

In all embodiments of all of the compounds herein $R^1$ is preferably halide or loweralkyl, most preferably Br, and the compounds are, with reference to formulae IV, 2- or 3-sulfonamides, particularly thiophene sulfonamides. In certain embodiments provided herein, $Ar^2$ is a benzo[b]thienyl, benzo[b]furyl or indolyl (benzo[b]pyrrolyl) group and the compounds provided herein are preferably benzo[b]thienyl-, benzo[b]furyl- or indolylsulfonamides. Benzo[b]thiophene, benzo[b]furyl and indolyl 2- or 3-sulfonamides are among the compounds preferred herein. The benzo[b]thiophene, benzo[b]furyl and indolyl 2- or 3-sulfonamides provided herein are selected with the proviso that the benzene group has at least one substituent and that substituent is other than 5-halo and 3-loweralkyl.

Compounds of particular interest include those of formula III in which $Ar^2$ is a phenyl, benzothienyl, benzofuryl or indolyl [benzopyrrolyl] group or in which $Ar^2$ is a substituted phenylaminocarbonylthienyl, substituted phenylaminocarbonylfuryl, substituted aminocarbonylpyrrolyl group in which there are at least two substituents or $Ar^2$ is phenylacetylthiophene, phenylacetylfuran, or phenylacetylpyrrole, is an acetoxystyrylthiophene, acetoxystyrylfuran or acetoxystyrylpyrrole.

The most preferred compounds provided herein have an $IC_{50}$ for $ET_A$ receptors in the assays exemplified herein less than 0.1 $\mu$M, more preferably less than 0.01 $\mu$M, and more preferably less than 0.001 (see, e.g., Table 1 for representative experimental results), when measured at 4° C., as described in the Examples. When measured at 24° C., the $IC_{50}$ concentrations are somewhat higher (2- to 10-fold; see, Table 1 for some comparative values).

Among the preferred compounds of interest herein are those in which $Ar^2$ has formula VI:

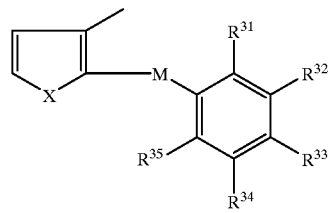

in which

M is $(CH_2)_mC(O)(CH_2)_r$, $(CH_2)_mC(O)NH(CH_2)_r$, $(CH_2)_m(CH=CH)(CH_2)_r$, $(CH_2)_mC(O)(CH_2)_sNH(CH_2)_r$, $(CH_2)_m(CH=CH)(CH_2)_r$, $C=N(OH)(CH_2)_r$, $(CH_2)$ $_mC(O)(CH=CH)_sNH(CH_2)_r$, $CH(OH)(CH_2)_r$, $CH(CH_3)C(O)(CH_2)_r$, $CH(CH_3)C(O)(CH_2)_m(CH=CH)(CH_2)_r$, $(CH_2)_r$, $(CH_2)_rO$, $C(O)O$, in which m,s and r are each independently 0 to 6, preferably 0 to 3, more preferably M is $(CH_2)_mC(O)(CH_2)_r$, $(CH_2)_mC(O)NH(CH_2)_r$, $(CH_2)_m(CH=CH)(CH_2)_r$, $(CH_2)_mC(O)(CH_2)_sNH(CH_2)_r$, $(CH_2)_m(CH=CH)(CH_2)_r$, $C=N(OH)(CH_2)_r$, $CH(OH)(CH_2)_r$, $(CH_2)_r$, $(CH_2)_rO$, $C(O)O$;

$R^{31}$, $R^{32}$, $R^{33}$, $R^{34}$ and $R^{35}$ are each independently selected from (i) or (ii) as follows:

(i) $R^{31}$, $R^{32}$, $R^{33}$, $R^{34}$ and $R^{35}$ are each independently selected from among H, OH, $NHR^{38}$, $CONR^{38}R^{39}$, $NO_2$, cyano, halide, pseudohalide, alkyl, alkenyl, alkynyl, aryl, arylalkyl, heteroaryl, alkoxy, alkylamino, alkylthio, haloalkyl, alkylsulfinyl, alkylsulfonyl, alkoxycarbonyl, alkylcarbonyl, alkenylthio, alkenylamino, alkenyloxy, alkenyl sulfinyl, alkenyisulfonyl, alkoxycarbonyl, arylaminocarbonyl, alkylaminocarbonyl, aminocarbonyl, (alkylaminocarbonyl)alkyl, carboxyl, carboxyalkyl, carboxyalkenyl, alkylsulfonylaminoalkyl, cyanoalkyl, acetyl, acetoxyalkyl, hydroxyalkyl, alkyloxyalkoxy, hydroxyalkyl, (acetoxy)alkoxy, (hydroxy)alkoxy and formyl; or (ii) at least two of $R^{31}$, $R^{32}$, $R^{33}$, $R^{34}$ and $R^{35}$, which substitute adjacent carbons on the ring, together form alkylenedioxy, alkylenethioxyoxy or alkylene-dithioxy (i.e. $—O—(CH_2)_n—O—$, $—S—(CH_2)_n—O—$, $—S—(CH_2)_n—S—$, where n is 1 to 4, preferably 1 or 2,) which is unsubstituted or substituted by replacing one or more hydrogens with halide, loweralkyl, loweralkoxy or halo loweralkyl, and the others of $R^{31}$, $R^{32}$, $R^{33}$, $R^{34}$ and $R^{35}$ are selected as in (i); and $R^{38}$ and $R^{39}$ are each independently selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl, and is preferably hydrogen, loweralkyl, loweralkoxy and lowerhaloalkyl, with the proviso that when M is $(CH_2)_mC(O)NH(CH_2)_r$, then at least two of $R^{31}$, $R^{32}$, $R^{33}$, $R^{34}$ and $R^{35}$ are not hydrogen.

M is most preferably

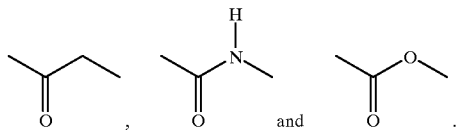

In general, however, in all of these compounds in which $Ar^2$ has formula V or VI or in which $R^8$ includes an aryl group, regardless of the selection of M, it is preferred that the aryl substituent have more than one substituent or at least one substituent in the ortho position. Aryl is preferably phenyl that is preferably substituted at the ortho position and, more preferably at at least one additional position, particularly 4 and 6, or adjacent positions, such as 3,4 or 4,5 when the substituents are linked to form an alkylenedioxy (or analog thereof in which one or both oxygens is(are) replaced with S.

In all compounds, at least one of $R^{31}$ and $R^{35}$ is other than hydrogen.

In more preferred compounds, M is $C(O)CH_2$, $C(O)NH$, $—CH=CH—$, $CH_2CH_2C(O)(CH)_2$, $CH_2CHC(O)CH_2$, and most preferably has formula VII:

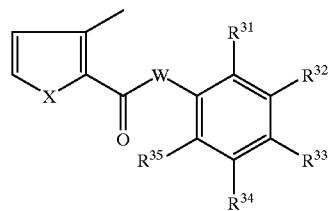

in which W is $CH_2$ or NH.

M is even more preferably selected from among:

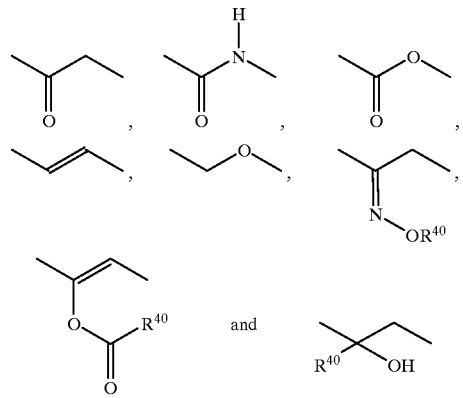

in which $R^{40}$ is preferably hydrogen, alkyl, alkoxy, alkoxyalkyl, haloalkyl, and more preferably loweralkyl, loweralkoxy, or halo loweralkyl, and is more preferably hydrogen or loweralkyl, particularly methyl or ethyl, and is most preferably hydrogen.

M is most preferably:

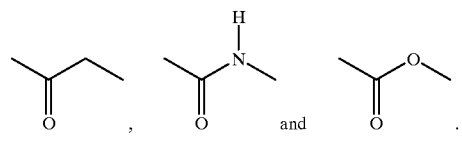

In preferred compounds $R^{31}$, $R^{32}$, $R^{33}$, $R^{34}$ and $R^{35}$ are selected from (i) or (ii):

(i) $R^{31}$, $R^{32}$, $R^{33}$, $R^{34}$ and $R^{35}$ are each independently selected from loweralkyl, haloloweralkyl, phenyl, alkoxy, loweralkylsulfonylaminoloweralkyl, cyanoloweralkyl, acetyl, loweralkoxycarbonyl, cyano, OH, acetoxyloweralkyl, hydroxy loweralkyl, acetoxy loweralkoxy or loweralkoxycarbonyl; or (ii) $R^{32}$ and $R^{33}$ or $R^{33}$ and $R^{34}$ form alkylene dioxy, preferably methylenedioxy, and the others of $R^{31}$, $R^{32}$, $R^{33}$, $R^{34}$ and $R^{35}$ are selected as in (i).

In preferred embodiments, $R^{31}$, $R^{33}$, $R^{35}$ are other then hydrogen and are preferably loweralkyl or lower alkoxy, or $R^{31}$ or $R^{35}$ is other than hydrogen, preferably loweralkyl or lower alkoxy, and $R^{32}$ and $R^{33}$ or $R^{33}$ and $R^{34}$ form methylenedioxy.

In all embodiments, preferred substituents also can be determined by reference to Table 1, which sets forth exemplary compounds. Preferred compounds are those of Table 1 that have the highest activities, and preferred substituents are those on the compounds with the highest activities.

TABLE 1

| COMPOUND | $ET_A$ ($\mu M$)* | $ET_B$ ($\mu M$)* |
|---|---|---|
| N-(3,4-dimethyl-5-isoxazolyl)-2-methylbenzo[b]thiophene-3-sulfonamide | 0.167 | 16.6 |
| N-(4-bromo-3-methyl-5-isoxazolyl)-2-methylbenzo[b]thiophene-3-sulfonamide | 0.0486 | 3.5 |
| N-(4-bromo-3-methyl-5-isoxazolyl)-2-ethylbenzo[b]thiophene-3-sulfonamide | 0.0067 | 5.13 |
| N-(4-bromo-3-methyl-5-isoxazolyl)-2-n-benzylbenzo[b]thiophene-3-sulfonamide | 0.0182 | ~1 |
| N-(4-bromo-3-methyl-5-isoxazolyl)-2-butylbenzo[b]thiophene-3-sulfonamide | 0.0226 | ~3 |
| N-(4-bromo-3-methyl-5-isoxazolyl)-2-i-propylbenzo[b]thiophene-3-sulfonamide | 0.005<br>0.03† | 5.7<br>10.7† |
| N-(4-bromo-3-methyl-5-isoxazolyl)-2-n-propylbenzo[b]thiophene-3-sulfonamide | 0.024<br>0.074† | 7.95<br>16.6† |
| N-(4-bromo-3-methyl-5-isoxazolyl)-2-(4-ethylbenzyl)benzo[b]thiophene-3-sulfonamide | 0.048† | 1.1 |
| N-(4-bromo-3-methyl-5-isoxazolyl)-2-[3,4-(methylenedioxy)-benzyl]benzo[b]thiophene-3-sulfonamide | 0.0015 ± 0.0014<br>0.0074 ± 0.0011† | 0.324 ± 0.78<br>0.939 ± 0.262† |
| N-(4-bromo-3-methyl-5-isoxazolyl)-2-(3,4,5-trimethoxybenzyl)-benzo[b]-thiophene-3-sulfonamide | 0.013† | 1.2† |
| N-(4-bromo-3-methyl-5-isoxazolyl)-2-ethyl-5-methylbenzo[b]thiophene-3-sulfonamide | 1.89 ± 0.431† | 54.3 ± 2.6† |
| N-(4-chloro-3-methyl-5-isoxazolyl)-2-[(3,4-methylenedioxy)benzyl]benzo[b]thiophene-3-sulfonamide | 0.011 ± 0.005† | 0.936 ± 0.095† |
| N-(4-bromo-3-methyl-5-isoxazolyl)-2-(3,4-dimethoxybenzyl)benzo[b]thiophene-3-sulfonamide | 0.021 ± 0.017† | 2.94 ± 1.32† |
| N-(4-bromo-3-methyl-5-isoxazolyl)-5-(benzo[b]thien-2-yl)thiophene-2-sulfonamide | 16† | 0.80† |
| N-(4-bromo-3-methyl-5-isoxazolyl)-2-(4-methoxybenzyl)benzo[b]thiophene-3-sulfonamide | 0.051 | 1.5† |
| N-(4-bromo-3-methyl-5-isoxazolyl)-2-(2-methoxybenzyl)-benzo[b]thiophene-3-sulfonamide | 0.19† | 2.2 |
| N-(3,4-dimethyl-5-isoxazolyl)-2-(4-chlorobenzyl)benzo[b]thiophene-3-sulfonamide | 0.21† | 4.7† |
| N-(4-chloro-3-methyl-5-isoxazolyl)-2-(4-dimethylaminobenzyl)benzo[b]thiophene-3-sulfonamide | 0.041†<br>0.014 | 1.3†<br>0.477 |
| N-(4-chloro-3-methyl-5-isoxazolyl)-2-ethylbenzo[b]furan-3-sulfonamide | 0.15† | 22† |
| N-(4-chloro-3-methyl-5-isoxazolyl)-2-phenylbenzo[b]thiophene sulfonamide | 0.932† | 46.8† |
| N-(4-chloro-3-methyl-5-isoxazolyl)-6-methoxy-2-[3,4-(methylenedioxy)benzyl]benzo[b]thiophene-3-sulfonamide | ~2$^{est†}$ | 2.39 |
| N-(4-chloro-5-methyl-3-isoxazolyl)-2-[3,4-(methylenedioxy)benzyl]benzo[b]thiophene-3-sulfonamide | 0.0055† | 0.364† |
| N-(4-chloro-3-methyl-5-isoxazolyl)-2-methoxycarbonylthiophene-3-sulfonamide | 0.631 | 53.2 |
| N-(4-bromo-3-methyl-5-isoxazolyl)-4-(4-propylphenyl)thiophene-2-sulfonamide | 0.962† | 0.435† |
| N-(4-bromo-3-methyl-5-isoxazolyl)-3-(phenylthio)thiophene-2-sulfonamide | 0.0801† | 3.68† |
| N-(3,4-dimethyl-5-isoxazolyl))-3-(phenylaminocarbonyl)thiophene-2-sulfonamide | 0.163 | >100 |
| N-(4-chloro-3-methyl-5-isoxazolyl)-2-[(4-tolyl)aminocarbonyl]thiophene-3-sulfonamide | 0.00116<br>0.0105† | 2.93<br>14† |
| N-(4-bromo-3-methyl-5-isoxazolyl)-5-(4-methoxyphenyl)thiophene-2-sulfonamide | 8.69<br>26.3† | 0.363<br>2.4† |
| N-(4-bromo-3-methyl-5-isoxazolyl)-5-(3-methoxyphenyl)thiophene-2-sulfonamide | 3.26<br>23.4† | 0.776<br>4.7† |
| N-(4-bromo-3-methyl-5-isoxazolyl)-5-(3-thienyl)thiophene-2-sulfonamide | 4.49 | 0.380 |
| N-(4-bromo-3-methyl-5-isoxazolyl)-3-methylthiophene-2-sulfonamide | 0.651 | 7.15 |
| N-(4-bromo-3-methyl-5-isoxazolyl)-3-(phenethyl)thiophene-2-sulfonamide | 0.16<br>0.676† | 10.77<br>37.2† |
| N-(4-bromo-3-methyl-5-isoxazolyl)-4-(phenethyl)thiophene-2-sulfonamide | 6.64 | 3.97 |
| N-(3,4-dimethyl-5-isoxazolyl)-2-[(4-methylphenyl)-aminocarbonyl]thiophene-3-sulfonamide | 0.00336 | 11.3 |
| N-(4-bromo-3-methyl-5-isoxazolyl)-2,5-dimethyl-4-phenylthiophene-3-sulfonamide | 1.40 | ~100 |
| N-(4-bromo-3-methyl-5-isoxazolyl)-2-[(methyl)phenylaminocarbonyl]thiophene-3-sulfonamide | 0.188 | 16.0 |
| N-(4-bromo-3-methyl-5-isoxazolyl)-2-(α- | 0.337 | 9.37 |

TABLE 1-continued

| COMPOUND | ET$_A$ ($\mu$M)* | ET$_B$ ($\mu$M)* |
|---|---|---|
| hydroxybenzyl)thiophene-3-sulfonamide | | |
| N-(4-bromo-5-methyl-3-isoxazolyl)-5-(4-methylphenyl)thiophene-2-sulfonamide | 7.10<br>15.8† | 0.3593<br>0.25† |
| N-(4-bromo-3-methyl-5-isoxazolyl)-5-phenylthiophene-2-sulfonamide | 3.53<br>36.6† | 0.417<br>2.4† |
| N-(4-bromo-3-methyl-5-isoxazolyl)-5-[4-(trifluoromethyl)phenyl]thiophene-2-sulfonamide | 6.39<br>6.31† | 0.0835<br>.282† |
| N,N'-bis(3-[(4-bromo-3-methyl-5-isoxazolyl)aminosulfonyl)thien-2-yl}urea | 0.0692<br>0.295† | 0.290<br>1.19† |
| N-(4-bromo-3-methyl-5-isoxazolyl)-2-(hydroxymethyl)thiophene-3-sulfonamide | 0.160<br>1.55† | 44.1<br>— |
| N-(4-bromo-3-methyl-5-isoxazolyl)-5-(2-formylphenyl)thiophene-3-sulfonamide | 3.46<br>12.31† | 0.529<br>1.28 ± 0.71† |
| N,N'-bis{3-[3,4-dimethyl-5-isoxazolyl)aminosulfonyl]thien-2-yl}urea | 1.01 ± 1.03<br>2.7† | 3.7 ± 2.7<br>5.9† |
| N-(3,4-dimethyl-5-isoxazolyl))-2-[(3-methoxyanilino)methyl]thiophene-3-sulfonamide | 0.214<br>0.933† | 5.34<br>7.7† |
| N-(4-bromo-3-methyl-5-isoxazolyl)-5-(3-aminophenyl)thiophene-2-sulfonamide | 0.537<br>1.44† | 1.07<br>2.63† |
| N-(4-bromo-3-methyl-5-isoxazolyl)-5-[3,5-bis(trifluoromethyl)phenyl]thiophene-2-sulfonamide | 0.794<br>5.9† | 12.0<br>15.5† |
| N-(4-bromo-3-methyl-5-isoxazolyl)-5-(3,3-dimethylbutyn-1-yl)thiophene-2-sulfonamide | 1.12<br>7.24† | 24.0<br>35.5† |
| N-(4-bromo-3-methyl-5-isoxazolyl)-5-(2-methoxyphenyl)thiophene-2-sulfonamide | 0.381 | 1.097 |
| N-(4-bromo-3-methyl-5-isoxazolyl)-5-(2-tolyl)thiophene-2-sulfonamide | 0.432 | 0.313 |
| N-(4-bromo-3-methyl-5-isoxazolyl)-2-[(3-carboxyphenyl)aminocarbonyl]thiophene-3-sulfonamide | 0.062† | >100† |
| N-(4-bromo-3-methyl-5-isoxazolyl)-2-[2-carboxylphenyl)aminocarbonyl]-thiophene-3-sulfonamide | 0.21† | 20† |
| N-(4-bromo-3-methyl-5-isoxazolyl)-2-(aminocarbonyl)thiophene-3-sulfonamide | 0.84† | >100† |
| N-(4-bromo-3-methyl-5-isoxazolyl)-2-[(5-dimethylamino-1-naphthyl)sulfonyl-aminocarbonyl]thiophene-3-sulfonamide | 0.97† | 3.9† |
| N-(4-bromo-3-methyl-5-isoxazolyl)-5-(5-methyl-2-thienyl)thiophene-2-sulfonamide | 17† | 0.21 |
| N-(4-bromo-3-methyl-5-isoxazolyl)-2-[(3,4-methylenedioxyphenyl)aminocarbonyl]thiophene-3-sulfonamide | 0.017† | 9.8† |
| N-(4-bromo-3-methyl-5-isoxazolyl)-2-[(3,4-methylenedioxy)phenoxycarbonyl]thiophene-3-sulfonamide | 0.0073† | 6.0† |
| N-(4-bromo-3-methyl-5-isoxazolyl)-3-[(3,4-methylenedioxy)phenyl]thiophene-2-sulfonamide | 0.50† | 79† |
| N-(4-bromo-3-methyl-5-isoxazolyl)-3-[(3,4-methylenedioxy)benzyl]thiophene-2-sulfonamide | 8.1 | 3.2† |
| N-(4-bromo-3-methyl-5-isoxazolyl)-3-benzylthiophene-2-sulfonamide | 1.6† | 39† |
| N-(4-bromo-3-methyl-5-isoxazolyl)-5-(3-tolyl)thiophene-2-sulfonamide | 15† | 4.2† |
| N-(4-bromo-3-methyl-5-isoxazolyl)-2-[(3,4-methylenedioxy)benzyl]thiophene-3-sulfonamide | 0.27† | 7.7† |
| N-(4-bromo-3-methyl-5-isoxazolyl)-2-[(3,4-methylenedioxy)benzoyl]thiophene-3-sulfonamide | 2.0† | 15† |
| N-(4-bromo-3-methyl-5-isoxazolyl)-2-((2-hydroxvphenyl)aminocarbonyl]thiophene-3-sulfonamide | 0.013† | 38† |
| N-(3,4-dimethyl-5-isoxazolyl)-2-[3,4-(methylenedioxy)phenoxycarbonyl]thiophene-3-sulfonamide | 6.1† | >~50† |
| N-(4-bromo-3-methyl-5-isoxazolyl)-5-(5-ethylthien-2-yl)thiophene-2-sulfonamide | 24† | 7.7† |
| N-(4-bromo-3-methyl-5-isoxazolyl)-2-[(3,4-methylenedioxy)benzoyl]aminocarbonyl]thiophene-3-sulfonamide | 0.089† | 37† |
| N-(4-chloro-3-methyl-5-isoxazolyl)-2-[3,4-(methylenedioxy)phenoxycarbonyl]thiophene-3-sulfonamide | 0.0065† | 7.4† |
| N-(4-bromo-3-methyl-5-isoxazolyl)-5-(1-pentynyl)thiophene-2-sulfonamide | 29† | 5.6† |
| N-(4-chloro-3-methyl-5-isoxazolyl)-5-(5-ethylthien-2-yl)thiophene-2-sulfonamide | 12† | 0.71 |
| N-(4-bromo-3-methyl-5-isoxazolyl)-2-[(3,4- | 0.0091† | 5.5† |

TABLE 1-continued

| COMPOUND | $ET_A$ ($\mu$M)* | $ET_B$ ($\mu$M)* |
|---|---|---|
| methylenedioxy)phenytacetyl]thiophene-3-sulfonamide | | |
| N-(4-bromo-3-methyl-5-isoxazolyl)-2-[3,4-(methylenedioxy)phenoxycarbonylamino]thiophene-3-sulfonamide | 0.087† | 5.9† |
| N-(4-bromo-3-methyl-5-isoxazolyl)-2-[(2-chloro-3,4-methylenedioxy)phenoxymethyl]thiophene-3-sulfonamide | 13† | 0.76† |
| N-(4-bromo-3-methyl-5-isoxazolyl)-2-[trans-(3,4-methylenedioxy)cinnamyl]thiophene-3-sulfonamide | 0.14† | 1.4† |
| N-(4-bromo-3-methyl-5-isoxazolyl)-5-(1-naphthyl)-thiophene-2-sulfonamide | 14† | 1.4† |
| N-(4-bromo-3-methyl-5-isoxazolyl)-5-(3-nitrophenyl)thiophene-2-sulfonamide | 26† | 4.5† |
| N-(4-bromo-3-methyl-5-isoxazolyl)-2-[(3,4-methylenedioxy)phenylureido]thiophene-3-sulfonamide | 0.57† | 1.3† |
| N-(4-chloro-3-methyl-5-isoxazolyl)-2-[(3,4-(methylenedioxy)phenylacetyl]thiophene-3-sulfonamide | 0.021† | 6.5 |
| N-(4-bromo-3-methyl-5-isoxazolyl)-5-(4-methyoxycarbonylphenyl)thiophene-2-sulfonamide | >100† | 17† |
| N-(4-bromo-3-methyl-5-isoxazolyl)-5-(4-carboxyphenyl)thiophene-2-sulfonamide | >100† | 31 |
| N-(4-bromo-3-methyl-5-isoxazolyl)-5-(4-totyl)aminocarbonyl)thiophene-2-sulfonamide | 28† | 8.6† |
| N-(4-bromo-3-methyl-5-isoxazolyl)-5-(2-methyfuranyl)thiophene-2-sulfonamide | 32† | 7.5 |
| N-(4-chloro-3-methyl-5-isoxazolyl)-2-[3,4-(methylenedioxy)benzyloxycarbonyl]thiophene-3-sultonamide | .42† | 12† |
| N-(4-chloro-3-methyl-5-isoxazolyl)-2-[2-(3,4-methylenedioxyphenyl)]ethoxycarbonyl-3-sulfonamide | .23† | 6.2† |
| N-(4-chloro-3-methyl-5-isoxazolyl)-2-{[4-(3,4-methylenedioxybenzyl)piperazin-1-yl]carbonyl}thiophene-3-sulfonamide | 20† | >~100† |
| N-(4-chloro-3-methyl-5-isoxazolyl)-2-aminothiophene-3-sulfonamide | 14† | 6.2† |
| N-(4-bromo-3-methyl-5-isoxazolyl)-5-(benzyloxymethyl)thiophene-2-sulfonamide | 12† | 9.0† |
| N-(4-chloro-3-methyl-5-isoxazolyl)-2-{1-cyano-1-[(3,4-methylenedioxy)phenyl)acetyl}thiophene-3-sulfonamide | 2.1 | 27† |
| N-(4-bromo-3-methyl-5-isoxazolyl)-2-[(3,4-methylenedioxy)phenethyl]thiophene-3-sulfonamide | 0.21 | 9.2 |
| N-(4-chloro-3-methyl-5-isoxazolyl)-2-[(3-dimethylamino)phenoxycarbonyl]thiophene-3-sulfonamide | 1.4† | 60† |
| N-(4-bromo-3-methyl-5-isoxazoly)-1-methylindole-2-sulfonamide | 77† | ~100† |
| N-(4-chloro-3-methyl-5-isoxozolyl-2-(cyclohexyloxycarbonyl)thiophene-3-sulfonamide | 0.44† | 34† |
| N-(4-chloro-3-methyl-5-isoxazolyl)-2-[β-hydroxy(3,4-methylenedioxy)phenylethyl]thiophene-3-sulfonamide | 0.053† | 16† |
| N-(4-bromo-3-methyl-5-isoxazolyl)-2-carboxyl-1-methylindole-3-sulfonamide | 0.59† | 104† |
| N-(4-chloro-3-methyl-5-isoxazolyl)-2-[(4-oxacyclohexyl)oxycarbonyl]thiophene-3-sulfonamide | 1.37† | - |
| N-2-[3,4-(methylenedioxy)phenylacetyl]thiophene-3-sulfonamide | 1.8† | 32.5† |
| N-(4-chloro-3-methyl-5-isoxazolyl)-{2-[3,4-(methylenedioxy)phenyl]acetyl}thiophene-3-sulfonamide oxime | — | — |
| N-(4-chloro-3-methyl-5-isoxazolyl)-2-[(4-tolyl)aminocarbonyl]-1-methylindole-3-sulfonamide | 31.3† | 14.7† |
| N-(4-chloro-3-methyl-5-isoxazolyl)-2-[(4-methoxyphenoxy)carbonyl]thiophene-3-sulfonamide | 0.023† | 15† |
| N-(4-bromo-3-methyl-5-isoxazolyl)-1-[3,4-(methylenedioxy)benzyl]indole-2-sulfonamide | 5.29† | 18.6† |
| N-(4-bromo-3-methyl-5-isoxazolyl)-2-[(4-methylphenoxy)carbonyl]thiophene-3-sulfonamide | 122† | 9.7† |
| N-(4-chloro-3-methyl-5-isoxazolyl)-2-[(4-methoxyphenyl)acetyl]thiophene-3-sulfonamide | 0.043† | 10.1† |
| N-(4-bromo-3-methyl-5-isoxazolyl)-3-[(4-methylphenoxy)methyl]thiophene-2-sulfonamide | 1.64† | 22.8† |

TABLE 1-continued

| COMPOUND | $ET_A$ ($\mu$M)* | $ET_B$ ($\mu$M)* |
|---|---|---|
| N-(4-bromo-3-methyl-5-isoxazolyl)-2-[(4-methylphenoxy)methyl]thiophene-3-sulfonamide | 1.2† | 15† |
| N-(4-bromo-3-methyl-5-isoxazolyl)-3-(4-methyl-trans-styryl)thiophene-2-sulfonamide | 0.94† | 0.66† |
| N-(4-bromo-3-methyl-5-isoxazolyl)-3-(4-methyl-phenethyl)thiophene-2-sulfonamide | 0.347† | 9.4† |
| N-(4-bromo-3-methyl-5-isoxazolyl)-2-[(4-methyl-phenyl)acetyl]thiophene-3-sulfonamide | 0.198† | 9.13† |
| N-(4-bromo-3-methyl-5-isoxazolyl)-2-[(3-methoxyphenyl)acetyl]thiophene-3-sulfonamide | 0.030† | 19.1† |
| N-(4-bromo-3-methyl-5-isoxazolyl)-3-(4-methyl-phenethyl)-5-(4-tolyl)thiophene-2-sulfonamide | 6.1† | 2.09† |
| N-(4-bromo-3-methyl-5-isoxazolyl)-3-(4-methylbenzyl)-5-(4-tolyl)thiophene-2-sulfonamide | 4.69† | 1.56† |
| N-(4-bromo-3-methyl-5-isoxazolyl)-3-(4-methyl-trans-styryl)-5-(4-tolyl)thiophene-2-sulfonamide | 6.9† | 1.58† |
| N-(4-chloro-3-methyl-5-isoxazolyl)-2-[β,β(ethylene-dioxy)-3,4-(methylenedioxy)phenethyl]thiophene-3-sulfonamide | 0.128† | 2.09† |
| N-(4-chloro-3-methyl-5-isoxazolyl)-2-[β-(dimethyl-amino)-3,4-(methylenedioxy)phenethy]thiophene-3-sulfonamide | 20.9† | ~100† |
| N-(4-chloro-3-methyl-5-isoxazolyl)-2-{a-hydroxy-[3,4-(methylenedioxy)phenyl]acetyl}thiophene-3-sulfonamide | 2.5† | 30† |
| N-(4-chloro-3-methyl-5-isoxazolyl)-2-[(5-methyl-3-isoxazolyl)aminocarbonyl]thiophene-3-sulfonamide | 0.056† | 92† |
| N-(4-bromo-3-methyl-5-isoxazolyl)-2-[(3-hydroxyl-6-pyridazinyl)aminocarbonyl]thiophene-3-sulfonamide | 0.066† | 81.3† |
| N-(4-chloro-3-methyl-5-isoxazolyl)2-{[2-acetyl-4,5-(methylenedioxy)phenyl]aminocarbonyl}thiophene-3-sulfonamide | 0.010† | 31.6† |
| N-(4-bromo-3-methyl-5-isoxazolyl)-3-{[3,4-(methylenedioxy)phenoxy]methyl}thiophene-2-sulfonamide | 0.513† | 9.6† |
| N-(4-bromo-3-methyl-5-isoxazolyl)-2-[(4-methyl)(cinnamyl)]thiophene-3-sulfonamide | 0.26† | 0.413† |
| N-(4-chloro-3-methyl-5-isoxazolyl)-2-[(4,5-dimethoxy-2-methoxycarbonylphenyl)aminocarbonyl]thiophene-3-sulfonamide | 0.55† | — |
| N-(4-chloro-3-methyl-5-isoxazolyl)-2-[(2-methyl-1,3,4-thiadiazol-5-yl)aminocarbonyl]thiophene-3-sulfonamide | 0.13† | — |
| N-(4-chloro-3-methyl-5-isoxazolyl)2-{[4,5-dimethoxy-2,4,5-dimethoxy-2-methoxycarbonyl)phenyl]phenylaminocarbonyl}thiophene-3-sulfonamide | 3.80† | — |
| N-(4-chloro-3-methyl-5-isoxazolyl)2-{[2-carboxyl-4,5-(methylenedioxy)phenyl]aminocarbonyl}thiophene-3-sulfonamide | 1.43† | - |
| N-(4-bromo-3-methyl-5-isoxazolyl)-3-[3,4-(methylenedioxy)phenethyl]thiophene-2-sulfonamide | 0.236† | 18† |
| N-(4-bromo-3-methyl-5-isoxazolyl)-3-[3,4-(methylenedioxy)-trans-styryl]thiophene-2-sulfonamide | 0.218† | 10† |
| N-(4-bromo-3-methyl-5-isoxazolyl)-2-[(4-methyl)-phenethyl]thiophene-3-sulfonamide | 0.106† | 40.1† |
| N-(3,4-dimethyl-5-isoxazolyl)-2-{[2-acetyl-4,5-(methylenedioxy)phenyl]aminocarbonyl}thiophene-3-sulfonamide | 0.032† | — |
| N-(4-chloro-3-methyl-5-isoxazolyl)-2-[4-methoxy-2-methylphenyl)aminocarbonyl]thiophene-3-sulfonamide | 0.027† | 0.14† |
| N-(4-chloro-3-methyl-5-isoxazolyl)-2-[(2-cyano-4,5-dimethoxyphenyl)aminocarbonyl]thiophene-3-sulfonamide | 0.0039† | 12.2† |
| N-(3,4-dimethyl-5-isoxazolyl)-2-(4-tolylacetylphenyl)-thiophene-3-sulfonamide | .0027† | 29.2 |
| N-(3,4-dimethyl-5-isoxazolyl)-2-[3,4-(methylene-dioxy)phenylacetyl]thiophene-3-sulfonamide | 0.0273† | 12.2† |
| N-(4-chloro-3-methyl-5-isoxazolyl)-2-[(2,4-dimethoxyphenyl)aminocarbonyl]thiophene-3-sulfonamide | 0.158† | 63.1† |
| N-(4-chloro-3-methyl-5-isoxazolyl)-2-((3-methyl-6-pyridyl)aminocarbonyl)thiophene-3-sulfonamide | 0.023† | 43.7† |
| N-(4-chloro-3-methyl-5-isoxazolyl)-2-[2-hydroxy-4-methylphenyl)aminocarbonyl]thiophene-3-sulfona- | .006 | — |

TABLE 1-continued

| COMPOUND | $ET_A$ ($\mu$M)* | $ET_B$ ($\mu$M)* |
| --- | --- | --- |
| mide | | |
| N-(4-chloro-3-methyl-5-isoxazolyl)-2-([2-cyano-4,5-(methylenedioxy)phenyl]aminocarbonyl)thiophene-3-sulfonamide | 0.0034† | 40.4† |
| N-(4-chloro-3-methyl-5-isoxazolyl)-2-[2-methyl-4,5-(methylenedioxy)phenylaminocarbonyl]thiophene-3-sulfonamide | 0.0030† | 355† |
| N-(4-chloro-3-methyl-5-isoxazolyl)-2-(2-carboxamido-4,5-dimethoxyphenylamino-carbonyl)thiophene-3-sulfonamide | 0.011† | 61† |
| N-(3,4-dimethyl-5-isoxazolyl)-2-(2,4-dimethylphenylacetyl)thiophene-3-sulfonamide | 0.0027† | 17.4† |
| N-(4-chloro-3-methyl-5-isoxazolyl)-2-(2,4-dimethyl-phenylacetyl)thiophene-3-sulfonamide | 0.0004† | 4.8† |
| N-(4-bromo-3-methyl-5-isoxazolyl)-2-(2,4-dimethylphenylacetyl)thiophene-3-sulfonamide | 0.0008†** | 3.6† |
| N-(4-chloro-3-methyl-5-isoxazolyl)-2-(3,4-(methylenedioxy)]phenylaminocarbonyl-3-thiophenesulfonamide | 0.0073† | 9.2† |
| N-(4-chloro-3-methyl-5-isoxazolyl)-2-[2-methyl-4,5-(methylenedioxy)phenylacetyl]thiophene-3-sulfonamide | 0.0032† | 9† |
| N-(4-chloro-3-methyl-5-isoxazolyl)-2-[3,4-(methylenedioxy)-6-(2-acetoxyethyl)phenylamino-carbonyl]thiophene-3-sulfonamide | 0.0045† | 25.7† |
| N-(4-chloro-3-methyl-5-isoxazolyl)-2-[3,4-(methylenedioxy)-6-(2-hydroxyethyl)phenyl-aminocarbonyl]thiophene-3-sulfonamide | 0.0056† | 16.8† |
| N-(4-chloro-3-methyl-5-isoxazolyl)-2-(3,5-dimethyl-phenylacetyl)thiophene-3-sulfonamide | 0.045† | 17.7† |
| N-(4-chloro-3-methyl-5-isoxazolyl)-2-(2,5-dimethylphenylacetyl)thiophene-3-sulfonamide | 0.007† | 18† |
| N-(4-chloro-3-methyl-5-isoxazolyl)-2-[2-methanesulfonylaminomethyl)-4,5-(methylenedioxy)phenylaminocarbonyl]thiophene-3-sulfonamide | 0.0068† | 19.8† |
| N-(4-chloro-3-methyl-5-isoxazolyl)-2-[2-cyanomethyl-4,5-(methylenedioxy)-6-cyanomethyl]-phenylaminocarbonyl-3-thiophenesulfonamide | 0.0038† | 25† |
| N-(4-chloro-3-methyl-5-isoxazolyl)-2-[2-hyroxyproyl-4,5-(methylenedioxy)phenylaminocarbonyl]-thiophene-3-sulfonamide | 0.0073† | 8.3† |
| N-(4-bromo-3-methyl-5-isoxazolyl)-3-[2-methyl-4,5-(methylenedioxy)cinnamyl]thiophene-2-sulfonamide | ~0.1†** | ~6†** |
| N-(4-bromo-3-methyl-5-isoxazolyl)-3-[2-methyl-4,5-(methylenedioxy)phenethyl]thiophene-2-sulfonamide | ~0.1†** | ~5†** |
| N-(4-bromo-3-methyl-5-isoxazolyl)-3-{[2-propyl-4,5-(methylenedioxy)phenoxylmethyl}thiophene-2-sulfonamide | ~0.2†** | ~1.5†** |
| N-(4-chloro-3-methyl-5-isoxazolyl)-2-[3,4-(methylenedioxy)-6-(2-acetoxyethoxy)]phenylamino-cavbonyl]thiophene-3-sulfonamide | ~0.02†** | ~18† |
| N-(4-chloro-3-methyl-5-isdoxazolyl)-2-[3,4-(methylenedioxy)-6-(2-hydroxyethoxy)phenyl-aminocarbonyl]thiophene-3-sulfonamide | ~0.01†** | 18† |
| N-(4-chloro-3-methyl-5-isoxazolyl)-2-[2-cyano-4,5-(methylenedioxy)phenylacetyl]thiophene-3-sulfonamide | ~0.3†** | ~0.7† |
| N-(4-chloro-3-methyl-5-isoxazolyl)-2-{2-[(dimethylamino)carbonylmethyl]-4,5-(methylene-dioxy)phenylaminocarbonyl}thiophene-3-sulfonamide | 0.009† | 13.8† |
| N-(4-chloro-3-methyl-5-isoxazolyl)-2-[2-methyl-4,5-(methylenedioxy)phenylhydroxylmino]thiophene-3-sulfonamide | 0.794† | 6.49† |
| N-(4-bromo-3-methyl-5-isoxazolyl)-2-[2-methyl-4,5-(methylenedioxy)phenethyl]thiophene-3-sulfonamide | 0.0619† | 8.90† |
| N-(4-bromo-3-methyl-5-isoxazolyl)-3-[2-(hydroxymethyl)-4,5-(methylenedioxy)cinnamyl]thiophene-2-sulfonamide | 0.0795† | 3.24† |
| N-(4-bromo-3-methyl-5-isoxazolyl)-3-{2-[(tetrahydro-4H-pyran-2-yloxy)methyl]-4,5-(methylenedioxy)cinnamyl}thiophene-2-sulfonamide | 0.0967† | 4.14 |
| N-(4-bromo-3-methyl-5-isoxazolyl)-3-(2,4-dimethylphenethyl)thiophene-2-sulfonamide | 0.1006† | 4.30† |
| N-(4-bromo-3-methyl-5-isoxazolyl)-3-(2,4-dimethylcinnamyl)thiophene-2-sulfonamide | 0.180† | 2.97† |

TABLE 1-continued

| COMPOUND | $ET_A$ ($\mu M$)* | $ET_B$ ($\mu M$)* |
| --- | --- | --- |
| N-(4-bromo-3-methyl-5-isoxazolyl)-2-(2,4-dimethylcinnamyl)thiophene-3-sulfonamide | 0.166† | 2.97† |
| N-(4-bromo-3-methyl-5-isoxazolyl}-3-[(2,4-dimethylphenoxy)methyl]thiophene-2-sulfonamide | 0.346† | 7.45 |
| N-(4-bromo-3-methyl-5-isoxazolyl)-2-[(2,4-dimethylphenoxy)methyl]thiophene-3-sulfonamide | 0.308† | 4.48† |
| N-(4-chloro-3-methyl-5-isoxazolyl)-5-(phenylaminocarbonyl)thiophene-2-sulfonamide | 28.1 | 60.6† |
| N-(4-chloro-3-methyl-5-isoxazolyl)-2-[β-acetoxy-2-methyl-4,5-(methylenedioxy)styryl]thiophene-3-sulfonamide | 0.00544 | 3.74† |
| N-(4-chloro-3-methyl-5-isoxazolyl)-2-[(2,3,4-trimethoxy-6-cyano)phenylaminocarbonyl]thiophene-3-sulfonamide | 0.000169† | 12.5† |
| N-(4-chloro-3-methyl-5-isoxazolyl)-2-[2-(cyano)phenyl]benzo[b]thiophene-3-sulfonamide | 6.33† | 8.82† |
| N-(4-chloro-3-methyl-5-isoxazolyl)-2-[3,4-(methylenedioxy)phenyl]benzo[b]thiophene-3-sulfonamide | 0.550† | 52.6† |
| N-(4-bromo-3-methyl-5-isoxazolyl)-3-(2-tolyl)thiophene-2-sulfonamide | 0.324† | 55.1 |
| N-(4-bromo-3-methyl-5-isoxazolyl)-3-(3-tolyl)thiophene-2-sulfonamide | 0.832† | 21.2† |
| N-(4-bromo-3-methyl-5-isoxazolyl)-3-(2-tolyl)thiophene-2-sulfonamide | 0.302† | 31% @ 100† |
| N-(4-bromo-3-methyl-5-isoxazolyl)-3-(3-methoxyphenyl)thiophene-2-sulfonamide | 0.334† | ** |
| N-(4-bromo-3-methyl-5-isoxazolyl)-3-(3-methoxyphenyl)thiophene-2-sulfonamide | 1.32† | 56.3† |
| N-(4-bromo-3-methyl-5-isoxazolyl)-3-(2-methoxyphenyl)thiophene-2-sulfonamide | 1.71† | 59.1† |
| N-(4-bromo-3-methyl-5-isoxazolyl)-3-(4-ethylphenyl)thiophene-2-sulfonamide | 0.184 | 43.9† |
| N-(4-bromo-3-methyl-5-isoxazolyl)-3-(4-propylphenyl)thiophene-2-sulfonamide | 0.0873 | 8.48† |
| N-(4-bromo-3-methyl-5-isoxazolyl)-3-(4-iso-propylphenyl)thiophene-2-sulfonamide | 0.218 | 28.3† |
| N-(4-bromo-3-methyl-5-isoxazolyl)-3-(4-butylphenyl)thiophene-2-sulfonamide | 0.160 | 6.11† |
| N-(3,4-dimethyl-5-isoxazolyl)-2-[2-methyl-4,5-(methylenedioxy)phenylacetyl]thiophene-3-sulfonamide | 0.00328† | 34.3† |
| N-(4-chloro-3-methyl-5-isoxazolyl)-2-(2,4,6-trimethylphenylaminocarbonyl)thiophene-3-sulfonamide | 0.000626† | 8.27† |
| N-(4-chloro-3-methyl-5-isoxazolyl)-2-(2,4,6-tri-methylphenylacetyl)thiophene-3-sulfonamide | 0.000238† | 3.82† |
| N-(4-chloro-5-methyl-3-isoxazolyl)-2-[2-methyl-4,5-(methylenedioxy)phenylacetyl]thiophene-3-sulfonamide | 0.000625† | 3.69† |
| N-(4-bromo-3-methyl-5-isoxazolyl)-2-[2-methyl-4,5-(methylenedioxy)cinnamyl]thiophene-3-sulfonamide | 0.0804† | 3.28† |
| N-(4-bromo-3-methyl-5-isoxazolyl)-2-(2,4-dimethylphenethyl)thiophene-3-sulfonamide | 0.0555† | 3.48† |
| N-(4-chloro-3-methyl-5-isoxazolyl)-2-[(4-methoxycarbonyl-2,6-dimethyl)-phenylaminocarbonyl]thiophene-3-sulfonamide | 0.000266† | 9.78† |
| N-(4-chloro-3-methyl-5-isoxazolyl)-2-(phenoxycarbonyl)thiophene-3-sulfonamide | 4.41 | 31% @ 100† |
| N-(4-bromo-3-methyl-5-isoxazolyl)-2-(phenoxycarbonyl)thiophene-3-sulfonamide | 2.71 | 20% @ 100† |
| N-(3,4-dimethyl-5-isoxazolyl)-2-{[3,4-(methylenedioxy)phenoxy]carbonyl}thiophene-3-sulfonamide | 3.61 | 30% @ 100† |
| N-(4-bromo-3-methyl-5-isoxazolyl)-2-[(2-methylphenoxy)carbonyl]thiophene-3-sulfonamide | 0.684† | 105† |
| N-(4-bromo-3-methyl-5-isoxazolyl)-2-[(3-methylphenoxy)carbonyl]thiophene-3-sulfonamide | 1.20† | 111† |
| N-(4-bromo-3-methyl-5-isoxazolyl)-2-((2,4-dimethylphenoxy)carbonyl]thiophene-3-sulfonamide | 0.291† | 43.2† |
| N-(4-bromo-3-methyl-5-isoxazolyl)-2-[(2-methoxylphenoxy)carbonyl]thiophene-3-sulfonamide | 0.761† | 29% @ 100† |

TABLE 1-continued

| COMPOUND | $ET_A$ ($\mu$M)* | $ET_B$ ($\mu$M)* |
|---|---|---|
| N-(4-bromo-3-methyl-5-isoxazolyl)-2-[(3-methoxylphenoxy)carbonyl]thiophene-3-sulfonamide | 0.78† | 90† |
| N-(4-bromo-3-methyl-5-isoxazolyl)-2-[(4-methoxylphenoxy)carbonyl]thiophene-3-sulfonamide | 1.73† | 111† |
| N-(3,4-dimethyl-5-isoxazolyl)-2-[(4-methoxylphenoxy)carbonyl]thiophene-3-sulfonamide | †0.324 | 68.5† |
| N-(3,4-dimethyl-5-isoxazolyl)-2-[(4-methylphenoxy)carbonyl]thiophene-3-sulfonamide | 0.324† | 68.5† |
| N-(4-chloro-3-methyl-5-isoxazolyl)-2-[(4-methylphenoxy)carbonyl]thiophene-3-sulfonamide | 2.52† | 19% @ 100† |
| N-(4-chloro-3-methyl-5-isoxazolyl)-2-[(2,4-dimethylphenoxy)carbonyl]thiophene-3-sulfonamide | 3.22† | 43% @ 100† |
| N-(3,4-dimethyl-5-isoxazolyl}-2-[(2,4-dimethylphenoxy)carbonyl]thiophene-3-sulfonamide | 0.648† | 68.5 |
| N-(4-bromo-3-methyl-5-isoxazolyl)-2-{[2-propyl-4,5-(methylenedioxy)phenoxy]carbonyl)thiophene-3-sulfonamide | 0.274† | 21% @ 100† |
| N-(4-chloro-3-methyl-5-isoxazolyl)-2-(3-methoxycarbonyl-2,4,6-trimethylphenylamino-carbonyl)thiophene-3-sulfonamide | 0.138† | 11.9† |
| N-(4-bromo-3-methyl-5-isoxazolyl)-3-(2,4-dimethylphenyl)thiophene-2-sulfonamide | 0.1002† | 60.3† |
| N-(3,4-dimethyl-5-isoxazolyl)-2-(phenoxycarbonyl)thiophene-3-sulfonamide | 2.85† | 31%† |
| N-(4-bromo-3-methyl-5-isoxazolyl)-3-(4-iso-butylphenyl)thiophene-2-sulfonamide | 0.0823† | 2.76† |
| N-(4-bromo-3-methyl-5-isoxazolyl)-3-(4-iso-pentylphenyl)thiophene-2-sulfonamide | 0.155† | 3.31† |
| N-(4-bromo-3-methyl-5-isoxazolyl)-3-[(2,4,6-trimethylphenoxy)methyl]thiophene-2-sulfonamide | 0.0457† | 4.68† |
| N-(4-bromo-3-methyl-5-isoxazolyl)-2-[(2,4,6-trimethylphenoxy)methyl]thiophene-3-sulfonamide | 0.0562† | 3.39† |
| N-(4-bromo-3-methyl-5-isoxazolyl)-3-(2,4,6-trimethylcinnamyl)thiophene-2-sulfonamide | 0.0490† | 1.86† |
| N-(4-bromo-3-methyl-5-isoxazolyl)-3-(2-methyl-4-propylphenyl)thiophene-2-sulfonamide | 0.0468† | 3.63† |
| N-(4-bromo-3-methyl-5-isoxazolyl)-3-(4-iso-butyl-2-methylphenyt)thiophene]-2-sulfonamide | 0.0468† | 1.66† |
| N-(4-bromo-3-methyl-5-isoxazolyl)-3-(4-iso-pentyl-2-methylphenyl)thiophene-2-sulfonamide | 0.107† | 2.40† |
| N-(4-bromo-3-methyl-5-isoxazolyl)-2-{[3,4-(methylenedioxy)phenoxy]methyl}thiophene-3-sulfonamide | 0.302† | 6.61† |
| N-(4-bromo-3-methyl-5-isoxazolyl)-2-{[4,5-(methylenedioxy)-2-propylphenoxy]methyl}thio-phene-3-sulfonamide | 0.107† | 0.407† |
| N-(4-bromo-3-methyl-5-isoxazolyl)-2-(2,4,6-trimethylphenethyl)thiophene-3-sulfonamide | 0.0417† | 1.23† |
| N-(4-bromo-3-methyl-5-isoxazolyl)-3-(2,4,6-trimethylphenethyl)thiophene-2-sulfonamide | 0.055† | 1.62† |
| N-(3,4-dimethyl-5-isoxazolyl)-2-[(2,4,6-trimethylphenoxy)carbonyl]thiophene-3-sutfonamide | 0.537† | 8% @ 100† |
| N-(4-chloro-3-methyl-5-isoxazolyl)-2-[(2,4,6-trimethylphenoxy)carbonyl]thiophene-3-sulfonamide | 0.0776† | 30.2 |
| N-(4-bromo-3-methyl-5-isoxazolyl)-2-[(2,4,6-trimethylphenoxy)carbonyl]thiophene-3-sulfonamide | 0.479† | 24.5† |

*results are generally the average of 2 to 5 experiments
**preliminary results or results in which one or more data points were only determined approximately
†assay performed with incubation at 24° C. As described in the Examples, incubation at the higher temperature reduces the activity by a factor of 2- to about 10-compared to the activity at 4° C.
— data not available or measured as % inhibition @ 100 $\mu$M
% = % inhibition @ 100 $\mu$M It is understood that 4-bromo or 4-chloro groups can be replaced by other 4-halo substituents or other suitable substituents for $R^1$, such as alkyl.

2. $Ar^2$ is a substituted 4-biphenyl group

Compounds of formulae I in which $Ar^1$ is N-(5-isoxazolyl) or N-(3-isoxazolyl) in which $Ar^2$ is selected from biphenyl derivatives. These compounds can be represented by the following formulae (VII):

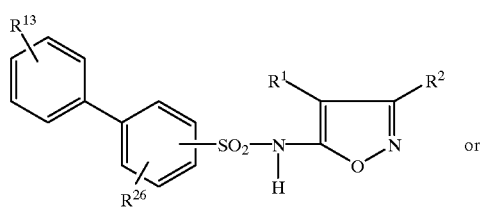

or

-continued

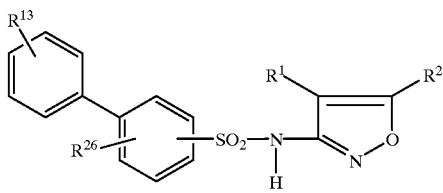

in which $R^{26}$ and $R^{13}$ are each independently selected from H, OH, OHNH, $NH_2$, $NO_2$, halide, pseudohalide, alkyl, alkenyl, alkynyl, aryl, arylalkyl, heteroaryl, alkoxy, alkylamino, dialkylamino, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, preferably from 1 to 6 atoms, and are either straight or branched chains or cyclic, and the aryl portions contain from about 4 to about 16 carbons, preferably 4 to 10 carbons. $R^{13}$ and $R^{26}$ are preferably each selected from from H, loweralkyl, haloalkyl and halide. Again, it is understood that $Ar^2$ may be substituted with more than one substituent, each of which is selected independently from the selections set forth for $R^{26}$ and $R^{13}$, and $R^2$ and $R^1$ are as defined above.

In the embodiments herein, the biphenyisulfonamides are substituted 4-biphenylsulfonamides, $R^{13}$ is preferably at the para position and $R^{26}$, if it is not hydrogen, is at any position except the 2-position.

In more preferred embodiments, $R^1$ is halide or methyl or higher ($C_9$–$C_{13}$) alkyl. $R^1$ is selected from halide, $CH_3$, $C_2H_5$, $CF_3$, $C_2F_5$, n-$C_3H_7$ and cyclo-$C_3H_7$, preferably halide or $CH_3$, and $R^2$ is selected from H, $CH_3$, $C_2H_5$, $CF_3$, $C_2F_5$, n-$C_3H_7$ and cyclo-$C_3H_7$, more preferably $R^1$ is halide or $CH_3$, and $R^2$ are selected from H, $CH_3$, $C_2H_5$, or $CF_3$.

In more preferred embodiments, $R^1$ is Cl or Br, or if greater $ET_B$ activity is preferred a higher alkyl ($C_9H_{19}$ to $C_{13}H_{27}$; $R^2$ is selected from H, $CH_3$, $C_2H_5$, $CF_3$, $C_2F_5$, n-$C_3H_7$, cyclo-$C_3H_7$, $nC_{13}H_{27}$ and $nC_9H_{19}$. In yet more preferred embodiments, $R^1$ is Br, Cl or $C_9H_{19}$ to $C_{13}H_{27}$; $R^2$ is H, $CH_3$, $C_2H_5$, or $CF_3$.

The biphenyl compounds provided herein are generally $ET_B$ active or $ET_B$ selective (see, e.g., Table 2); i.e. the compounds provided herein inhibit binding of endothelin to $ET_B$ receptors at concentrations about 10- to about 30-fold less than they inhibit binding of endothelin to $ET_A$ receptors. In particular the 4-biphenylsulfonamides are $ET_B$ selective.

In general in all embodiments herein, 4-haloisoxazolyl sulfonamides exhibit substantially enhanced activity with respect to at least one of the ET receptors (about two-fold to twenty-fold greater activity), as assessed by assays, such as those provided herein, that measure binding to $ET_A$ and/or $ET_B$ receptors, compared to corresponding sulfonamides in which the substituent at the 4 position in the isoxazolyl is other than halo, such as alkyl. For example: the $IC_{50}$ of N-(3,4-dimethyl-5-isoxazolyl)-2-biphenylsulfonamide for $ET_A$ receptors is about 0.008 μM, whereas, the $IC_{50}$ of N-(4-bromo-3-methyl-5-isoxazolyl)-2-biphenylsulfonamide is about 0.0016 μM (see, Table below); and (3) the $IC_{50}$ of N-(3,4-dimethyl-5-isoxazolyl)-3-biphenylsulfonamide for $ET_B$ receptors is about 3.48 μM; whereas, the $IC_{50}$ of N-(4-bromo-3-methyl-5-isoxazolyl)-3-biphenylsulfonamide for $ET_B$ receptors is about 0.76 μM and the $IC_{50}$ of N-(4-chloro-3-methyl-5-isoxazolyl)-3-biphenylsulfonamide for $ET_B$ receptors is about 0.793 μM (see, Table below).

Exemplary biphenyi sulfonamides are the following and those set forth in Table 2, and include, but are not limited to: N-(3-methyl-5-isoxazolyl)-4'-methylphenyl-4-biphenylsulfonamide, N-(4-bromo-3-methyl-5-isoxazolyl)-4'-methylphenyl-4-biphenylsulfonamide, N-(4-chloro-3-methyl-5-isoxazolyl)-4'-methylphenyl-4-biphenylsulfonamide, (3-methyl-5-isoxazolyl)-4'-trifluorophenyl-4-biphenylsulfonamide, (4-bromo-3-methyl-5-isoxazolyl)-4'-trifluorophenyl-4-biphenylsulfonamide, (3-methyl-5-isoxazolyl)-4'-methyoxyphenyl-4-biphenylsulfonamide, (4-bromo-3-methyl-5-isoxazolyl)-4'-methoxyphenyl-4-biphenylsulfonamide, (4-bromo-3-methyl-5-isoxazolyl)-3'-methoxyphenyl-4-biphenylsulfonamide, (4-bromo-3-methyl-5-isoxazolyl)-2'-methoxyphenyl-4-biphenylsulfonamide, N-(4-bromo-3-methyl-5-isoxazolyl)-3',4'-methylenedioxyphenyl-4-biphenylsulfonamide and (4-bromo-3-methyl-5-isoxazolyl)-3'-methylphenyl-4-biphenylsulfonamide. Corresponding 4-chloro and 4-fluoro isoxazolyl compounds are also encompassed herein.

Exemplary biphenyl compounds were tested using the exemplified assays (see, EXAMPLES) and the results, which are intended to be exemplary or provided for comparison with compounds provided herein, and are not limiting, are as set forth in the following table (Table 2):

TABLE 2

| COMPOUND | $ET_A$ (μM)* | $ET_B$ (μM)* |
|---|---|---|
| N-(4-bromo-3-methyl-5-isoxazolyl)-4-biphenylsulfonamide | 3.3<br>49† | ~0.17<br>1.23† |
| N-(4-bromo-5-methyl-3-isoxazolyl)-4-biphenylsulfonamide | 6.4 ± 2<br>49† | 0.29 ± 0.02<br>1.78† |
| N-(4-chloro-3-methyl-5-isoxazolyl)-4-biphenylsulfonamide | 4.93 ± 3 | 0.29 ± 0.1 |
| N-(3,4-dimethyl-5-isoxazolyl)-4-biphenylsufonamide | 9.9 ± 1.4<br>6.3† | 0.77 ± 0.32<br>0.15† |
| N-(4-chloro-5-methyl-3-isoxazolyl)-4-biphenylsulfonamide | 3.7<br>18.6† | 0.23 ± 0.01<br>1.29† |
| N-(4-Methyl-3-trifluoromethyl-5-isoxazolyl)-4-biphenylsulfonamide | 19.0<br>- | 1.7<br>5.62† |
| N-(4-Tridecyl-3-trifluoromethyl-5-isoxazolyl)-4-biphenylsulfonamide | 34.0 ± 9<br>33.0† | 0.99 ± 0.2<br>0.95† |
| N-(3,4-dimethyl-5-isoxazolyl)-2-biphenylsulfonamide | 0.0083 ± 0.0014 | 12.8 |

TABLE 2-continued

| COMPOUND | ET$_A$ ($\mu$M)* | ET$_B$ ($\mu$M)* |
| --- | --- | --- |
| N-(4-bromo-3-methyl-5-isoxazolyl)-2-biphenylsulfonamide | 0.00127** | 8.54** |
| N-(4-chloro-3-methyl-5-isoxazolyl)-2-biphenlsulfonamide | 0.00123** | ~14** |
| N-(3,4-dimethyl-5-isoxazolyl)-3-biphenylsulfonamide | >0.03** | 3.48** |
| N-(4-bromo-3-methyl-5-isoxazolyl)-3-biphenylsulfonamide | ~0.03** | 0.76** |
| N-(4-chloro-3-methyl-5-isoxazolyl)-3-biphenylsulfonamide | >0.03** | 0.793** |
| N-(4-bromo-3-methyl-5-isoxazolyl)-4'-methylphenyl-4-biphenylsulfonamide | 14.53 ± 9.6<br>22.17 ± 3.77† | 0.046 ± 0.044<br>0.168 ± 0.0032† |
| N-(4-bromo-3-methyl-5-isoxazolyl)-4'-trifluorophenyl-4-biphenylsulfonamide | 5.4 ± 0.3<br>25.91 ± 37† | 0.083 ± 0.02<br>0.71 ± 0.43† |
| N-(4-bromo-3-methyl-5-isoxazolyl)-4'-methoxyphenyl-4-biphenylsulfonamide | 14.7 ± 5.6<br>121.5 ± 2.12† | 1.15 ± 0.44<br>3.94 ± 0.89† |
| N-(4-bromo-3-methyl-5-isoxazolyl)-3'-methoxyphenyl-4-biphenylsulfonamide | 4.97 ± 3.4<br>162.6 ± 7.14† | 0.66 ± 0.25<br>2.08 ± 0.23† |
| N-(4-bromo-3-methyl-5-isoxazolyl)-2'-methoxyphenyl-4-biphenylsulfonamide | 3.3 ± 3.5 | 0.41 ± 0.14 |
| N-(4-bromo-3-methyl-5-isoxazolyl)-3',4'-methylenedioxyphenyl-4-biphenylsulfonamide | 38.2 ± 4.95† | 3.0 ± 0.78† |
| N-(4-bromo-3-methyl-5-isoxazolyl)-3'-methylphenyl-4-biphenylsulfonamide | — | — |

*results generally from 1, 2 or 3 experiments with the same preparation
**preliminary results Preferred compounds are those in which Ar$^2$ is a 4-biphenyl in which, referring to formula VII, at least one substituent R$^{13}$ is at the para position. Preferred substitutents are loweralkyl, halo loweralkyl and lower alkoxy. Such compounds are ET$_B$ active.

The preparation of the above and other compounds that possess the requisite activities are set forth in the Examples.

B. Preparation of the Compounds

The preparation of some of the above and other compounds that possess the requisite activities are set forth in the Examples. Compounds whose synthesis is not explicitly exemplified can be synthesized by routine modification of one or more methods described in detail in the Examples by substituting appropriate readily available reagents.

The preparation of the above compounds are described in detail in the examples. Any such compound or similar compound may be synthesized according to a method discussed in general below and set forth in the Examples by selecting appropriate starting materials as exemplified.

In general, most of the syntheses involve the condensation of a sulfonyl chloride with an aminoisoxazole in dry pyridine or in tetrahydrofuran (THF) and sodium hydride. The sulfonyl chorides and aminoisoxazoles either can be obtained commercially or synthesized according to methods described in the Examples or using other methods available to those of skill in this art (see, e.g., U.S. Pat. Nos. 4,659,369, 4,861,366 and 4,753,672).

The N-(alkylisoxazolyl)sulfonamides can be prepared by condensing an aminoisoxazole with a sulfonyl chloride in dry pyridine with or without the catalyst 4-(dimethylamino) pyridine. The N-(3,4-dimethyl-5-isoxazolyl)sulfonamides and N-(4,5-dimethyl-5-isoxazolyl)sulfonamides can be prepared from the corresponding aminodimethylisoxazole, such as 5-amino-3,4-dimethylisoxazole. For example, N-(3,4-dimethyl-5-isoxazolyl)-2-(carbomethoxy)thiophene-3-sulfonamide was prepared from 2-methoxycarbonylthiophene-3-sulfonyl chloride and 5-amino-3,4-dimethylisoxazole in dry pyridine.

The N-(4-haloisoxazolyl)sulfonamides can be prepared by condensation of amino-4-haloisoxazole with a sulfonyl chloride in THF with sodium hydride as a base. For example, N-(4-bromo-3-methyl-5-isoxazolyl)thiophene-2-sulfonamide was prepared from 5-amino-4-bromo-3-methylisoxazole and thiophene-2-sulfonyl chloride in THF and sodium hydride. N-(4-bromo-3-methyl-5-isoxazolyl)-5-(3-isoxazolyl)thiophene-2-sulfonamide was prepared from 5-amino-4-bromo-3-methylisoxazole and 5-(3-isoxazolyl) thiophene-2-sulphonyl chloride.

Alternatively, compounds, such as those in which Ar$^2$ is thienyl, furyl and pyrrolyl herein, may be prepared by reacting an appropriate sulfonyl chloride with a 5-aminoisoxazole substituted at the 3 and 4 positions, such as 5-amino-4-bromo-3-methylisoxazole, in tetrahydrofuran (THF) solution containing a base, such as sodium hydride. Following the reaction, the THF is removed under reduced pressure, the residue dissolved in water, acidified and extracted with methylene chloride. The organic layer is washed and then dried over anhydrous magnesium sulfate, the solvents are evaporated and the residue is purified by recrystallization using hexanes/ethylacetate to yield pure product.

These sulfonamides also can be prepared from the corresponding sulfonyl chloride and the aminoisoxazole in pyridine with or without a catalytic amount of 4-dimethylaminopyridine (DMAP). In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature. For example:

(a) N-(4-bromo-3-methyl-5-isoxazolyl)-2-(N-phenylaminocarbonyl)thiophene-3-sulfonamide was prepared from N-(4-bromo-3-methyl-5-isoxazolyl)-2-carboxylthiophene-3-sulfonamide and aniline and 1-ethyl-3'-[3-dimethylaminopropyl]carbodiimide (EDCl). N-(4-bromo-3-methyl-5-isoxazolyl)-2-[(4-methoxyphenyl)aminocarbonyl]thiophene-3-sulfonamide was prepared from 4-methoxyaniline, N,N'-diisopropylethylamine and N-(4-bromo-3- methyl-5-isoxazolyl)-2-carboxylthiophene-3-sulfonamide. N-(4-bromo-3-methyl-5-isoxazolyl)-2-(benzylaminocarbonyl)thiopane-3-sulfonamide was prepared from N-(4-bromo-3-methyl-5-isoxazolyl)-2-carboxylthiophene-3-sulfonamide and benzylamine as described above.

N-(4-bromo-3-methyl-5-isoxazolyl)-2-carboxylthiophene-3-sulfonamide was prepared from N-(4-bromo-3-methyl-5-isoxazolyl)-2-(carbomethoxy)thiophene-3-sulfonamide, which was prepared from the condensation of 5-amino-4-bromo-3-methylisoxazole and 2-(carbomethoxy)thiophene-3-sulfonyl chloride.

(b) N-(4-bromo-3-methyl-5-isoxazolyl)-1-(4'-isopropylphenyl)pyrrole-2-sulfonamide and N-(4-bromo-3-methyl-5-isoxazolyl)-1-(4'-isopropylphenyl) pyrrole-3-sulfonamide were prepared from 5-amino-4-bromo-3-methylisoxazole and a mixture of 1-(4'-isopropylphenyl)pyrrole-2-sulfonyl chloride and 1-(4'-isopropylphenyl)pyrrole-3-sulfonyl chloride. These sulfonyl chlorides were prepared from 1-(4'-isopropylphenyl)pyrrole-2-sulfonic acid in phosphorus oxychloride and phosphorus pentachloride. 1-(4'-isopropylphenyl)pyrrole-2-sulfonic acid was prepared from 1-(4'-isopropylphenyl)pyrrole and chiorosulfonic acid. 1-(4'-isopropylphenyl)pyrrole was prepared from 4-isopropylaniline and 2,5-dimethoxytetrahydrofuran.

Prodrugs and other derivatives of the compounds suitable for administration to humans may also be designed and prepared by methods known to those of skill in the art (see, e.g., Nogrady (1985) *Medicinal Chemistry A Biochemical Approach,* Oxford University Press, New York, pages 388–392).

Compounds described herein have been synthesized and tested for activity in in vitro assays and, in some cases, in in vivo animal models. Nuclear magnetic resonance spectroscopic (NMR), mass spectrometric, infrared spectroscopic and high performance liquid chromatographic analyses indicated that the synthesized compounds have structures consistent with those expected for such compounds and are generally at least about 98% pure. All of the compounds exemplified or described herein exhibited activity as endothelin antagonists.

C. Evaluation of the Bioactivity of the Compounds

Standard physiological, pharmacological and biochemical procedures are available for testing the compounds to identify those that possess any biological activities of an endothelin peptide or the ability to interfere with or inhibit endothelin peptides. Compounds that exhibit in vitro activities, such as the ability to bind to endothelin receptors or to compete with one or more of the endothelin peptides for binding to endothelin receptors can be used in the methods for isolation of endothelin receptors and the methods for distinguishing the specificities of endothelin receptors, and are candidates for use in the methods of treating endothelin-mediated disorders.

Thus, other preferred compounds of formulas I and II, in addition to those specifically identified herein, that are endothelin antagonists or agonists may be identified using such screening assays.

1. Identifying compounds that modulate the activity of an endothelin peptide

The compounds are tested for the ability to modulate the activity of endothelin-1. Numerous assays are known to those of skill in the art for evaluating the ability of compounds to modulate the activity of endothelin (see, e.g., U.S. Pat. No. 5,114,918 to Ishikawa et al.; EP A1 0 436 189 to BANYU PHARMACEUTICAL CO., LTD. (Oct. 7, 1991); Borges et al. (1989) *Eur. J. Pharm.* 165: 223–230; Filep et al. (1991) *Biochem. Biophys. Res. Commun.* 177: 171–176). In vitro studies may be corroborated with in vivo studies (see, e.g., U.S. Pat. No. 5,114,918 to Ishikawa et al.; EP A1 0 436 189 to BANYU PHARMACEUTICAL CO., LTD. (Oct. 7, 1991)) and pharmaceutical activity thereby evaluated. Such assays are described in the Examples herein and include the ability to compete for binding to $ET_A$ and $ET_B$ receptors present on membranes isolated from cell lines that have been genetically engineered to express either $ET_A$ or $ET_B$ receptors on their cell surfaces.

The properties of a potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E., "Tissue selectivity of endothelin," *Eur. J. Pharmacol* 165:223–230, (1989)). The ability to act as an endothelin antagonist in vivo can be tested in hypertensive rats, ddy mice or other recognized animal models (see, Kaltenbronn et al. (1990) *J. Med. Chem.* 33:838–845, see, also, U.S. Pat. No. 5,114,918 to Ishikawa et al.; and EP A1 0 436 189 to BANYU PHARMACEUTICAL CO., LTD (Oct. 7, 1991); see, also Bolger et al. (1983) *J. Pharmacol. Exp. Ther.* 225291–309). Using the results of such animal studies, pharmaceutical effectiveness may be evaluated and pharmaceutically effective dosages determined. A potential agonist may also be evaluated using in vitro and in vivo assays known to those of skill in the art.

Endothelin activity can be identified by the ability of a test compound to stimulate constriction of isolated rat thoracic aorta (Borges et al. (1989) "Tissue selectivity of endothelin" *Eur. J. Pharmacol.* 165: 223–230). To perform the assay, the endothelium is abraded and ring segments mounted under tension in a tissue bath and treated with endothelin in the presence of the test compound. Changes in endothelin induced tension are recorded. Dose response curves may be generated and used to provide information regarding the relative inhibitory potency of the test compound. Other tissues, including heart, skeletal muscle, kidney, uterus, trachea and vas deferens, may be used for evaluating the effects of a particular test compound on tissue contraction.

Endothelin isotype specific antagonists may be identified by the ability of a test compound to interfere with endothelin binding to different tissues or cells expressing different endothelin-receptor subtypes, or to interfere with the biological effects of endothelin or an endothelin isotype (Takayanagi et al. (1991) *Reg. Pep.* 32: 23–37, Panek et al. (1992) *Biochem. Biophys. Res. Commun.* 183: 566–571). For example, $ET_B$ receptors are expressed in vascular endothelial cells, possibly mediating the release of prostacyclin and endothelium-derived relaxing factor (De Nucci et al. (1988) *Proc. Natl. Acad. Sci. USA* 85:9797). $ET_A$ receptors are not detected in cultured endothelial cells, which express $ET_B$ receptors.

The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.g., Filep et al. (1991) *Biochem. and Biophys Res. Commun.* 177: 171–176). Thus, the relative affinity of the compounds for different endothelin receptors may be evaluated by determining the inhibitory dose response curves using tissues that differ in receptor subtype.

Using such assays, the relative affinities of the compounds for $ET_A$ receptors and $ET_B$ receptors have been and can be assessed. Those that possess the desired properties, such as specific inhibition of binding of endothelin-1, are selected. The selected compounds that exhibit desirable activities may be therapeutically useful and are tested for such uses using the above-described assays from which in vivo effectiveness may be evaluated (see, e.g., U.S. Pat. Nos. 5,248,807; 5,240,910; 5,198,548; 5,187,195; 5,082,838; 5,230,999; published Canadian Application Nos. 2,067,288 and 2071193; published Great Britain Application No. 2,259, 450; Published International PCT Application No. WO 93/08799; Benigi et al. (1993) *Kidney International* 44:440–444; and Nirei et al. (1993) *Life Sciences* 52:1869–1874). Compounds that exhibit in vitro activities that correlate with in vivo effectiveness will then be formulated in suitable pharmaceutical compositions and used as therapeutics.

The compounds also may be used in methods for identifying and isolating endothelin-specific receptors and aiding in the design of compounds that are more potent endothelin antagonists or agonists or that are more specific for a particular endothelin receptor.

2. Isolation of endothelin receptors

A method for identifying endothelin receptors is provided. In practicing this method, one or more of the compounds is linked to a support and used in methods of affinity purification of receptors. By selecting compounds with particular specificities, distinct subclasses of ET receptors may be identified.

One or more of the compounds may be linked to an appropriate resin, such as Affi-gel, covalently or by other linkage, by methods known to those of skill in the art for linking endothelin to such resins (see, Schvartz et al. (1990) *Endocrinology* 126: 3218–3222). The linked compounds can be those that are specific for $ET_A$ or $ET_B$ receptors or other subclass of receptors.

The resin is pre-equilibrated with a suitable buffer generally at a physiological pH (7 to 8). A composition containing solubilized receptors from a selected tissue are mixed with the resin to which the compound is linked and the receptors are selectively eluted. The receptors can be identified by testing them for binding to an endothelin isopeptide or analog or by other methods by which proteins are identified and characterized. Preparation of the receptors, the resin and the elution method may be performed by modification of standard protocols known to those of skill in the art (see, e.g., Schvartz et al. (1990) *Endocrinology* 126: 3218–3222).

Other methods for distinguishing receptor type based on differential affinity to any of the compounds herein are provided. Any of the assays described herein for measuring the affinity of selected compounds for endothelin receptors may also be used to distinguish receptor subtypes based on affinity for particular compounds provided herein. In particular, an unknown receptor may be identified as an $ET_A$ or $ET_B$ receptor by measuring the binding affinity of the unknown receptor for a compound provided herein that has a known affinity for one receptor over the other. Such preferential interaction is useful for determining the particular disease that may be treated with a compound prepared as described herein. For example, compounds with high affinity for $ET_A$ receptors and little or no affinity for $ET_B$ receptors are candidates for use as hypertensive agents; whereas, compounds that preferentially interact with $ET_B$ receptors are candidates for use as anti-asthma agents.

D. Formulation and Administration of the Compositions

Effective concentrations of one or more of the sulfonamide compounds of formula I or II or pharmaceutically acceptable salts, esters or other derivatives thereof are mixed with a suitable pharmaceutical carrier or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as salts of the compounds or prodrugs of the compounds may also be used in formulating effective pharmaceutical compositions.

The concentrations or the compounds are effective for delivery of an amount, upon administration, that ameliorates the symptoms of the endothelin-mediated disease. Typically, the compositions are formulated for single dosage administration.

Upon mixing or addition of the sulfonamide compound (s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients.

The active compounds can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., U.S. Pat. No. 5,114,918 to Ishikawa et al.; EP A1 0 436 189 to BANYU PHARMACEUTICAL CO., LTD (Oct. 7, 1991); Borges et al. (1989) *Eur. J. Pharm.* 165: 223–230;: Filep et al. (1991) *Biochem. Biophys. Res. Commun.* 177: 171–176) and then extrapolated therefrom for dosages for humans.

The concentration of active compound in the drug composition will depend on absorption, inactivation and excretion rates of the active compound, the dosage schedule, and amount administered as well as other factors known to those of skill in the art. For example, the amount that is delivered is sufficient to treat the symptoms of hypertension. The effective amounts for treating endothelin-mediated disorders are expected to be higher than the amount of the sulfonamide compound that would be administered for treating bacterial infections.

Typically a therapeutically effective dosage should produce a serum concentration of active ingredient of from about 0.1 ng/ml to about 50–100 µg/ml. The pharmaceutical compositions typically should provide a dosage of from about 0.01 mg to about 2000 mg of compound per kilogram of body weight per day. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the compound is used for treating asthma or hypertension, it may be used with other bronchodilators and antihypertensive agents, respectively.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

The compounds may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The compounds may be formulated as aerosols for topical application, such as by inhalation (see, e.g., U.S. Pat. Nos. 4,044,126, 4,414,209, and 4,364,923, which describe aerosols for delivery of a steroid useful for treatment inflammatory diseases, particularly asthma).

Finally, the compounds may be packaged as articles of manufacture containing packaging material, a compound provided herein, which is effective for antagonizing the effects of endothelin, ameliorating the symptoms of an endothelin-mediated disorder, or inhibiting binding of an endothelin peptide to an ET receptor with an $IC_{50}$ of less than about 10 μM, within the packaging material, and a label that indicates that the compound or salt thereof is used for antagonizing the effects of endothelin, treating endothelin-mediated disorders or inhibiting the binding of an endothelin peptide to an ET receptor.

The following examples are included for illustrative purposes only and are not intended to limit the scope of the invention.

EXAMPLE 1

N-(4-Bromo-3-methyl-5-isoxazolyl)thiophene-2-sulfonamide

A solution of 5-amino-4-bromo-3-methylisoxazole (177 mg, 1.0 mmol) in dry tetrahydrofuran (THF, 2 ml) was added to a suspension of sodium hydride (60% dispersion in mineral oil, 90 mg, 2.2 mmol) in dry THF (1 ml) at 0–5° C. After stirring at 0–5° C. for 5 min., the reaction was stirred at room temperature for 10 min to complete the reaction. The reaction mixture was re-cooled to 0° C. and thiophene-2-sulfonyl chloride (200 mg, 1.1 mmol) dissolved in dry THF (2 ml) was added dropwise. Stirring was continued for 1 h; during this period the reaction mixture slowly attained ambient temperature. THF was removed under reduced pressure. The residue was dissolved in water (10 ml), the pH was adjusted to 10–11 by adding 5 N sodium hydroxide solution, and was extracted with ethyl acetate (3×10 ml) to remove the neutral impurities. The aqueous layer was acidified with concentrated HCl (pH 2–3) and extracted with methylene chloride (3×10 ml). The combined organic layers was dried over anhydrous magnesium sulfate and concentrated under reduced pressure to give N-(4-bromo-3-methyl-5-isoxazolyl)thiophene-2-sulfonamide. The pure material was obtained by recrystallization using hexanes/ethyl acetate (110 mg, 34% yield), m.p. 125–127° C.

EXAMPLE 2

N-(4-Bromo-3-methyl-5-isoxazolyl)-5-(3-isoxazolyl) thiophene-2-sulfonamide

A solution of 5-amino-4-bromo-3-methylisoxazole (177 mg, 1.0 mmol) in dry THF (2 ml) was added to a suspension of sodium hydride (60% dispersion in mineral oil, 90 mg, 2.2 mmol) in dry THF (1 ml) at 0–5° C. After stirring at 0–5° C. for 5 min, the reaction was warmed to room temperature for 10 min to complete the reaction. The reaction mixture was re-cooled to 0° C., and 5-(3-isoxazolyl)thiophene-2-sulphonyl chloride (273 mg, 1.1 mmol), which had been dissolved in dry THF (2 ml), was added slowly. Stirring was continued for 1 h; during this period the reaction mixture slowly attained ambient temperature. THF was removed under reduced pressure. The residue was dissolved in water (10 ml), the pH was adjusted to 2–3 by adding concentrated HCl, and was extracted with methylene chloride (3×10 ml). The combined organic layers was dried over anhydrous magnesium sulfate and concentrated under reduced pressure to give N-(4-bromo-3-methyl-5-isoxazolyl)-5-(3-isoxazolyl)thiophene-2-sulfonamide. The pure material was obtained by recrystallization using hexanes/ethyl acetate (160 mg, 41% yield), m.p. 120–123° C.

EXAMPLE 3

N-(4-Bromo-3-methyl-5-isoxazolyl)-5-(2-pyridyl) thiophene-2-sulfonamide

N-(4-bromo-3-methyl-5-isoxazolyl)-5-(2-pyridyl) thiophene-2-sulfonamide was prepared in the same manner as described in Example 2 from 5-amino-4-bromo-3-methylisoxazole and 5-(2-pyridyl)thiophene-2-sulphonyl chloride in 40% yield. Purification was achieved by recrystallization from ethyl acetate to give a crystalline solid, m.p. 186–188° C.

EXAMPLE 4

N-(4-Bromo-3-methyl-5-isoxazolyl)-4,5-dibromothiophene-2-sulfonamide

N-(4-bromo-3-methyl-5-isoxazolyl)-4,5-dibromothiophene-2-sulfonamide was prepared in the same manner as described in Example 2 from 5-amino-4-bromo-3-methylisoxazole and 4,5-dibromothiophene-2-sulphonyl chloride in 45% yield. Purification was achieved by recrystallization from ethyl acetate/hexanes to give a crystalline solid, m.p. 153–155° C.

EXAMPLE 5

N-(4-Bromo-3-methyl-5-isoxazolyl)-5-chloro-3-methylbenzo[b]thiophene-2-sulfonamide N-(4-bromo-3-methyl-5-isoxazolyl)-5-chloro-3-methylbenzo[b]thiophene-2-sulfonamide was prepared in the same manner as described in Example 2 from 5-amino-4-bromo-3-methylisoxazole and 5-chloro-3-methylbenzo[b]thiophene-2-sulphonyl chloride in 18% yield. Purification was achieved by recrystallization from ethyl acetate/hexanes to give a crystalline solid, m.p. 153–155° C.

EXAMPLE 6

N-(4-Bromo-3-methyl-5-isoxazolyl)-5-(4-chlorobenzamidomethyl)thiophene-2-sulfonamide N-(4-Bromo-3-methyl-5-isoxazolyl)-5-(4-chlorobenzamidomethyl)thiophene-2-sulfonamide was prepared in the same manner as described in Example 2 from 5-amino-4-bromo-3-methylisoxazole and 5-(4-chlorobenzamidomethyl)thiophene-2-sulphonyl chloride in 27% yield. The crude product was passed through a silica gel column using hexanes/ethyl acetate as eluent. Purification was effected by recrystallization from ethyl acetate/hexanes to give a crystalline solid, m.p. 210° C. (dec).

EXAMPLE 7

N-(4-Bromo-3-methyl-5-isoxazolyl)-4-(benzenesulfonyl)thiophene-2-sulfonamide

N-(4-Bromo-3-methyl-5-isoxazolyl)-4-(benzenesulfonyl) thiophene-2-sulfonamide was prepared in the same manner as described in Example 2 from 5-amino-4-bromo-3-methylisoxazole and 4-benzenesulfonylthiophene-2-sulphonyl chloride in 26% yield. Purification was achieved by recrystallization from ethyl acetate/hexanes to give a crystalline solid, m.p. 181–184° C.

EXAMPLE 8

N-(4-Bromo-3-methyl-5-isoxazolyl)-4-bromo-5-chloro-thiophene-2-sulfonamide

N-(4-Bromo-3-methyl-5-isoxazolyl)-4-bromo-5-chloro-thiophene-2-sulfonamide was prepared in the same manner as described in Example 2 from 5-amino-4-bromo-3-methylisoxazole and 4-bromo-5-chlorothiophene-2-sulphonyl chloride in 25% yield. Purification was achieved by recrystallization from ethyl acetate/hexanes to give a crystalline solid, m.p. 143–145° C.

EXAMPLE 9

N-(4-Bromo-3-methyl-5-isoxazolyl)-2,5-dichlorothiophene-3-sulfonamide

N-(4-Bromo-3-methyl-5-isoxazolyl)-2,5-dichlorothiophene-3-sulfonamide was prepared in the same manner as described in Example 2 from 5-amino-4-bromo-3-methylisoxazole and 2,5-dichlorolthiophene-3-sulphonyl chloride in 47% yield. Purification was achieved by recrystallization from ethyl acetate/hexanes to give a crystalline solid, m.p. 135–138° C.

EXAMPLE 10

N-(4-Bromo-3-methyl-5-isoxazolyl)-2,5-dimethylthiophene-3-sulfonamide

N-(4-Bromo-3-methyl-5-isoxazolyl)-2,5-dimethylthiophene-3-sulfonamide was prepared in the same manner as described in Example 1 from 5-amino-4-bromo-3-methylisoxazole and 2,5-dimethylthiophene-3-sulphonyl chloride in 55% yield. Purification was achieved by recrystallization from ethyl acetate/hexanes to give a crystalline solid, m.p. 77–80° C.

EXAMPLE 11

N-(4-Bromo-3-methyl-5-isoxazolyl)-4,5-dichlorothiophene-2-sulfonamide

N-(4-Bromo-3-methyl-5-isoxazolyl)-4,5-dichlorothiophene-2-sulfonamide was prepared in the same manner as described in Example 1 from 5-amino-4-bromo-3-methylisoxazole and 4,5-dichlorothiophene-2-sulphonyl chloride in 42% yield. Purification was achieved by recrystallization from ethyl acetate/hexanes to give a crystalline solid, m.p. 135–138° C.

EXAMPLE 12

N-(4-Bromo-3-methyl-5-isoxazolyl)-2,5-dichloro-4-bromothiophene-3-sulfonamide N-(4-Bromo-3-methyl-5-isoxazolyl)-2,5-dichloro-4-bromothiophene-3-sulfonamide was prepared in the same manner as described in Example 1 from 5-amino-4-bromo-3-methylisoxazole and 4-bromo-2,5-dichlorothiophene-3-sulfonyl chloride in 58% yield. Purification was achieved by recrystallization from ethyl acetate/hexanes to give a crystalline solid, m.p. 146–149° C.

EXAMPLE 13

N-(4-Bromo-3-methyl-5-isoxazolyl)-2-{3-[1-methyl-5-(trifluoromethyl)pyrazolyl]}thiophene-5-sulfonamide N-(4-Bromo-3-methyl-5-isoxazolyl)-2-{3-[1-methyl-5-(trifluoromethyl)pyrazolyl]}thiophene-5-sulfonamide was prepared in the same manner as described in Example 1 from 5-amino-4-bromo-3-methylisoxazole and 2-{3-[1-methyl-5-(trifluoromethyl)pyrazolyl]}thiophene-5-sulphonyl chloride in 30% yield. Purification was achieved by recrystallization from ethyl acetate/hexanes to give a crystalline solid, m.p. 121–123° C.

EXAMPLE 14

N-(4-Bromo-5-methyl-3-isoxazolyl)thiophene-2-sulfonamide

Thiophene-2-sulfonyl chloride (183 mg, 1 mmol) was added to a solution of 3-amino-4-bromo-5-methylisoxazole (177 mg, 1 mmol) in dry pyridine (0.5 ml). The reaction mixture was stirred at room temperature for 3 h. Pyridine was removed under reduced pressure and the residue was partitioned between water and ethyl acetate. The organic layer was washed with 1N HCl (3×10 ml), brine (10 ml) and dried over anhydrous magnesium sulfate. Evaporation of the solvents left an oily residue which was solidified at −20° C. and then purified by recrystallization from ethyl acetate/hexanes, to give the pure product (51% yield) as a tan solid, m.p. 156–158° C.

EXAMPLE 15

N-(4-Bromo-3-methyl-5-isoxazolyl)-5-(benzenesulfonyl)thiophene-2-sulfonamide N-(4-Bromo-3-methyl-5-isoxazolyl)-5-(benzenesulfonyl)thiophene-2-sulfonamide was prepared in the same manner as described in Example 2 from 5-amino-4-bromo-3-methylisoxazole and 5-benzenesulfonylthiophene-2-sulfonyl chloride in 59% yield. Purification was achieved by recrystallization from ethyl acetate/hexanes to give a crystalline solid, m.p. 139–142° C.

EXAMPLE 16

N-(4-Bromo-3-methyl-5-isoxazolyl)-2-(carbomethoxy)thiophene-3-sulfonamide

N-(4-Bromo-3-methyl-5-isoxazolyl)-2-(carbomethoxy)thiophene-3-sulfonamide was prepared in the same manner as described in Example 2 from 5-amino-4-bromo-3-methylisoxazole and 2-(carbomethoxy)thiophene-3-sulfonyl chloride in 73% yield. Purification was achieved by recrystallization from ethyl acetate/hexanes to give a crystalline solid, m.p. 198–200° C.

EXAMPLE 17

N-(4-Bromo-3-methyl-5-isoxazolyl)-2-(carboxyl)thiophene-3-sulfonamide

N-(4-Bromo-3-methyl-5-isoxazolyl)-2-(carbomethoxy)thiophene-3-sulfonamide (Example 16) (1.5 g, 3.95 mmol) was dissolved in methanol (10 ml). Sodium hydroxide pellets (1 g, 25 mmol) and a few drops of water were then added. The resultant solution was stirred for 16 h at ambient temperature. Methanol was removed under reduced pressure. The residue was diluted with water and was extracted with ethyl acetate (2×10 ml). The aqueous layer was acidified (pH=2) with concentrated hydrochloric acid and was extracted with ethyl acetate (2×60 ml). The combined organic layers was dried over anhydrous magnesium sulfate and filtered. Removal of the solvent gave N-(4-bromo-3-methyl-5-isoxazolyl)-2-(carbomethoxy)thiophene-3-sulfonamide (1.2 g, 82% yield), which was purified by silica gel column chromatography using ethyl acetate as eluent, m.p. 188–194° C.

EXAMPLE 18

N-(4-Bromo-3-methyl-5-isoxazolyl)-2-(N-phenylaminocarbonyl)thiophene-3-sulfonamide Aniline (0.093 g, 1 mmol) and 1-ethyl-3'[3-dimethylaminopropyl]-carbodiimide (EDCl) (0.191 g, 1 mmol) were added to N-(4-bromo-3-methyl-5-isoxazolyl)-2-(carboxyl)thiophene-3-sulfonamide (0.368 g, 1 mmol) that had been suspended in methylene chloride (5 ml) to produce a clear solution. Stirring was continued for 1 h at ambient temperature. The reaction mixture was diluted with methylene chloride (50 ml) and washed with 3 N hydrochloric acid solution (3×50 ml). The combined organic layers was dried over anhydrous magnesium sulfate and filtered. Removal of the solvent under reduced pressure gave N-(4-bromo-3-methyl-5-isoxazolyl)-2-(N-phenylaminocarbonyl)thiophene-3-sulfonamide. The crude product thus obtained was purified by column chromatography using ethyl acetate as eluent to yield the product (0.32 g, 72% yield, m.p. 168–170° C.

EXAMPLE 19

N-(4-Bromo-3-methyl-5-isoxazolyl) 1-(4'-isopropylphenyl)pyrrole-2-sulfonamide and N-(4-bromo-3-methyl-5-isoxazolyl) 1-(4'-isopropylphenyl)pyrrole-3-sulfonamide A. 1-(4'-isopropylphenyl)pyrrole Glacial acetic acid (100 ml) was added to a mixture of 4-isopropylaniline (10 ml, 72.4 mmol) and 2,5-dimethoxytetrahydrofuran (9.6 ml, 72.4 mmol) and the resulting mixture was refluxed for 1.5 h. The reaction mixture was allowed to cool and acetic acid was removed under reduced pressure. The resulting brown syrup was dissolved in ethyl acetate (200 ml) and washed with water (2×200 ml). The organic layer was dried over magnesium sulfate and filtered. Removal of the solvent gave 1-(4'-isopropylphenyl)pyrrole (13.28 g, 99% yield) as a brown syrup.

B. 1-(4'-isopropylphenyl)pyrrole-2-sulfonic acid

Chlorosulfonic acid (1.82 ml, 27.08 mmol) was slowly added to a solution of 1-(4'-isopropylphenyl)pyrrole (5.01 g, 27.08 mmol) in chloroform (100 ml) at 0° C. The resulting solution was stirred at 0° C. for 1 h and for an additional 1 h at room temperature. Chloroform was removed under reduced pressure. The resultant brown liquid was diluted with ethyl acetate (200 ml) and washed with 1 N sodium hydroxide. The aqueous layer was then acidified with concentrated hydrochloric acid (pH<1) and then extracted with chloroform (2×150 ml). The combined organic layers was dried over magnesium sulfate and was filtered. Removal of the solvent gave 1-(4'-isopropylphenyl)pyrrole-2-sulfonic acid as a brown syrup (3 g, 42% yield).

C. 1-(4'-isopropylphenyl)pyrrole-2-sulfonyl chloride and 1-(4'-isopropylphenyl)pyrrole-3-sulfonyl chloride Phosphorus pentachloride (4.7 g, 22.64 mmol) was slowly added to a solution of 1-(4'-isopropylphenyl)pyrrole-2-sulfonic acid (3 g, 11.32 mmol) in phosphorus oxychloride (8.4 ml, 90.57 mmol). The resulting mixture was heated at 70° C. for 10 h. The reaction mixture was allowed to cool to room temperature, then carefully poured on to crushed ice (500 g) and extracted with chloroform (200 ml). The combined organic layers was dried over anhydrous magnesium sulfate. This was filtered and removal of the solvent yielded a 4:1 mixture of 1-(4'-isopropylphenyl)pyrrole-2-sulfonyl chloride and 1-[4'-isopropylphenyl)pyrrole-3-sulfonyl chloride (2.5 g, 78%) as a brown oil.

D. N-(4-bromo-3-methyl-5-isoxazolyl) 1-(4'-isopropylphenyl)pyrrole-2-sulfonamide and N-(4-bromo-3-methyl-5-isoxazolyl) 1-(4'-isopropylphenyl)pyrrole-3-sulfonamide N-(4-bromo-3-methyl-5-isoxazolyl) 1-(4'-isopropylphenyl)pyrrole-2-sulfonamide and N-(4-bromo-3-methyl-5-isoxazolyl) 1-(4'-isopropylphenyl)pyrrole-3-sulfonamide were prepared in the same manner as described in Example 2 from 5-amino-4-bromo-3-methylisoxazole and a mixture of 1-(4'-isopropylphenyl)pyrrole-2-sulfonyl chloride and 1-(4'-isopropylphenyl)pyrrole-3-sulfonyl chloride in 65% combined yield. The mixture was subjected to preparative HPLC to give N-(4-bromo-3-methyl-5-isoxazolyl) 1-(4'-isopropylphenyl)pyrrole-2-sulfonamide (retention time 22.85 min, 5% to 95% acetonitrile in water with 0.1% TFA over 30 min period, $C_{18}$ analytical column) and N-(4-bromo-3-methyl-5-isoxazolyl) 1-(4'-isopropylphenyl)pyrrole-3-sulfonamide (retention time 24.56 min, 5% to 95% acetonitrile in water with 0.1% TFA over 30 min period, $C_{18}$ analytical column) as oils.

EXAMPLE 20

N-(4-Bromo-3-methyl-5-isoxazolyl)-5-bromothiophene-2-sulfonamide

N-(4-Bromo-3-methyl-5-isoxazolyl)-5-bromothiophene-2-sulfonamide was prepared in the same manner as described in Example 2 from 5-amino-4-bromo-3-methylisoxazole and 5-bromothiophene-2-sulfonyl chloride in 30% yield. Purification was achieved by recrystallization from ethyl acetate/hexanes to give a crystalline solid, m.p. 240° C. (dec).

EXAMPLE 21

N-(4-Bromo-3-methyl-5-isoxazolyl)-2-[N-(4-methoxyphenyl)aminocarbonyl]-thiophene-3-sulfonamide 4-Methoxyaniline (0.246 g, 2 mmol), bromo-tris-pyrrolidinophosphonium hexafluorophosphate (PyBrop) (0.466 g, 1 mmol) and N,N'-diisopropylethylamine (0.15 ml) were added to N-(4-bromo-3-methyl-5-isoxazolyl)-2-(carboxyl)thiophene-3-sulfonamide (0.368 g, 1 mmol), which had been suspended in methylene chloride (3 ml), resulting in a clear solution. Stirring was continued for 24 h at ambient temperature. The reaction mixture was diluted with methylene chloride (50 ml) and washed with 3 N hydrochloric acid solution (3×50 ml) followed by 5% sodium carbonate solution (2×50 ml). The combined organic layers was dried over anhydrous magnesium sulfate and filtered. Removal of the solvent under reduced pressure gave N-(4-bromo-3-methyl-5-isoxazolyl)-2-[N-(4-methoxyphenyl)aminocarbonyl]thiophene-3-sulfonamide. The crude product thus obtained was purified by column chromatography using ethyl acetate as eluent. This was recrystallized from ethyl acetate/hexanes to give a crystalline solid, m.p. 202–205° C. (0.08 g, 17% yield).

EXAMPLE 22

N-(4-Bromo-3-methyl-5-isoxazolyl)-2-[N-(3-methoxyphenyl)aminocarbonyl]thiophene-3-sulfonamide N-(4-Bromo-3-methyl-5-isoxazolyl)-2-[N-(3-methoxyphenyl)aminocarbonyl]thiophene-3-sulfonamide was prepared in the same manner as described in Example 21 from N-(4-bromo-3-methyl-5-isoxazolyl)-2-(carboxyl)thiophene-3-sulfonamide and 3-methoxyaniline in 23% yield. The crude product was purified by column chromatography using ethyl acetate as eluent. This was recrystallized from ethyl acetate/hexanes to give a crystalline solid, m.p. 200–202° C.

EXAMPLE 23

N-(4-Bromo-3-methyl-5-isoxazolyl)-2-[N-(2-methoxyphenyl)aminocarbonyl]thiophene-3-sulfonamide N-(4-bromo-3-methyl-5-isoxazolyl)-2-[N-(2-methoxyphenyl)aminocarbonyl]thiophene-3-sulfonamide was prepared in the same manner as described in Example 21 from N-(4-bromo-3-methyl-5-isoxazolyl)-2-(carboxyl)thiophene-3-sulfonamide and 2-methoxyaniline in 26% yield. The crude product was purified by column chromatography using ethyl acetate as eluent. This was recrystallized from ethyl acetate/hexanes to give a crystalline solid, m.p. 74–80° C.

EXAMPLE 24

N-(4-Bromo-3-methyl-5-isoxazolyl)-2-(N-benzylaminocarbonyl)thiophene-3-sulfonamide Benzylamine (0.214 g, 2 mmol), benzotriazole-1-yl-oxy-tris(dimethylamino)phosphonium hexafluorophosphate (Bop) (0.442 g, 1 mmol) and N,N'-diisopropylethylamine (0.15 ml) were added to N-(4-bromo-3-methyl-5-isoxazolyl)-2-(carboxyl)thiophene-3-sulfonamide (0.368 g, 1 mmol), which had been suspended in methylene chloride (3 ml). The resultant solution was stirred for 14 h at ambient temperature. This was diluted with methylene chloride (50 ml) and washed with 3 N hydrochloric acid (3×50 ml) followed by 5% sodium carbonate solution (2×50 ml). The combined organic layers was dried over anhydrous magnesium sulfate and filtered. Removal of the solvent under reduced pressure gave N-(4-bromo-3-methyl-5-isoxazolyl)-2-(N-benzylaminocarbonyl)thiophene-3-sulfonamide. The crude product was purified by column chromatography using ethyl acetate as eluent. Recrystallization from ethyl acetate/hexanes gave a crystalline solid, m.p. 186–190° C. (0.14 g, 30% yield).

EXAMPLE 25

N-(4-Bromo-3-methyl-5-isoxazolyl)-2-[N-(4-ethylphenyl)aminocarbonyl]-thiophene-3-sulfonamide N-(4-bromo-3-methyl-5-isoxazolyl)-2-[N-(4-ethylphenyl)aminocarbonyl]thiophene-3-sulfonamide was prepared in the same manner as described in Example 24 from N-(4-bromo-3-methyl-5-isoxazolyl)-2-(carboxyl) thiophene-3-sulfonamide and 4-ethylaniline in 31% yield. The crude product was purified by column chromatography using ethyl acetate as eluent. This was recrystallized from ethyl acetate/hexanes to give a crystalline solid, m.p. 187–190° C.

EXAMPLE 26

N-(4-Bromo-3-methyl-5-isoxazolyl)-2-[N-(4-biphenyl)aminocarbonyl]-thiophene-3-sulfonamide N-(4-bromo-3-methyl-5-isoxazolyl)-2-[N-(4-biphenyl) aminocarbonyl]-thiophene-3-sulfonamide compound was prepared in the same manner as described in Example 24 from N-(4-bromo-3-methyl-5-isoxazolyl)-2-(carboxyl) thiophene-3-sulfonamide and 4-phenylaniline in 26% yield. The crude product was purified by column chromatography using ethyl acetate as eluent. This was recrystallized from ethyl acetate/hexanes to give a crystalline solid, m.p. 205–212° C. (dec).

EXAMPLE 27

N-(3,4-dimethyl-5-isoxazolyl)-2-(carbomethoxy) thiophene-3-sulfonamide

2-Methoxycarbonylthiophene-3-sulfonyl chloride (2.50 g, 10.05 mmol) was added to a solution of 5-amino-3,4-dimethylisoxazole(0.98 g, 8.75 mmol) in dry pyridine (5.0 ml). The reaction mixture was stirred at room temperature for 16 h. Pyridine was removed under reduced pressure and the residue was partitioned between water and dichloromethane. The organic layer was washed with 1 N HCl (2×50 ml) and dried over anhydrous magnesium sulfate. Evaporation of the solvents left an oily residue, which, after purification by column chromatography over silica gel (1:1 hexanes/ethyl acetate as eluent), yielded 2.20 mg (65%) of a brown solid. Further purification was achieved by recrystallization from ethyl acetate/hexanes, giving the pure product as a white solid, m.p. 113–116° C.

EXAMPLE 28

N-(3,4-dimethyl-5-isoxazolyl)-2-(carboxyl) thiophene-3-sulfonamide

N-(3,4-dimethyl-5-isoxazolyl)-2-(carboxyl)thiophene-3-sulfonamide was prepared in the same manner as described in Example 17 from N-(3,4-dimethyl-5-isoxazolyl)-2-(carbomethoxy)thiophene-3-sulfonamide by basic hydrolysis in 94% yield. Purification was achieved by recrystallization from ethyl acetate/hexanes to give a crystalline solid, m.p. 202–203° C.

EXAMPLE 29

N-(3,4-dimethyl-5-isoxazolyl)-2-(N-phenylaminocarbonyl)thiophene-3-sulfonamide

N-(3,4-dimethyl-5-isoxazolyl)-2-(N-phenylaminocarbonyl)thiophene-3-sulfonamide was prepared in the same manner as described in Example 18 from N-(3,4-dimethyl-5-isoxazolyl)-2-(carboxyl)thiophene-3-sulfonamide in 40% yield. Purification was achieved by recrystallization from ethyl methanol/water to give a crystalline solid, m.p. 176–178° C.

EXAMPLE 30

N-(4-Bromo-3-methyl-5-isoxazolyl)-5-(2-thienyl) thiophene-2-sulfonamide

A. 5-bromo-2,2'-bithiophene

N-Bromosuccinimide (NBS, 1.12 g, 6.3 mmol) was added in small portions to a stirred solution of 1.0 g (6.01 mmol) of 2,2'-bithiophene in 10 ml of glacial acetic acid and 10 ml of chloroform. After stirring for 1 h at room temperature, the mixture was poured into ice-water and extracted into chloroform (75 ml). The organic layer was washed with aqueous sodium bicarbonate solution, water, and then dried over magnesium sulfate and evaporated. The residue was subjected to flash chromatography on silica gel using hexane to give 1.3 g (88%) of a light green solid, m.p. 55–56° C.

B. 5-Chlorosulfonyl-2,2'-bithiophene

A stirred solution of 5-bromo-2,2'-bithiophene (1.5 g, 6.1 mmol) in 10 ml of dry ether was placed under an argon atmosphere, cooled to −78° C. and 4.3 ml of a 1.7 M solution of t-butyllithium was added over 20 min. Stirring was continued at this temperature for an additional 20 min. Sulfur dioxide gas was then bubbled in at −78° C. until a yellow precipitate formed. Bubbling of the sulfur dioxide gas was continued for an additional 3 min and was immediately followed by a dropwise addition of N-chlorosuccinimide (NCS, 902 mg, 6.76 mmol) that had been dissolved in THF. The mixture was warmed to room temperature and stirring was continued for an additional 1.5 h. The mixture was then concentrated and the residue dissolved in ether. The organic layer was washed with water, brine solution and dried over magnesium sulfate. Evaporation of solvent left a pale yellow solid, which was recrystallized from hexane to give 700 mg (44%) of a yellow solid, m.p. 63–64° C.

C. N-(4-Bromo-3-methyl-5-isoxazolyl)-5-(2-thienyl) thiophene-2-sulfonamide

N-(4-bromo-3-methyl-5-isoxazolyl)-5-(2-thienyl) thiophene-2-sulfonamide was prepared in the same manner as described in Example 2. Reaction of 2-chlorosulfonyl-5, 2'-bithiophene (300 mg, 1.14 mmol) with 5-amino-4-bromo-3-methylisoxazole (183 mg, 1.03 mmol) yielded, after flash chromatography using 10% MeOH/CHCl$_3$, 430 mg (94%) of a pale brown solid, m.p. 210° C.

EXAMPLE 31

N-(4-Bromo-3-methyl-5-isoxazolyl)thiophene-3-sulfonamide

A. Thiophene-3-sulfonyl chloride

A stirred solution of 3-bromothiophene (1.5 g, 9.2 mmol) in 10 ml of dry ether was placed under an argon atmosphere and cooled to −78° C. Over the course of 20 min, a solution of t-butyllithium (5.6 ml of a 1.7 M) was added and stirring was continued at this temperature for an additional 20 min. Sulfur dioxide gas was then bubbled in at −78° C. and the solution was warmed to 0° C., whereupon NCS (1.47 g, 12 mmol) in 8 ml of THF, was added dropwise. After warming to room temperature, stirring was continued for an additional 1 hour, after which, evaporation of solvents left 1.55 g of a brown oil. Flash chromatography over silica gel using hexanes yielded 1.24 g (74%) of a yellow oil which solidified on standing to give a yellow crystalline solid, m.p. 38–39° C.

B. N-(4-Bromo-3-methyl-5-isoxazolyl)thiophene-3-sulfonamide

N-(4-bromo-3-methyl-5-isoxazolyl)thiophene-3-sulfonamide was prepared in the same manner as described in Example 2 from thiophene-3-sulfonyl chloride with 5-amino-4-bromo-3-methylisoxazole in 22% yield. Purification by column chromatography using 10% MeOH/CHCl$_3$ as eluent gave a pale brown oil.

EXAMPLE 32

N-(3,4-dimethyl-5-isoxazolyl)-5-phenylthiophene-2-sulfonamide

A. N-(3,4-dimethyl-5-isoxazolyl)-5-bromothiophene-2-sulfonamide

A solution of 5-bromothiophene-2-sulfonyl chloride (2.75 g, 10 mmol) and 5-amino-3,4-dimethylisoxazole (1.07 g, 9.57 mmol) in pyridine containing a catalytic amount of 4-dimethylaminopyridine (DMAP, 10 mg) was stirred at room temperature for a period of 3 h. The solution was heated at 50° C. for an additional 1.5 h to drive the reaction to completion as judged by TLC. The pyridine was removed under reduced pressure and the residue, after extraction into ethyl acetate, was washed with 1 N HCl (2×25 ml), water (1×25), brine solution, (1×25 ml) and dried over magnesium sulfate. Evaporation of solvent left a viscous brown gum, which was subjected to flash chromatography. Elution with 3% methanol hexanes gave 246 mg (10%) of pure sulfonamide.

B. N-(methoxyethoxymethyl)-N-(3,4-dimethyl-5-isoxazolyl)-5-bromothiophene-2-sulfonamide N-(3,4-dimethyl-5-isoxazolyl)-5-bromothiophene-2-sulfonamide (680 mg, 2 mmol) in dry THF (2 ml) was added to sodium hydride (121 mg of a 60% oil dispersion, 3 mmol) in dry THF (1 ml). The resulting suspension was cooled to 0° C. and methoxyethoxymethyl chloride (334 mg, 2.68 mmol) was added dropwise via syringe. The solution was warmed to room temperature, and stirring continued overnight. Evaporation of solvent left an oil that was extracted into ethyl acetate, washed with brine, dried over magnesium sulfate and evaporated. Flash chromatography of the residue on silica gel using 10–15% ethylacetate/hexanes yielded 480 mg (56%) of a colorless oil.

C. N-(methoxyethoxymethyl)-N-(3,4-dimethyl-5-isoxazolyl)-5-phenylthiophene-2-sulfonamide Sodium carbonate (2 ml of a 2 M aqueous solution) followed by phenyl boronic acid (86 mg, 0.71 mmol) in 2 ml of 95% ethanol were added to a solution of N-(methoxyethoxymethyl)-N-(3,4-dimethyl-5-isoxazolyl)-5-bromothiophene-2-sulfonamide (200 mg, 0.47 mmol) and tetrakis (triphenylphosphine) palladium (0) (23 mg, 0.02 mmol) in dry benzene (4 ml) under argon. The mixture was refluxed for 12 h, diluted with 5 ml of water and extracted into ethyl acetate (3×25 ml). The combined organic extracts was washed with brine (1×25 ml), dried and evaporated. The residue was flash chromatographed on silica gel using 25% ethylacetate/hexanes to afford 123 mg (62%) of the sulfonamide as a colorless gum.

D. N-(3,4-dimethyl-5-isoxazolyl)-5-phenylthiophene-2-sulfonamide

HCl (3 ml of a 3 N aqueous solution) was added to a solution of N-(methoxyethoxymethyl)-N-(3,4-dimethyl-5-isoxazolyl)-5-phenylthiophene-2-sulfonamide (100 mg, 0.24 mmol) in 3 ml of 95% ethanol and the resulting mixture was refluxed for 6 h. The mixture was then concentrated, diluted with 5 ml of water, neutralized with saturated aqueous sodium bicarbonate solution and acidified to pH 4 using glacial acetic acid. The mixture was extracted with ethyl acetate (2×25 ml) and the combined organic extract was washed with brine (1×5 ml), dried and evaporated. Flash chromatography of the residue on silica gel using 2% MeOH/CHCl$_3$ and further purification by reverse phase HPLC yielded 33.4 mg (42%) of the pure sulfonamide as a white powder, m.p. 176–178° C.

EXAMPLE 33

N-(4-Bromo-3-methyl-5-isoxazolyl)-5-(4-ethylphenyl)thiophene-2-sulfonamide

A. N-(5-bromothiophene-2-sulfonyl)-pyrrole

Sodium hydride (60% oil dispersion, 191 m.g., 4.78 mmol) was suspended in dry tetrahydrofuran (2 ml) and the resulting cloudy suspension was cooled to 0° C. in an ice bath. Pyrrole (385 mg, 5.75 mmol) in dry tetrahydrofuran (2 ml) was added dropwise over a period of 10 min. The ice bath was removed and the solution was stirred at room temperature until gas evolution ceased (15 minutes), whereupon 5-bromothiophene-2-sulfonyl chloride (1.0 g, 3.82 mmol) previously dissolved in tetrahydrofuran (4.0 ml) was added dropwise through a steel cannula. After stirring for 1 h at room temperature, the mixture was filtered through Celite. The filter pad was rinsed with tetrahydrofuran, and the filtrate was evaporated, which left a light brown solid that was recrystallized from methanol to produce the sulfonamide (821 mg, 74% yield) as a white powder.

B. 4-Ethylphenylboronic acid

A solution of 1-bromo-4-ethyl benzene (2.0 g, 11 mmol) in dry ether (5 ml) was added to magnesium turnings (311 mg, 13 mmol), which had been suspended in dry ether, by dropwise addition. After addition was complete, the suspension was refluxed for a period of 15 min, by which time nearly all of the magnesium had reacted. The solution was then added to trimethyl borate (1.12 g, 11 mmol), previously dissolved in ether (5 ml) at −78° C., warmed to room temperature and stirred for 90 min. The reaction was quenched by the addition of 10% aqueous HCl (2 ml) and the solution was extracted with ether. The combined ether extract was extracted with 1 M NaOH (2×20 ml), the aqueous extracts were acidified with dilute HCl to pH 2 and extracted with ether (2×25 ml). The resulting combined ether extract was washed once with water (10 ml), dried and evaporated to produce a white solid (676 mg, 38% yield), m.p. 138–140° C.

C. N-[5-(4-ethylphenyl)thiophene-2-sulfonyl]pyrrole

N-[5-(4-ethylphenyl)thiophene-2-sulfonyl]pyrrole was prepared, in the same manner as described in Example 32C, from 4-ethylphenylboronic acid and N-(5-bromothiophenesulfonyl)pyrrole. Purification by column chromatography using 10% ethyl acetate/hexanes gave the pure sulfonamide as a tan solid in 81% yield.

D. 5-Chlorosulfonyl-2-(4-ethylphenyl)thiophene

A solution of N-[5-(4-ethylphenyl)thiophene-2-sulfonyl] pyrrole (100 mg, 0.32 mmol) and 6 N sodium hydroxide (1 ml) in methanol (1.5 ml) was refluxed for approximately 6 h. Evaporation of solvents and drying in vacuo resulted in an oil. Phosphorus oxychloride (258 ml, 2.52 mmol) and phosphorus pentachloride (131 mg, 0.63 mmol) were added to the oil and the resulting brown suspension was heated at 50° C. for 3 h. The resulting clear brown solution was carefully added to about 20 ml of crushed ice and then extracted with ethyl acetate (3×25 ml). The combined organic layers was washed with brine (2×5 ml), dried (MgSO$_4$) and evaporated to leave an oily residue. Flash chromatography over silica gel using 2% ethyl acetate/hexanes yielded (53 mg, 59%) of the pure sulfonyl chloride as a pale yellow oil.

E. N-(4-bromo-3-methyl-5-isoxazolyl)-5-(4-ethylphenyl)thiophene-2-sulfonamide N-(4-bromo-3-methyl-5-isoxazolyl)-5-(4-ethylphenyl) thiophene-2-sulfonamide was prepared in the same manner as described in Example 2. Reaction of 5-chlorosulfonyl-2-(4-ethylphenyl) thiophene (47.1 mg, 11.16 mmol) with 5-amino-4-bromo-3-methyl isoxazole (29 mg, 0.16 mmol) yielded, after flash chromatography using 10% MeOH/CHCl$_3$, a pale brown solid (46 mg, 66% yield), m.p. 172–175° C.

EXAMPLE 34

N-(3,4-dimethyl-5-isoxazolyl)benzo[b]thiophene-2-sulfonamide

A. Benzo[b]thiophene-2-sulfonyl chloride

Benzo[b]thiophene (1.50 g, 11.2 mmol) was stirred at 0° C. in 20 ml of THF. t-Butyllithium (1.7 M, 16.8 mmol, 9.9 ml) was slowly added over a 5 minute period. Fifteen minutes later, SO$_2$ was flushed into the reaction flask and a thick white precipitate formed. The reaction mixture was stirred for 15 minutes at 0° C. and then NCS (1.64 g, 12.3 mmol) was added. The reaction was warmed to 25° C. and stirred for 30 min. It was then poured into ethyl acetate (150 ml) and washed with brine (3×100 ml). The organic phase was dried with MgSO$_4$, filtered and concentrated to collect 2.29 g of a brown oil. The brown oil was subjected to flash chromatography (5% ethyl acetate/hexanes), which provided a yellow tan solid (1.39 g, 53% yield).

B. N-(3,4-Dimethyl-5-isoxazolyl)benzo[b]thiophene-2-sulfonamide 3,4-Dimethyl-5-amino-isoxazole (0.224 g, 2.0 mmol) and 50 mg of DMAP were stirred in 5 ml of pyridine at 25° C. The benzo[b]thiophene-2-sulfonyl chloride (0.16 g, 2.6 mmol) was added and the dark brown-yellow reaction mixture was stirred for 18 h at ambient temperature, poured into 100 ml of ethyl acetate and washed with 2% HCl (3×50 ml). The organic phase was dried with MgSO$_4$, filtered and concentrated to collect 0.61 g of a brown oil/solid. The brown oil/solid was subjected to flash chromatography (30% ethyl acetate/hexanes) to provide 0.37 g of a light brown solid. This was stirred in 10 ml of methanol and 0.5 g of NaOH. The methanolic solution was heated for reflux for 1 h, then cooled to 25° C. and the methanol was removed in vacuo. The resulting residue was acidified to pH 1 with 2% HCl (100 ml) and extracted with ethyl acetate (2×50 ml) The organic phase was dried with MgSO$_4$, filtered and concentrated to collect 0.225 g of a yellow-orange solid. This was recrystallized from CHCl$_3$/hexanes to produce a light tan-yellow solid (0.194 g, 31% yield), m.p. 157–160° C.

EXAMPLE 35

N-(3,4-Dimethyl-5-isoxazolyl)benzo[b]furan-2-sulfonamide

A. Benzo[b]furan-2-sulfonyl chloride

Benzo[b]furan-2-sulfonyl chloride was prepared as in Example 34A from benzo[b]furan (1.61 g, 13.6 mmol), t-BuLi (1.7 M, 17.7 mmol, 10.4 ml) and NCS (2.0 g, 15.0 mmol). Flash chromatography (5% ethyl acetate/hexanes) yielded a brown solid (1.84 g, 62% yield).

B. N-(3,4-Dimethyl-5-isoxazolyl)benzo[b]furan-2-sulfonamide

N-(3,4-Dimethyl-5-isoxazolyl)benzo[b]furan-2-sulfonamide was prepared, in the same manner as described in Example 34B, from 3,4-dimethyl-5-amino isoxazole (78 mg, 0.70 mmol) and benzo[b]furan-2-sulfonyl chloride (0.46 g, 2.1 mmol). Flash chromatography (30% ethyl acetate/hexanes) provided 0.186 g of a light yellow solid, which was treated with 31 mg of NaOH in 10 ml of methanol at 25° C. for 30 minutes. Recrystallization from CHCl$_3$/hexanes yielded a light tan solid (90 mg, 44% yield), m.p. 160.5–163° C.

EXAMPLE 36

N-(3,4-dimethyl-5-isoxazolyl)furan-2-sulfonamide

A. Furan-2-sulfonyl chloride

Furan-2-sulfonyl chloride was prepared as in Example 34A from furan (0.96 g, 14.2 mmol), t-BuLi (1.7 M, 17 mmol, 10 ml) and NCS (2.27 g, 17 mmol) using ether (30 ml) as the solvent. Flash chromatography (5% ethyl acetate/hexanes) produced a yellow liquid (1.22 g, 52% yield).

N-(3,4-dimethyl-5-isoxazolyl)furan-2-sulfonamide

N-(3,4-dimethyl-5-isoxazolyl)furan-2-sulfonamide was prepared as described in Example 34B from 3,4-dimethyl-5-amino isoxazole (0.122 g, 1.0 mmol), furan-2-sulfonyl chloride (0.50 g, 3.0 mmol) and NaOH (64 mg). Flash chromatography (50% ethyl acetate/hexanes) yielded 70 mg of a yellow solid. Recrystallization from CHCl$_3$/hexanes produced an off-white solid (46 mg, 29% yield), m.p 107–110° C.

EXAMPLE 37

N-(3,4-Dimethyl-5-isoxazolyl)-3-methoxy-2-thiophene sulfonamide

A. 3-methoxy-2-thiophenesulfonyl chloride

Chlorosulfonic acid (ClSO$_3$H, 2.31 g, 19.62 mmol) was slowly added to a solution of 3-methoxythiophene (2.29 g, 19.62 mmol) in CHCl$_3$ (80 ml) at 0° C. The resulting mixture was stirred at 0° C. for 30 min. The solvent was evaporated under reduced pressure at room temperature, the residue was suspended in POCl$_3$ (15 ml, 156.96 mmol), and PCl$_5$ (8.2 g, 39.24 mmol) was added slowly. The reaction was stirred at 60° C. for 18 h, then cooled to room temperature and poured onto crushed ice (200 g). The aqueous mixture was extracted with CHCl$_3$ (2×150 ml) and the combined organic layers was dried (MgSO$_4$). The solid was removed by filtration and the filtrate was concentrated to give 3-methoxy-2-thiophenesulfonyl chloride as a brown oil (1.81 g, 43% yield).

B. N-(3,4-dimethyl-5-isoxazolyl)-3-methoxy-2-thiophene sulfonamide

Sodium hydride (1.02 g, 25.56 mmol, 60% dispersion in mineral oil) was slowly added to a solution of 3-methoxy-2-thiophenesulfonyl chloride (1.18 g, 8.52 mmol) and 3,4-dimethyl-5-aminoisoxazole (1.05 g, 9.37 mmol) in THF (20 ml) at room temperature. The resulting mixture was refluxed for 4 h. THF was removed under reduced pressure. The residue was dissolved in water (10 ml), the pH was adjusted to 10–11 by adding 5 N sodium hydroxide solution, and was extracted with ethyl acetate (3×10 ml) to remove the neutral impurities. The aqueous layer was acidified with concentrated HCl (pH 2–3) and extracted with methylene chloride (3×10 ml). The combined organic layers was dried over anhydrous magnesium sulfate to produce a crude oil. Further purification by reverse phase HPLC yielded a yellow oil (retention time 14.94 min, 5% to 95% acetonitrile in H$_2$O with 0.1% TFA over 30 min period, C$_{18}$ analytical column).

EXAMPLE 38

N-(4-Bromo-3-methyl-5-isoxazolyl)-3-phenyl-2-thiophene sulfonamide and N-(4-bromo-3-methyl-5-isoxazolyl)-4-phenyl-2-thiophene sulfonamide

A. 3-phenyl-2-thiophenesulfonyl chloride and 4-phenyl-2-thiophenesulfonyl chloride n-Butyllithium (2.38 M, 17.2 ml, 41.03 mmol) was slowly added to a solution of 3-phenylthiophene (5.47 g, 34.2 mmol) in Et$_2$O (25 ml) at 0° C. The ice bath was removed, the mixture was stirred at room temperature for 2 h, cooled to −30° C. (CO$_2$/acetone) and SO$_2$ gas was bubbled through the reaction mixture for 20 min. A solution of NCS (6.06 g, 44.5 mmol) in THF (20 ml) was then added. The reaction was allowed to warm to room temperature and stirred for 16 h. The crude mixture was filtered, and the solid was washed with Et$_2$O. The combined organic layers was concentrated and the residue was chromatographed (hexanes/CHCl$_3$) to give 3-phenyl-2-thiophenesulfonyl chloride and 4-phenyl-2-thiophenesulfonyl chloride as a 1:1 mixture (1.46 g, 16.5%, while solid).

B. N-(4-Bromo-3-methyl-5-isoxazolyl)-3-phenyl-2-thiophene sulfonamide and N-(4-bromo-3-methyl-5-isoxazolyl)-4-phenyl-2-thiophene sulfonamide N-(4-bromo-3-methyl-5-isoxazolyl)-3-phenyl-2-thiophene sulfonamide and N-(4-bromo-3-methyl-5-isoxazolyl)-4-phenyl-2-thiophene sulfonamide were prepared as described in Example 1. A fraction of the crude mixture of products was purified by HPLC to give N-(4-bromo-3-methyl-5-isoxazolyl)-3-phenyl-2-thiophene sulfonamide (light brown solid, retention time 20.48 min, 5% to 95% acetonitrile in water with 0.1% TFA over 30 min C$_{18}$ analytical column, m.p. 105–107° C.) and N-(4-bromo-3-methyl-5-isoxazolyl)-4-phenyl-2-thiophene sulfonamide (dull yellow solid, m.p. 108–110° C., retention time 21.35 min, same conditions).

EXAMPLE 39

4-tert-Butyl-N-(4-bromo-3-methyl-5-isoxazolyl) benzenesulfonamide

A solution of 5-amino-4-bromo-3-methylisoxazole (354 mg, 2.0 mmol) in dry THF (1 ml) was added to a suspension of sodium hydride (60% dispersion in mineral oil, 188 mg, 4.4 mmol) in dry THF (1 ml) at 0–5° C. After stirring at 0–5° C. for 10 min., the reaction was warmed to room temperature for 10 min. to complete the reaction. The reaction mixture was re-cooled to 0° C. and 4-tert-butylbenzenesulfonyl chloride (512 mg, 2.2 mmol) was added slowly. Stirring was continued for 20 min. at 0–5° C. Excess sodium hydride was decomposed by addition of methanol (0.4 ml) followed by water (0.5 ml). The mixture was acidified with hydrochloric acid and extracted with dichloromethane. The extract was dried over anhydrous magnesium sulfate and the solvent was removed under reduced pressure to give a crude product, which was purified by recrystallization from ethyl acetate/hexanes to give a white solid in 21% yield, m.p. 170° C. (dec.).

EXAMPLE 40

N-(3,4-Dimethyl-5-isoxazolyl)-2-methylbenzo[b] thiophene-3-sulfonamide

A. 2-Methylbenzo[b]thiophene t-BuLi (1.7 M, 26 mmoles, 15 ml) was added to a stirred solution of benzo[b]thiophene (17 mmoles, 2.3 g) and THF (30 ml) at −50° C. The resulting bright yellow reaction mixture was warmed to −30° C., and iodomethane (26 mmoles, 1.6 ml) was added. After 10 min. at −30° C, the solution was warmed to ambient temperature and stirred an additional 30 min., then diluted with ether (100 ml) and washed with brine (2×100 ml). The organic phase was dried (MgSO$_4$), filtered and concentrated to collect 2.48 g (98%) of 2-methylbenzo[b]thiophene as a light yellow solid.

B. 2-Methylbenzo[b]thiophene-3-sulfonyl chloride

Sulfuryl chloride (9.5 mmoles, 0.76 ml) was added to a stirred solution of dimethylformamide (DMF; 11.2 mmoles, 0.87 ml) at 0° C., and the resulting faint yellow solution was stirred for 20 min at 0° C. 2-Methylbenzo[b]thiophene (5.6 mmoles, 0.83 g) was then added, the reaction mixture was diluted with 2 ml of DMF, and then heated to 85° C. After 2.5 hrs at 85° C., the brown reaction mixture was cooled to ambient temperature and added to ice (≈100 ml). The aqueous phase was extracted with ethyl acetate (100 ml), and the organic phase was dried (MgSO$_4$), filtered and concentrated to collect an orange-brown solid. Flash chromatography (4% ethyl acetate/hexanes) provided 0.89 g (64%) of 2-methylbenzo[b]thiophene-3-sulfonyl chloride as a yellow solid.

C. N-(3,4-Dimethyl-5-isoxazolyl)-2-methylbenzo[b] thiophene-3-sulfonamide

2-Methylbenzo[b]thiophene-3-sulfonyl chloride (1.7 mmoles, 0.41 g) was added to a solution of 3,4-dimethyl-5-aminoisoxazole (0.75 mmoles, 84 mg), 4-dimethylaminopyridine (DMAP; 50 mg) and pyridine (5 ml) at ambient temperature. After 24 h, the reaction mixture was diluted with ethyl acetate (50 ml) and washed with 2% HCl (3×50 ml). The organic phase was dried (MgSO$_4$), filtered and concentrated to collect a brown-orange solid, which was dissolved in a solution of methanol (10 ml) and NaOH (60 mg). The solution was stirred 1 h at ambient temperature, then the methanol was evaporated and the resulting residue was diluted with 2% HCl (50 ml), and extracted with ethyl acetate (75 ml). The organic phase was dried (MgSO$_4$), filtered and concentrated to collect a tan solid. Recrystallization from chloroform and hexanes resulted in 93 mg (38%) of N-(3,4-dimethyl-5-isoxazolyl)-2-methylbenzo[b]thiophene-3-sulfonamide as light yellow crystals, m.p. 174–176° C.

EXAMPLE 41

N-(4-Bromo-3-methyl-5-isoxazolyl)-2-methylbenzo[b]thiophene-3-sulfonamide

NaH (60% oil dispersion, 2.5 mmoles, 100 mg) was added to a solution of 4-bromo-3-methyl-5-aminoisoxazole (1.0 mmoles, 0.177 g). THF (5 ml) at 0° C. was added, and the resulting reaction mixture was stirred 10 min at 0° C. 2-Methylbenzo[b]thiophene-3-sulfonyl chloride (1.2 mmoles, 0.28 g) was added, and the reaction mixture was stirred for 20 min at 0° C., then warmed to ambient temperature for 1 hr followed by addition of 2 ml of water. The mixture was diluted with ethyl acetate (100 ml) and washed with 2% HCl (2×50 ml), then brine (50 ml). The organic phase was dried (MgSO$_4$), filtered and concentrated. Recrystallization of the crude reaction mixture resulted in 0.24 g (63%) of N-(4-bromo-3-methyl-5-isoxazolyl)-2-methylbenzo[b]thiophene-3-sulfonamide as an off-white solid, m.p. 131–133° C.

EXAMPLE 42

N-(4-Bromo-3-methyl-5-isoxazolyl)-2-ethylbenzo[b]thiophene-3-sulfonamide

A. 2-Ethylbenzo[b]thiophene

2-Ethylbenzo[b]thiophene was prepared by the method of Example 40A with benzo[b]thiophene (7.5 mmoles, 1.0 g), t-BuLi (1.7 M, 8.9 mmoles, 5.3 ml), iodoethane (8.9 mmoles, 0.72 ml) and THF (20 ml). 1.2 g (99%) of a yellow liquid was isolated.

B. 2-Ethylbenzo[b]thiophene-3-sulfonyl chloride

2-Ethylbenzo[b]thiophene-3-sulfonyl chloride compound was prepared by the method of Example 40B with dimethylformamide (DMF; 13.6 mmoles, 1.1 ml), sulfonyl chloride (11.5 mmoles, 0.93 ml). Flash chromatography (2% ethyl acetate/hexanes) provided 1.34 g (76%) of a light yellow solid.

C. N-(4-bromo-3-methyl-5-isoxazolyl)-2-ethylbenzo[b]thiophene-3-sulfonamide

N-(4-bromo-3-methyl-5-isoxazolyl)-2-ethylbenzo[b]thiophene-3-sulfonamide was prepared by the method of Example 41 with 4-bromo-3-methyl-5-aminoisoxazole (1.0 mmoles, 0.177 g), NaH (2.5 mmoles, 100 mg), 2-ethylbenzo[b]thiophene-3-sulfonyl chloride (1.2 mmoles, 0.31 g) and THF (7 ml). Recrystallization from chloroform and hexanes provided 0.24 g (60%) of a tan crystalline solid, m.p. 118.5–120° C.

EXAMPLE 43

N-(4-Bromo-3-methyl-5-isoxazolyl)-2-benzylbenzo[b]thiophene-3-sulfonamide

A. 2-Benzylbenzo[b]thiophene

2-Benzylbenzo[b]thiophene was prepared by the method of Example 40A with benzo[b]thiophene (7.5 mmoles, 1.0 g), t-BuLi (1.7 M, 11.2 mmoles, 6.6 ml), benzyl bromide (10.2 mmoles, 1.3 ml) and THF (20 ml). Flash chromatography (hexanes) provided 0.66 g (39%) of a yellow solid.

B. 2-Benzylbenzo[b]thiophene-3-sulfonyl chloride

2-Benzylbenzo[b]thiophene-3-sulfonyl chloride was prepared by the method of Example 40B with DMF (5.4 mmoles, 0.41 ml), sulfuryl chloride (4.6 mmoles, 0.37 ml) and 2-benzylbenzo[b]thiophene. Flash chromatography (5% ethyl acetate/hexanes) provided 0.55 g (64%) of a yellow solid.

C. N-(4-bromo-3-methyl-5-isoxazolyl)-2-benzylbenzo[b]thiophene-3-sulfonamide

N-(4-bromo-3-methyl-5-isoxazolyl)-2-benzylbenzo[b]thiophene-3-sulfonamide was prepared by the method of Example 41 with 4-bromo-3-methyl-5-aminoisoxazole (1.0 mmoles, 0.177 g), NaH (2.5 mmoles, 100 mg), 2-benzylbenzo[b]thiophene-3-sulfonyl chloride (1.2 mmoles, 0.39 g) and THF (7 ml). Flash chromatography (5% methanol/chloroform) followed by recrystallization from chloroform and hexanes provided 0.11 g (24%) of a tan crystalline solid, m.p. 120–123° C.

EXAMPLE 44

N-(4-Bromo-3-methyl-5-isoxazolyl)-2-butylbenzo[b]thiophene-3-sulfonamide

A. 2-Butylbenzo[b]thiophene 2-n-Butylbenzo[b]thiophene was prepared by the method of Example 40A with benzo[b]thiophene (7.5 mmoles, 1.0 g), t-BuLi (1.7 M, 9.7 mmoles, 5.7 ml), 1-bromobutane (9.7 mmoles, 1.0 ml) and THF (20 ml). 0.65 g (46%) of a yellow liquid was isolated.

B. 2-n-Butylbenzo[b]thiophene-3-sulfonyl chloride 2-n-Butylbenzo[b]thiophene-3-sulfonyl chloride was prepared by the method of Example 40B with DMF (6.6 mmoles, 0.51 ml), sulfuryl chloride (5.6 mmoles, 0.45 ml) and 2-n-butylbenzo[b]thiophene (3.3 mmoles, 0.63 g). Flash chromatography (2% ethyl acetate/hexanes) provided 0.68 g (71%) of an orange solid.

C. N-(4-bromo-3-methyl-5-isoxazolyl)-2-n-butylbenzo[b]thiophene-3-sulfonamide

N-(4-bromo-3-methyl-5-isoxazolyl)-2-n-butylbenzo[b]thiophene-3-sulfonamide was prepared by the method of Example 41 with 4-bromo-3-methyl-5-aminoisoxazole (1.0 mmoles, 0.177 g), NaH (2.5 mmoles, 100 mg), 2-n-butylbenzo[b]thiophene-3-sulfonyl chloride (1.2 mmoles, 0.35 g) and THF (6 ml). Recrystallization from ethyl acetate and hexanes provided 0.24 g (56%) of a yellow solid, m.p. 124.5–126° C.

EXAMPLE 45

N-(4-Bromo-3-methyl-5-isoxazolyl)-2-n-propylbenzo[b]thiophene-3-sulfonamide

A. 2-n-propylbenzo[b]thiophene 2-n-Propylbenzo[b]thiophene was prepared by the method of Example 40A with benzo[b]thiophene (7.5 mmoles, 1.0 g), t-BuLi (1.7 M, 9.7 mmoles, 5.7 ml), n-bromopropane (9.7 mmoles, 0.88 ml) and THF (20 ml). 1.11 g (85%) of a light yellow liquid was isolated.

B. 2-propylbenzo[b]thiophene-3-sulfonyl chloride

2-Propylbenzo[b]thiophene-3-sulfonyl chloride was prepared by the method of Example 40B with DMF (3.6 mmoles, 0.28 ml), sulfuryl chloride (3.1 mmoles, 0.25 ml) and 2-propylbenzo[b]thiophene (1.8 mmoles, 0.32 g). Flash chromatography (3% ethyl acetate/hexanes) provided 0.28 g (56%) of a yellow solid.

C. N-(4-bromo-3-methyl-5-isoxazolyl)-2-n-propylbenzo[b]thiophene-3-sulfonamide N-(4-bromo-3-methyl-5-isoxazolyl)-2-n-propylbenzo[b]thiophene-3-sulfonamide was prepared by the method of Example 41 with 4-bromo-3-methyl-5-aminoisoxazole (0.68 mmoles, 0.12 g) NaH (1.7 mmoles, 6.8 mg), 2-n-propylbenzo[b]thiophene-3-sulfonyl chloride (0.82 mmoles, 0.23 g) and THF (3 ml). Recrystallization from chloroform and hexanes provided 0.19 g (67%) of a yellow crystalline solid, m.p. 136–138° C.

EXAMPLE 46

N-(4-Bromo-3-methyl-5-isoxazolyl)-2-i-propylbenzo[b]thiophene-3-sulfonamide

A. 2-i-propylbenzo[b]thiophene 2-i-Propylbenzo[b]thiophene was prepared by the method of Example 40A with benzo[b]thiophene (7.5 mmoles, 1.0 g), t-BuLi (1.7 M, 11.2 mmoles, 6.6 ml), 2-iodopropane (11.2 mmoles, 1.12 ml) and THF (20 ml) with stirring at ambient temperature for 24 hrs. It was isolated as a yellow oil (1.11 g; 85% yield).

B. 2-i-propylbenzo[b]thiophene-3-sulfonyl chloride 2-i-propylbenzo[b]thiophene-3-sulfonyl chloride compound was prepared by the method of Example 40B with DMF (5.2 mmoles, 0.40 ml), using sulfuryl chloride (4.2 mmoles, 0.34 ml) and 2-i-propylbenzo[b]thiophene (2.1 mmoles, 0.37 g). Flash chromatography (1% ethyl acetate/hexanes) provided 0.17 g (29%) of a yellow solid.

C. N-(4-bromo-3-methyl-5-isoxazolyl)-2-i-propylbenzo[b]thiophene-3-sulfonamide N-(4-bromo-3-methyl-5-isoxazolyl)-2-i-propylbenzo[b]thiophene-3-sulfonamide was prepared by the method of Example 41 using 4-bromo-3-methyl-5-aminoisoxazole (0.55 mmoles, 9.7 mg), NaH (1.4 mmoles, 5.5 mg), 2-i-propylbenzo[b]thiophene-3-sulfonyl chloride (0.60 mmoles, 0.17 g) and THF (2 ml). Recrystallization from chloroform and hexanes provided 89 mg (39%) of a tan crystalline solid, m.p. 157.5–159° C.

EXAMPLE 47

N-(4-Bromo-3-methyl-5-isoxazolyl)-2-(4-ethylbenzyl)benzo[b]-thiophene-3-sulfonamide

A. α-(2-benzo[b]thiophene)-4-ethylbenzyl alcohol

α-(2-Benzo[b]thiophene)-4-ethylbenzyl alcohol was prepared by the method of Example 40A with benzo[b]thiophene (7.5 mmoles, 1.0 g), t-BuLi (9.7 mmoles, 1.7 M, 5.7 ml), 4-ethylbenzaldehyde (8.9 mmoles, 1.22 ml) and THF (20 ml). Flash chromatography (10% ethyl acetate/hexanes) provided 1.79 g (89%) of a yellow solid.

B. 2-(4-ethylbenzyl)benzo[b]thiophene

To a solution of α-(2-benzo[b]thiophene)-4-ethylbenzyl alcohol (4.0 mmoles, 1.1 g), triethylsilane (4.4 mmoles, 0.11 ml) and CH$_2$Cl$_2$ (20 ml) at 0° C. was added TFA (8.1 mmoles, 0.62 ml). The solution was stirred 30 min at 0° C., then diluted with ether (100 ml) and washed with sat. NaHCO$_3$ (100 ml). The organic phase was dried (MgSO$_4$), filtered and concentrated. Flash chromatography (2% ethyl acetate/hexanes) provided 0.69 g (68%) of a white solid.

C. 2-(4-Ethylbenzyl)benzo[b]thiophene-3-sulfonyl chloride 2-(4-Ethylbenzyl)benzo[b]thiophene-3-sulfonyl chloride was prepared by the method of Example 40B with DMF (5.4 mmoles, 0.42 ml), sulfuryl chloride (4.6 mmoles, 0.37 ml) and 2-(4-ethylbenzyl)benzo[b]thiophene (2.7 mmoles, 0.69 g). Flash chromatography (2% ethyl acetate/hexanes) provided 0.43 g (45%) of an orange solid.

D. N-(4-bromo-3-methyl-5-isoxazolyl)-2-(4-ethylbenzyl)benzo[b]-thiophene-3-sulfonamide N-(4-bromo-3-methyl-5-isoxazolyl)-2-(4-ethylbenzyl)benzo[b]-thiophene-3-sulfonamide was prepared by the method of Example 41 using 4-bromo-3-methyl-5-aminoisoxazole (1.0 mmoles, 0.177 g), NaH (2.5 mmoles, 100 mg), 2-(4-ethylbenzyl)benzo[b]thiophene-3-sulfonyl chloride (1.2 mmoles, 0.42 g) and THF (6 ml). Flash chromatography (50% ethyl acetate/hexanes) followed by recrystallization from chloroform and hexanes provided 0.21 g (43%) of a tan solid, m.p. 128–130° C.

EXAMPLE 48

N-(4-Bromo-3-methyl-5-isoxazolyl)-2-[3,4-(methylenedioxy)benzyl]-benzo[b]thiophene-3-sulfonamide

A. α-(2-benzo[b]thienyl)-3,4-(methylenedioxy)benzyl alcohol

α-(2-Benzo[b]thienyl)-3,4-(methylenedioxy)benzyl alcohol was prepared by the method of Example 40A using benzo[b]thiophene (7.5 mmoles, 1.0 g), t-BuLi (1.7 M, 9.7 mmoles, 5.7 ml), piperonal (8.9 mmoles, 1.0 g) and THF (20 ml). Flash chromatography (20% ethyl acetate/hexanes) provided 1.6 g (74%) of a yellow solid.

B. 2-[3,4-(methylenedioxy)benzyl]benzo[b]thiophene

2-[3,4-(methylenedioxy)benzyl]benzo[b]thiophene was prepared by the method of Example 47B using α-(2-benzo[b]thienyl)-3,4-(methylenedioxy)benzyl alcohol (6.2 mmoles, 1.8 g), triethylsilane (6.8 mmoles, 1.1 ml) CH$_2$Cl$_2$ (50 ml) and TFA (12.4 mmoles, 0.95 ml). Recrystallization from hexanes provided 1.2 g (73%) of a light orange solid.

C. 2-[3,4-(methylenedioxy)benzyl]benzo[b]thiophene-3-sulfonyl chloride

2-[3,4-(methylenedioxy)benzyl]benzo[b]thiophene-3-sulfonyl chloride was prepared by the method of Example 40B using DMF (9.1 mmoles, 0.70 ml), sulfuryl chloride (7.7 mmoles, 0.62 ml) and 2-[3,4-(methylenedioxy)benzyl]benzo[b]thiophene (4.6 mmoles, 1.2 g). Flash chromatography (5% ethyl acetate/hexanes) provided 0.71 g (42%) of a light yellow solid.

D. N-(4-bromo-3-methyl-5-isoxazolyl)-2-[3,4-(methylenedioxy)benzyl]-benzo[b]thiophene-3-sulfonamide N-(4-bromo-3-methyl-5-isoxazolyl)-2-[3,4-(methylenedioxy)benzyl]-benzo[b]thiophene-3- sulfonamide was prepared by the method of Example 41 using 4-bromo-3-methyl-5-aminoisoxazole (1.0 mmoles, 0.177 g), NaH (2.5 mmoles, 100 mg), 2-[3,4-(methylenedioxy)benzyl]benzo[b]thiophene-3-sulfonyl chloride (1.1 mmoles, 0.40 g) and THF (7 ml). Flash chromatography (50% ethyl acetate/hexanes) followed by recrystallization from chloroform and hexanes provided 0.23 g (45%) of a tan crystalline solid, m.p. 164–165° C.

EXAMPLE 49

N-(4-Bromo-3-methyl-5-isoxazolyl)benzo-2,1,3-thiadiazole-4-sulfonamide

N-(4-bromo-3-methyl-5-isoxazolyl)benzo-2,1,3-thiadiazole-4-sulfonamide was prepared from 5-amino-4-bromo-3-methylisoxazole and 2,1,3-thiadiazole-4-sulfonyl chloride according to the procedures described in Example 39. The crude product was purified by recrystallization from ethyl acetate/hexanes to give a crystalline solid, m.p. 177–179° C., yield 34%.

EXAMPLE 50

N-(4-Bromo-3-methyl-5-isoxazolyl)-1-methylindole-2-sulfonamide

A. 2-Methylindole-2-sulfonyl chloride

2-Methylindole-2-sulfonyl chloride was prepared by the method of Example 34 with 1-methylindole (7.8 mmols, 1.0 ml), t-BuLi (1.7 m, 9.4 mmols, 5.5 ml), sulfur dioxide, NCS (8.6 mmols, 1.2 g) and THF (15 ml). Flash chromatography (2% ethyl acetate/hexanes) provided 0.66 g (36%) of a yellow solid.

B. N-(4-bromo-3-methyl-5-isoxazolyl)-1-methylindole-2-sulfonamide

N-(4-bromo-3-methyl-5-isoxazolyl)-1-methylindole-2-sulfonamide was prepared by the method of Example 41 with 4-bromo-3-methyl-5-aminoisoxazole (1.0 mmols, 0.18 g), NaH (2.5 mmols, 60 mg), 1-methylindole-2-sulfonyl chloride (1.2 mmols, 0.26 g) and THF (7 ml). Recrystallization from chloroform and hexane provided 0.28 g (77%) of a brown solid, m.p. 132–134° C.

EXAMPLE 51

N-(3,4-Dimethyl-5-isoxazolyl)-2-dibenzofuransulfonamide

A. 2-Dibenzofuransulfonyl chloride

2-Dibenzofuransulfonic acid (12.8 mmol) was heated at 70° C. with phosphorus oxychloride (1.30 ml, 14.0 mol) for 2 h. Excess phosphorus oxychloride was removed under reduced pressure. The residue was decomposed with ice water and extracted with ethyl acetate. The extract was washed with 5% sodium bicarbonate solution, dried over anhydrous magnesium sulfate and concentrated to yield 2.9 g crude 2-dibenzofuransulfonyl chloride.

B. N-(3,4-Dimethyl-5-isoxazolyl)-2-dibenzofuransulfonamide

The 2-benzofuransulfonyl chloride from step (a) was added to a solution of 5-amino-3,4-dimethylisoxazole (250 mg, 2.2 mmol) and 4-(dimethyl)aminopyridine (5 mg) in dry pyridine (2.0 ml). The reaction mixture was stirred at room temperature for 4 h. Pyridine was removed under reduced pressure and the residue was partitioned between water and ethyl acetate. The organic layer was washed with 1N HCl (2×25 ml), brine (25 ml) and dried over anhydrous magnesium sulfate. Evaporation of the solvents left an oily residue that, after purification by column chromatography over silica gel (1% methanol in chloroform as eluent), yielded white solid (32% yield). Purification was achieved by recrystallization from chloroform/hexanes to give a white "cotton-like" solid, m.p. 173–175° C. (dec.).

EXAMPLE 52

N-(4-chloro-3-methyl-5-isoxazolyl)-2-[2-(3,4-methylenedioxy)phenyl]-ethoxycarbonyl-3-sulfonamide N-(4-chloro-3-methyl-5-isoxazolyl)-2-[2-(3,4-methylenedioxy)phenyl]ethoxycarbonyl-3-sulfonamide was prepared by the same method as described in Example 97 with the exception that 2-(3,4-methylenedioxy) phenylethanol was used instead of sesamol. The final product was obtained by HPLC purification as a yellowish oil, (500 mg, 25% yield).

EXAMPLE 53

N-(4-Bromo-3-methyl-5-isoxazolyl)-2-phenylthiophene-3-sulfonamide

A. 3-bromo-2-phenyl-thiophene

Tetrakis (triphenylphosphine) palladium (400 mg), $Na_2CO_3$ (4 M, 80 ml, 320 mmol) and phenylboric acid (3.81 g, 30.3 mmol) as a solution in ethanol (80 ml) were sequentially added to a solution of 2,3-dibromothiophene (7.33 g, 30.3 mmol) in benzene (100 ml). The mixture was heated at reflux for 12 hours. The aqueous layer of the crude mixture was removed and the organic layer was diluted with $Et_2O$ (200 ml), washed with 1N NaOH (2×150 ml) and was dried ($MgSO_2$), filtered and the solvent was evaporated. The residue was chromatographed using hexane as the eluent to give 3-bromo-2-phenylthiophene as a clear oil (3.31 g, 47% yield).

B. 2-Phenylthiophene-3-sulfonylchloride n-BuLi (2.38 M, 11.5 ml, 27.28 mmol) was slowly added to a solution of 3-bromo-2-phenyl-thiophene (22.73 mmol) in ether (50 ml) at 0° C. The reaction was stirred at 0° C. for 1 h. $SO_2$ was bubbled through the mixture for 15 minutes at 0° C. followed by the addition of NCS (3.95 g, 29.55 mmol) as a suspension in THF (20 ml). The crude products were purified by column chromatography (hexanes) to give 2-phenylthiophene-3-sulfonylchloride as a white solid (1.23 g, 34% yield).

C. N-(4-bromo-3-methyl-5-isoxazolyl)-2-phenylthiophene-3-sulfonamide

N-(4-bromo-3-methyl-5-isoxazolyl)-2-phenyl-thiophene-3-sulfonamide was prepared from 2-phenyl-3-thiophene sulfonylchloride using the method described in Example 1. The product was purified by HPLC, 77% yield, reddish solid, mp 86–89° C.

EXAMPLE 54

3-Phenoxy-N-(4-bromo-3-methyl-5-isoxazolyl) thiophene-2-sulfonamide

A. 3-Phenoxythiophene.

Cuprous chloride (3.08 g, 31.1 mmol) and phenol (8.78 g, 93.3 mmol) were sequentially added to a solution of 3-bromothiophene (5.06 g, 31.1 mmol) in pyridine (150 ml). Sodium hydride (3.73 g, 93.3 mmol, 60% dispersion in mineral oil) was then slowly added. The reaction was heated at reflux for 20 hours under Argon. The pyridine was removed under reduced pressure. The residue was diluted with Et$_2$O (200 ml) and washed with 1 N NaOH (3×100 ml), 1 N HCl (2×150 ml) and 1 N NaOH (150 ml). The organic layer was dried (MgSO$_4$), filtered, and the solvent was evaporated. The residue was chromatographed using hexanes to give 3-phenoxy-thiophene as a clear oil (4.0 g, 74% yield).

B. 3-Phenoxythiophene-2-sulfonyl chloride

BuLi (2.38 M, 11.5 ml, 27.28 mmol) was slowly added to a solution of 3-phenoxythiophene (4.0 g, 22.73 mmol) in ether (50 ml) at 0° C. The reaction was stirred at 0° C. for 1 h. SO$_2$ was bubbled through the mixture for 15 minutes at 0° C. followed by the addition of NCS (3.95 g, 29.55 mmol) as a suspension in THF (20 ml). The mixture was allowed to warm up to 25° C. and stirred for 2 more h. The precipitate was filtered, and the filtrate was concentrated and chromatographed (hexanes) to give 3-phenoxythiophene-2-sulfonyl chloride as a yellowish solid (1.03 g, 17% yield).

C. N-(4-bromo-3-methyl-5-isoxazolyl)-3-phenoxythiophene-2-sulfonamide

N-(4-bromo-3-methyl-5-isoxazolyl)-3-phenoxythiophene-2-sulfonamide was prepared from 3-phenoxythiophene-2-sulfonyl chloride and 5-amino-4-bromo-3-methylisoxazole using the method described in Example 1. The product was recrystallized from acetonitrile/H$_2$O to give a solid m.p. 121–123° C., 61% yield.

EXAMPLE 55

N-(4-Bromo-3-methyl-5-isoxazolyl)-2-[N-(4-isopropylphenyl)aminocarbonyl]-thiophene-3-sulfonamide N-(4-bromo-3-methyl-5-isoxazolyl)-2-[N-(4-isopropylphenyl)aminocarbonyl]thiophene-3-sulfonamide was prepared in the same manner as described in Example 24 from N-(4-bromo-3-methyl-5-isoxazolyl)-2-(carboxyl)thiophene-3-sulfonamide and 4-isopropylaniline in 19% yield. The crude product was passed through silica gel column using ethyl acetate as eluent. This was further purified by HPLC (5% CH$_3$CN to 100% CH$_3$CN over 30 min.) to give a solid.

EXAMPLE 56

N-(4-Bromo-3-methyl-5-isoxazolyl)-2-[N-(4-sec-butylphenyl)aminocarbonyl]thiophene-3-sulfonamide N-(4-bromo-3-methyl-5-isoxazolyl)-2-[N-(4-sec-butylphenyl)aminocarbonyl]thiophene-3-sulfonamide was prepared in the same manner as described in Example 24 from N-(4-bromo-3-methyl-5-isoxazolyl)-2-(carboxyl)thiophene-3-sulfonamide and 4-sec-butylaniline in 25% yield. The crude product was passed through silica gel column using ethyl acetate as eluent. This was further purified by HPLC (5% CH$_3$CN to 100% CH$_3$CN over 30 min.) give a solid, m.p. 205–208° C.

EXAMPLE 57

N-(4-Bromo-3-methyl-5-isoxazolyl)-2-[N-(4-tert-butylphenyl)aminocarbonyl]thiophene-3-sulfonamide N-(4-bromo-3-methyl-5-isoxazolyl)-2-[N-(4-tert-butylphenyl)aminocarbonyl]thiophene-3-sulfonamide was prepared in the same manner as described in Example 24 from N-(4-bromo-3-methyl-5-isoxazolyl)-2-(carboxyl)thiophene-3-sulfonamide and 4-tert-butylaniline in 28% yield. The crude product was passed through silica gel column using ethyl acetate as eluent. This was further purified by HPLC (5% CH$_3$CN to 100% CH$_3$CN over 30 min.) give a solid, m.p. 76–86° C.

EXAMPLE 58

N-(4-Bromo-3-methyl-5-isoxazolyl)-2-[N-(4-butylphenyl)aminocarbonyl]-thiophene-3-sulfonamide N-(4-bromo-3-methyl-5-isoxazolyl)-2-[N-(4-butylphenyl)aminocarbonyl]thiophene-3-sulfonamide was prepared in the same manner as described in Example 24 from N-(4-bromo-3-methyl-5-isoxazolyl)-2-(carboxyl)thiophene-3-sulfonamide and 4-butylaniline in 18% yield. The crude product was passed through silica gel column using ethyl acetate as eluent. This was further Purified by HPLC (5% CH$_3$CN to 100% CH$_3$CN over 30 min.) give a solid.

EXAMPLE 59

N-(4-bromo-3-methyl-5-isoxazolyl)thiazole-2-sulfonamide

A. Thiazole-2-sulfonyl chloride

Thiazole (0.51 g, 6 mmol) was dissolved in THF (5 ml) and cooled to −78° C. under argon atmosphere. n-Butyllithium (2.5 M solution in hexane, 2.4 ml, 6 mmol) was added dropwise under constant stirring. The resultant reaction mixture was stirred at −78° C. for 40 min. Sulfur dioxide was bubbled through the reaction mixture for 15 min at −78° C. The reaction mixture was allowed to attain ambient temperature slowly and stirred for 30 min. NCS was added and stirring was continued for 30 min. The reaction mixture was diluted with water (50 ml), extracted with ethyl acetate (2×50 ml) and the combined organic layers was dried over anhydrous MgSO$_4$. Removal of the solvent under reduced pressure gave crude product which was purified by column chromatography, using hexane as eluent, to give thiazole-2-sulfonyl chloride as a liquid(0.6 g, 54% yield).

B. N-(4-bromo-3-methyl-5-isoxazolyl)thiazole-2-sulfonamide

N-(4-bromo-3-methyl-5-isoxazolyl)thiazole-2-sulfonamide was prepared in the same manner as described in Example 2 from 5-amino-4-bromo-3-methylisoxazole and thiazole-2-sulfonyl chloride in 57% yield. This was purified by HPLC (5% CH$_3$CN to 100% CH$_3$CN over 30 min.) to give a solid., m.p. 175–177° C.

EXAMPLE 60

N-(4-chloro-3-methyl-5-isoxazolyl)thiazole-2-sulfonamide

N-(4-chloro-3-methyl-5-isoxazolyl)thiazole-2-sulfonamide was prepared in the same manner as described in Example 2 from 5-amino-4-chloro-3-methylisoxazole and thiazole-2-sulfonyl chloride in 33% yield. This was purified by HPLC (5% CH$_3$CN to 100% CH$_3$CN over 30 min.) to give a solid, m.p. 171–173° C.

EXAMPLE 61

N-(3,4-dimethyl-5-isoxazolyl)thiazole-2-sulfonamide

N-(3,4-methyl-5-isoxazolyl)thioazole-2-sulfonamide was prepared in the same manner as described in Example 14 from 5-amino-3,4-dimethylisoxazole and thiazole-2-sulfonyl chloride in 37% yield. This was purified by HPLC (5% CH$_3$CN to 100% CH$_3$CN over 30 min.) give a solid, m.p. 118–120° C.

EXAMPLE 62

5-benzyl-N-(4-Bromo-3-methyl-5-isoxazolyl)thiophene-2-sulfonamide

A. 1-(2-Thienyl)benzyl alcohol

Sodium borohydride (0.37 g, 10 mmol) was added to 2-benzoylthiophene (1.88 g, 10 mmol) dissolved in methanol/THF mixture (1:10 ratio, 11 ml). This was stirred at room temperature for 10 h. The reaction mixture was decomposed by addition of saturated ammonium chloride solution (50 ml) and was extracted with ethyl acetate (2×50 ml). The combined organic layers was dried over anhydrous MgSO$_4$. Removal of the solvent gave 1-(2-thienyl)benzyl alcohol as a solid (1.75 g, 92% yield).

B. 2-Benzylthiophene

Acetic anhydride (5 ml) was added to a solution of 1-(2-thienyl)benzyl alcohol in pyridine. The resultant solution was stirred at 70° C. for 3 h. Water (50 ml) was added and the reaction mixture was stirred at room temperature for 2 h. This was extracted with ethyl acetate (2×50 ml) and the combined organic layers dried over anhydrous MgSO$_4$. Removal of the solvent gave crude product, which was purified by passing through silica gel using 3:1 hexane/ethyl acetate mixture to give 1-(2-thienyl)benzyl acetate.

A solution of 1-(2-thienyl)benzyl acetate in THF (5 ml) was added carefully to dry liquid ammonia (100 ml). Lithium metal was added in small portions until the blue color persisted. The resulting reaction mixture was stirred for 30 min, and the reaction was quenched by addition of solid ammonium chloride. The residue, after complete evaporation of liquid ammonia, was dissolved in water (50 ml) and was extracted with methylene chloride (2×50 ml). The combined organic layers was dried over MgSO$_4$ and filtered. Removal of the solvent gave crude product, which was purified by column chromatography using hexane as eluent to give 2-benzylthiophene (1.2 g, 68% yield).

C. 5-Benzylthiophene-2-sulfonyl chloride

To a solution of 2-benzylthiophene (0.875 g, 5 mmol) in chloroform (2 ml) at 0° C. was added chlorosulfonic acid dropwise and the reaction was stirred at 0° C. for 30 min. The reaction mixture was decomposed by pouring onto crushed ice (20 g). The mixture was extracted with ethyl acetate, dried over MgSO$_4$ and filtered. The solvent was removed under reduced pressure to give 5-benzylthiophene-2-sulfonic acid.

Phosphorous pentachloride (2.08 g, 40 mmol) was added to a solution of 5-benzylthiophene-2-sulfonic acid in phosphorous oxychloride (6.0 g, 40 mmol) at 0° C. The reaction mixture was kept at 50° C. for 1 h, cooled to room temperature, then poured onto crushed ice (50 g) and extracted with ethyl acetate (2×30 ml). Removal of the solvent under reduced pressure gave a crude product, which was purified by column chromatography using 3% ethyl acetate in hexane to give 2-benzylthiophene-5-sulfonyl chloride (0.6 g, 39% yield).

D. N-(4-bromo-3-methyl-5-isoxazolyl)-5-benzylthiophene-2-sulfonamide

N-(4-Bromo-3-methyl-5-isoxazolyl)-5-benzylthiophene-2-sulfonamide was prepared in the same manner as described in Example 2 from 5-amino-4-bromo-3-methylisoxazole and 5-benzyl-2-thiophenesulfonyl chloride in 22% yield. The product was purified by HPLC (5% CH$_3$CN to 100% CH$_3$CN over 30 min.) to give a solid, m.p. 49–50° C.

EXAMPLE 63

N-(4-Bromo-3-methyl-5-isoxazolyl)-3-phenethylthiophene-2-sulfonamide

A. 1-(3-Thienyl)phenethyl alcohol

Benzyl bromide (25.65 g, 150 mmol) was added dropwise over 8 h to a suspension of magnesium (3.6 g, 150 mmol) in ether (75 ml) dissolved in ether (30 ml). The resulting mixture was cooled to −10° C. 3-thiophenecarboxaldehyde in ether (45 ml) over 30 min was then added and the resultant reaction mixture was stirred at room temperature for 6 h. This was cooled to 0° C. and the reaction mixture was decomposed by addition of 0.1 N HCl. The ether layer was separated and the aqueous phase was extracted with ethyl acetate (2×50 ml). The combined organic layers was dried over MgSO$_4$ and filtered. Removal of the solvent gave 1-(3-thienyl)phenethyl alcohol (16 g, 78% yield).

B. 1-(3-Thienyl)phenethyl acetate 1-(3-Thienyl)phenethyl alcohol (10 g, 49 mmol) was dissolved in a 2:1 pyridine and acetic anhydride mixture (50 ml). This was stirred at 80° C. for 4 h. Excess of pyridine and acetic anhydride mixture was removed under reduced pressure and the residue was dissolved in water (100 ml). This was extracted with methylene chloride (3×75 ml) and the combined organic layers was dried over MgSO$_4$ and filtered. Removal of the solvent gave 1-(3-thienyl)phenethyl acetate (10.2 g, 84% yield).

C. 3-Phenethylthiophene 1-(3-thienyl)phenylethyl acetate dissolved in THF (20 ml) was added carefully to dry liquid ammonia (300 ml). Lithium metal was added in small portions until the blue color persisted. The resulting reaction mixture was stirred for 30 min and the reaction was quenched by addition of solid ammonium chloride. The residue, after the complete evaporation of liquid ammonia, was dissolved in water (100 ml) and was extracted with methylene chloride (4×50 ml). The combined organic layers was dried over MgSO$_4$ and filtered. Removal of the solvent gave a crude product, which was purified by column chromatography using hexane followed by mixture of ethyl acetate in hexane as eluent to give 3-phenethylthiophene (3.2 g, 34% yield) and 1-(3-thienyl)phenethyl acetate (starting material, 7 g).

D. 3-Phenethylthiophene-2-sulfonyl chloride and 4-phenethylthiophene-2-sulfonyl chloride 3-Phenethylthiophene (0.94 g, 5 mmol) was dissolved in THF (12 ml) and cooled to −78° C. under argon atmosphere. n-Butyllithium (2.5 M solution in hexane, 4.4 ml, 5.5 mmol) was added dropwise with constant stirring under an argon atmosphere. The resultant reaction mixture was stirred at −10° C. to 0° C. for 3 h, cooled to −78° C. and sulfur dioxide was bubbled through the reaction mixture for 15 min. The reaction mixture was allowed to attain ambient temperature slowly and stirring continued for 30 min. NCS (1 g) was added and stirring was continued for 1 h. The reaction mixture was diluted with water (50 ml), extracted with methylene chloride (2×50 ml) and the combined organic layers was dried over anhydrous MgSO$_4$. Removal of the solvent under reduced pressure gave a crude product which was purified by column chromatography, using 0.2% ethyl acetate in hexane as eluent, to give 3-phenethyl-2-thiophenesulfonyl chloride (0.06 g, 4% yield) and 4-phenethyl-2-thiophenesulfonyl chloride (0.72 g, 45% yield).

E. N-(4-bromo-3-methyl-5-isoxazolyl)-3-phenethylthiophene-2-sulfonamide

N-(4-bromo-3-methyl-5-isoxazolyl)-3-phenethylthiophene-2-sulfonamide was prepared in the same manner as described in Example 2 from 5-amino-4-bromo-3-methylisoxazole and 3-phenethyl-2-thiophenesulfonyl chloride in 48% yield. This was purified by HPLC (5% CH$_3$CN to 100% CH$_3$CN over 30 min.) to give a solid.

EXAMPLE 64

N-(4-Bromo-3-methyl-5-isoxazolyl)-4-phenethylthiophene-2-sulfonamide

N-(4-bromo-3-methyl-5-isoxazolyl)-4-phenethylthiophene-2-sulfonamide was prepared in the same manner as described in Example 2 from 5-amino-4-bromo-3-methylisoxazole and 4-phenethyl-2-thiophenesulfonyl chloride in 32% yield. This was purified by HPLC (5% CH$_3$CN to 100% CH$_3$CN over 30 min.) to give a gum.

EXAMPLE 65

N-(4-Bromo-3-methyl-5-isoxazolyl)-5-(3-methoxyphenyl)thiophene-2-sulfonamide

A. 5-bromothiophene-2-sulfonyl chloride

Chlorosulfonic acid was added dropwise over 20 min. to a cold solution (−78° C.) of 2-bromothiophene (16.3 g, 100 mmol) in methylene chloride (50 ml) was added After addition of chlorosulfonic acid was complete, the cold bath was removed. The reaction mixture was allowed to attain room temperature slowly (2 h), was added dropwise onto the crushed ice (1000 g) and was extracted with methylene chloride (4×100 ml). The combined organic layers was dried over MgSO$_4$, filtered and the solvent was removed under reduced pressure to give a crude product. This was purified by column chromatography using hexane as eluent to give 5-bromothiophene-2-sulfonyl chloride (22 g, 75% yield).

B. N-(5-bromothiophene-2-sulfonyl)pyrrole

N-(5-bromothiophene-2-sulfonyl)pyrrole was prepared in the same manner as described in Example 33A from 5-bromothiophene-2-sulfonyl chloride and pyrrole in 88% yield. This was purified by recrystallization using hexane/ethyl acetate as a solvent.

C. 3-Methoxyphenylboronic acid

3-Methoxyphenylboronic acid was prepared in the same manner as described in Example 33B from 3-bromoanisole and triisopropyl borate in 82% yield. This was used in the next step without any further purification.

D. N-[5-(3-methoxyphenyl)thiophene-2-sulfonyl]pyrrole

N-[5-(3-methoxyphenyl)thiophene-2-sulfonyl]pyrrole was prepared in the same manner as described in Example 32C from 3-methoxyphenylboronic acid and N-(5-bromothiophene-2-sulfonyl)pyrrole in 93% yield. This was purified by recrystallization using hexane/ethyl acetate as solvent.

E. 5-(3-Methoxyphenyl)thiophene-2-sulfonyl chloride

To a suspension of N-[5-(3-methoxyphenyl)thiophene-2-sulfonyl]pyrrole (1.4 g, 4.5 mmol) in ethanol (15 ml) was added 6 N sodium hydroxide solution (15 ml) and the resultant reaction mixture refluxed for 14 h. The reaction mixture was cooled to room temperature. Ethanol was removed under reduced pressure and the resultant precipitate was filtered and dried under vacuum (1.1 g, 91% yield).

Phosphorous pentachloride (2.08 g, 10 mmol) was added to the suspension of sodium slat of sulfonic acid (0.62 g, 2.5 mmol) (obtained from above step) in phosphorousoxy chloride (0.93 ml, 10 mmol) and the resultant reaction mixture stirred at room temperature for 3 h. This was decomposed by adding on to crushed ice and the product was extracted with methylene chloride (2×50 ml). The combined organic layers dried over MgSO$_4$ and filtered. Removal of the solvent gave the crude product which was purified by column chromatography using 2% ethyl acetate in hexane to give 5-(3-methoxyphenyl)thiophene-2-sulfonyl chloride (0.51 g, 75%).

F. N-(4-bromo-3-methyl-5-isoxazolyl)-5-(3-methoxyphenyl)thiophene-2-sulfonamide N-(4-bromo-3-methyl-5-isoxazolyl)-5-(3-methoxyphenyl)thiophene-2-suffonamide was prepared in the same manner as described in Example 2 from 5-amino-4-bromo-3-methylisoxazole and 5-(3-methoxyphenyl)thiophene-2-sulfonyl chloride in 48% yield. This was purified by HPLC (5% CH$_3$CN to 100% CH$_3$CN over 30 min.) give a solid.

EXAMPLE 66

N-(4-Bromo-3-methyl-5-isoxazolyl)-5-(2-methylfuranyl)thiophene-2-sulfonamide

A. N-(pyrrole)-5-(2-methylfuranyl)thiophene-2-sulfonamide t-BuLi (1.7 m solution in hexane, 7.9 ml, 14.6 mmol) was added dropwise under constant stirring under a nitrogen atmosphere to a solution of 2-methyl furan (1.0 g, 12 mmol) in THF (20 ml) at −78° C. The solution was then warmed to −10° C. and stirring was continued for 45 min. The solution was then added to a solution of zinc chloride (27 ml of a 0.5 M solution in THF) at −30° C. and then warmed to room temperature where stirring continued for 1 hr. resulting in a pale yellow clear solution. The solution was then transferred via a steel canula under nitrogen to a solution of N-(pyrrole)-5-bromothiophene-2-sulfonamide (Example 33A, 3.5 g, 12 mmol) and tetrakis(triphenylphosphine)palladium (0) (693 mg, 0.6 mmol) in THF (15 ml) at −78° C. The solution was then warmed to room temperature and stirred for a period of 2 hours. Purification by column chromatography using 2% ethyl acetate gave 680 mg of N-(pyrrole)-5-(2-methylfuranyl)thiophene-2-sulfonamide as a pale yellow powder (19% yield).

B. 2-(2-methylfuranyl)thiophene-5-sulfonyl chloride 2-(2-methylfuranyl)thiophene-5-sulfonyl chloride was prepared as in the same manner as described in Example 33D from N-(pyrrole)-5-(2-methylfuranyl)thiophene-2-sulfonamide (300 mg, 1.02 mmol). Purification by column chromatography using 2% ethyl acetate/hexanes gave 145 mg (53%) of the sulfonyl chloride as a pale yellow solid.

C. N-(4-bromo-3-methyl-5-isoxazolyl)-5-(2-methyl-furanyl)thiophene-2-sulfonamide N-(4-bromo-3-methyl-5-isoxazolyl)-5-(2-methylfuranyl)thiophene-2-sulfonamide was prepared in the same manner as described in Example 2. Reaction of 2-(2-methylfuranyl)thiophene-5-sulfonyl chloride (55 mg, 0.21 mmol) with 5-amino-4-bromo-3-methyl isoxazole (41 mg, 0.21 mmol), after purification by column chromatography using 10% MeOH/CHCl$_3$, gave 45 mg of the pure sulfonamide as a brown semisolid, 54% yield, m.p. 123–124° C.

EXAMPLE 67

N-(4-Bromo-3-methyl-5-isoxazolyl)-5-(4-methoxyphenyl)thiophene-2-sulfonamide

A. N-[5-(4-methoxyphenyl)thiophene-2-sulfonyl]pyrrole

N-[5-(4-methoxyphenyl)thiophene-2-sulfonyl]pyrrole was prepared, in the same manner as described in Example 32C, from 4-methoxyphenylboronic acid and N-(5-bromothiophene-2-sulfonyl)pyrrole. Recrystallization using hexane/ethyl acetate gave a solid in quantitative yield.

B. 5-chlorosulfonyl-2-(4-methoxyphenyl)thiophene

A solution of N-[5-(4-methoxyphenyl)thiophene-2-sulfonyl]pyrrole (1.4 g, 4.5 mmol) was suspended in ethanol (15 ml). A 6N sodium hydroxide solution was added, and the resulting suspension was refluxed for 14 hr. to give a clear solution. This was cooled to room temperature. Ethanol was removed under reduced pressure. A precipitate was formed on standing at room temperature which was filtered and washed with methylene chloride and dried under vacuum giving a solid (1.2 g, 91%).

The solid (0.67 g, 2.5 mmol) was suspended in phosphorous oxychloride (0.92 ml, 10 mmole) and phosphorous pentachloride (2.08 g, 10 mmole) was added. The resulting mixture was stirred at room temperature for 3 hr. The reaction mixture was decomposed by pouring onto crushed ice (50 g). The mixture was extracted with methylene chloride (2×50 ml) and the combined organic layers was dried over MgSO$_4$. Removal of solvent under reduced pressure gave a crude product which was purified by column chromatography using 2% EtOAc in hexane as solvent to give 5-chlorosulfonyl-2-(4-methoxyphenyl)thiophene (530 mg, 86%).

C. N-(4-bromo-3-methyl-5-isoxazolyl)-5-(4-methoxyphenyl)thiophene-2-sulfonamide

N-(4-bromo-3-methyl-5-isoxazolyl)-5-(4-methoxyphenyl)thiophene-2-sulfonamide was prepared in the same manner as described in Example 1. Reaction of 5-chlorosulfonyl-2-(4-methoxyphenyl)thiophene with 5-amino-4-bromo-3-methylisoxazole gave N-(4-bromo-3-methyl-5-isoxazolyl)-5-(4-methoxyphenyl)thiophene-2-sulfonamide in 50% yield, m.p. 128–130° C.

EXAMPLE 68

N-(4-Bromo-3-methyl-5-isoxazolyl)-5-(3-thienyl)thiophene-2-sulfonamide

A. 3-Thiopheneboric acid n-Butyllithium (2.5 M solution in hexane, 20 ml, 50 mmol) was added dropwise to a solution of 3-bromothiophene (8.15 g, 50 mmol) in THF (20 ml) at −78° C. under an argon atmosphere. The resulting solution was stirred at −78° C. for 45 min, and then added to a solution of triisopropyl borate (9.4 g, 50 mmol) in THF at −78° C. over 30 min through a steel cannula. The resulting reaction mixture was stirred at room temperature for 12 h and was decomposed by the addition of 100 ml 1N HCl. The aqueous layer was extracted with ether (2×100 ml) and the combined organic layers was extracted with 1 M NaOH (3×30 ml), the aqueous extract was acidified with concentrated HCl to pH 2 and extracted with ether (3×50 ml). The combined ether extract was washed once with water, dried over MgSO$_4$ and filtered. Removal of the solvent gave 3-thienylboronic acid as a solid (5.2 g, 80% yield).

B. N-[5-(3-thienyl)thiophene-2-sulfonyl]pyrrole

N-[5-(3-thienyl)thiophene-2-sulfonyl]pyrrole was prepared in the same manner as described in Example 32C from 3-thienylboronic acid and N-(5-bromothiophene-2-sulfonyl) pyrrole in quantitative yield. This was purified by recrystallization using hexane/ethyl acetate as solvent.

C. 5-(3-Thienyl)thiophene-2-sulfonyl chloride 5-(3-thienyl)thiophene-2-sulfonyl chloride was prepared in the same manner as described in Example 64E from N-[5-(4-methoxyphenyl)thiophene-2-sulfonyl]pyrrole in 74% yield.

D. N-(4-bromo-3-methyl-5-isoxazolyl)-5-(3-thienyl)thiophene-2-sulfonamide

N-(4-bromo-3-methyl-5-isoxazolyl)-5-(3-thienyl)thiophene-2-sulfonamide was prepared in the same manner as described in Example 2 from 5-amino-4-bromo-3-methylisoxazole and 5-(3-thienyl)thiophene-2-sulfonyl chloride in 40% yield. This was purified by HPLC (5% CH$_3$CN to 100% CH$_3$CN over 30 min.) give a solid.

EXAMPLE 69

N-(4-Bromo-3-methyl-5-isoxazolyl)furan-2-sulfonamide

N-(4-bromo-3-methyl-5-isoxazolyl)furan-2-sulfonamide was prepared by the method of Example 1 with 5-amino-4-bromo-3-methylisoxazole (0.266 g, 1.5 mmol), NaH (60% oil dispersion) (0.15 g, 3.8 mmol) and furan-2-sulfonyl chloride (Example 36A) (0.30 mg, 1.8 mmol). Flash chromatography (50% EtOAc/hexane) and recrystallization from CHCl$_3$ and hexane provided 90 mg (20% yield) of light yellow crystals (m.p. 117–119° C.).

EXAMPLE 70

N-(4-bromo-3-methyl-5-isoxazolyl)-5-(phenylthio)furan-2-sulfonamide

A. 2-(phenylthio)furan t-BuLi (1.7 m, 10 ml, 1.7 mmol) was added to a solution of furan (1.24 ml, 17 mmol) in 20 ml of THF at −60° C. Thirty minutes later diphenyidisulfide (3.7 g, 17 mmol) was added via cannula in 8 ml of THF. The reaction was warmed to ambient temperature for 30 minutes, then diluted with 150 ml of ether and washed with 3% NaOH (3×100 ml). The organic was dried (MgSO$_4$), filtered and concentrated to collect 2.92 g (97% yield) of a light yellow liquid.

B. 5-phenylthiofuran-2-sulfonyl chloride 5-phenylthiofuran-2-sulfonyl chloride was prepared by the method of Example 34A with 5-phenylthiofuran (1.5 g, 8.5 mmol), t-BuLi (1.2 m, 8.9 mmol, 5.3 ml) and NCS (1.14 g, 8.5 mmol). Flash chromatography (5% EtOAc/hexane) provided 1.61 g (69% yield) of a yellow-orange liquid.

C. N-(4-bromo-3-methyl-5-isoxazolyl)-5-(phenylthio)furan-2-sulfonamide

N-(4-bromo-3-methyl-5-isoxazolyl)-5-(phenylthio)furan-2-sulfonamide was prepared by the method of Example 1 with 4-bromo-3-methyl-2-aminoisoxazole (0.354 g, 2.0 mmol), NaH (60% oil dispersion) (0.20 g, 5.0 mmol) and 5-phenylthiofuran-2-sulfonyl chloride (0.66 g, 2.4 mmol). Flash chromatography (50% EtOAc/hexane) and recrystallization from CHCl$_3$/hexane provided 82 mg (10% yield) of a tan solid (m.p. 90–91.5° C.).

EXAMPLE 71

N-(4-Bromo-3-methyl-5-isoxazolyl)-5-phenylfuran-2-sulfonamide

A. 2-Phenylfuran 2-phenylfuran was prepared by the method of Example 32C from 2-bromofuran (0.93 g, 6.3 mmol), sodium carbonate (18 ml of 2 M aqueous solution), phenyl boric acid (0.93 g, 7.6 mmol) and tetrakis (triphenylphosphine) palladium (0) (0.36 g, 0.32 mmol). Flash chromatography with hexane provided 0.79 g (87% yield) of a colorless liquid.

B. 5-phenylfuran-2-sulfonyl chloride 5-phenylfuran-2-sulfonyl chloride was prepared by the method of Example 34A with 2-phenylfuran (0.79 g, 5.5 mmol), t-BuLi (1.7 m, 6.0 mmol, 3.6 ml) and NCS (0.73 g, 5.5 mmol). Flash chromatography (5% EtOAc/hexane) provided 0.84 g (63% yield) of a light red solid.

C. N-(4-bromo-3-methyl-5-isoxazolyl)-5-phenylfuran-2-sulfonamide

N-(4-bromo-3-methyl-5-isoxazolyl)-5-phenylfuran-2-sulfonamide was prepared by the method of Example 1 with 4-bromo-3-methyl-2-amino isoxazole (0.354 g, 2.0 mmol), NaH (60% oil dispersion) (0.20 g, 5.0 mmol) and 5-phenylfuran-2-sulfonyl chloride (0.58 g, 2.4 mmol). Flash chromatography (50% EtOAc/hexane) and recrystallization from CHCl$_3$/hexane provided 0.23 g (29% yield) of light yellow crystals (m.p. 124–126° C.).

EXAMPLE 72

N-(4-Bromo-3-methyl-5-isoxazolyl)-5-(4-isopropylphenyl)thiophene-2-sulfonamide

A. 4-isopropylphenyl boronic acid

4-Isopropylphenyl boronic acid was prepared in the same manner as described in Example 33B from 1-bromo-4-ethyl benzene. The boronic acid was isolated as a white powder in 63% yield, m.p. 133–135° C.

B. N-[5-(4-isopropylphenyl)thiophene-2-sulfonyl]pyrrole

N-[5-(4-isopropylphenyl)thiophene-2-sulfonyl]pyrrole was prepared in the same manner as described in Example 33C, from 4-isopropylphenyl boronic acid and N-(5-bromothiophene sulfonyl)-pyrrole. Purification by column chromatography using 10% ethyl acetate/hexanes gave the pure sulfonamide as an off white colored solid in 84% yield, m.p. 112–114° C.

C. 5-chlorosulfonyl-2-(4-ethylphenyl)thiophene 5-chlorosulfonyl-2-(4-ethylphenyl)thiophene was prepared in the same manner as described in Example 33D. Hydrolysis of 526 mg (1.59 mmol) of N-[5-(4-isopropylthiophene)-2-sulfonyl]pyrrole with 6N sodium hydroxide followed by chlorination using phosphorous oxychloride and phosphorous pentachloride gave the crude sulfonyl chloride as dark oil. Flash column chromatography over silica gel using 2% ethyl acetate/hexanes yielded 262 mg (55%) of the pure sulfonyl chloride as a light brown oil.

D. N-(4-bromo-3-methyl-5-isoxazolyl)-5-(4-isopropylphenyl)thiophene-2-sulfonamide N-(4-bromo-3-methyl-5-isoxazolyl)-5-(4-isopropylphenyl)thiophene-2-sulfonamide was prepared in the same manner as described in Example 2. Reaction of 5-chlorosulfonyl-2-(4-isopropyl)thiophene (260 mg, 0.87 mmol) with 5-amino-4-bromo-3-methylisoxazole (161 mg, 0.91 mmol) yielded after flash chromatography using 10% MeOH/CHCl$_3$ a pale brown solid (265 mg) which was further purified using preparative HPLC to give the pure sulfonamide as a light tan colored solid, m.p. 114–116° C.

EXAMPLE 73

N-(4-Bromo-3-methyl-5-isoxazolyl)-5-(4-propylphenyl)thiophene-2-sulfonamide

A. 1-bromo-4-propylbenzene

A solution of 1-bromopropane (1.32 g, 0.6 mmol) was added dropwise at room temperature at a rate such that a gentle reflux was maintained to a suspension of magnesium (258 mg, 12 mmol) in dry tetrahydrofuran. The cloudy suspension was stored at room temperature for an additional 30 minutes to produce a gray solution that was then added dropwise over 15 minutes to a mixture of 1-iodo-4-bromobenzene (3.0 g, 10.6 mmol) and tetrakis (triphenylphosphine) palladium (0) in 50 mL of dry benzene at room temperature. The mixture was stirred for 2 hours, diluted with 50 mL of water, the organic layer was separated and the aqueous layer was extracted with ether (2×50 mL). The combined organic extracts was dried and evaporated to yield 1.69 g (80%) of a light brown oil, which was used in the next step without further purification.

B. 4-propylphenyl boronic acid

To a suspension of magnesium shavings (217 mg, 8.9 mmol) in 3 mL of dry tetrahydrofuran under argon, a crystal of iodine along with a solution of 4-bromopropylbenzene (1.69 g, 8.5 mmol) dissolved in 6 mL of tetrahydrofuran was added at such a rate that a gentle reflux was maintained. The solution was refluxed for an additional 0.5 h, cooled to room temperature and added in portions over 10 min to a solution of trimethylborate (924 mg, 8.9 mmol) previously dissolved in 4 mL of dry ether at −78° C. After 30 minutes, the solution was warmed to room temperature; and stirring was continued for 90 min. The reaction was then quenched by the addition of 2 mL of a 10% hydrochloric acid solution. The tetrahydrofuran was removed under reduced pressure and the remaining residue was extracted into diethyl ether (3×25 mL). The combined ether extracts was extracted with 1 M NaOH (3×25 mL) and the resulting aqueous layer was acidified to pH 2.0 using 6N HCl, then reextracted back into diethyl ether (3×25 mL). The combined organic layers was washed with water (1×25 mL), brine (1×25 mL) and dried over magnesium sulfate. Evaporation of solvent left a brown solid which was filtered through a small plug of silica gel using 10% MeOH/CHC₃. Evaporation left 448 mg (32%) of a brown solid, m.p. 90–93° C.

C. N-[5-(4-propylphenyl)thiophene-2-sulfonyl] pyrrole

N-[5-(4-propylphenyl)thiophene-2-sulfonyl]pyrrole was prepared in the same manner as described in Example 33C, from 4-propylphenyl boronic acid and N-(5-bromothiophenesulfonyl)pyrrole. Purification by column chromatography using 10% ethyl acetate/hexanes gave the pure sulfonamide as a white solid in 55% yield, m.p. 106–108° C.

D. 5-chlorosulfonyl-2-(4-propylphenyl)thiophene 5-chlorosulfonyl-2-(4-propylphenyl)thiophene was prepared in the same manner as described in Example 33D. Hydrolysis of 240 mg (0.73 mmol) of N-[5-(4-propylphenylthiophene)-2-sulfonyl]pyrrole with 6N NaOH followed by chlorination using phosphorous oxychloride and phosphorous pentachloride gave the crude sulfonyl chloride as a greenish-brown oil. Flash chromatography over silica gel using 2% ethyl acetate/hexanes yielded 83 mg (81%) of the pure sulfonyl chloride as a pale yellow oil.

E. N-(4-bromo-3-methyl-5-isoxazolyl)-5-(4-propylphenyl)thiophene-2-sulfonamide N-(4-bromo-3-methyl-5-isoxazolyl)-5-(4-propylphenyl)thiophene-2-sulfonamide was prepared in the same manner as described in Example 2. Reaction of 5-chlorosulfonyl-2-(4-isopropyl)thiophene (260 mg, 0.87 mmol) with 5-amino-4-bromo-3-methylisoxazole (161 mg, 0.91 mmol) yielded after flash chromatography using 10% MeOH/CHCl₃ a brown solid (76.1 mg) which was further purified using preparative HPLC to give the pure sulfonamide as a tan colored oil.

EXAMPLE 74

N-(4-Bromo-3-methyl-5-isoxazolyl)-2-(3,4,5-trimethoxybenzyl)-benzo[b]-thiophene-3-sulfonamide

A. α-(2-benzo[b]thienyl)-3,4,5-trimethoxybenzyl alcohol

α-(2-benzo[b]thienyl)-3,4,5-trimethoxybenzyl alcohol was prepared in the same manner as described in Example 40A. Reaction of benzo[b]thiophene (7.5 mmoles, 1.0 g), t-BuLi (1.7 m, 9.7 mmoles, 5.7 mls) and 3,4,5-trimethoxybenzaldehyde (8.9 mmoles, 1.8 g) in THF (20 ml) yielded, after flash chromatography using 50% ethyl acetate/hexanes, 2.4 g (97%) of a yellow-white solid.

B. 2-(3,4,5-trimethoxybenzyl)-benzo[b]thiophene 2-(3,4,5-trimethoxybenzyl)-benzo[b]thiophene was prepared in the same manner as described in Example 47B. Reaction of α-(2-benzo[b]-thienyl)-3,4,5-trimethoxybenzyl alcohol (4.5 mmoles, 1.5 g), triethylsilane (5.0 mmoles, 0.80 mls), CH₂Cl₂ (50 ml) and TFA (9.1 mmoles, 0.70 mls) yielded, after flash chromatography using 20% ethyl acetate/hexanes, 0.77 g (54%) of a white solid.

C. 2-(3,4,5-trimethoxybenzyl)-benzo[b]thiophene-3-sulfonylchloride 2-(3,4,5-trimethoxybenzyl)-benzo[b]thiophene-3-sulfonylchloride was prepared in the same manner as described in Example 40B. Reaction of dimethylformamide (DMF; 4.8 mmoles, 0.40 mls), sulfuryl chloride (4.1 mmoles, 0.33 mls) and 2-(3,4,5-trimethoxybenzyl)-benzo[b] thiophene (2.4 mmoles, 0.75 g) yielded, after flash chromatography using 20% ethyl acetate/hexanes, 0.29 g (30%) of a yellow-orange oil.

D. N-(4-bromo-3-methyl-5-isoxazolyl)-2-(3,4,5-trimethoxybenzyl)benzo[b]thiophene-3-sulfonamide N-(4-bromo-3-methyl-5-isoxazolyl)-2-(3,4,5-trimethoxybenzyl)benzo[b]thiophene-3-sulfonamide was prepared in the same manner as described in Example 41. Reaction of 4-bromo-3-methyl-5-aminoisoxazole (0.55 mmoles, 97 mg), NaH (1.4 mmoles, 55 mg), and 2-(3,4,5-trimethoxylbenzyl)-benzo[b]thiophene-3-sulfonyl chloride (0.66 mmoles, 0.27 g) in THF (2 ml) yielded, after flash chromatography using 50% ethyl acetate/hexanes and recrystallization from chloroform and hexanes, 94 mg of a tan solid, m.p. 154–156° C.

EXAMPLE 75

N-(4-bromo-3-methyl-5-isoxazolyl) 2-ethyl-5-methylbenzo[b]thiophene-3-sulfonamide

A. 2-ethyl-5-methylbenzo[b]thiophene 2-ethyl-5-methylbenzo[b]thiophene was prepared in the same manner as described in Example 40A. Reaction of 5-methylbenzo[b]thiophene (3.4 mmoles, 0.50 g), t-BuLi (1.7 m, 5.1 mmoles, 3.0 ml) and ethyl iodide (6.8 mmoles, 0.54 ml) in THF (10 ml) yielded 0.58 g (97%) of a light yellow liquid.

B. 2-ethyl-5-methylbenzo[b]thiophene-3-sulfonylchloride 2-ethyl-5-methylbenzo[b]thiophene-3-sulfonylchloride was prepared in the same manner as described in Example 40B. Reaction of DMF (6.5 mmoles, 0.50 ml), sulfurylchloride (5.5 mmoles, 0.44 ml) and 2-ethyl-5-methylbenzo[b] thiophene (3.2 mmoles, 0.57 g) yielded, after flash chromatography, using 2% ethyl acetate/hexanes, 0.58 g (66%) of an orange solid.

C. N-(4-bromo-3-methyl-5-isoxazolyl)-2-ethyl-5-methylbenzo[b]thiophene-3-sulfonamide N-(4-bromo-3-methyl-5-isoxazolyl)-2-ethyl-5-methylbenzo[b]thiophene-3-sulfonamide was prepared in the same manner as described in Example 41. Reaction of 4-bromo-3-methyl-5-aminoisoxazole (1.0 mmole, 0.18 g), NaH (2.5 mmoles, 0.10 g), and 2-ethyl-5-methylbenzo[b] thiophene-3-sulfonylchloride (1.3 mmoles, 0.36 g) in THF (6 ml) yielded, after recrystallization from chloroform and hexanes, 0.25 g (60%) of a light brown crystalline solid, m.p. 176–178° C.

EXAMPLE 76

N-(4-chloro-3-methyl-5-isoxazolyl)-2-[3,4-(methylenedioxy)benzyl]-benzo[b]thiophene-3-sulfonamide N-(4-chloro-3-methyl-5-isoxazolyl)-2-[3,4-(methylenedioxy)benzyl]-benzo[b]thiophene-3-sulfonamide was prepared in the same manner as described in Example 41. Reaction of 4-chloro-3-methyl-5-aminoisoxazole (0.61 mmoles, 81 mg), NaH (1.5 mmoles), 61 mg), and 2-[3,4-(methylenedioxy)benzyl]benzo[b]thiophene-3-sulfonyl chloride (0.74 mmoles, 0.27 g) in THF (4 ml) yielded, after flash chromatography using 50% ethyl acetate/hexanes followed by recrystallization from ethyl acetate and hexanes, 0.23 g (81%) of a light brown solid, m.p. 178–181° C.

EXAMPLE 77

N-(4-Bromo-3-methyl-5-isoxazolyl)-2-(3,4-dimethoxybenzyl)benzo[b]thiophene-3-sulfonamide

A. α-(2-benzo[b]thienyl)-3,4-dimethylbenzyl alcohol

α-(2-benzo[b]thienyl)-3,4-dimethylbenzyl alcohol was prepared in the same manner as described in Example 40A. Reaction of benzo[b]-thiophene (7.5 mmoles, 1.0 g), t-BuLi (1.7 m, 97 mmoles, 5.7 ml) and 3,4-dimethoxybenzaldehyde (8.9 mmoles, 1.5 g) in THF (20 ml) yielded, after flash chromatography using 30% ethyl acetate/hexanes, 2.25 g (≈100%) of a white gummy solid.

B. 2-(3,4-dimethoxybenzyl)benzo[b]thiophene 2-(3,4-dimethoxybenzyl)benzo[b]thiophene was prepared in the same manner as described in Example 47B. Reaction of α-(2-benzo[b]thienyl)-3-4-dimethoxybenzyl alcohol (7.5 mmoles, 2.25 g), triethylsilane (8.2 mmoles, 1.3 ml) and $CH_2Cl_2$ (20 ml) in TFA (15 mmoles, 1.2 mls) yielded, after flash chromatography using 10% ethyl acetate/hexanes, 1.77 g (84%) of a colorless oil.

C. 2-(3,4-dimethoxybenzyl)-benzo[b]thiophene-3-sulfonylchloride 2-(3,4-dimethoxybenzyl)-benzo[b]thiophene-3-sulfonylchloride was prepared in the same manner as described in Example 40B. Reaction of DMF (90 mmoles, 7 ml) and 2-(3,4-dimethoxybenzyl)-benzo[b]thiophene (6.0 mmoles, 1.7 g) yielded, after flash chromatography using 15% ethyl acetate/hexanes, 1.24 g (54%) of a green oil.

D. N-(4-bromo-3-methyl-5-isoxazolyl)-2-(3,4-dimethoxybenzyl)benzo[b]thiophene-3-sulfonamide N-(4-bromo-3-methyl-5-isoxazolyl)-2-(3,4-dimethoxybenzyl)benzo[b]thiophene-3-sulfonamide was prepared in the same manner as described in Example 41. Reaction of 4-bromo-3-methyl-5-aminoisoxazole (1.0 mmoles, 0.18 g), NaH (2.5 mmoles, 60 mg), and 2-(3,4-dimethoxybenzyl)benzo[b]thiophene-3-sulfonylchloride (1.2 mmoles, 0.44 g) in THF (6 ml), after recrystallization from chloroform and hexanes, yielded 0.42 g (80%) of a brown solid, m.p. 151–153° C.

EXAMPLE 78

N-(3,4-dimethyl-5-isoxazolyl)-2-(3,4-methylenedioxy)benzo[b]thiophene-3-sulfonamide N-(3,4-dimethyl-5-isoxazolyl)-2-(3,4-methylenedioxy)benzo[b]thiophene-3-sulfonamide was prepared in the same manner as described in Example 41. Reaction of 3,4-dimethyl-5-aminoisoxazole (1.0 mmoles, 0.11 g), NaH (2.5 mmoles, 60 mg) and 2-[3,4-(methylenedioxy)benzyl]-benzo[b]thiophene-3-sulfonylchloride (1.1 mmoles, 0.40 g) in THF (6 ml) yielded, after flash chromatography using 50% ethyl acetate/hexanes followed by recrystallization from chloroform and hexanes, 0.35 g (79%) of a tan solid, m.p. 135–137° C.

EXAMPLE 79

N-(4-Bromo-3-methyl-5-isoxazolyl)-2-(4-methoxybenzyl)benzo[b]-thiophene-3-sulfonamide

A. α-(2-benzo[b]thienyl)-4-methyoxybenzol alcohol

α-(2-benzo[b]thienyl)-4-methyoxybenzol alcohol was prepared by the method of Example 40A with benzo[b]thiophene (7.5 mmoles. 1.0 g), t-BuLi (1.7 m, 10.4 mmoles, 6.1 ml), 4-methoxy-benzaldehyde (8.9 mmoles, 1.1 ml) and THF (20 ml). Flash chromatography (20% ethyl acetate/hexanes) provided 1.75 g (87%) of a yellow solid.

B. 2-(4-methyoxybenzyl)-benzo[b]thiophene 2-(4-methyoxybenzyl)-benzo[b]thiophene was prepared by the method of Example 47B with α-(2-benzo[b]thienyl)-4-methoxybenzyl alcohol (1.9 mmoles) 0.50 g), triethylsilane (2.0 mmoles, 0.32 mls), $CH_2Cl_2$ (20 ml) and TFA (3.7 mmoles, 0.30 ml). Recrystallization with hexanes and chloroform provided 0.40 (85%) of a pink solid.

C. 2-(4-methoxybenzyl)-benzo[b]thiophene-3-sulfonylchloride 2-(4-methoxybenzyl)-benzo[b]thiophene-3-sulfonylchloride was prepared by the method of Example 40B with DMF (3.2 mmoles, 0.24 ml), sulfurylchloride (2.7 mmoles, 0.22 ml) and 2-(4-methoyxybenzyl)benzo[b]thiophene (1.6 mmoles. 0.4 g). Flash chromatography using 2% ethyl acetate/hexanes provided 0.19 g (33%) of a light yellow solid.

D. N-(4-bromo-3-methyl-5-isoxazolyl)-2-(4-methoxybenzyl)benzo[b]thiophene-3-sulfonamide N-(4-bromo-3-methyl-5-isoxazolyl)-2-(4-methoxybenzyl)benzo[b]thiophene-3-sulfonamide was prepared by the method of Example 41 with 4-bromo-3-methyl-5-aminoisoxazole (0.48 mmoles, 85 mg), NaH (1.2 mmoles, 48 mg), 2-(4-methoxybenzyl)-benzo[b]thiophene-3-sulfonylchloride (0.53 mmoles, 0.19 g) and THF (3 ml). Flash chromatography (50% ethyl acetate/hexanes) followed by recrystallization from methanol and water provided 46 mg (20%) of a white crystalline solid, m.p. 120–122° C.

EXAMPLE 80

N-(4-Bromo-3-methyl-5-isoxozolyl)-2-(2-methoxybenzyl)benzo[b]thiophene-3-sulfonamide

A. α-(2-benzo[b]thiophene)-2-methoxybenzyl alcohol

α-(2-Benzo[b]thiophene)-2-methoxybenzyl alcohol was prepared by the method of Example 47A with benzo[b]thiophene (7.5 mmoles, 1.0 g) t-BuLi (1.7 m, 9.7 mmoles, 5.7 ml), 2-methoxybenzaldehyde (8.9 mmoles, 1.1 ml) and THF (20 ml). Flash chromatography (20% ethyl acetate/hexanes) provided 1.9 g (96%) of a yellow oil.

B. 2-(2-Methoxybenzyl)-benzo[b]thiophene 2-(2-Methoxybenzyl)-benzo[b]thiophene was prepared by the method of Example 47B α-(2-benzo[b]thiophene)-2-methoxybenzyl alcohol (7.1 mmoles, 1.9 g), triethylsilane (7.9 mmoles, 1.3 ml) and $CH_2Cl_2$ (30 ml) at 0° C. was added TFA (14.3 mmoles, 1.1 ml). Flash chromatography (2% ethyl acetate/hexanes) provided 1.31 g (72%) of a yellow solid.

C. 2-(2-methoxybenzyl)-benzo[b]thiophene-3-sulfonyl chloride 2-(2-methoxybenzyl)-benzo[b]thiophene-3-sulfonyl chloride was prepared by the method of Example 40B with sulfuryl chloride (8.4 mmoles, 0.7 ml), DMF (9.8 mmoles, 0.8 ml) and 2-(2-methoxybenzyl)benzo[b]thiophene (4.9 mmoles, 1.25 g). Flash chromatography (2% ethyl acetate/hexanes) provided 0.94 g (54%) of a yellow solid.

D. N-(4-bromo-3-methyl-5-isoxozolyl)-2-(2-methoxybenzyl)benzo[b]thiophene-3-sulfonamide N-(4-bromo-3-methyl-5-isoxozolyl)-2-(2-methoxybenzyl)-benzo[b]-thiophene-3-sulfonamide was prepared by the method of Example 41 with 5-amino-4-bromo-3-methylisoxazole (1.0 mmoles, 0.18 g), NaH (2.5 mmoles, 100 mg), 2-(2-methoxybenzyl)-benzo[b]thiophene-3-sulfonyl chloride (1.4 mmoles, 0.49 g) and THF (7 ml). Flash chromatography (50% ethyl acetate/hexanes) followed by recrystallization from chloroform and hexanes provided 0.30 g (61%) of a brown solid, m.p. 80–84° C.

EXAMPLE 81

N-(3,4-dimethyl-5-isoxazolyl)-2-(4-chlorobenzyl)-benzo[b]thiophene-3-sulfonamide

A. α-(2-benzo[b]thienyl)-4-chlorobenzyl alcohol

α-(2-benzo[b]thienyl)-4-chlorobenzyl alcohol was prepared by the method of Example 40A with benzo[b]thiophene (7.5 mmoles, 1.0 g), t-BuLi (1.7 m, 9.7 mmoles, 5.7 ml), 4-chlorobenzaldehyde (9.7 mmoles, 1.4 g) and THF (20 ml). The crude material (2.45 g) was taken forward without further purification.

B. 2-(4-chlorobenzyl)benzo[b]thiophene 2-(4-chlorobenzyl)benzo[b]thiophene was prepared by the method of Example 47B with α-(2-benzo[b]thiophene)-4-chlorobenzyl alcohol (8.9 mmoles, 2.45 g), triethylsilane (9.8 mmoles, 1.6 ml), CH$_2$Cl$_2$ (40 ml) and TFA (13.4 mmoles, 1.0 ml). Flash chromatography (1% ethyl acetate/hexanes) provided 1.3 g (67%—2 steps) of an off-white solid.

C. 2-(4-chlorobenzyl)benzo[b]thiophene-3-sulfonylchloride 2-(4-chlorobenzyl)benzo[b]thiophene-3-sulfonylchloride was prepared by the method of Example 40B with DMF (70 mmoles, 5.4 ml), sulfurylchloride (2.3 mmoles, 1.9 ml) and 2-(4-chlorobenzyl)-benzo[b]thiophene (4.6 mmoles, 1.2 g). Flash chromatography (2% ethyl acetate/hexanes) provided 0.51 g (31%) of an orange-yellow oil.

D. N-(3,4-dimethyl-5-isoxazolyl)-2-(4-chlorobenzyl)-benzo[b]thiophene-3-sulfonamide N-(3,4-dimethyl-5-isoxazolyl)-2-(4-chlorobenzyl)-benzo[b]thiophene-3-sulfonamide was prepared by the method of Example 41 with 3,4-dimethyl-5-aminoisoxazole (1.2 mmoles, 1.4 g), NaH (3.0 mmoles, 73 mg), 2-(4-chlorobenzyl)-benzo[b]thiophene-3-sulfonylchloride (1.4 mmoles, 0.50 g) and THF (8 ml). Flash chromatography (50% ethyl acetate/hexanes) followed by recrystallization from methanol and water provided 1.04 g (27%) of a yellow solid, m.p. 100–102° C.

EXAMPLE 82

N-(4-chloro-3-methyl-5-isoxazolyl)-2-(4-dimethylaminobenzyl)benzo [b]thiophene-3-sulfonamide

A. α-(2-benzo[b]thienyl)-4-dimethylaminobenzyl alcohol

α-(2-benzo[b]thienyl)-4-dimethylaminobenzyl alcohol was prepared by the method of Example 40A with benzo[b]thiophene (7.5 mmoles, 1.0 g), t-BuLi (1.7 M, 8.9 mmoles, 5.3 ml), 4-dimethylaminobenzaldehyde (8.9 mmoles, 1.3 g) and THF (20 ml). The crude product (2.4 g) was carried forward without further purification.

B. 2-(4-dimethylaminobenzyl)benzo[b]thiophene 2-(4-dimethylaminobenzyl)benzo[b]thiophene was prepared by the method of Example 47B with α-(2-benzo[b]thienyl)-4-dimethylaminobenzyl alcohol (7.5 mmoles, 2.1 g), triethylsilane (2.8 mmoles, 1.3 ml), CH$_2$Cl$_2$ (50 ml) and TFA (11.2 mmoles, 0.9 ml). Flash chromatography (10% ethyl acetate/hexanes) provided 1.5 g (73%—for two steps) of a white solid.

C. 2-(4-dimethylaminobenzyl)-benzo[b]thiophene-3-sulfonylchloride

Chlorosulfonic acid (9.4 mmoles, 0.6ml) was added to 2-(4-dimethylaminobenzyl)-benzo[b]thiophene (3.7 mmoles, 1.0 g) in CH$_2$Cl$_2$ (100 ml) at −78° C. The solution was stirred 20 min. at −78° C. Phosphorous oxychloride (11.2 mmoles, 1.0 ml) and phosphorous pentachloride (11.2 mmoles, 2.3 g) were added to the reaction mixture. The reaction mixture was warmed to ambient temperature and stirring was continued an additional 1.5 hr. followed by dilution with ice (≈200 ml) and extraction with ethyl acetate (200 ml). The organic layer was washed carefully with sat. NaHCO$_3$ (3×100 ml), then dried (MgSO$_4$), filtered and concentrated. Flash chromatography (5% ethyl acetate/hexanes) provided 0.61 g (45%) of a yellow solid.

D. N-(4-chloro-3-methyl-5-isoxazolyl)-2-(4-dimethylaminobenzyl)benzo[b]thiophene-3-sulfonamide N-(4-chloro-3-methyl-5-isoxazolyl)-2-(4-dimethylaminobenzyl)benzo[b]thiophene-3-sulfonamide was prepared by the method of Example 41 with 4-chloro-3-methyl-5-aminoisoxazole (0.52 mmoles, 69 mg), NaH (1.3 mmoles, 31 mg), 2-(4-dimethylaminobenzyl)-benzo[b]thiophene-3-sulfonylchloride (0.58 mmoles, 0.21 g) and THF (4 ml). Flash chromatography (5% methanol/chloroform) provided 0.16 g (66%) of a yellow gummy solid, m.p. 105–110° C.

EXAMPLE 83

N-(4-bromo-3-methyl-5-isoxazolyl)-2,5-dimethylfuran-3-sulfonamide

A. 2,5-dimethyl-furan-3-sulfonylchloride 2,5-dimethyl-furan-3-sulfonylchloride was prepared by the method of Example 40B with DMF (28 mmoles, 2.2 ml), sulfurylchloride (24 mmoles, 1.9 ml) and 2,5-dimethyl-furan (14 mmoles, 1.5 ml). Flash chromatography (5% ethyl acetate/hexanes) provided 0.61 g (22%) of a yellow liquid.

B. N-(4-bromo-3-methyl-5-isoxazolyl)-2,5-dimethyl-furan-3-sulfonamide

N-(4-bromo-3-methyl-5-isoxazolyl)-2,5-dimethyl-furan-3-sulfonamide was prepared by the method of Example 41 with 4-bromo-3-methyl-5-amino-isoxazole (2.0 mmoles, 0.35 g), NaH (5.0 mmoles, 200 mg), 2,5-dimethyl-furan-3-sulfonylchloride (2.4 mmoles, 0.47 g) and THF (9 ml). Flash chromatography (5% methanol/chloroform) followed by recrystallization from chloroform and hexanes provided 0.21 g (31%) of a light brown solid, m.p. 85.5–87° C.

EXAMPLE 84

N-(4-Bromo-3-methyl-5-isoxazolyl)-2,5-dimethyl-4-phenylthiophene-3-sulfonamide

A. 2,5-dimethyl-3,4-dibromothiophene

NBS (13.2 mmoles, 2.4 g) was added to 2,5-dimethylthiopene (5.3 mmoles, 0.59 g) in $CHCl_3$ (30 ml). The reaction mixture was stirred at ambient temperature for 1.5 hr., then diluted with ether (50 ml) and washed with water (3×50 ml). The organic was dried ($MgSO_4$), filtered and concentrated. Flash chromatography (hexanes) provided 1.2 g (84%) of a white solid.

B. 2,5-dimethyl-3-bromo-4-phenylthiophene

Phenyl boronic acid (5.0 mmoles, 0.61 g) was added to 2,5-dimethyl-3,4-bromothiophene (4.5 mmoles, 1.2 g), tetrakis (triphenylphosphine) palladium (0) (0.23 mmoles, 0.26 g) and $Na_2CO_3$ (2 M, 26 mmoles, 13 ml) in benzene (20 ml). The biphasic reaction mixture was heated to reflux for 24 hr. then cooled to ambient temperature and diluted with ether (100 ml) and washed with water (100 ml). The organic later was dried ($MgSO_4$), filtered and concentrated. Flash chromatography (hexanes) provided 0.60 g (49%) of a yellow solid.

C. 2,5-dimethyl-4-phenyl-3-chlorosulfonyl-thiophene t-BuLi (1.7 M, 2.7 mmoles, 1.6 ml) was added to 2,5-dimethyl-3-bromo-4-phenyl thiophene (2.2 mmoles, 0.59 g) in THF (8 mls.) at −30° C. The solution was stirred 20 min. at −30° C., then the flask was evacuated with sulfur dioxide, and warmed to −20° C. upon which NCS (2.2 mmoles, 0.30 g) was added. The reaction mixture was warmed to ambient temperature for 30 min., then diluted with ethyl acetate (50 ml) and washed with water (2×50 ml). The organic layer was dried ($MgSO_4$), filtered and concentrated. Flash chromatography (2% ethyl acetate/hexanes) provided 0.26 g (41%) of a light yellow solid.

D. N-(4-bromo-3-methyl-5-isoxazole)-2,5-dimethyl-4-phenylthiophene-3-sulfonamide N-(4-bromo-3-methyl-5-isoxazole)-2,5-dimethyl-4-phenylthiophene-3-sulfonamide was prepared by the method of Example 41 with 4-bromo-3-methyl-5-amino isoxazole (0.79 mmoles, 0.14 g), NaH (2.0 mmoles, 80 mg), 2.5-dimethyl-4-phenylthiophene-3-sulfonylchloride (0.91 mmoles, 0.26 g) and THF (3 ml). Recrystallization twice from chloroform and hexanes provided 0.15 g (45%) of a white crystalline solid, m.p. 166–168° C.

EXAMPLE 85

N-(4-Bromo-3-methyl-5-isoxazolyl)-2-(hydroxymethyl thiophene-3-sulfonamide $BH_3$THF (3.62 ml, 1 M in THF) was added to a solution of N-(4-bromo-3-methyl-5-isoxazolyl)-2-carboxylthiophene-3-sulfonamide (1.0 g, 2.72 mmol) in dry THF (15 ml) at room temperature. After stirring at room temperature for 10 minutes, the mixture was refluxed for 1 hour. The reaction was cooled with an ice-bath and 1N HCl (10 ml) was added. The resulting mixture was concentrated. The aqueous residue was then partitioned between 1N HCl and EtOAc. The organic layer was dried ($MgSO_4$). The solid was filtered and the filtrate concentrated. The residue was treated with MeOH and concentrated again. This process was repeated 3 more times to give N-(4-bromo-3-methyl-5-isoxazolyl)-2-(hydroxymethyl)thiophene-3-sulfonamide (680 mg, 71% yield) as a yellow oil.

EXAMPLE 86

N-(4-Bromo-3-methyl-5-isoxazolyl)-2-[(3-methoxyphenyl)aminomethyl]-thiophene-3-sulfonamide $BH_3$ THF (15 ml, 1 M in THF) was added to a solution of N-(4-bromo-3-methyl-5-isoxazolyl)-2-[N-(3-methoxyphenyl)aminocarbonyl]thiophene-3-sulfonamide (Example 22) (1.0 g, 2.12 mmol) in dry THF (15 ml). The mixture was refluxed for 8 hours and cooled. THF was evaporated on a rotavap and MeOH was added to the residue. The resulting solution was concentrated. The final residue was purified by HPLC to give N-(4-bromo-3-methyl-5-isoxazolyl)-2-[(3-methoxyphenyl)aminomethyl]thiophene-3-sulfonamide (113 mg., 12% yield) as a grey powder, m.p. 70–73° C.

EXAMPLE 87

N-(4-bromo-3-methyl-5-isoxazolyl)-2-[N-(3-carboxyphenylaminocarbonyl]-thiophene-3-sulfonamide $Et_3N$ (2.27 ml. 16. mmol), ethyl 3-aminobenzoate (836 ml, 5.44 mmol) and phosphonitrilic chloride trimer (1.89 g, 5.44 mmol) were sequentially added to a solution of N-(4-bromo-3-methyl-5-isoxazolyl)-2-(carbonyl)thiophene-3-sulfonamide (Example 17) (1 g, 2.27 mmol) in dry THF (20 ml). The reaction was stirred at room temperature for 1 hour and cooled. Water (5 ml) was added to quench the reaction. The resulting solution was concentrated on a rotavap. The residue was diluted with EtOAc and washed with 2N HCl (2×150 ml). The organic layer was dried ($MgSO_4$). The solid was filtered off and the filtrate was concentrated. The residue was treated with 1N NaOH (200 ml) and stirred at 0° C. for 15 minutes. The mixture was then acidified with conc. HCl to pH~1. The resulting yellow precipitate was filtered off and recrystallized from $CH_3CN/H_2O$ to give N-(4-bromo-3-methyl-5-isoxazolyl)-2-[N-(3-carboxyphenyl)aminocarbonyl]thiophene-3-sulfonamide (153 mg., 11.6%) as a yellowish powder, m.p. 183–185° C.

EXAMPLE 88

N-(4-Bromo-3-methyl-5-isoxazolyl)-2-[N-(2-carboxylphenyl)aminocarbonyl]thiophene-3-sulfonamide N-(4-bromo-3-methyl-5-isoxazolyl)-2-[N-(2-carboxylphenyl)aminocarbonyl]thiophene-3-sulfonamide was prepared by the same method as described in Example 87, with the exception of using ethyl-2-aminobenzoate instead of ethyl-3-aminobenzoate.

EXAMPLE 89

N-(4-bromo-3-methyl-5-isoxazolyl)-2-(aminocarbonyl)thiophene-3-sulfonamide

Carbonyldiimidazole (485 mg, 2.99 mmol) was added to a solution of N-(4-bromo-3-methyl-5-isoxazolyl)-2-carboxylthiophene-3-sulfonamide (1 g, 2.72 mmol) in THF (10 ml) at room temperature. The mixture was stirred for 15 minutes. Aqueous $NH_3$ (5 ml) was then added, and the mixture was stirred at room temperature for 30 minutes. The solvent was evaporated and the residue was partitioned between EtOAc and 1N HCl. The organic layer was dried (MgSO$_4$). The solid was filtered and the filtrate concentrated. The oily residue was recrystallized from EtOAc to give N-(4-bromo-3-methyl-5-isoxazolyl)-2-(aminocarbonyl)thiophene-3-sulfonamide (946 mg, 95% yield) as a white solid, m.p. 168–170° C.

EXAMPLE 90

N-(4-Bromo-3-methyl-5-isoxazolyl)-2-[(5-dimethylamino-1-naphthyl)sulfonylaminocarbonyl] thiophene-3-sulfonamide Dansylchloride (90.2 mg, 0.328 mmol) was added to a solution of N-(4-bromo-3-methyl-5-isoxazolyl)-2-(aminocarbonyl)thiophene-3-sulfonamide (Example 89) (100 mg, 0.273 mmol) and NaH (43.7 mg, 60% dispersion in mineral oil, 1.10 mmol). The reaction was stirred at room temperature for 1 hour. Water was added to quench the reaction and THF was stripped off on a rotavap. The aqueous residue was partitioned between 1N HCl and EtOAc. The organic layer was dried (MgSO$_4$). The solid was filtered and the filtrate concentrated. The residue was recrystalized from EtOAc to give N-(4-bromo-3-methyl-5-isoxazolyl)-2-[(5-dimethylamino-1-naphthyl)sulfonylaminocarbonyl] thiophene-3-sulfonamide (55 mg., 34% yield) as a white powder (m.p. 184–186° C.).

EXAMPLE 91

N-(4-Bromo-3-methyl-5-isoxazolyl)-2-[(3,4-methylenedioxyphenyl)aminocarbonyl]thiophene-3-sulfonamide N-(4-bromo-3-methyl-5-isoxazolyl)-2-[(3,4-methylenedioxyphenyl)aminocarbonyl]thiophene-3-sulfonamide was prepared by the same method as described in Example 89 with the exception that 3,4-methylenedioxyaniline was used in place of ammonium hydroxide. N-(4-bromo-3-methyl-5-isoxazolyl)-2-[(3,4-methylenedioxyphenyl)aminocarbonyl]thiophene-3-sulfonamide was purified by HPLC to give 15% yield of the desired product as a dark grey powder, m.p. 138–140° C.

EXAMPLE 92

N-(4-Bromo-3-methyl-5-isoxazolyl)-2-[(3,4-methylenedioxy)phenoxycarbonyl]thiophene-3-sulfonamide Carbonyldiimidazole (530 mg., 3.26 mmol.) was added to a solution of N-(4-bromo-3-methyl-5-isoxazolyl)-2-carboxylthiophene-3-sulfonamide (Example 17) (1.0 g, 2.72 mmol) in dry THF (10 ml). The mixture was stirred at room temperature for 15 minutes. Sesamol (767 mg., 5.44 mmol) and imidazole (185 mg, 2.72 mmol) were added simultaneously. The resulting mixture was refluxed for 1 hour and allowed to cool to room temperature. The solvent was evaporated. The residue was partitioned between 1N HCl and EtOAc. The organic layer was dried (MgSO$_4$). The solid was filtered and the filtrate concentrated to give a yellow oil which was recrystalized from EtOAc/Et$_2$O/Hexane. N-(4-bromo-3-methyl-5-isoxazolyl)-2-[(3,4-methylenedioxy) phenoxycarbonyl]thiophene-3-sulfonamide was obtained as a white powder (494 mg, 37% yield), m.p. 174–176° C.

EXAMPLE 93

N-(4-Bromo-3-methyl-5-isoxazolyl)-2-[(3,4-methylenedioxy)benzoyl]-thiophene-3-sulfonamide A. N-(4-bromo-3-methyl-5-isoxazolyl)-2-[(N-methoxy-N-methyl)aminocarbonyl]thiophene-3-sulfonamide N-(4-bromo-3-methyl-5-isoxazolyl)-2-[(N-methoxy-N-methyl)carboxamide]thiophene-3-sulfonamide was prepared by the same method as described in Example 89 with the exception that N,O-dimethylhydroxylamine was used in place of ammonium hydroxide. The yield was 90%.

B. N-(4-Bromo-3-methyl-5-isoxazolyl)-2-[(3,4-methylenedioxy)benzoyl]thiophene-3-sulfonamide Freshly prepared (3,4-methylenedioxy)phenyl magnesium bromide (1.28 g of (3,4-methylenedioxy) bromobenzene and 172 mg Mg turnings) was added to a solution of N-(4-bromo-3-methyl-5-isoxazolyl)-2-[(N-methoxy-N-methyl)aminocarbonyl]thiophene-3-sulfonamide (A) (652 mg, 1.59 mmol) in THF (10 ml) at room temperature. The resulting mixture was refluxed for 30 minutes. To workup, the mixture was allowed to cool to room temperature and was quenched with 1N HCl (10 ml). THF was then evaporated. The aqueous residue was partitioned between 1N HCl and EtOAc. The organic layer was concentrated and the residue was purified by HPLC to give N-(4-bromo-3-methyl-5-isoxazolyl)-2-[(3,4-methylenedioxy)benzoyl]thiophene-3-sulfonamide (90 mg, 12% yield) as a dark yellow powder, m.p. 47–49° C.

EXAMPLE 94

N-(4-Bromo-3-methyl-5-isoxazolyl)-2-[(2-hydroxyphenyl)aminocarbonyl]-thiophene-3-sulfonamide N-(4-bromo-3-methyl-5-isoxazolyl)-2-[(2-hydroxyphenyl)aminocarbonyl]thiophene-3-sulfonamide was prepared by the same method as described in Example 89 with the exception that 3-aminophenol was used in place of ammonium hydroxide. The product was purified by HPLC to give N-(4-bromo-3-methyl-5-isoxazolyl)-2-[(2-hydroxyphenyl)aminocarbonyl]thiophene-3-sulfonamide (50 mg, 18% yield) as a dull yellow solid, m.p. 42–44° C.

EXAMPLE 95

N-(3,4-dimethyl-5-isoxazolyl)-2[(3,4-methylenedioxy)phenoxycarbonyl]thiophene-3-sulfonamide N-(3,4-dimethyl-5-isoxazolyl)-2[3,4-(methylenedioxy) phenoxycarbonyl]thiophene-3-sulfonamide was prepared by the same method as described in Example 92 with the exception that N-(3,4-dimethyl-5-isoxazolyl)-2-carboxylthiophene-3-sulfonamide was used instead of N-(3-bromo-4-methyl-5-isoxazolyl)-2-carboxylthiophene-3-sulfonamide. N-(3,4-dimethyl-5-isoxazolyl)-2[(3,4-methylenedioxy)phenoxycarbonyl]thiophene-3-sulfonamide was purified by HPLC and was obtained as an orange oil (200 mg., 15% yield).

EXAMPLE 96

N-(4-Bromo-3-methyl-5-isoxazolyl)-2-{[(3,4-methylenedioxy)benzoyl]-aminocarbonyl}thiophene-3-sulfonamide Carbonyldiimidazole (213 mg. 1.31 mmol) was added to a solution of piperonylic acid (181.5 mg., 1.09 mmol) in dry THF (10 ml). The resulting mixture was stirred for 15 minutes. N-(4-bromo-3-methyl-5-isoxazolyl)-2-aminocarbonylthiophene-3-sulfonamide (Example 89) (400 mg, 1.09 mmol) and NaH (175 mg, 60% in mineral oil, 4.37 mmol) were added sequentially. The mixture was stirred at room temperature for 8 hours. Water was added to destroy the excess NaH. The solvent was then evaporated and the residue was partitioned between 1N HCl and EtOAc. The organic layer was dried (MgSO$_4$), the solid filtered and the filtrate concentrated. The residue was recrystalized from EtOAc to give N-(4-bromo-3-methyl-5-isoxazolyl)-2-{[(3,4-methylenedioxy)benzoyl]aminocarbonyl}thiophene-3-sulfonamide (20 mg, 3.6% yield) as a yellowish powder (m.p. 90–93° C.).

EXAMPLE 97

N-(4-chloro-3-methyl-5-isoxazolyl)-2-[(3,4-methylenedioxy)phenoxycarbonyl]thiophene-3-sulfonamide N-(4-chloro-3-methyl-5-isoxazolyl)-2-[(3,4-methylenedioxy)phenoxycarbonyl]thiophene-3-sulfonamide was prepared by the same method as described in Example 93 with the exception that N-(4-chloro-3-methyl-5-isoxazolyl)-2-carboxylthiophene-3-sulfonamide was used instead of N-(4-bromo-3-methyl-5-isoxazolyl)-2-carboxylthiophene-3-sulfonamide. N-(4-chloro-3-methyl-5-isoxazolyl)-2-[(3,4-methylenedioxy)phenoxycarbonyl]-thiophene-3-sulfonamide was recrystalized from EtOAc (49% mg, 20% yield) as a white solid, m.p. 189–191° C.

EXAMPLE 98

N-(4-Bromo-3-methyl-5-isoxazolyl)-2-[(3,4-methylenedioxy)phenylacetyl]thiophene-3-sulfonamide N-(4-bromo-3-methyl-5-isoxazolyl)-2-[(3,4-methylenedioxy)phenylacetyl]thiophene-3-sulfonamide was prepared by the same method as described in Example 93 with the exception that piperonylmagnesium chloride was used instead of (3,4-methylenedioxy)phenylmagnesium bromide and the reaction mixture was stirred overnight at room temperature instead of refluxing for 30 minutes. The crude mixture was purified by HPLC to give N-(4-bromo-3-methyl-5-isoxazolyl)-2-[3,4-(methylenedioxy)phenylacetyl]thiophene-3-sulfonamide (20 mg, 40% yield) as a yellow oil.

EXAMPLE 99

N-(4-Bromo-3-methyl-5-isoxazolyl)-2-[(3,4-methylenedioxy)phenoxycarbonylamino]thiophene-3-sulfonamide Triethylamine (2.28 ml, 16.35 mmol) and diphenylphosphorylazide (773 mg., 2.72 mmol) were sequentially added to a solution of N-(4-bromo-3-methyl-5-isoxazolyl)-2-carboxylthiophene-3-sulfonamide (Example 17) (1.0 g, 2.72 mmol) in dry THF (40 ml). The mixture was stirred for 8 hours. Sesamol (1.54 g, 10.9 mmol) was added and the mixture was refluxed for 2 hr. The mixture was allowed to cool to room temperature. The solvent was stripped off on a rotavap and the residue was partitioned between EtOAc and 1N HCl. The organic layer was dried (MgSO$_4$). The solid was filtered and the filtrate concentrated. The residue was purified by HPLC to afford N-(4-bromo-3-methyl-5-isoxazolyl)-2-[3,4-(methylenedioxy)phenoxycarbonylamino]thiophene-3-sulfonamide (400 mg, 29% yield) as a beige powder, m.p. 39–43° C.

EXAMPLE 100

N-(4-Bromo-3-methyl-5-isoxazolyl)-2-[(3,4-methylenedioxy)phenylureido]thiophene-3-sulfonamide N-(4-bromo-3-methyl-5-isoxazolyl)-2-[(3,4-methylenedioxy)phenylureido]thiophene-3-sulfonamide was prepared by the same method as described in Example 99 with the exception that 3,4-methylenedioxyaniline was used instead of sesamol. N-(4-bromo-3-methyl-5-isoxazolyl)-2-[3,4-(methylenedioxy)phenylureido]thiophene-3-sulfonamide (157 mg, 12% yield) was obtained via HPLC purification as a brownish-greyish powder, m.p. 62–65° C.

EXAMPLE 101

N-(4-chloro-3-methyl-5-isoxazolyl)-2-[(3,4-methylenedioxy)benzyloxycarbonyl]thiophene-3-sulfonamide N-(4-chloro-3-methyl-5-isoxazolyl)-2-[(3,4-methylenedioxy)benzyloxycarbonyl]thiophene-3-sulfonamide was prepared by the same method as described in Example 97 with the exception that piperonyl alcohol was used instead of sesamol. N-(4-chloro-3-methyl-5-isoxazolyl)-2-[(3,4-(methylenedioxy)benzyloxycarbonyl]thiophene-3-sulfonamide (210 mg, 15% yield) was obtained via HPLC purification as a yellowish powder, m.p. 35–38° C.

EXAMPLE 102

N-(4-chloro-3-methyl-5-isoxazolyl)-2-[(3,4-methylenedioxy)phenylacetyl]thiophene-3-sulfonamide N-(4-chloro-3-methyl-5-isoxazolyl)-2-[(3,4-methylenedioxy)phenylacetyl]thiophene-3-sulfonamide was prepared by the same method as described in Example 98 with the exception that N-(4-chloro-3-methyl-5-isoxazolyl)-2-carboxylthiophene-3-sulfonamide was used instead of N-(4-bromo-3-methyl-5-isoxazolyl)-2-carboxylthiophene-3-sulfonamide. N-(4-chloro-3-methyl-5-isoxazolyl)-2-[(3,4-methylenedioxy)phenylacetyl]thiophene-3-sulfonamide (3 g, 50% yield) was obtained via HPLC purification as a yellow solid, m.p. 35–38° C.

EXAMPLE 103

N-(4-chloro-3-methyl-5-isoxazolyl)-2-[(3,4-methylenedioxy)phenethyloxycarbonyl]thiophene-3-sulfonamide N-(4-chloro-3-methyl-5-isoxazolyl)-2-[(3,4-methylenedioxy)phenethyloxycarbonyl]thiophene-3-sulfonamide was prepared by the same method as described in Example 97 with the exception that (3,4-methylenedioxy)phenethyl alcohol was used instead of sesamol. N-(4-chloro-3-methyl-5-isoxazolyl)-2-[3,4-(methylenedioxy)phenethyloxycarbonyl]thiophene-3-sulfonamide (500 mg, 34% yeild) was obtained via HPLC purification as a yellowish oil.

EXAMPLE 104

N-(4-chloro-3-methyl-5-isoxazolyl)-2-{[4-(3,4-methylenedioxybenzyl)piperazin-1-yl]carbonyl}thiophene-3-sulfonamide N-(4-chloro-3-methyl-5-isoxazolyl)-2-{[4-(3,4-methylenedioxybenzyl)piperazin-1-yl]carbonyl}thiophene-3-sulfonamide was prepared by the same method as described in Example 89 with the exception that N-(4-chloro-3-methyl-5-isoxazolyl)-2-carboxylthiophene-3-sulfonamide was used instead of N-(4-bromo-3-methyl-5-isoxazolyl)-2-carboxylthiophene-3-sulfonamide, and 1-piperonylpiperazine was used instead of ammonium hydroxide. N-(4-chloro-3-methyl-5-isoxazolyl)-2-{[4-(3,4-methylenedioxybenzyl)piperazin-1-yl]carbonyl}thiophene-3-sulfonamide (872 mg, 54% yield) was obtained via HPLC purification as a white powder, m.p. 221–223° C.

EXAMPLE 105

N-(4-chloro-3-methyl-5-isoxazolyl)-2-aminothiophene-3-sulfonamide

N-(4-chloro-3-methyl-5-isoxazolyl)-2-aminothiophene-3-sulfonamide was prepared by the same method as described in Example 99 except that the mixture was refluxed without the addition of sesamol. N-(4-chloro-3-methyl-5-isoxazolyl)-2-aminothiophene-3-sulfonamide (298 mg, 31% yield) was obtained via HPLC as a yellow solid, m.p. 39–42° C.

EXAMPLE 106

N-(4-chloro-3-methyl-5-isoxazolyl)-2-{1-cyano-1-[(3,4-methylenedioxy)phenyl]acetyl}thiophene-3-sulfonamide Carbonyidiimidazole (603 mg, 3.72 mmol) was added to a solution of N-(4-chloro-3-methyl-5-isoxazolyl)-2-carboxylthiophene-3-sulfonamide (Example 17) (1.0 g, 3.1 mmol) in dry THF (40 ml). The mixture (I) was stirred at room temperature for 15 minutes.

NaH (868 mg, 60% in mineral oil, 21.7 mmol) was added to a solution of (3,4-methylenedioxy)phenylacetonitrile in THF (100 ml). The mixture (II) was refluxed for 30 minutes and then allowed to warm to room temperature.

The mixture (I) was then cannulated into mixture (II) while cooled by ice-bath and the resulting mixture was allowed to warm to room temperature. Water was added to quench excess NaH. THF was then stripped off on a rotavap. The residue was partitioned between 1N NaOH and Et$_2$O. The aqueous layer was acidified with concentrated HCl with cooling to pH~1 and extracted with EtOAc. The organic layer was dried (MgSO$_4$), the solid filtered and the filtrate concentrated. The residue was purified by HPLC to give N-(4-chloro-3-methyl-5-isoxazolyl)-2-{1-cyano-1-[3,4-(methylenedioxy)phenyl]acetyl}thiophene-3-sulfonamide (277 mg, 19% yield) as a yellowish powder, m.p. 142–142° C.

EXAMPLE 107

N-(4-chloro-3-methyl-5-isoxazolyl)-2-[3-(dimethylamino)phenoxycarbonyl]thiophene-3-sulfonamide N-(4-chloro-3-methyl-5-isoxazolyl)-2-[3-(dimethylamino)phenoxycarbonyl]thiophene-3-sulfonamide was prepared by the same method as described in Example 97 with the exception that 3-dimethylaminophenol was used instead of sesamol. N-(4-chloro-3-methyl-5-isoxazolyl)-2-[3-(dimethylamino)phenoxycarbonyl]thiophene-3-sulfonamide (50 mg, 7.3% yield) was obtained via HPLC purification as a dark brown oil.

EXAMPLE 108

N-(4-chloro-3-methyl-5-isoxazolyl)-2-(cyclohexyloxycarbonyl)thiophene-3-sulfonamide N-(4-chloro-3-methyl-5-isoxazoyl)-2-(cyclohexyloxycarbonyl)thiophene-3-sulfonamide was prepared by the same method as described in Example 97 with the exception that cyclohexanol was used instead of sesamol. N-(4-chloro-3-methyl-5-isoxazoyl)-2-(cyclohexyloxycarbonyl)thiophene-3-sulfonamide (29 mg, 5% yield) was obtained via HPLC purification as an off-white solid, m.p. 134–137° C.

EXAMPLE 109

N-(4-chloro-3-methyl-5-isoxazolyl)-2-[β-hydroxy(3,4-methylenedioxy)phenylethyl]thiophene-3-sulfonamide LiBH$_4$ (36.6 mg, 1.68 mmol) was added slowly to a solution of N-(4-chloro-3-methyl-5-isoxazolyl)-2-[3,4-methylenedioxy)phenylacetyl]thiophene-3-sulfonamide (Example 102) (74 mg, 0.168 mmol) in the THF (10 ml). The resulting mixture was stirred for 8 hours. Saturated NH$_4$Cl (aq) was added to quench the excess LiBH$_4$. The resulting mixture was concentrated on a rotavap. The residue was partitioned between EtOAc and 1N HCl. The organic layer was dried (MgSO$_4$), and the solid was filtered.

EXAMPLE 110

N,N'-bis{3-[(3,4-dimethyl-5-isoxazolyl)aminosulfonyl]thien-2-yl}urea

Triethylamine (1.4 ml, 9.93 mmol) and diphenylphosphorylazide (9.39 mg., 3.31 mmol) were sequentially added to a solution of N-(3,4-dimethyl-5-isoxazolyl)-2-(carboxyl)thiophene-3-sulfonamide (Example 17) (1.0 g, 3.31 mmol) in THF (50 ml). The resulting mixture was stirred for 30 minutes at room temperature and then refluxed for 1 hour. The mixture was allowed to cool to room temperature. THF was stripped off by use of a rotavap. The residue was partitioned between EtOAc and 1N HCl. The organic layer was dried (MgSO$_4$), the solid filtered, and the filtrate concentrated. N,N'-bis{3-[(3,4-dimethyl-5-isoxazolyl)aminosulfonyl]thien-2-yl}urea (140 mg, 14% yield) was obtained via HPLC purification as a pale powder, m.p. 112–114° C.

EXAMPLE 111

N,N'-bis{3-[(4-bromo-3-methyl-5-isoxazolyl)aminosulfonyl]thien-2-yl}urea

N,N'-bis{3-[(4-bromo-3-methyl-5-isoxazolyl)aminosulfonyl]thien-2-yl}urea was prepared by the same method as described in Example 110 with the exception that N-(4-bromo-3-methyl-5-isoxazolyl)-2-carboxythiophene-3-sulfonamide was used instead of N-(3,4-dimethyl-5-isoxazolyl)-2-carboxylthiophene-3-sulfonamide. N,N'-bis{3-[(4-bromo-3-methyl-5-isoxazolyl)aminosulfonyl]thien-2-yl}urea (80 mg, 15.5% yield) was obtained via HPLC purification as an off-white solid, m.p. 127–129° C.

EXAMPLE 112

N-(4-Bromo-3-methyl-5-isoxazolyl)-5-(benzyloxymethyl)thiophene-2-sulfonamide

A. 2-(benzyloxymethyl)thiophene

Sodium hydride (0.41 mg, 20 mmol) was added to a solution of 2-thiophene methanol (2.0 g, 0.18 mmol) in THF (20 ml) at −40° C. The reaction was stirred at −40° C. for 25 min., then neat benzylbromide (3.6 g, 20 mmol) was added by syringe. The solution was stirred at −40° C. for 0.5 hr, then at room temperature for 1 hr. The THF was evaporated off and the remaining residue was taken up in ether (~50 ml). The organic solution was washed with water (1×10 ml), brine (1×10 ml) and dried over MgSO$_4$. Evaporation of solvents left an oil which was purified by column chromatography using 1% ether-hexanes to give 2.6 g of the thiophene as a pale yellow oil (78% yield).

B. 2-chlorosulfonyl-5-(benzyloxymethyl)thiophene 2-chlorosulfonyl-5-(benzyloxymethyl)thiophene was prepared in the same manner as described in Example 132A from 2-(benzyloxymethyl)thiophene (1.0 g, 5.25 mmol). Purification by column chromatography using 2.5% ethyl acetate/hexanes gave 520 mg of the pure thiophene as a brown oil (32% yield).

C. N-(4-bromo-3-methyl-5-isoxazolyl)-5-(benzyloxymethyl)thiophene-2-sulfonamide

N-(4-bromo-3-methyl-5-isoxazolyl)-5-(benzyloxymethyl)thiophene-2-sulfonamide was prepared as described in Example 2 from 2-chlorosulfonyl-5-(benzyloxymethyl)thiophene (520 mg, 1.72 mmol) and 5-amino-4-bromo-3-methyl isoxazole (319 mg, 1.8 mmol). Purification by column chromatography using 10% MeOH/CHCl$_3$) gave 238 mg of pure N-(4-bromo-3-methyl-5-isoxazolyl)-5-(benzyloxymethyl)thiophene-2-sulfonamide as brown semisolid (31% yield, m.p. 92° C.).

EXAMPLE 113

N-(4-Chloro-3-methyl-5-isoxazolyl)-2-ethylbenzo[b]furan-3-sulfonamide

A. 2-Ethylbenzo[b]furan

2-Ethylbenzo[b]furan was prepared by the method of example 40A with benzo[b]furan (7.3 mmols), 0.86 g) t-BuLi (1.7 m, 9.4 mmols) iodoethane (4 mmols, 0.9 mls) and THF (15 ml). 1.0 g (95%) of a yellow liquid was isolated.

B. 2-Ethylbenzo[b]furan-3-sulfonyl chloride

2-Ethylbenzo[b]furan-3-sulfonyl chloride was prepared by the method of Example 82C with 2-ethylbenzo[b]furan (6.9 mmols, 1.0 g), chlorosulfonic acid (8.9 mmols, 0.6 ml) phosphorous oxychloride (21 mmols, 1.9 ml), phosphorous pentachloride (6.9 mmols, 1.4 g) and CH$_2$Cl$_2$ (10 ml). Flash chromatography (2% ethyl acetate/hexanes) provided 0.71 g (42%) of an orange solid.

C. N-(4-chloro-3-methyl-5-isoxazolyl)-2-ethylbenzol[b]furan-3-sulfonamide

N-(4-chloro-3-methyl-5-isoxazolyl)-2-ethylbenzo[b]furan-3-sulfonamide compound was prepared by the method of Example 41 with 4-chloro-3-methyl-5-amino-isoxazole (1.0 mmols, 0.13 g), NaH (2.5 mmols, 60 mg), 2-ethylbenzo[b]furan-3-sulfonyl chloride (1.2 mmols, 0.28 g) and THF (7 ml). Flash chromatography (20% ethyl acetate/hexanes) followed by recrystallization from chloroform and hexane provided 97 mg (28%) of a white solid, m.p. 132–133.5° C.

EXAMPLE 114

N-(4-Bromo-3-methyl-5-isoxazolyl)-2-[(3,4-methylenedioxy)benzyl])thiophene-3-sulfonamide A. N-(2-carbomethoxythiophene-3-sulfonyl)pyrrole N-(2-carbomethoxythiophene-3-sulfonyl)pyrrole was prepared in the same manner as described in Example 33A by reacting 2-carbomethoxythiophene-3-sulfonyl chloride with pyrrole, 50% yield.

B. N-[(2-hydroxymethyl)thiophene-3-sulfonyl]pyrrole

To a stirred solution of N-(2-carbomethoxythiophene-3-sulfonyl)pyrrole (3.0 g, 11.02 mmole) in a mixture of THF and methanol (3:1 mixture, 40 ml) was added sodium borohydride (1.2 g) in six lots over a 30 min. period (exothermic reaction) with constant stirring. The solvent was removed under reduced pressure and the residue was dissolved in saturated ammonium chloride solution (50 ml). The crude product was extracted with ethyl acetate, and the combined organic layers was dried over MgSO$_4$, and evaporated to give a crude product (2.4 g, 90%), which was used directly in the next step.

C. N-[2-(bromomethyl)thiophene-3-sulfonyl]pyrrole

Bromine was added to a stirred mixture of triphenylphosphine (3.1 g, 12 mmole) in methylene chloride (50 ml) at 0° C. under nitrogen atmosphere with stirring until the yellow color persisted. A few crystals of triphenylphosphine were added to consume excess bromine followed by pyridine (1.21 ml), and N-[(2-hydroxymethyl)-3-sulfonyl]pyrrole dissolved in methylene chloride (10 ml) was added. The reaction was stirred at 0° C. for 1 hr and concentrated to give a crude product. The crude product was purified by flash chromatography on silica gel using 10:1 hexane in ethyl acetate to give N-[2-(bromomethyl)thiophene-3-sulfonyl]pyrrole (2.7 g, 80% yield).

D. N-{2-[(3,4-methylenedioxy)benzyl]thiophene-3-sulfonyl]}pyrrole

N-{2-[(3,4-methylenedioxy)benzyl]thiophene-3-sulfonyl]}pyrrole was prepared in the same manner as described in Example 32C using N-[2-(bromomethyl)thiophene-3-sulfonyl]pyrrole and 3,4-methylenedioxyphenylboronic acid, 53% yield.

E. 3-chlorosulfonyl-2-[(3,4-methylenedioxy)benzyl]thiophene 3-chlorosulfonyl-2-(3,4-methylenedioxybenzyl)thiophene was prepared in the same manner as described in Example 65E from N-{2-[(3,4-methylenedioxy)benzyl]-3-sulfonyl}pyrrole by basic hydrolysis of the sulfonamide to the sodium salt of sulfonic acid and by conversion of this salt to the corresponding sulfonyl chloride, 54% yield.

F. N-(4-bromo-3-methyl-5-isoxazolyl)-2-[(3,4-methylenedioxybenzyl]thiophene-3-sulfonamide N-(4-bromo-3-methyl-5-isoxazolyl)-2-[(3,4-methylenedioxy)benzyl]thiophene-3-sulfonamide was prepared in the same manner as described in Example 2 by reacting 5-amino-4-bromo-3-methylisoxazole and 3-chlorosulfonyl-2-[(3,4-methylenedioxy)benzyl]thiophene. The crude product was purified by HPLC, 37% yield.

EXAMPLE 115

N-(4-Bromo-3-methyl-5-isoxazolyl)-5-(2-methoxyphenyl)thiophene-2-sulfonamide

A. N-[5-(2-methoxyphenyl)thiophene-2-sulfonyl]pyrrole

N-[5-(2-methoxyphenyl)thiophene-2-sulfonyl]pyrrole was prepared in the same manner as described in Example 32C using 2-methoxyphenylboronic acid and N-(5-bromothiophenesulfonyl)pyrrole, 74% yield.

B. 5-chlorosulfonyl-2-(2-methoxyphenyl)thiophene 5-chlorosulfonyl-2-(2-methoxyphenyl)thiophene was prepared in the same manner as described in Example 65E from N-[5-(2-methoxyphenyl)thiphene-2-sulfonyl]pyrrole by hydrolysis of the sulfonamide to the sodium salt of sulfonic acid (83%) followed by conversion of the salt to the corresponding sulfonyl chloride, resulting in a 24% yield.

C. N-(4-bromo-3-methyl-5-isoxazolyl)-5-(2-methoxyphenyl)thiophene-2-sulfonamide N-(4-bromo-3-methyl-5-isoxazolyl)-5-(2-methoxyphenyl)thiophene-2-sulfonamide was prepared in the same manner as described in Example 1. Reaction of 2-chlorosulfonyl-5-(2-methoxyphenyl)thiophene with 5-amino-4-bromo-3-methylisoxazole gave N-(4-bromo-3-methyl-5-isoxazolyl)-5-(2-methyoxyphenyl)thiophene-2-sulfonamide in 32% yield, m.p. 114–117° C.

EXAMPLE 116

N-(4-Bromo-3-methyl-5-isoxazolyl)-5-(2-tolyl)thiophene-2-sulfonamide

A. 2-(2-tolyl)thiophene

Sodium carbonate (5 ml., 2M aqueous solution) followed by 2-methylphenylboronic acid (0.294 g, 2.4 mmol) were added to a solution of 2-bromothiophene (0.542 g, 2 mmol) and tetrakis(triphenylphosphine)-palladium (0) (100 mg) in toluene (5 ml) and ethanol (5 ml) under nitrogen. The mixture was refluxed for 2 hours, cooled to room temperature and extracted with ethyl acetate (2×50 ml). The combined organic layers was dried over MgSO$_4$ and evaporated. The residue was flash chromatographed on silica gel using hexane as eluent to afford 1.2 g of 2-(2-tolyl)thiophene as a colorless gum.

B. 2-chlorosulfonyl-5-(2-tolyl)thiophene

To the cold (−5 to 0° C.) solution of 2-(2-tolyl)thiophene (0.87 g, 5 mmole) was added chlorosulfonic acid (0.33 ml, 5 mmole) over a 15 min. period with constant stirring. After 10 min., phosphorous oxychloride (2 ml) and phosphorous pentachloride were added. The reaction mixture was slowly allowed to attain ambient temperature and stirred for 3 hours. The mixture was then poured onto crushed ice (50 g) and was extracted with ethyl acetate (2×50 ml). The combined organic layers was dried over MgSO$_4$ and evaporated. The residue was purified by flash column chromatography on silica gel using 2% ethyl acetate in hexane to give 2-chlorosulfonyl-5-(2-tolyl)thiophene, (1.1 g, 72% yield).

C. N-(4-bromo-3-methyl-5-isoxazolyl)-5-(2-tolyl)thiophene-2-sulfonamide

N-(4-bromo-3-methyl-5-isoxazolyl)-5-(2-tolyl)thiophene-2-sulfonamide was prepared in the same manner as described in Example 2. Reaction of 5-chlorosulfonyl-2-(2-tolyl)thiophene with 5-amino-4-bromo-3-methylisoxazole gave the crude product which was purified by column chromatography giving the pure product (gum). This gum was dissolved in 5 ml of NH$_4$OH, concentrated and dried under high vacuum to get the ammonium salt of N-(4-bromo-3-methyl-5-isoxazolyl)-5-(2-tolyl)thiophene-2-sulfonamide in 67% yield, m.p. 180–184° C. (NH$_3^+$ salt).

EXAMPLE 117

N-(4-Bromo-3-methyl-5-isoxazolyl)-5-(3-tolyl)thiophene-2-sulfonamide

A. 2-(3-tolyl)thiophene 2-(3-tolyl)thiophene was prepared in the same manner as described in Example 117A using 2-bromothiophene and 3-methylphenylboronic acid. The crude product was purified by flash chromatography on silica gel using hexane as the eluent (86% yield).

B. 2-chlorosulfonyl-5-(3-tolyl)thiophene 2-chlorosulfonyl-5-(3-tolyl)thiophene was prepared in the same manner as described in Example 117B from 2-(3-tolyl)thiophene, 22% yield.

C. N-(4-bromo-3-methyl-5-isoxazolyl)-5-(3-tolyl)thiophene-2-sulfonamide

N-(4-bromo-3-methyl-5-isoxazolyl)-5-(3-tolyl)thiophene-2-sulfonamide was prepared in the same manner as described in the Example 117C using 2-chlorosulfonyl-5-(3-tolyl)thiophene and 5-amino-4-bromo-3-methylisoxazole. To obtain the ammonium salt of the final product, aqueous NH$_4$OH was used (31% yield; hygroscopic).

EXAMPLE 118

N-(4-Bromo-3-methyl-5-isoxazolyl)-3-benzylthiophene-2-sulfonamide

A. 3-benzylthiophene 3-benzylthiophene was prepared in the same manner as described in Example 32C using 3-thienylboronic acid and benzyl bromide, 74% yield.

B. 2-chlorosulfonyl-3-benzylthiophene 2-chlorosulfonyl-3-benzylthiophene was prepared in the same manner as described in Example 117B using 3-benzylthiophene, 78% yield.

C. N-(4-bromo-3-methyl-5-isoxazolyl)-3-benzylthiophene-2-sulfonamide

N-(4-bromo-3-methyl-5-isoxazolyl)-3-benzylthiophene-2-sulfonamide was prepared in the same manner as described in Example 2 by reacting 2-chlorosulfonyl-3-benzylthiophene with 5-amino-4-bromo-3-methylisoxazole resulting in a 24% yield, m.p. 180–183° C.

EXAMPLE 119

N-(4-Bromo-3-methyl-5-isoxazolyl)-5-(2-methylfuranyl)thiophene-2-sulfonamide

A. N-[5-(2-methyl-5-furyl)thiophene-2-sulfonyl]pyrrole t-BuLi (1.7 m solution in hexane, 7.9 ml, 14.6 mmol) was added dropwise under constant stirring under a nitrogen atmosphere to a solution of 2-methylfuran (1.0 g, 12 mmol) in THF (20 ml) at −78° C. The solution was then warmed to −10° C. and stirring continued for 45 min. The solution was then added to a solution of zinc chloride (27 ml of a 0.5 M solution in THF) at −30° C. and then warmed to room temperature where stirring continued for 1 hr. resulting in a pale yellow clear solution. The solution was then transferred via a steel canula under nitrogen to a solution of N-(5-bromothiophene-2-sulfonyl)pyrrole (Example 33A, 3.5 g, 12 mmol) and tetrakis(triphenylphosphine)-palladium (0) (693 mg, 0.6 mmol) in THF (15 ml) at −78° C. The solution was then wanned to room temperature and stirred for a period of 2 hours. Purification by column chromatography using 2% ethyl acetate gave 680 mg of N-[5-(2-methyl-5-furyl)thiophene-2-sulfonyl]pyrrole as a pale yellow powder (19% yield).

B. 2-(2-methyl-5-furyl)thiophene-5-sulfonyl chloride 2-(2-methyl-5-furyl)thiophene-5-sulfonyl chloride was prepared in the same manner as described in Example 33D from N-[5-(2-methyl-5-furyl)thiophene-2-sulfonyl]pyrrole (300 mg, 1.02 mmol). Purification by column chromatography using 2% ethyl acetate/hexanes gave 145 mg (53%) of the sulfonyl chloride as a pale yellow solid.

C. N-(4-bromo-3-methyl-5-isoxazolyl)-5-(2-methyl-5-furyl)thiophene-2-sulfonamide N-(4-bromo-3-methyl-5-isoxazolyl)-5-(2-methyl-5-furyl)thiophene-2-sulfonamide was prepared in the same manner as described in Example 2. Reaction of 2-(2-methyl-5-furyl)thiophene-5-sulfonyl chloride (55 mg, 0.21 mmol) with 5-amino-4-bromo-3-methylisoxazole (41 mg, 0.21 mmol), after purification by column chromatography using 10% MeOH/CHCl$_3$, gave 45 mg of the pure sulfonamide as a brown semisolid (54% yield, m.p. 123–124° C.).

EXAMPLE 120

N-(4-Bromo-3-methyl-5-isoxazolyl)-4-(phenethyl)thiophene-2-sulfonamide

N-(4-bromo-3-methyl-5-isoxazolyl)-4-(phenethyl)thiophene-2-sulfonamide was prepared in the same manner as described in Example 2 using 5-amino-4-bromo-3-methyl-isoxazole (132.75 mg, 0.75 mmole) and 4-(phenethyl)thiophene-2-sulfonyl chloride (Example 119D; 225.62 mg, 0.75 mmol). The product was purified by HPLC (5–95% acetonitrile with 0.1% TFA over 30 min.) to give N-(4-bromo-3-methyl-5-isoxazolyl)-4-(phenethyl)thiophene-2-sulfonamide as a brownish oil 72.3mg, 32% yield.

EXAMPLE 121

N-(3,4-dimethyl-5-isoxazolyl)-2-[(4-methylphenyl)aminocarbonyl]thiophene-3-sulfonamide Phosphonitrilic chloride trimer dissolved in THF (5 ml) was added to a suspension of N-(3,4-dimethyl-5-isoxazolyl)-2-(carboxyl)thiophene-3-sulfonamide (2.0 g, 6.6 mmol) (Example 28) in THF (5 ml) and Et$_3$N at 0° C. The cold bath was removed and the reaction mixture stirred at room temperature for 2 hours. The mixture was diluted with water (150 ml) and acidified to pH 2 using concentrated hydrochloric acid. The reaction mixture was then extracted with methylene chloride (2×100 ml), and the combined organic layers was washed with 2N hydrochloric acid (3×100 ml), dried over MgSO$_4$, and concentrated be get crude product. The crude product was dissolved in ether and allowed to stand at room temperature to give a precipitate which was filtered and washed with cold ether giving N-(3,4-dimethyl-5-isoxazolyl)-2-[(4-methylphenyl)aminocarbonyl]thiophene-3-sulfonamide (1.6 g, 61% yield).

EXAMPLE 122

N-(4-Bromo-3-methyl-5-isoxazolyl)-5-[(4-tolyl)aminocarbonyl]thiophene-2-sulfonamide N-(4-bromo-3-methyl-5-isoxazolyl)-5-[(4-tolyl)aminocarbonyl]thiophene-2-sulfonamide was prepared in the same manner as described in Example 24 from N-(4-bromo-3-methyl-5-isoxazolyl)-5-(4-carboxybenzene)thiophene-2-sulfonamide (Example 148), 110 mg, 0.25 mmol) and 4-methylaniline (53 mg, 0.49 mmol). Purification by recrystallization from methanol/water gave 91 mg of the pure sulfonamide as a light tan powder (61% yield, m.p. 188° C.).

EXAMPLE 123

N-(4-chloro-3-methyl-5-isoxazolyl)-2-[(4-tolyl)aminocarbonyl]thiophene-3-sulfonamide

A. N-(4-chloro-3-methyl-5-isoxazolyl)-2-(carboxyl)thiophene-3-sulfonamide

N-(4-chloro-3-methyl-5-isoxazolyl)-2-(carboxyl)thiophene-3-sulfonamide was prepared in the same manner as described in Example 17 using N-(4-chloro-3-methyl-5-isoxazolyl)-2-(carbomethoxy)thiophene-3-sulfonamide (Example 123), 78% yield.

B. N-(4-chloro-3-methyl-5-isoxazolyl)-2-[(4-tolyl)aminocarbonyl]thiophene-3-sulfonamide N-(4-chloro-3-methyl-5-isoxazolyl)-2-[(4-tolyl)aminocarbonyl]thiophene-3-sulfonamide was prepared in the same manner as described in Example 122 using N-(4-chloro-3-methyl-5-isoxazolyl)-2-(carboxyl)thiophene-3-sulfonamide. The crude product was dissolved in a small quantity of EtOAc (2 ml) and ether (15 ml) was added. The resulting precipitate was filtered and washed with cold ether (50 ml) giving N-(4-chloro-3-methyl-5-isoxazolyl)-2-[(4-tolyl)aminocarbonyl]thiophene-3-sulfonamide in 53% yield (m.p. 177–179°).

EXAMPLE 124

N-(4-Bromo-3-methyl-5-isoxazolyl)-2-[(N-methyl)-N-phenylaminocarbonyl]thiophene-3-sulfonamide A solution of N-(4-bromo-3-methyl-5-isoxazolyl)-2-(carboxyl)thiophene-3-sulfonamide (183.6 mg, 0.5 mmol) in dry THF (1 ml) was added to a solution of N-methyl-4-methylaniline (0.066 ml, 0.6 mmol) in THF (0.5 ml). Triethylamine (0.63 ml, 4.2 mmol) was added to the mixture and, after 10 min., a solution of phosphonitrilic chloride trimer (210.7 mg, 0.6 mmol) was added. The mixture was stirred for 1 hr. at 50° C., cooled, neutralized with 10 ml 1N HCl (pH 3) and extracted with ethyl acetate. The extract was dried over anhydrous magnesium sulfate and the solvent was removed under reduced pressure to give a crude product which was purified by HPLC (5–95% acetonitrile with 0.1% TFA over 30 min.) resulting in N-(4-bromo-3-methyl-5-isoxazolyl)-2-[(N-methyl)-N-phenylaminocarbonyl]thiophene-3-sulfonamide as a white solid (92.1 mg, 39.4% yield, m.p. 51–55° C.).

EXAMPLE 125

N-(4-Bromo-3-methyl-5-isoxazolyl)-3-[3,4-(methylenedioxy)phenyl]thiophene-2-sulfonamide

A. 3-bromothiophene-2-sulfonyl chloride

Chlorosulfonic acid (20 ml, 300 mmol) was added to a solution of 3-bromothiophene (8.15 g, 50 mmol) in methylene chloride (50 ml) at −78° C. over a 20 min. period. After the completion of addition, the cold bath was removed and stirring continued at ambient temperature for 1 hr. The reaction mixture was carefully added, dropwise, to crushed ice (100 g). The mixture was extracted with methylene chloride (2×100 ml). The combined organic layers was dried over MgSO$_4$ and evaporated. The crude product was purified by flash chromatography on silica gel using hexane as the eluent resulting in 3-bromothiophene-2-sulfonyl chloride (4 g, 30% yield) and 4-bromothiophene-2-sulfonyl chloride (200mg, ≦1%).

B. N-(3-bromothiophene-2-sulfonyl)pyrrole

N-(3-bromothiophene-2-sulfonyl)pyrrole was prepared in the same manner as described in Example 33A by reacting 3-bromothiophene-2-sulfonylchloride with pyrrole (for 16 hr.). N-(3-bromothiophene-2-sulfonyl)pyrrole was obtained in 54% yield.

C. N-{[3-(3,4-methylenedioxy)phenyl]thiophene-2-sulfonyl}pyrrole

N-{[3-(3,4-methylenedioxy)phenyl]thiophene-2-sulfonyl}pyrrole was prepared in the same manner as described in Example 32C using 3,4-methylenedioxyphenylboronic acid and N-(3-bromothiophene-2-sulfonyl)pyrrole. The crude product was purified by flash column chromatography on silica gel using 2% EtOAc in hexane as the eluent resulting in N-{[3-(3,4-methylenedioxy)phenyl]thiophene-2-sulfonyl}-pyrrole in a 90% yield.

D. 2-chlorosulfonyl-3-[3,4-(methylenedioxy)phenyl]thiophene 2-chlorosulfonyl-3-[3,4-(methylenedioxy)phenyl]thiophene was prepared in the same manner as described in Example 112B using N-{[3-(3,4-methylenedioxy)phenyl]thiophene-2-sulfonyl)pyrrole by basic hydrolysis of the sulfonamide to the sodium sulfonate (100% yield) followed by conversion of the salt to the corresponding sulfonyl chloride resulting in a 34% yield of the final product.

E. N-(4-bromo-3-methyl-5-isoxazolyl)-3-[3,4-(methylenedioxy)phenyl]thiophene-2-sulfonamide N-(4-bromo-3-methyl-5-isoxazolyl)-3-[3,4-(methylenedioxy)phenyl]thiophene-2-sulfonamide was prepared in the same manner as described in Example 1 by reaction of 2-chlorosulfonyl-3-[3,4-(methylenedioxy)phenyl]thiophene with 5-amino-4-bromo-3-methylisoxazole resulting in a 60% yield, m.p. 183–186° C.

EXAMPLE 126

N-(4-Bromo-3-methyl-5-isoxazolyl)-2-[(2-chloro-3,4-methylenedioxy)phenoxymethyl]thiophene-3-sulfonamide

A. N-{2-[(3,4-methylenedioxy)phenoxymethyl]thiophene-3-sulfonyl}pyrrole

Sodium hydride (100 mg, 5 mmole) was added to a stirred solution of 3,4-methylenedioxyphenol (0.607 g, 4.5 mmol) in DMF (dry, 5 ml) at 0° C. under a nitrogen atmosphere with stirring. The reaction mixture was permitted to attain room temp and stirring continued for 1 hr. The reaction mixture was cooled to 0° C. and N-[(2-bromomethyl)thiophene-3-sulfonyl]pyrrole was added. Stirring was continued at ambient temperature for 16 hr. The reaction mixture was diluted with water (100 ml), extracted with ethyl acetate (2×50 ml) and washed with 1N NaOH (2×25 ml) to remove phenol derivative. The mixture was dried over MgSO$_4$ and concentrated resulting in N-{2-[(3,4-methylenedioxy)phenoxymethyl]thiophene-3-sulfonyl}pyrrole, which was recrystallized using hexane/EtOAc (1.0 g, 92% yield).

B. 3-chlorosulfonyl-2-[(2-chloro-3,4-methylenedioxy)phenoxymethyl]thiophene 3-chlorosulfonyl-2-[(2-chloro-3,4-methylenedioxy)phenoxymethyl]thiophene was prepared in the same manner as described in Example 64E using N-{2-[(3,4-methylenedioxy)phenoxymethyl]thiophene-3-sulfonyl}pyrrole by conducting a basic hydrolysis (using potassium hydroxide in iso-propanol) to the potassium sulfonate followed by conversion of the salt to the corresponding sulfonyl chloride in an overall yield of 50%.

C. N-(4-bromo-3-methyl-5-isoxazolyl)-2-[(2-chloro-3,4-methylenedioxy)phenoxymethyl]thiophene-3-sulfonamide N-(4-bromo-3-methyl -5-isoxazolyl)-2-[(2-chloro-3,4-methylenedioxyphenoxy)methyl]thiophene-3-sulfonamide was prepared in the same manner as described in Example 1 by reaction of 3-chlorosulfonyl-2-[(2-chloro-3,4-methylenedioxyphenoxy)methyl]thiophene with 5-amino-4-bromo-3-methylisoxazole, 47% yield, m.p. 152–154° C.

EXAMPLE 127

N-(4-Bromo-3-methyl-5-isoxazolyl)-2-[trans-3,4-(methylenedioxy)cinnamyl]thiophene-3-sulfonamide

A. Diethyl 2-{3-[(N-pyrrolyl)sulfonyl]thienylmethyl}phosphonate

N-[2-bromomethyl)thiophene-3-sulfonyl]pyrrole (0.915 g, 3 mmol) was suspended in triethylphosphite (5 ml) and was heated to 140° C. for 1 hr. with stirring under nitrogen atmosphere. Excess triethylphosphate was removed under reduced pressure and the residue was dried under vacuum resulting in 0.9 g, 83% yield of diethyl 2-{3-[(N-pyrrolyl)sulfonyl]thienylmethyl}phosphonate.

B. N-{2-[trans-3,4-(methylenedioxy)cinnamyl]thiophene-3-sulfonyl}pyrrole

Sodium hydride (200 mg, 60% dispersion) was added in two lots to the stirred solution of diethyl 2-{3-[(N-pyrrolyl)sulfonyl]thienylmethyl}phosphonate (900 mg, 2.48 mmol) in dry THF (10 ml) at 0° C. The mixture was stirred at room temperature for 1 hr. then piperonal (600 mg) was added. Stirring was continued for 12 hours. The mixture was diluted with water (100 ml) and extracted with methylene chloride (2×50 ml). The combined organic layers was dried over MgSO$_4$, evaporated, and the residue was flash chromatographed on silica gel using 0.5% ethyl acetate in hexane to give N-{2-[trans-(3,4-methylenedioxy)cinnamyl]thiophene-3-sulfonyl}pyrrole (750 mg, 84% yield).

C. 3-chlorosulfonyl-2-[trans-3,4-(methylenedioxy)cinnamyl]thiophene 3-chlorosulfonyl-2-[trans-3,4-(methylenedioxy)cinnamyl]thiophene was prepared in the same manner as described in Example 64E from N-{2-[trans-3,4-

(methylenedioxy)cinnamyl]thiophene-3-sulfonyl}pyrrole by basic hydrolysis (using isopropanol and potassium hydroxide) to the corresponding potassium sulfonate (100%) followed by conversion of the salt to the corresponding sulfonyl chloride in a 31% overall yield.

D. N-(4-bromo-3-methyl-5-isoxazolyl)-2-[trans-3,4-(methylenedioxy)cinnamyl]thiophene-3-sulfonamide N-(4-bromo-3-methyl-5-isoxazolyl)-2-[trans-3,4-(methylenedioxy)cinnamyl]thiophene-3-sulfonamide was prepared in the same manner as described in Example 1 by reaction of 3-chlorosulfonyl-2-[trans-3,4-(methylenedioxy)cinnamyl]thiophene with 5-amino-4-bromo-3-methylisoxazole. The crude product was purified by HPLC resulting in a 33% yield, m.p. 147–149° C.

EXAMPLE 128

N-(4-Bromo-3-methyl-5-isoxazolyl)-2-[3,4-(methylenedioxy)phenethyl]thiophene-3-sulfonamide A. N-{2-[3,4-(methylenedioxy)phenethyl]thiophene-3-sulfonyl}pyrrole An ethyl acetate (15 ml) solution of N-{2-[trans-3,4-(methylenedioxy)cinnamyl]thiophene-3-sulfonyl}pyrrole (Example 127B, 0.6 g, 1.67 mmol) was subjected to catalytic hydrogenation using 10% Pd—C (100 mg) at 55 psi for 14 hr. The catalyst was filtered and the filtrate concentrated to resulting in N-{2-[3,4-(methylenedioxy)phenethyl]thiophene-3-sulfonyl}pyrrole (0.55 g, 91% yield).

B. 3-chlorosulfonyl-2-[3,4-(methylenedioxy)phenethyl]thiophene 3-chlorosulfonyl-2-[3,4-(methylenedioxy)phenethyl]thiophene was prepared in the same manner as described in the Example 64E using N-{2-[3,4-(methylenedioxy)phenethyl]thiophene-3-sulfonyl}pyrrole by conducting basic hydrolysis (iso-propanol and potassium hydroxide) of the sulfonamide to the potassium salt of sulfonic acid (93%) followed by conversion of the salt to the corresponding sulfonyl chloride in a 42% yield.

C. N-(4-bromo-3-methyl-5-isoxazolyl)-2-[3,4-(methylenedioxy)phenethyl]thiophene-3-sulfonamide N-(4-bromo-3-methyl-5-isoxazolyl)-2-[3,4-(methylenedioxy)phenethyl]thiophene-3-sulfonamide was prepared in the same manner as described in Example 2. By reacting 3-chlorosulfonyl-2-[3,4-(methylenedioxy)phenethyl]thiophene with 5-amino-4-bromo-3-methylisoxazole and purifying the crude product by HPLC, N-(4-bromo-3-methyl-5-isoxazolyl)-2-[3,4-(methylenedioxy)phenethyl]thiophene-3-sulfonamide was obtained in a 30% yield, m.p. 180° (dec.).

EXAMPLE 129

N-(4-Bromo-3-methyl-5-isoxazolyl)-3-(phenylthio)thiophene-2-sulfonamide

A. 3-phenylthiothiophene-2-sulfonyl chloride

A stirred solution of 3-(phenylthio)thiophene (1.0 g, 5.2 mmol) in 5 ml of dry THF was placed under an argon atmosphere and cooled to −78° C. n-butyl lithium (2.78 ml of 2.3M solution) was added over 20 min. and stirring was continued at this temperature for an additional 20 min. Sulfur dioxide gas was then bubbled in at −78° C. for a period of 30 min., resulting in the formation of a yellow precipitate. This was immediately followed by dropwise addition of N-chlorosuccinimide (764 mg, 5.72 mmol) dissolved in THF. The mixture was warmed to room temperature and stirring continued for an additional 1.5 hr. The mixture was then concentrated and the residue dissolved in ether. The organic layer was washed with water, brine solution and dried over magnesium sulfate. Evaporation of solvents left a light brown oil which was subjected to flash chromatography. Elution with 2% ethylacetate-hexanes gave 840 mg (56%) of a pale yellow solid.

B. N-(4-bromo-3-methyl-6-isoxazolyl)-3-(phenylthio)thiophene-2-sulfonamide

N-(4-bromo-3-methyl-6-isoxazolyl)-3-(phenylthio)thiophene-2-sulfonamide was prepared in the same manner as described in Example 2 using 5-amino-4-bromo-3-methylisoxazole (192 mg, 1.1 mmol) and 3-phenylthiothiophene-2-sulfonyl chloride (300 mg, 1.0 mmol). Purification by column chromatography using 10% MeOH/CHCl$_3$ yielded 358 mg (83%) of the pure sulfonamide as a brown oil.

EXAMPLE 130

N-(3,4 dimethyl-5-isoxazolyl)-3-(phenylaminocarbonyl)thiophene-2-sulfonamide

A. N-(3,4-dimethyl-5-isoxazolyl)thiophene-2-sulfonamide

N-(3,4-dimethyl-5-isoxazolyl)thiophene-2-sulfonamide was prepared in the same manner as described in Example 14 using thiophene-2-sulfonyl chloride and 3,4-dimethylaminoisoxazole. Purification by column chromatography using 3% MeOH/CHCl$_3$ yielded 48% N-(3,4-dimethyl-5-isoxazolyl)thiophene-2-sulfonamide.

B. N-(methyoxyethoxymethyl)-N-(3,4-dimethyl-5-isoxazolyl)thiophene-2-sulfonamide N-(methyoxyethoxymethyl)-N-(3,4-dimethyl-5-isoxazolyl)thiophene-2-sulfonamide was prepared in the same manner as described in Example 32B using N-(3,4-dimethyl-5-isoxazolyl)thiophene-2-sulfonamide and methoxyethoxymethyl chloride resulting in 34% yield. HPLC analysis of the crude oil obtained after workup showed that the oil was approximately 96% pure and so was used in the next step without further purification.

C. N-(methyoxyethoxymethyl)-N-(3,4-dimethyl-5-isoxazolyl)-5-trimethylsilyl)thiophene-2-sulfonamide A stirred solution of N-(methoxyethoxymethyl)-N-(3,4-dimethyl-5-isoxazolyl)thiophene-2-sulfonamide (300 mg, 0.87 mmol) in 5.0 ml of dry THF was placed under an argon atmosphere and cooled to −78° C. Over the course of 20 min, a solution of t-BuLi in hexanes (461 ml of a 2.25 M solution) was added dropwise and stirring was continued at this temperature for about 25 min. Then neat trimethylsilyl-chloride (135 ml, 1 mmol) was added dropwise and the solution was stirred at −78° C. for 15 min. then at room temp. for 1.5 hr. TLC (1% CHCl$_3$ in MeOH) showed complete reaction of starting material at this time thus, the reaction was quenched by addition of 2.0 ml of water. After evaporation of solvents the remaining residue was extracted into ethyl acetate, washed with brine solution and dried over magnesium sulfate. Purification by column chromatography using 20% ethyl acetate/hexanes gave the pure sulfonamide as a clear oil (52% yield).

D. N-(methoxyethoxymethyl)-N-(3,4-dimethylisoxazolyl)-3-(phenylaminocarbonyl)-5-(trimethylsilyl)thiophene-2-sulfonamide A stirred solution of N-(methyoxyethoxymethyl)-N-(3,4-dimethyl-5-isoxazolyl)-5-trimethylsilyl)thiophene-2-sulfonamide (180 mg, 0.43 mmol) in 4 ml of dry THF was placed under an argon atmosphere and cooled to −78° C. At this temperature a solution of t-BuLi in hexanes (215 µl at a 2.55 M solution) was added dropwise and stirring was continued at −78° C. for 0.5 hr. resulting in a clear yellow solution. Phenylisocyanate (77 µl, 0.65 mmol) was added dropwise at −78° C. and the solution allowed to reach room temperature. The solution was then worked up as above in part C. Purification of the final product was achieved by column chromatography using 30% ethyl acetate/hexanes to give 108 mg of the sulfonamide a 54% yield.

E. N-(3,4 dimethyl-5-isoxazolyl)-3-(phenylaminocarbonyl)thiophene-2-sulfonamide N-(3,4 dimethyl-5-isoxazolyl)-3-(phenylaminocarbonyl)thiophene-2-sulfonamide was prepared in the same manner as described in Example 32D using N-(methoxyethoxymethyl)-N-(3,4-dimethylisoxazolyl)-3-(N-phenylcarboxamide-5-trimethylsilyl)thiophene-2-sulfonamide (108 mg, 0.23 mmol). Purification was achieved by recrystallization from acetonitrile/water to give 62 mg (71% yield) N-(3,4 dimethyl-5-isoxazolyl)-3-(phenylaminocarbonyl)thiophene-2-sulfonamide as a brown powder, m.p. 152° C.

EXAMPLE 131

N-(3,4-dimethyl-5-isoxazolyl)-2-(α-hydroxybenzyl)thiophene-3-sulfonamide

A. Thiophene-3-sulfonyl chloride n-BuLi (2.38M, 17 ml) was slowly added to a solution of 3-bromothiophene (6.5 g, 40 mmol) in ether (30 ml) at −78° C. The reaction was stirred at −78° C. for 45 min. $SO_2$ was bubbled through the mixture for 15 minutes at −78° C. followed by the addition of NCS (6.4 g, 48 mmol) as a suspension in THF (40 ml). The crude product was purified by column chromatography using 5% ethyl acetate/hexanes to give 3.92 g thiophene-3-sulfonyl chloride as a pale yellow solid (54% yield).

B. N-(3,4-dimethyl-5-isoxazolyl)thiophene-3-sulfonamide

N-(3,4-dimethyl-5-isoxazolyl)thiophene-3-sulfonamide was prepared in the same manner as described in Example 14 using thiophene-3-sulfonyl chloride and 3,4-dimethylaminoisoxazole resulting in 66% yield as a pale brown solid.

C. 2-[2-(trimethylsilyl)ethoxymethyl]-N-(3,4-dimethyl-5-isoxazolyl)thiophene-3-sulfonamide N,N-diisoproplyethylamine (222 µl, 128 mmol) was added to a solution of N-(3,4-dimethyl-5-isoxazolyl)thiophene-3-sulfonamide (300 mg, 1.16 mmol) in methylene chloride (5 ml), and the mixture was stirred at room temperature for 15 min. The mixture was then cooled to 0° C. and 2-(trimethylsilyl)ethoxy methyl chloride (SEM chloride) (226,µl, 1.28 mmol) was added dropwise via syringe, and the resultant yellow solution was stirred at room temperature for 5 hours. Evaporation of solvents left an oil which was extracted into ethyl acetate, washed with water and brine solution and dried over magnesium sulfate. Flash chromatography of the residue using 10% ethyl acetate/hexanes yielded 321 mg 2-[2-(trimethylsilyl)ethoxymethyl]-N-(3,4-dimethyl-5-isoxazolyl)thiophene-3-sulfonamide as a clear colorless oil which solidified into a white solid upon standing (71% yield).

D. 2-[2-(trimethylsilyl)ethoxymethyl]-N-(3,4-dimethyl-5-isoxazolyl)-2-(α-hydroxybenzyl)thiophene-3-sulfonamide n-BuLi (2.39 M, 177 µl) was slowly added to a solution of (2-trimethylsilylethoxymethyl)-N-(3,4-dimethyl-5-isoxazolyl)thiophene-3-sulfonamide (156 mg, 0.38 mmol) in THF at −78° C. under nitrogen. The reaction was stirred at −78° C. for 45 min., then benzaldehyde (45 µl, 0.42 mmol) was added in one lot at −78° C. and the solution was allowed to come to room temperature. Stirring was continued for 1 hr. Purification was achieved by column chromatography using 10% ethyl acetate/hexanes to give 179 mg 2-[2-(trimethylsilyl)ethoxymethyl]-N-(3,4-dimethyl-5-isoxazolyl)-2-(α-hydroxybenzyl)thiophene-3-sulfonamide as a yellow viscous oil (90% yield).

E. N-(3,4-dimethyl-5-isoxazolyl)-2-(α-hydroxybenzyl)thiophene-3-sulfonamide To a solution of 2-[2-(trimethylsilyl)ethoxymethyl]-N-(3, 4-dimethyl-5-isoxazolyl)-2-(α-hydroxybenzyl)thiophene-3-sulfonamide (70 mg, 0–14 mmol) in DMF (2 ml) was added cesium fluoride (26 mg, 0.17 mmole) in one portion. The resulting mixture was heated to 100° C. for 10 hours. The solvents were removed by evaporation under vacuum and the remaining residue was extracted into ethyl acetate, washed with water, brine, and dried over $MgSO_4$. The product was then purified by chromatography using 50–70% ethyl acetate/hexanes to give 26.2 mg N-(3,4-dimethyl-5-isoxazolyl)-2-(α-hydroxybenzyl)thiophene-3-sulfonamide as a pale white semisolid (51% yield).

EXAMPLE 132

N-(4-Bromo-5-methyl-3-isoxazolyl)-5-(4-methylphenyl)thiophene-2-sulfonamide

A. N-[5-(4-methylphenyl)thiophene-2-sulfonyl]pyrrole

N-[5-(4-methylphenyl)thiophene-2-sulfonyl]pyrrole was prepared in the same manner as described in Example 32C using 4-methyl-phenylboronic acid and N-(5-bromothiophenesulfonyl)pyrrole. Purification by column chromatography using 2% ethyl acetate/hexanes gave N-[5-(4-methylphenyl)thiophene-2-sulfonyl]pyrrole as a pale yellow solid in 77% yield.

B. 2-chlorosulfonyl-5-(4-methylphenyl)thiophene 2-chlorosulfonyl-5-(4-methylphenyl)thiophene was prepared in the same manner as described in Example 33D using N-[5-(4-methylphenyl)thiophene-2-sulfonyl]pyrrole. Purification by column chromatography using 2% ethyl acetate/hexanes gave 2-chlorosulfonyl-5-(4-methylphenyl)thiophene as a pale yellow powder (61% yield).

C. N-(4-bromo-3-methyl-5-isoxazolyl)-5-(4-methylphenyl)thiophene-2-sulfonamide N-(4-bromo-3-methyl-5-isoxazolyl)-5-(4-methylphenyl) thiophene-2-sulfonamide was prepared in the same manner as described in Example 2. Reaction of 2-chlorosulfonyl-5-(4-methylphenyl)thiophene (100 mg, 0.37 mmol) with 5-amino-4-bromo-3-methylisoxazole (65 mg, 0.37 mmol) yielded, after column chromatography using 10% MeOH/CHCl$_3$, 96 mg final product as a pale yellow solid, (63% yield, m.p. 175° C.).

EXAMPLE 133

N-(4-Bromo-3-methyl-5-isoxazolyl)-5-(4-phenyl)thiophene-2-sulfonamide

A. N-(pyrrole)-5-(4-phenyl)thiophene-2-sulfonamide

N-(pyrrole)-5-(4-phenyl)thiophene-2-sulfonamide was prepared in the same manner as described in Example 32C using phenyl boronic acid and N-(5-bromothiophenesulfonyl)pyrrole. Purification by column chromatography using 2% ethyl acetate/hexanes gave the pure sulfonamide as a yellow powder in 67% yield.

B. 2-chlorosulfonyl-5-(4-phenyl)thiophene 2-chlorosulfonyl-5-(4-phenyl)thiophene was prepared in the same manner as in Example 33D from N-(pyrrole)-5-(4-phenyl)thiophene-2-sulfonamide. Purification by column chromatography using 2% ethyl acetate/hexanes gave the pure thiophene in 77% yield as a yellow powder.

C. N-(4-bromo-3-methyl-5-isoxazolyl)-5-(4-phenyl)thiophene-2-sulfonamide

N-(4-bromo-3-methyl-5-isoxazolyl)-5-(4-phenyl) thiophene-2-sulfonamide was prepared in the same manner as described in Example 2. Reaction of 2-chlorosulfonyl-5-(4-phenyl)thiophene (94 mg, 0.36 mmol) with 5-amino-4-bromo-3-methyl isoxazole (64 mg, 0.36 mmol) yielded after column chromatography using 10% MeOH/CHCl$_3$, 85 mg of N-(4-bromo-3-methyl-5-isoxazolyl)-5-(4-phenyl) thiophene-2-sulfonamide as a light brown solid, (59% yield, m.p. 132° C.).

EXAMPLE 134

N-(4-bromo-3-methyl-5-isoxazolyl)-5-[4-(trifluoromethyl)phenyl]thiophene-2-sulfonamide

A. N-{5-[4-(trifluoromethyl)phenyl]thiophene-2-sulfonyl}pyrrole

N-{5-[4-(trifluoromethyl)phenyl]thiophene-2-sulfonyl}pyrrole was prepared in the same manner as described in Example 32C using 4-trifluoromethylbenzene boronic acid and N-(5-bromothiophene sulfonyl)pyrrole. Purification by column chromatography using 2% ethyl acetate/hexanes gave the pure sulfonamide as a white powder in 75% yield.

B. 2-chlorosulfonyl-5-[4-(trifluoromethyl)phenyl]thiophene 2-chlorosulfonyl-5-[4-(trifluoromethyl)phenyl]thiophene was prepared in the same manner as Example 33D from N-{5-[4-(trifluoromethyl)phenyl]thiophene-2-sulfonyl}pyrrole. Purification by column chromatography using 2% ethyl acetate/hexanes gave the pure thiophene as a white powder in 41% yield.

C. N-(4-bromo-3-methyl-5-isoxazolyl)-5-[4-(trifluoromethyl)phenyl]thiophene-2-sulfonamide N-(4-bromo-3-methyl-5-isoxazolyl)-5-[4-(trifluoromethyl)phenyl]thiophene-2-sulfonamide was prepared in the same manner as described in Example 2. Reaction of 2-chlorosulfonyl-5-[4-(trifluoromethyl)phenyl] thiophene (100 mg, 0.31 mmol) with 5-amino-4-bromo-3-methyl isoxazole (54 mg, 0.31 mmol) yielded, after column chromatography, 39 mg of N-(4-bromo-3-methyl-5-isoxazolyl)-5-[4-(trifluoromethyl)phenyl]thiophene-2-sulfonamide as a pale yellow powder, (27% yield, m.p. 132° C.).

EXAMPLE 135

N-(4-Bromo-3-methyl-5-isoxazolyl)-5-(2-formylphenyl)thiophene-2-sulfonamide

A. N-(3-methyl-5-isoxazolyl)-5-bromothiophene-2-sulfonamide

N-(3-methyl-5-isoxazolyl)-5-bromothiophene-2-sulfonamide was prepared in the same manner as described in Example 14 from 5-bromothiophene-2-sulfonyl chloride and 5-amino-3-methyl isoxazole. Purification was achieved by extraction of the crude sulfonamide into aqueous 2N NaOH, washing of the aqueous layer with ethyl acetate and acidification, using concentrated HCl, to pH~2. Re-extraction into ethyl acetate was followed by washing of the organic material with water, brine and drying over magnesium sulfate. After evaporation of solvents, a brownish solid remained which was sufficiently pure to use in the next step.

B. N-(3-methyl-5-isoxazolyl)-5-(2-formylphenyl)thiophene-2-sulfonamide

N-(3-methyl-5-isoxazolyl)-5-(2-formylphenyl)thiophene-2-sulfonamide was prepared in the same manner as described in Example 32C from 2-formylbenzeneboronic acid (281 mg, 1.87 mmol) and N-(3-methyl-5-isoxazolyl)-5-bromothiophene-2-sulfonamide (550 mg, 1.7 mmol). Purification by column chromatography using 15% MeOH/CHCl$_3$ gave 163 mg (28%) of the pure sulfonamide as a brown oil.

C. N-(4-bromo-3-methyl-5-isoxazolyl)-5-(2-formylphenyl)thiophene-2-sulfonamide N-bromosuccinamide (81 mg, 0.45 mmol) was added to a solution of N-(3-methyl-5-isoxazolyl)-5-(2-formylphenyl) thiophene-2-sulfonamide (155 mg, 0.45 mmol) in CHCl$_3$ (5 ml). The resulting brownish solution was stirred at room temperature for 3 hours. The solvent was stripped off and the material extracted into ethyl acetate and washed with brine solution. Evaporation of solvents gave 85 mg of the product (45% yield). A portion of this was further purified by preparative HPLC. N-(4-bromo-3-methyl-5-isoxazolyl)-5-(2-formylphenyl)thiophene-2-sulfonamide was isolated as a pale brown oil.

EXAMPLE 136

N-(4-Bromo-3-methyl-5-isoxazolyl)-5-(3-aminophenyl)thiophene-2-sulfonamide

A. N-(3-methyl-5-isoxazolyl)-5-(3-aminophenyl)thiophene-2-sulfonamide

N-(3-methyl-5-isoxazolyl)-5-(3-aminophenyl)thiophene-2-sulfonamide was prepared in the same manner as described in Example 32C from 3-amino benzene boronic acid (256 mg, 1.87 mmol) and N-(3-methyl-5-isoxazolyl)-5-bromothiophene-2-sulfonamide (55 mg, 1.7 mmol). Purification by column chromatography using 15% MeOH/CHCl₃ gave 318 mg (56%) of the product.

B. N-(4-bromo-3-methyl-5-isoxazolyl)-5-(3-aminophenyl)thiophene-2-sulfonamide N-(4-bromo-3-methyl-5-isoxazolyl)-5-(3-aminophenyl)thiophene-2-sulfonamide was prepared in the same manner as described in Example 30A (without acetic acid) using N-(3-methyl-5-isoxazolyl)-5-(3-aminophenyl)thiophene-2-sulfonamide resulting in a 33% yield. Further purification was achieved using preparative HPLC giving pure N-(4-bromo-3-methyl-5-isoxazolyl)-5-(3-aminophenyl) thiophene-2-sulfonamide as a clear colorless oil.

EXAMPLE 137

N-(4-Bromo-3-methyl-5-isoxazolyl)-5-(3,3-dimethylbutyn-1-yl)thiophene-2-sulfonamide

A. N-[5-(3,3-dimethylbutyn-1-yl)thiophene-2-sulfonyl]pyrrole

A mixture of N-(5-bromothiophene-2-sulfonyl)pyrrole (600 mg, 2.05 mmol), 3,3-dimethyl-1-butyne (338 mg, 4.1 mmol), copper iodide (39 mg, 0.21 mmol), tetrakistriphenylphosphine palladium [Pd(PPh₃)₄] (118 mg, 0.1 mmol) and piperidine (5 ml) was stirred at room temperature for a period of 24 hours under a nitrogen atmosphere. The mixture was then diluted with water (10 ml) and extracted with 3×25 ml portions of ether. The combined ether extracts are washed with brine and dried over MgSO₄. The solvent was removed under reduced pressure and crude product purified by column chromatography using 2% ethyl acetate/hexanes to give 423 mg N-[5-(3,3-dimethylbutyn-1-yl)thiophene-2-sulfonyl]pyrrole as a yellow powder (70% yield).

B. 2-chlorosulfonyl-5-(3,3-dimethylbutyn-1-yl)thiophene 2-chlorosulfonyl-5-(t-butylethynyl)thiophene was prepared in the same manner as described in Example 33D from N[5-(3,3-dimethylbutyn-1-yl)thiophene-2-sulfonamide. Purification by column chromatography using 2% ethyl acetate/hexanes gave the pure sulfonamide in 33% yield.

C. N-(4-bromo-3-methyl-5-isoxazolyl)-5-(3,3-dimethylbutyn-1-yl)thiophene-2-sulfonamide N-(4-bromo-3-methyl-5-isoxazolyl)-5-(3,3-dimethylbutyn-1-yl)thiophene-2-sulfonamide was prepared in the same manner as described in Example 2. Reaction of 2-chlorosulfonyl-5-(3,3-dimethylbutyn-1-yl)thiophene (120 mg. 0.46 mmol) with 5-amino-4-bromo-3-methylisoxazole (85 mg, 0.48 mmol) yielded, after column chromatography using 10% MeOH/CHCl₃, 116 mg N-(4-bromo-3-methyl-5-isoxazolyl)-5-(3,3-dimethylbutyn-1-yl)thiophene-2-sulfonamide as a viscous clear oil (63%).

EXAMPLE 138

N-(4-Bromo-3-methyl-5-isoxazolyl)-5-[3,5-bis(trifluoromethyl)phenyl]thiophene-2-sulfonamide

A. N-{5-[3,5-bis(trifluoromethyl)phenyl]thiophene-2-sulfonyl}pyrrole

N-{5-[3,5-bis(trifluoromethyl)phenyl]thiophene-2-sulfonyl}pyrrole was prepared in the same manner as described in Example 32C from 3,5-bis(trifluoromethyl)benzeneboronic acid (619 mg, 2.26 mmol) and N-[5-bromothiophene-2-sulfonyl]pyrrole (60 mg, 2.05 mmol). Purification by column chromatography using 2% ethyl acetate/hexanes gave the pure sulfonamide as a white solid in 93% yield.

B. 2-chlorosulfonyl-5-[3,5-bis(trifluoromethyl)phenyl]thiophene 2-chlorosulfonyl-5-[3,5-bis(trifluoromethyl)phenyl]thiophene was prepared in the same manner as described in Example 33D from N-{5-[3,5-bis(trifluoromethyl)phenyl]thiophene-2-sulfonyl}pyrrole. Purification by column chromatography using 2% ethyl acetate/hexanes gave the pure thiophene in 73% yield as a brownish clear oil.

C. N-(4-bromo-3-methyl-5-isoxazolyl)-5-[3,5 bis(trifluoromethyl)phenyl]thiophene-2-sulfonamide N-(4-bromo-3-methyl-5-isoxazolyl)-5-[3,5 bis(trifluoromethyl)phenyl]thiophene-2-sulfonamide was prepared in the same manner as in Example 2. Reaction of 2-chlorosulfonyl-5-[3,5-bis(trifluoromethyl)phenyl] thiophene (250 mg, 0.63 mmol) with 5-amino-4-bromo-3-methylisoxazole (118 mg, 0.67 mmol) yielded, after column chromatography using 5% MeOH/CHCl₃, 115.2 mg N-(4-bromo-3-methyl-5-isoxazolyl)-5-[3,5 bis(trifluoromethyl)phenyl]thiophene-2-sulfonamide as a white powder (34% yield). A portion of this sample was further purified by preparative HPLC, m.p. 140° C.

EXAMPLE 139

N-(4-Bromo-3-methyl-5-isoxazolyl)-5-(5-methyl-2-thienyl)thiophene-2-sulfonamide

A. 2-methylthiophene-5-boronic acid n-BuLi (2.38 M, 16 ml) was slowly added to a solution of 2-methyl thiophene (3.0 g, 31 mmol) in THF (20 ml) at −78° C. The solution was kept at −78° C. for 10 min. then warmed to 0° C. for an additional 0.5 hr. The solution was then transferred by steel canula under nitrogen into a vessel containing triisopropylborate (6.3 g, 33 mmol) in ether (15 ml) at −78° C. The resulting milky white solution was stirred at −78° C. for 20 min. then at room temperature for 2 hours. The reaction was quenched by the addition of 10% aqueous HCl (5.0 ml) and the solution was extracted into ether. The combined ether extracts were extracted with 10 M NaOH (2×30 ml), the aqueous extracts were acidified with dilute HCl to pH 2 and extracted into ether (3×25 ml). The combined ether extracts were washed once with water (10 ml), once with brine (10 ml) and dried and evaporated to give 3.91 g 2-methylthiophene-5-boronic acid as a light brown solid. This was used in the next step with no further purification.

B. N-[5-(5-methyl-2-thienyl)thiophene-2-sulfonyl]pyrrole

N-[5-(5-methyl-2-thienyl)thiophene-2-sulfonyl]pyrrole was prepared in the same manner as described in Example 32C from 2-methylthiophene-5-boronic acid and N-(5-bromothiophene-2-sulfonyl)pyrrole. Purification by column chromatography using 2% ether/hexanes gave the pure sulfonamide in 72% yield as a white solid.

C. 2-chlorosulfonyl-5-(5-methyl-2-thienyl)thiophene 2-chlorosulfonyl-5-(5-methyl-2-thienyl)thiophene was prepared in the same manner as described in Example 33D from N-[5-(5-methyl-2-thienyl)thiophene-2-sulfonyl]pyrrole (570 mg, 1.84 mmol). Purification by column chromatography using 2% ethyl acetate/hexanes gave 258 mg (50%) of the sulfonyl chloride as a light green solid.

D. N-(4-bromo-3-methyl-5-isoxazolyl)-5-(5-methyl-2-thienyl)thiophene-2-sulfonamide N-(4-bromo-3-methyl-5-isoxazolyl)-5-(5-methyl-2-thienyl)thiophene-2-sulfonamide was prepared in the same manner as described in Example 2. Reaction of 2-chlorosulfonyl-5-(5-methyl-2-thienyl)thiophene (200 mg, 0.72 mmol) with 5-amino-4-bromo-3-methylisoxazole (127 mg, 0.72 mmol) yielded 273 mg (90%) of the crude sulfonamide. After passing through a small plug of silica gel, a portion of the product was further purified by preparative HPLC to give the pure sulfonamide as a white powder, m.p. 161–162° C.

EXAMPLE 140

N-(4-Bromo-3-methyl-5-isoxazolyl)-5-(5-ethyl-2-thienyl)thiophene-2-sulfonamide

A. 2-ethylthiophene-5-boronic acid 2-ethylthiophene-5-boronic acid was prepared in the same manner as described in Example 140A from 2-ethylthiophene (2.0 g, 18 mmol). Evaporation of solvents after workup gave 2.16 g (78%) of 2-ethylthiophene-5-boronic acid as a white sold which was used on the next step with no further purification.

B. N-[5-(5-ethyl-2-thienyl)thiophene-2-sulfonyl]pyrrole

N-[5-(5-ethyl-2-thienyl)thiophene-2-sulfonyl]pyrrole was prepared in the same manner as described in Example 32C from 2-ethylthiophene-5-boronic acid (411 mg, 2.64 mmol) and N-(5-bromothiophene-2-sulfonyl)pyrrole (700 mg, 2.39 mmol). Purification by column chromatography using 2% ethyl acetate/hexanes gave 6.30 mg of the pure product as a dark brown solid (90% yield).

C. 2-chlorosulfonyl-5-(5-ethyl-2-thienyl)thiophene 2-chlorosulfonyl-5-(5-ethyl-2-thienyl)thiophene was prepared in the same manner as described in Example 33D from N-(pyrrole)-5-(5-ethyl-2-thienyl)thiophene-2-sulfonamide (630 mg, 2.16 mmol). Purification by column chromatography using 1% ethyl acetate/hexanes gave 400.3 mg of the pure sulfonyl chloride as a bright yellow solid (57% yield).

D. N-(4-bromo-3-methyl-5-isoxazolyl)-5-(5-ethyl-2-thienyl)thiophene-2-sulfonamide N-(4-bromo-3-methyl-5-isoxazolyl)-5-(5-ethyl-2-thienyl)thiophene-2-sulfonamide was prepared in the same manner as described in Example 2. Reaction of 2-chlorosulfonyl-5-(5-ethyl-2-thienyl)thiophene (200 mg, 0.68 mmol) with 5-amino-4-bromo-3-methyl isoxazole (121 mg, 0.68 mmol) yielded 174 mg N-(4-bromo-3-methyl-5-isoxazolyl)-5-(5-ethyl-2-thienyl)thiophene-2-sulfonamide (59% yield). After passing through a small plug of silica gel with elution using 10% MeOH/CHCl$_3$, a small fraction of the product was further purified using preparative HPLC to give the sulfonamide as a light tan colored powder, m.p. 126° C.

EXAMPLE 141

N-(4-chloro-3-methyl-5-isoxazolyl)-5-(5-ethyl-2-thienyl)thiophene-2-sulfonamide

N-(4-chloro-3-methyl-5-isoxazolyl)-5-(5-ethyl-2-thienyl)thiophene-2-sulfonamide was prepared in the same manner as in Example 2. Reaction of 2-chlorosulfonyl-5-(5-ethyl-2-thienyl)thiophene (Example 141C, 200 mg, 0.68 mmol) with 5-amino-4-chloro-3-methylisoxazole (91 mg, 0.68 mmol) yielded 188 mg of the final product (71% yield). A small portion of the product was further purified by preparative HPLC to give the pure sulfonamide as a tan colored solid.

EXAMPLE 142

N-(4-Bromo-3-methyl-5-isoxazolyl)-5-(benzo[b]thien-2-yl)thiophene-2-sulfonamide

A. Benzo[b]thiophene-2-boronic acid

Benzo[b]thiophene-2-boronic acid was prepared in the same manner as described in Example 140A from benzo[b]thiophene except that t-BuLi was used as the base in place of n-BuLi resulting in a tan solid in 78% yield.

B. N-[5-(benzo[b]thien-2-yl)thiophene-2-sulfonyl]pyrrole

N-[5-(benzo[b]thien-2-yl)thiophene-2-sulfonyl]pyrrole was prepared in the same manner as described in Example 32C from benzo[b]thiophene-2-boronic acid (426 mg, 2.39 mmol) and N-(5-bromothiophene-2-sulfonyl)pyrrole (700 mg, 2.39 mmol). Purification by column chromatography using 2% ethyl acetate/hexanes gave the pure sulfonamide in 68% yield as a brownish-red solid.

C. 2-chlorosulfonyl-5-(benzo[b]thien-2-yl)thiophene 2-chlorosulfonyl-5-(benzo[b]thien-2-yl)thiophene was prepared in the same manner as in Example 33D from N-[5-(benzo[b]thien-2-yl)thiophene-2-sulfonyl]pyrrole (520 mg, 1.5 mmol). Purification by column chromatography using 2% ethyl acetate/hexanes gave 153 mg (32% yield) of the pure sulfonyl chloride as a white solid.

D. N-(4-bromo-3-methyl-5-isoxazolyl)-5-(benzo[b]thien-2-yl)thiophene-2-sulfonamide N-(4-bromo-3-methyl-5-isoxazolyl)-5-(benzo[b]thien-2-yl)thiophene-2-sulfonamide was prepared in the same manner as in Example 2. Reaction of 2-chlorosulfonyl-5-(benzo]thien-2-yl)thiophene (150 mg, 0.48 mmol) with 5-amino-4-bromo-3-methyl isoxazole (84 mg, 0.48 mmol) resulted in 97 mg of pure N-(4-bromo-3-methyl-5-isoxazolyl)-5-(benzo[b]thien-2-yl)thiophene-2-sulfonamide as a light tan powder, (45% yield, m.p. 164° C.).

EXAMPLE 143

N-(Bromo-3-methyl-5-isoxazolyl)-5-(1-pentynyl)thiophene-2-sulfonamide

A. N-[5-(1-pentynyl)thiophene-2-sulfonyl)pyrrole

N-[5-(1-pentynyl)thiophene-2-sulfonyl)pyrrole was prepared as in Example 138A from N-(5-bromothiophene-2-sulfonyl)pyrrole (600 mg, 2.05 mmol) and 1-pentynel (280 mg, 4.1 mmol). Purification by column chromatography using 2% ethyl acetate/hexanes gave 424 mg of the pure sulfonamide as a brown oil (74% yield).

B. 2-chlorosulfonyl-5-(1-pentynyl)thiophene 2-chlorosulfonyl-5-(1-pentynyl)thiophene was prepared in the same manner as described in Example 33D from N-[5-(1-pentynyl)thiophene-2-sulfonyl]pyrrole (420 mg, 1.5 mmol). Purification by column chromatography using 1% ethyl acetate/hexanes gave 55 mg of the pure thiophene as a brown oil (15% yield).

C. N-(bromo-3-methyl-5-isoxazolyl)-5-(1-pentynyl) thiophene-2-sulfonamide

N-(bromo-3-methyl-5-isoxazolyl)-5-(1-pentynyl) thiophene-2-sulfonamide was prepared in the same manner as described in Example 2. Reaction of 2-chlorosulfonyl-5-(1-pentynyl)thiophene (55 mg. 0.22 mmol) with 5-amino-4-bromo-3-methylisoxazole (43 mg, 0.22 mmol) yielded 75 mg of N-(bromo-3-methyl-5-isoxazolyl)-5-(1-pentynyl) thiophene-2-sulfonamide (87% yield). A portion of the product was further purified by preparative HPLC to give the pure sulfonamide as a light brown oil.

EXAMPLE 144

N-(4-Bromo-3-methyl-5-isoxazolyl)-5-(1-naphthyl) thiophene-2-sulfonamide

A. N-[5-(1-naphthyl)thiophene-2-sulfonyl]pyrrole

N-[5-(1-naphthyl)thiophene-2-sulfonyl]pyrrole was prepared in the same manner as described in Example 32C from 1-naphthaleneboronic acid (353 mg, 2.05 mmol) and N-(5-bromothiophene-2-sulfonyl)pyrrole (600 mg, 2.05 mmol). Purification by column chromatography using 2% ethyl acetate/hexanes gave the pure sulfonamide in 87% yield as a pale yellow clear oil.

B. 2-chlorosulfonyl-5-(1-naphthyl)thiophene 2-chlorosulfonyl-5-(1-naphthyl)thiophene was prepared as described in Example 33D from N-[5-(1-naphthyl) thiophene-2-sulfonyl]pyrrole (604 mg, 1.28 mmol). Purification by column chromatography using 2% ethyl acetate/hexanes gave 376 mg of the pure thiophene in 68% yield.

C. N-(4-bromo-3-methyl-5-isoxazolyl)-5-(1-naphthyl)thiophene-sulfonamide

N-(4-bromo-3-methyl-5-isoxazolyl)-5-(1-naphthyl) thiophene-sulfonamide was prepared in the same manner as described in Example 2. Reaction of 2-chlorosulfonyl-5-(1-naphthyl)thiophene (200 mg, 0.65 mmol) with 5-amino-4-bromo-3-methylisoxazole (0.65 mmol), after purification by column chromatography using 1% MeOH/CHCl$_3$, gave 65.3 mg of pure N-(4-bromo-3-methyl-5-isoxazolyl)-5-(1-naphthyl)thiophene-sulfonamide as a brown solid, (22% yield, m.p. 118° C.).

EXAMPLE 145

N-(4-Bromo-3-methyl-5-isoxazolyl)-5-(3-nitrophenyl)thiophene-2-sulfonamide

A. N-(3-methyl-5-isoxazolyl)-5-(3-nitrophenyl) thiophene-2-sulfonamide

N-(3-methyl-5-isoxazolyl)-5-(3-nitrophenyl)thiophene-2-sulfonamide was prepared in the same manner as described in Example 32C from 3-nitrobenzene boronic acid (362 mg, 2.17 mmol) and N-(3-methyl-5-isoxazolyl)-5-bromothiophene-2-sulfonamide (700 mg, 2.17 mmol). Purification by column chromatography using 10% MeOH/CHCl$_3$ gave 166 mg of the pure sulfonamide (21% yield).

B. N-(4-bromo-3-methyl-5-isoxazolyl)-5-(3-nitrophenyl)thiophene-2-sulfonamide N-(4-bromo-3-methyl-5-isoxazolyl)-5-(3-nitrophenyl) thiophene-2-sulfonamide was prepared in the same manner as described in Example 136C. Reaction of N-(3-methyl-5-isoxazolyl)-5-(3-nitrophenyl)thiophene-2-sulfonamide (328 g, 0.90 mmol) with N-bromosuccinamide (160 mg, 0.90 mmol) gave the final product. A fraction of this material was further purified by preparative HPLC to give the pure sulfonamide as a brown solid, m.p. 132° C.

EXAMPLE 146

N-(4-Bromo-3-methyl-5-isoxazolyl)-5-(4-methyoxycarbonylphenyl)thiophene-2-sulfonamide

A. 2-(4-methoxycarbonylphenyl)thiophene 2-(4-methoxycarbonylphenyl)thiophene was prepared in the same manner as described in Example 32C from thiophene-2-boronic acid (1.0 g, 7.81 mmol) and methyl-4-bromobenzoate (1.68 g, 7.81 mmol). Purification by column chromatography using 2% ethyl acetate/hexanes gave 1.1 g of 2-(4-methoxycarbonylphenyl)thiophene as a white solid (65% yield).

B. 2-chlorosulfonyl-5-(4-methoxycarbonylphenyl) thiophene

Chlorosulfonic acid (1.06 g, 9.16 mmol) was slowly added to a solution of 2-(4-methoxycarbonylphenyl) thiophene (500 mg, 2.29 mmol) in CH$_2$Cl$_2$ (10 ml) at −78° C. The resulting solution was stirred at −78° C. for 1 hr. by which time the sulfonic acid had completely formed as judged by TLC using 10% ethyl acetate/hexanes. Phosphorous oxychloride (2 ml) was then added at −78° C. followed immediately by addition of phosphorous pentachloride (954 mg, 4.58 mmol). The resulting solution was stirred at −78° C. for 0.5 hr. and then at room temperature for 25 min. The solution was then carefully poured onto crushed ice (100 g) and extracted into diethyl ether (100 ml). The combined organic layers was washed with brine (1×25 ml) and dried over MgSO$_4$. After filtration, removal of solvents left a light greenish solid which was further purified by column chromatography using 2% ethyl acetate/hexanes to give 620 mg of pure 2-chlorosulfonyl-5-(4-methoxycarbonylphenyl) thiophene as a pale yellow solid (85% yield).

C. N-(4-bromo-3-methyl-5-isoxazolyl)-5-(4-methoxycarbonylphenyl)thiophene-2-sulfonamide N-(4-bromo-3-methyl-5-isoxazolyl)-5-(4-methoxycarbonylphenyl)thiophene-2-sulfonamide was prepared in the same manner as described in Example 2 from 2-chlorosulfonyl-5-(4-methoxycarbonylphenyl)thiophene (646 mg, 2.04 mmol) and 5-amino-4-bromo-3-methylisoxazole (361 mg, 2.04 mmol). Purification by column chromatography using 10% MeOH/CHCl$_3$ gave 384 mg of N-(4-bromo-3-methyl-5-isoxazolyl)-5-(4-methoxycarbonylphenyl)thiophene-2-sulfonamide as a brown oil (41% yield).

EXAMPLE 147

N-(4-Bromo-3-methyl-5-isoxazolyl)-5-(4-carboxyphenyl)thiophene-2-sulfonamide Lithium hydroxide (13.3 mg, 0.32 mmol) in methanol (2 ml) was added to a solution of N-(4-bromo-3-methyl-5-isoxazolyl)-5-(4-methoxycarbonylphenyl)thiophene-2-sulfonamide (Example 147C, 121 mg, 0.27 mmol) previously dissolved in methanol (5 ml). The solution was stirred at room temperature for a period of 18 hours. The methanol was removed in vacuo and the remaining residue dissolved in water. 4N HCl was added until pH 2.0 was reached, and then the aqueous solution was extracted with ethyl acetate (3×25ml). The combined organic layers was washed with water (1×10 ml), brine (1×10 ml) and dried over MgSO$_4$. Evaporation left 50 mg (43% yield) of a pale yellow residue which was further purified by preparative HPLC to give N-(4-bromo-3-methyl-5-isoxazolyl)-5-(4-carboxyphenyl) thiophene-2-sulfonamide as a white solid, m.p. 219–228° C.

EXAMPLE 148

N-(4-chloro-3-methyl-5-isoxazolyl)2-{[2-acetyl-4,5-(methylenedioxy)phenyl]aminocarbonyl}thiophene-3-sulfonamide Carbonyldiimidazole (553 mg, 3.41 mmol) was added to a solution of N-(4-chloro-3-methyl-5-isoxazolyl)-2-carboxylthiophene-3-sulfonamide (1.0 g, 3.1 mmol) in dry DMF (10 ml). The mixture was stirred at room temperature for 15 minutes to give mixture (I).

NaH (60% dispersion in mineral oil, 521 mg, 13.02 mmol) was added to a solution of 2'-amino-4',5'-(methylenedioxy)acetophenone (1.13 g, 6.2 mmol) in dry DMF (10 ml) at 0° C. The mixture was stirred at 0° C. for 15 minutes to give mixture (II). Mixture (I) was slowly cannulated into mixture (II) at 0° C. The resulting mixture was stirred at 0° C. for 4 hours. The reaction mixture was poured into 2 N HCl (aq., 200 ml) and the resulting precipitate was filtered. The solid was washed with water (2×10 ml) and ethyl ether (2×10 ml) to give N-(4-chloro-3-methyl-5-isoxazolyl)2-{[2-acetyl-4,5-(methylenedioxy) phenyl]aminocarbonyl}thiophene-3-sulfonamide (730 mg, 49% yield) as a dull yellow powder, m.p. 191–193° C.

EXAMPLE 149

N-(4-chloro-3-methyl-5-isoxazolyl)-2-[(4,5-dimethoxy-2-methoxycarbonylphenyl) aminocarbonyl]thiophene-3-sulfonamide and N-(4-chloro-3-methyl-5-isoxazolyl)2-{[4,5-dimethoxy-2] 4,5-dimethoxy-2-methoxycarbonyl)phenyl] phenylaminocarbonyl}thiophene-3-sulfonamide The title compounds were prepared by the method set forth for N-(4-chloro-3-methyl-5-isoxazolyl)2-{[2-acetyl-4, 5-(methylenedioxy)phenyl]aminocarbonyl}thiophene-3-sulfonamide (EXAMPLE 148) except that methyl-2-amino-4,5-dimethoxybenzoate was used instead of 2'-amino-4',5'-(methylenedioxy)acetophenone. The crude product was purified via HPLC to give N-(4-chloro-3-methyl-5-isoxazolyl)-2[(4,5-dimethoxy-2-methoxycarbonylphenyl) aminocarbonyl]thiophene-3-sulfonamide as a yellow powder (13% yield, m.p. 167–168° C.) and N-(4-chloro-3-methyl-5-isoxazolyl)2-{[4,5-dimethoxy-2,4,5-dimethoxy-2-methoxycarbonyl)phenyl]phenylaminocarbonyl}thiophene-3-sulfonamide as a dull yellow solid (1% yield, m.p. 228–230° C.).

EXAMPLE 150

N-(4-chloro-3-methyl-5-isoxazolyl)-2-[(2-methyl-1,3,4-thiadiazol-5-yl)aminocarbonyl]thiophene-3-sulfonamide Carbonyldiimidazole (553 mg, 3.41 mmol) was added to a solution of N-(4-chloro-3-methyl-5-isoxazolyl)-2-carboxyl-thiophene-3-sulfonamide (10 g, 3.1 mmol) in dry DMF (10 ml). The mixture was stirred at room temperature for 15 minutes before the sequential addition of 2-amino-5-methyl-1,3,4-thiadiazole (736 mg, 6.2 mmol) and pyridine (10 ml). The resulting mixture was stirred at room temperature overnight. To work up, the reaction mixture was poured into 1 N HCl (150 ml) and extracted with EtOAC. The organic layer was dried (MgSO4), the solid was filtered and the filtrate was concentrated. The residue was purified via HPLC to give N-(4-chloro-3-methyl-5-isoxazolyl)-2-[(2-methyl-1,3,4-thiadiazol-5-yl)aminocarbonyl]thiophene-3-sulfonamide as a white powder (15% yield, m.p. 192–194° C.).

EXAMPLE 151

N-(4-chloro-3-methyl-5-isoxazolyl)2-{[2-carboxyl-4,5-(methylenedioxy)phenyl] aminocarbonyl}thiophene-3-sulfonamide NaOH (1.5 N, 250 ml) was added to N-(4-chloro-3-methyl-5-isoxazolyl)-2-[(4,5-dimethoxy-2-methoxycarbonylphenyl)aminocarbonyl]thiophene-3-sulfonamide (EXAMPLE 149); 410 mg). The resulting suspension was stirred at room temperature overnight to give a clear solution. The mixture was acidified using concentrated HCl with cooling. The resulting precipitate was filtered, washed with water (3×50 ml) and dried on a lyophilyzer to give N-(4-chloro-3-methyl-5-isoxazolyl)2-{[2-carboxyl-4,5-(methylenedioxy)phenyl]aminocarbonyl}) thiophene-3-sulfonamide as a yellow powder (87% yield, m.p. 192–195° C.).

EXAMPLE 152

N-(3,4-dimethyl-5-isoxazolyl)-2-{[2-acetyl-4,5-(methylenedioxy)phenyl]aminocarbonyl}thiophene-3-sulfonamide N-(3,4-dimethyl-5-isoxazolyl)-2-{[2-acetyl-4,5-(methylenedioxy)phenyl]aminocarbonyl}thiophene-3-sulfonamide was prepared by the method set forth for N-(4-chloro-3-methyl-5-isoxazolyl)2-{[2-acetyl-4,5-(methylenedioxy)phenyl]aminocarbonyl}thiophene-3-sulfonamide (EXAMPLE 148) except that N-(3,4-dimethyl-5-isoxazolyl)-2-carboxylthiophene-3-sulfonamide was used instead of N-(4-chloro-3-methyl-5-isoxazolyl)-2-carboxylthiophene-3-sulfonamide. N-(3,4-dimethyl-5-isoxazolyl)-2-{[2-acetyl-4,5-(methylenedioxy)phenyl] aminocarbonyl}thiophene-3-sulfonamide was obtained as a yellow powder (8% yield, m.p. 228–231° C.).

EXAMPLE 153

N-(4-chloro-3-methyl-5-isoxazolyl)-2-[(4-methoxy-2-methylphenyl)aminocarbonyl]thiophene-3-sulfonamide N-(4-chloro-3-methyl-5-isoxazolyl)-2-[(4-methoxy-2-methylphenyl)aminocarbonyl]thiophene-3-sulfonamide was prepared by the method set forth for N-(4-chloro-3-methyl-5-isoxazolyl)-2-[(2-methyl-1,3,4-thiadiazol-5-yl) aminocarbonyl]thiophene-3-sulfonamide (EXAMPLE 150), except that 4-methoxy-2-methylaniline was used instead of 2-amino-5-methyl-1,3,4-thiadiazole and that pyridine was not used. The title compound was obtained via HPLC purification as a dull yellow powder (66% yield, m.p. 58–62° C.).

EXAMPLE 154

N-(4-chloro-3-methyl-5-isoxazolyl)-2-[(2-cyano-4,5-dimethoxyphenyl)aminocarbonyl]thiophene-3-sulfonamide N-(4-chloro-3-methyl-5-isoxazolyl)-2-[(2-cyano-4,5-dimethoxyphenyl)aminocarbonyl]thiophene-3-sulfonamide was prepared by the method set forth for N-(4-chloro-3-methyl-5-isoxazolyl)2-{[2-acetyl-4,5-(methylenedioxy) phenyl]aminocarbonyl}thiophene-3-sulfonamide (EXAMPLE 148) except that 2-amino-4,5-dimethoxybenzonitrile was used in stead of 2'-amino-4',5'-(methylenedioxy)acetophenone. N-(4-chloro-3-methyl-5-isoxazolyl)-2-[{2-cyano-4,5-dimethoxyphenyl) aminocarbonyl]thiophene-3-sulfonamide was obtained via HPLC purification as a light brown powder (36% yield, m.p. 53–56° C.).

EXAMPLE 155

N-(4-chloro-3-methyl-5-isoxazolyl)-2-[(2,4-dimethoxyphenyl)aminocarbonyl]thiophene-3-sulfonamide N-(4-chloro-3-methyl-5-isoxazolyl)-2-[(2,4-dimethoxyphenyl)aminocarbonyl]thiophene-3-sulfonamide was prepared by the method set forth for N-(4-chloro-3-methyl-5-isoxazolyl)-2-[4-methoxy-2-methylphenyl) aminocarbonyl]thiophene-3-sulfonamide (EXAMPLE 153), except that 2,4-dimethoxyaniline was used in stead of 4-methoxy-2-methylaniline. N-(4-chloro-3-methyl-5-isoxazolyl)-2-[(2,4-dimethoxyphenyl)aminocarbonyl] thiophene-3-sulfonamide was obtained via recrystalization (CH3CN/H2O) as yellow crystals (16% yield, m.p. 162–164° C.).

EXAMPLE 156

N-(4-chloro-3-methyl-5-isoxazolyl)-2-[(3-methyl-6-pyridyl)aminocarbonyl]thiophene-3-sulfonamide N-(4-chloro-3-methyl-5-isoxazolyl)-2-[(3-methyl-6-pyridyl)aminocarbonyl]thiophene-3-sulfonamide was prepared by the method set forth for N-(4-chloro-3-methyl-5-isoxazolyl)2-{[2-acetyl-4,5-(methylenedioxy)phenyl] aminocarbonyl}thiophene-3-sulfonamide (EXAMPLE 148), except that 2-amino-5-picoline was used in stead of 2'-amino-4',5'-(methylenedioxy)acetophenone, N-(4-chloro-3-methyl-5-isoxazolyl)-2-[(3-methyl-6-pyridyl) aminocarbonyl]thiophene-3-sulfonamide was obtained, via HPLC purification of the crude reaction mixture, as a bright yellow powder (17% yield, m.p. 158–160° C.).

EXAMPLE 157

N-(4-bromo-3-methyl-5-isoxazolyl)-2-[(4-methylphenyl)acetyl]thiophene-3-sulfonamide N-(4-bromo-3-methyl-5-isoxazolyl)-2-[(4-methylphenyl) acetyl]thiophene-3-sulfonamide was prepared in the same manner as described in Example 93B by reacting 4-methylbenzylmagnesium chloride with N-(4-bromo-3-methyl-5-isoxazolyl)-2-[N-methoxy (methylaminocarbonyl)]thiophene-3-sulfonamide in THF (see Example 93A) at –78° C. to room temperature, resulting in 78% yield. m.p. 146–150° C.8

EXAMPLE 158

N-(4-bromo-3-methyl-5-isoxazolyl)-2-[(4-methyl) (cinnamyl)]thiophene-3-sulfonamide A. N-[2-(4-methyl-trans-styryl)-3-sulfonyl]pyrrole N-[2-(4-methyl-trans-styryl)-3-sulfonyl]pyrrole was prepared in the same manner as described in example 127B using diethyl{3-[(N-pyrroly])sulfonyl]-thien-2-[yl] methyl}phosphonate and 4-methylbenzaldehyde in 30% yield.

B. 2-(4-methyl-trans-styryl)thiophene-3-sulfonyl chloride 2-(4-methyl-trans-styryl)thiophene-3-sulfonyl chloride was prepared in the same manner as described in Example 64E from N-[2-(4-methyl-trans-styryl)-3-sulfonyl}pyrrole by basic hydrolysis (using ethanol and sodium hydroxide) to the corresponding sodium sulfonate followed by conversion to the corresponding sulfonyl chloride in 13% yield.

C. N-(4-bromo-3-methyl-5-isoxazolyl)-2-(4-methyl-trans-styryl)thiophene-3-sulfonamide N-(4-bromo-3-methyl-5-isoxazolyl)-2-(4-methyl-trans-styryl)thiophene-3-sulfonamide was prepared in the same manner as described in Example 2 by reaction of 2-(4-methyl-trans-styryl)thiophene-3-sulfonyl chloride with 5-amino-4-bromo-3-methylisoxazole. The crude product was purified by HPLC followed by crystallization resulting in a 34% yield, m.p. 101–105° C.

EXAMPLE 159

N-(4-bromo-3-methyl-5-isoxazolyl)-2-[(4-methyl) phenethyl]thiophene-3-sulfonamide A. N-{2-[(4-methyl)phenethyl]thiophene-3-sulfonyl}pyrrole N-{2-[(4-methyl)phenethyl]thiophene-3-sulfonyl}pyrrole was prepared as described in Example 128A by the catalytic hydrogenation of N-[2-(4-methyl-trans-styryl)-3-sulfonyl}pyrrole in 80% yield.

B. 2-[(4-methyl)phenethyl]thiophene-3-sulfonylchloride

2-[(4-methyl)phenethyl]thiophene-3-sulfonylchloride was prepared, as described in Example 64E, using N-{2-[(4-methyl)phenethyl]thiophene-3-sulfonyl}pyrrole by basic hydrolysis (KOH/ethanol) of the sulfonamide to this potassium salt followed by conversion of salt to the corresponding sulfonyl chloride in 51% yield.

C. N-(4-bromo-3-methyl-5-isoxazolyl)-2-[(4-methyl)phenethyl]thiophene-3-sulfonamide N-(4-bromo-3-methyl-5-isoxazolyl)-2-[(4-methyl) phenethyl]thiophene-3-sulfonamide was prepared, as described in Example 2, using 2-[(4-methyl)phenethyl] thiophene-3-sulfonylchloride and 5-amino-4-bromo-3-methylisoxazole in 52% yield.

EXAMPLE 160

N-(4-bromo-3-methyl-5-isoxazolyl)-2-[(4-methylphenoxy)methyl]thiophene-3-sulfonamide A. N-{2-[(4-methylphenoxy)methyl]thiophene-3-sulfonyl}pyrrole N-{2-[(4-methylphenoxy)methyl]thiophene-3-sulfonyl}pyrrole was prepared, as described in Example 126A, by reacting N-[2-bromo-methyl)thiophene-3-sulfonyl]pyrrole with 4-methylphenol, in 81% yield.

B. 2-[(4-methylphenoxy)methyl]thiophene-3-sulfonyl chloride

2-[(4-methylphenoxy)methyl]thiophene-3-sulfonyl chloride was prepared, as described in Example 64E, using N-{2-[(4-methylphenoxymethyl]thiophene-3-sulfonyl}pyrrole by basic hydrolysis (NaOH/EtOH) followed by conversion to the corresponding sulfonyl chloride, in 46% yield.

C. N-(4-bromo-3-methyl-5-isoxazolyl)-2-[(4-methylphenoxy)methyl]thiophene-3-sulfonamide N-(4-bromo-3-methyl-5-isoxazolyl)-2-[(4-methylphenoxy)methyl]thiophene-3-sulfonamide was prepared, as described in Example 2, by reacting 3-chlorosulfonyl-2-[(4-methylphenoxy)methyl]thiophene with 5-amino-4-bromo-3-methylisoxazole, resulting in a 64% yield, m.p. 128–130° C.

EXAMPLE 161

N-(3,4-dimethyl-5-isoxazolyl)-2-(4-tolylacetylphenyl)thiophene-3-sulfonamide

A. N-(3,4-dimethyl-5-isoxazolyl)-2-[N-methoxy(methylaminocarbonyl)thiophene-3-sulfonamide N-(3,4-dimethyl-5-isoxazolyl)-2-[N-methoxy(methylaminocarbonyl)thiophene-3-sulfonamide was prepared, as described in Example 93A, by reacting N-(3,4-dimethyl-5-isoxazolyl)-2-(carboxyl)thiophene-3-sulfonamide with N-O-dimethylhydroxylamine hydrochloride using triethylamine as base and carbonyidiimidazole, resulting in a 23% yield. Crude product purified by column chromatography using 1:1 hexanes/EtOAc as the eluent.

B. N-(3,4-dimethyl-5-isoxazolyl)-2-(4-tolylacetyl)thiophene-3-sulfonamide

N-(3,4-dimethyl-5-isoxazolyl)-2-(4-tolylacetyl)thiophene-3-sulfonamide was prepared, as described in Example 93B, by reacting N-(3,4-dimethyl-5-isoxazolyl)-2-[N-methoxy(methylaminocarbonyl)]thiophene-3-sulfonamide with 4-tolylmagnesium chloride, resulting in a 65% yield, m.p. 95–100° C.

EXAMPLE 162

N-(3,4-dimethyl-5-isoxazolyl)-2-[3,4-(methylenedioxy)phenylacetyl]thiophene-3-sulfonamide N-(3,4-dimethyl-5-isoxazolyl)-2-[3,4-(methylenedioxy)phenylacetyl]thiophene-3-sulfonamide was prepared, as described in Example 93B, by reacting N-(3,4-dimethyl-5-isoxazolyl)-2-[N-methoxy(methylaminocarbonyl)]thiophene-3-sulfonamide with 3,4-methylenedioxy)phenylmagnesium chloride, resulting in a 65% yield, m.p. 95–100° C.

EXAMPLE 163

N-(4-chloro-3-methyl-5-isoxazolyl)-2-{[2-cyano-4,5-(methylenedioxy)phenyl]aminocarbonyl}thiophene-3-sulfonamide N-(4-chloro-3-methyl-5-isoxazolyl)-2-{[2-cyano-4,5-(methylenedioxy)phenyl]aminocarbonyl}thiophene-3-sulfonamide was prepared as described in EXAMPLE 148, except that 2'-amino-4',5'-(methylenedioxy)benzonitrile was used instead of 2'-amino-4',5'-(methylenedioxy)acetophenone. It was obtained via HPLC purification as a yellowish solid in ~40% yield, m.p. 167–168° C.

EXAMPLE 164

N-(4-chloro-3-methyl-5-isoxazolyl)-2-(3-methoxycarbonyl-2,4,6-trimethyl)phenylaminocarbonyl-3-thiophenesulfonamide A. Methyl 3-amino-2,4,6-trimethylbenzoate Methyl 3-amino-2,4,6-trimethylbenzoate was synthesized in the same manner as (3,4-methylenedioxy)-6-methylaniline (see Example 177, below).

B. N-(4-chloro-3-methyl-5-isoxazolyl)-2-(3-methoxycarbonyl-2,4,6-trimethyl)phenylaminocarbonyl-3-thiophenesulfonamide N-(4-chloro-3-methyl-5-isoxazolyl)-2-(3-methoxycarbonyl-2,4,6-trimethyl)phenylaminocarbonyl-3-thiophenesulfonamide was synthesized in the same manner as for Example 94 except that DMF was used instead of THF and the reaction was heated at 80° C. for 5 hours. The crude product was purified via preparative HPLC to give N-(4-chloro-3-methyl-5-isoxazolyl)-2-(3-methoxycarbonyl-2,4,6-trimethyl)phenylaminocarbonyl-3-thiophenesulfonamide as an off-white powder (48 mg, 1% yield, m.p. 66–70° C.).

EXAMPLE 165

N-(4-chloro-3-methyl-5-isoxazolyl)-2-(2,4,6-trimethyl)phenylacetyl-3-thiophenesulfonamide N-(4-chloro-3-methyl-5-isoxazolyl)-2-(2,4,6-trimethyl)phenylacetyl-3-thiophenesulfonamide was synthesized in the same manner as for Example 102 using 2,4,6-trimethylbenzyl chloride and N-(4-chioro-3-methyl-5-isoxazolyl)-2-(N-methyl-N'-methoxy)aminocarbonyl-3-thiophenesulfonamide. The crude product was purified by flash column chromatography (eluent 1% methanol in $CH_2Cl_2$) to give N-(4-chloro-3-methyl-5-isoxazolyl)-2-(2,4,6-trimethyl)phenylacetyl-3-thiophenesulfonamide as a solid (31% yield, m.p. 42–46° C.).

EXAMPLE 166

N-(4-chloro-3-methyl-5-isoxazolyl)-2-(2,4,6-trimethyl)phenylaminocarbonyl-3-thiophenesulfonamide N-(4-chloro-3-methyl-5-isoxazolyl)-2-(2,4,6-trimethyl)phenylaminocarbonyl-3-thiophenesulfonamide was synthesized in the same manner as Example 94. The crude product was purified via preparative HPLC to give N-(4-chloro-3-methyl-5-isoxazolyl)-2-(2,4,6-trimethyl)phenylaminocarbonyl-3-thiophenesulfonamide as a yellowish-brownish powder (410 mg, 30% yield, m.p. 45–48° C.).

EXAMPLE 167

N-(3,4-dimethyl-5-isoxazolyl)-2-(2,4-dimethyl)phenylacetyl-3-thiophenesulfonamide N-(3,4-dimethyl-5-isoxazolyl)-2-(2,4-dimethyl)phenylacetyl-3-thiophenesulfonamide was synthesized by the same method as described for Example 102 using 2,4-dimethylbenzyl chloride and N-(3,4-dimethyl-5-isoxazolyl)-2-(N-methyl-N'-methoxy)aminocarbonyl-3-thiophenesulfonamide. The crude product was purified by flash column chromatography (eluent 1% methanol in $CH_2Cl_2$) and further by preparative HPLC to give N-(3,4-dimethyl-5-isoxazolyl)-2-(2,4-dimethyl)phenylacetyl-3-thiophenesulfonamide as a semi-solid (34% yield).

EXAMPLE 168

N-(4-chloro-3-methyl-5-isoxazolyl)-2-(2,4-dimethyl)phenylacetyl-3-thiophenesulfonamide N-(4-chloro-3-methyl-5-isoxazolyl)-2-(2,4-dimethyl)phenylacetyl-3-thiophenesulfonamide was synthesized in the same manner as for Example 102 using 2,4-dimethylbenzyl chloride and N-(4-chloro-3-methyl-5- isoxazolyl)-2-(N-methyl-N'-methoxy)aminocarbonyl-3-thiophenesulfonamide. The crude product was purified by flash column chromatography (eluent 1% methanol in CH$_2$Cl$_2$) to give N-(4-chloro-3-methyl-5-isoxazolyl)-2-(2,4-dimethyl)phenylacetyl-3-thiophenesulfonamide as a solid (52% yield, m.p. 48–54° C.).

EXAMPLE 169

N-(4-bromo-3-methyl-5-isoxazolyl)-2-(2,4-dimethyl)phenylacetyl-3-thiophenesulfonamide N-(4-bromo-3-methyl-5-isoxazolyl)-2-(2,4-dimethyl) phenylacetyl-3-thiophenesulfonamide was synthesized in the same manner as for Example 102 using 2,4-dimethylbenzyl chloride and N-(4-bromo-3-methyl-5-isoxazolyl)-2-(N-methyl-N'-methoxy)aminocarbonyl-3-thiophenesulfonamide. The crude product was purified by flash column chromatography (eluent 1% methanol in CH$_2$Cl$_2$) and further by preparative HPLC to give N-(4-bromo-3-methyl-5-isoxazolyl)-2-(2,4-dimethyl) phenylacetyl-3-thiophenesulfonamide as a solid (28% yield, m.p. 58–63° C.).

EXAMPLE 170

N-(4-chloro-3-methyl-5-isoxazolyl)-2-(3,5-dimethyl)phenylacetyl-3-thiophenesulfonamide N-(4-chloro-3-methyl-5-isoxazolyl)-2-(3,5-dimethyl) phenylacetyl-3-thiophenesulfonamide was synthesized in the same manner as for Example 102 using 3,5-dimethylbenzyl bromide and N-(4-chloro-3-methyl-5-isoxazolyl)-2-(N-methyl-N'-methoxy)aminocarbonyl-3-thiophenesulfonamide. The crude product was purified by flash column chromatography (eluent 2% methanol in CH$_2$Cl$_2$) to give N-(4-chloro-3-methyl-5-isoxazolyl)-2-(3,5-dimethyl)phenylacetyl-3-thiophenesulfonamide as a solid (57% yield, m.p. 45–50° C.).

EXAMPLE 171

N-(4-chloro-3-methyl-5-isoxazolyl)-2-(2,5-dimethyl)phenylacetyl-3-thiophenesulfonamide N-(4-chloro-3-methyl-5-isoxazolyl)-2-(2,5-dimethyl) phenylacetyl-3-thiophenesulfonamide was synthesized in the same manner as for Example 102 using 2,5-dimethylbenzyl chloride and N-(4-chloro-3-methyl-5-isoxazolyl)-2-(N-methyl-N'-methoxy)aminocarbonyl-3-thiophenesulfonamide. The crude product was purified by flash column chromatography (eluent 2% methanol in CH$_2$Cl$_2$) to give N-(4-chloro-3-methyl-5-isoxazolyl)-2-(2,5-dimethyl)phenylacetyl-3-thiophenesulfonamide as a solid (33% yield, m.p. 72–76° C.).

EXAMPLE 172

N-(4-chloro-3-methyl-5-isoxazolyl)-2-[3,4-(methylenedioxy)-6-(2-acetoxyethyl)]phenylaminocarbonyl-3-thiophenesulfonamide A. 2-(3,4-methylenedioxy)phenyl-1-ethanol To a solution of 2-(3,4-methylenedioxy)phenylacetic acid (5 g, 25.75 mmol) in anhydrous THF (20 ml) at 0° C. was added BH$_3$ THF (40 ml, 1.0 M in THF). The mixture was stirred at room temperature for 1 h. To work up, THF was evaporated on a rotavap. The residue was treated with water (100 ml) Acidified and extracted with ether (2×100 ml). Removal of the solvent under reduced pressure gave 2-(3,4-methylenedioxy)phenyl-1-ethanol as an oil (4.7 g, 98% yield).

B. 1-acetoxy-2-[(3,4-methylenedioxy)phenyl]ethane

To a stirred solution of 2-(3,4-methylenedioxy)phenyl-1-ethanol (1.68 g, 10 mmol) in dry pyridine was added acetic anhydride and the resultant reaction mixture was stirred at 80° C. for 1 h. The reaction mixture was poured into ice-water and was extracted with ether (2×75 ml). The combined ether extract was washed with water (2×50 ml), 5% Hcl (2×50 ml) and then with 5% NaHCO$_3$ (2×50 ml). The organic layer was dried over magnesium sulfate and the solvent was removed under reduced pressure to give 1-acetoxy-2-[(3,4-methylenedioxy)phenyl]ethane as a solid (1.7 g, 81% yield).

C. 1-acetoxy-2-[(3,4-methylenedioxy)-6-nitrophenyl]ethane

To a stirred solution of 1-acetoxy-2-[(3,4-methylenedioxy)phenyl]ethane (1.7 g, 8.09 mmol) in acetic acid (10 ml) was added, dropwise, concentrated HNO$_3$ (4.5 ml). This was stirred at room temperature for 30 min. The reaction mixture was poured into water (100 ml). The precipitated solid was filtered, washed with water and dried under high vacuum to get 1-acetoxy-2-[(3,4-methylenedioxy)-6-nitrophenyl]ethane (1.8 g, 88% yield).

D. 1-acetoxy-2-[(3,4-methylenedioxy)-6-aminophenyl]ethane

The solution of 1-acetoxy-2-[(3,4-methylenedioxy)-6-nitrophenyl]ethane (0.8 g, 3.13 mmol) in ethyl acetate (25 ml) was subjected to catalytic hydrogenation using 10% palladium on carbon (100 mg) at 50 psi for 30 min. The catalyst was filtered and the solvent was removed under reduced pressure to give 1-acetoxy-2-[(3,4-methylenedioxy)-6-aminophenyl]ethane as a solid (0.69 g, 98% yield).

E. N-(4-chloro-3-methyl-5-isoxazolyl)-2-[3,4-(methylenedioxy)-6-(2-acetoxyethyl)]phenylaminocarbonyl-3-thiophenesulfonamide N-(4-chloro-3-methyl-5-isoxazolyl)-2-[3,4-(methylenedioxy)-6-(2-acetoxyethyl)]phenylaminocarbonyl-3-thiophenesulfonamide was synthesized in the same manner as Example 87. The crude product was purified by preparative HPLC to give N-(4-chloro-3-methyl-5-isoxazolyl)-2-[3,4-(methylenedioxy)-6-(2-acetoxyethyl)]phenylaminocarbonyl-3-thiophenesulfonamide as a dull yellow powder (12% yield, m.p. 78–82° C.).

EXAMPLE 173

N-(4-chloro-3-methyl-5-isoxazolyl)-2-[3,4-(methylenedioxy)-6-(2-hydroxyethyl)]phenylaminocarbonyl-3-thiophenesulfonamide To a stirred solution of N-(4-chloro-3-methyl-5-isoxazolyl)-2-[3,4-(methylenedioxy)-6-(2-acetoxyethyl)]phenylaminocarbonyl-3-thiophenesulfonamide (35 mg, 0.066 mmol) in methanol was added NaOH powder (40 mg) and stirred at room temperature for 30 min. HPLC analysis showed complete consumption of starting material. The reaction mixture was diluted with water and acidified to pH 2–3. This was extracted with ethyl acetate (2×25 ml). The combined organic layer was dried over magnesium sulfate and the solvent removed under reduced pressure to give N-(4-chloro-3-methyl-5-isoxazolyl)-2-[3,4 (methylenedioxy)-6-(2-hydroxyethyl)]phenylaminocarbonyl-3-thiophenesulfonamide as a solid (84% yield, m.p. 47–52° C.).

EXAMPLE 174

N-(4-chloro-3-methyl-5-isoxazolyl)-2-[3,4-(methylenedioxy)-6-(2-acetoxyethoxy)]phenylaminocarbonyl-3-thiophenesulfonamide A. Methyl 2-[3,4-(methylenedioxy)phenoxy]acetate and 2-[3,4-(methylenedioxy)phenoxylacetic acid The mixture of sesamol (13.8 g, 100 mmol, methyl bromoacetate (15.3 g, 100 mmol) and potassium carbonate in acetone (200 ml) was refluxed for 24 h with stirring. Acetone was removed under reduced pressure. The residue was dissolved in water (200 ml) and was extracted with ether (2×100 ml). The combined organic layer was dried over magnesium sulfate and the solvent removed under reduced pressure to give methyl 2-[3,4-(methylenedioxy)phenoxy]acetate as an oil (12 g, 57% yield). The aqueous phase was neutralized to pH 2–3 with concentrated HCl and the precipitated solid was filtered to get 2-(3,4-(methylenedioxy)phenoxy]acetic acid as a solid (6 g, 31% yield).

B. 2-3,4-(methylenedioxy)phenoxy-1-ethanol 2-(3,4-methylenedioxy)phenoxy-1-ethanol was synthesized in the same manner as for Example 172(A) using 2-[3,4-(methylenedioxy)phenoxy]acetic acid and BH$_3$.THF complex. The reaction was carried out for 12 hours at room temperature (98% yield).

C. 1-acetoxy-2-[3,4-(methylenedioxy)phenoxy]ethane

1-Acetoxy-2-[3,4-(methylenedioxy)phenoxy]ethane was synthesized in the same manner as for Example 172(B) by acetylation of 2-(3,4-methylenedioxy)phenoxy-1-ethanol using acetic anhydride and pyridine (92% yield).

D. 1-acetoxy-2-[3,4-(methylenedioxy)-6-nitrophenoxy]ethane 1-acetoxy-2-[3,4-(methylenedioxy)-6-nitrophenoxy]ethane was synthesized in the same manner as for Example 172(C) by nitration of 1-acetoxy-2-[3,4-(methylenedioxy)phenoxylethane. The reaction was carried out between 0° C. and 5° C. for 30 min (78% yield).

E. 1-acetoxy-2-[3,4-(methylenedioxy)-6-aminophenoxy]ethane 1-acetoxy-2-[3,4-(methylenedioxy)-6-aminophenoxy]ethane was synthesized in the same manner as for Example 172(D) by reduction of 1-acetoxy-2-[3,4-(methylenedioxy)-6-nitrophenoxy]ethane (100% yield).

F. N-(4-chloro-3-methyl-5-isoxazolyl)-2-[3,4-(methylenedioxy)-6-(2-acetoxyethoxy)]phenylaminocarbonyl-3-thiophenesulfonamide N-(4-chloro-3-methyl-5-isoxazolyl)-2-[3,4-(methylenedioxy)-6-(2-acetoxyethoxy)]phenylaminocarbonyl-3-thiophenesulfonamide was synthesized in the same manner as Example 87 using 1-acetoxy-2-[3,4-(methylenedioxy)-6-aminophenoxy]ethane and N-(4-chloro-3-methyl-5-isoxazolyl)-2-carboxylthiophene-3-sulfonamide. The crude product was purified by preparative HPLC to give N-(4-chloro-3-methyl-5-isoxazolyl)-2-[3,4-(methylenedioxy)-6-(2-acetoxyethoxy)]phenylaminocarbonyl-3-thiophenesulfonamide as a dull yellow powder (21% yield, m.p. 117–119° C.).

EXAMPLE 175

N-(4-chloro-3-methyl-5-isoxazolyl)-2-[3,4-(methylenedioxy)-6-(2-hydroxyethoxy)]phenylaminocarbonyl-3-thiophenesulfonamide N-(4-chloro-3-methyl-5-isoxazolyl)-2-[3,4-(methylenedioxy)-6-(2-hydroxyethoxy)]phenylaminocarbonyl-3-thiophenesulfonamide was synthesized in the same manner as Example 173 by basic hydrolysis of N-(4-chloro-3-methyl-5-isoxazolyl)-2-[3,4-(methylenedioxy)-6-(2-acetoxyethoxy)]phenylaminocarbonyl-3-thiophenesulfonamide (86% yield, m.p. 158–161° C.).

EXAMPLE 176

N-(4-chloro-3-methyl-5-isoxazolyl)-2-(4-methoxycarbonyl-2,6-dimethyl)phenylaminocarbonyl-3-thiophenesulfonamide A. N-(4-chloro-3-methyl-5-isoxazolyl)-N-(methoxyethoxymethyl)-2-carboxylthiophene-3-sulfonamide To a mixture of N-(4-chloro-3-methyl-5-isoxazolyl)-2-carboxylthiophene-3-sulfonamide (3.23 g, 100 mmol) and diisopropylethyl amine (3 ml) in ethyl acetate (20 ml) was added methoxyethoxymethyl chloride and the resultant reaction mixture was stirred at room temperature or 12 hours. This was diluted with ethyl acetate (100 ml) and washed with 1 N HCl (2×50 ml). The organic layer was dried over magnesium sulfate and the solvent removed under reduced pressure to give N-(4-chloro-3-methyl-5-isoxazolyl)-N-(methoxyethoxymethyl)-2-(carbomethoxy)-thiophene-3-sulfonamide as light brown oil.

The crude N-(4-chloro-3-methyl-5-isoxazolyl)-N-(methoxyethoxymethyl)-2-(carbomethoxy)thiophene-3-sulfonamide was dissolved in methanol (50 ml) and potassium hydroxide (5 g) and water (5 ml) were added. The reaction mixture was stirred at room temperature for 12 hours and extracted with ethyl acetate (2×50 ml). The aqueous phase was neutralized to pH 2–3 and was extracted with ethyl acetate (2×50 ml). The combined organic layer was dried over magnesium sulfate and solvent removed to give N-(4-chloro-3-methyl-5-isoxazolyl)-N-(methoxyethoxymethyl)-2-carboxylthiophene-3-sulfonamide as light brown solid (3.5 g, 85% yield).

B. 4-Carbomethoxy-2,6-dimethylaniline

To a warm solution of 3,5-dimethyl benzoic acid (5 g, 33.33 mmol) in acetic acid (30 ml) was added fuming nitric acid (30 ml), dropwise. After completion of the addition the reaction mixture was warmed with a heat gun. This was stirred for an additional 2 hours during which period a solid was precipitated. The reaction mixture was diluted with water (200 ml) and filtered. The solid was dried under reduced pressure.

To the above solid was added 20 ml of oxalyl chloride and a catalytic amount of DMF (2 drops). This was stirred at room temperature for 3 hours during which period a clear solution was formed. Excess oxalyl chloride was removed under reduced pressure to give yellow solid.

To the yellow solid was added dry methanol (100 ml) and the mixture stirred at room temperature for 1 hour. Excess methanol was removed under reduced pressure and the residue dissolved in ether (200 ml). This was washed with water (100 ml) followed by saturated NaHCO$_3$ solution (100 ml). The organic layer was dried over magnesium sulfate and the solvent removed giving 4-carbomethoxy-2,6-dimethylnitrobenzene as a yellow solid (5.8 g, 83% yield).

4-carbomethoxy-2,6-dimethylnitrobenzene (2 g, 9.5 mmol) was dissolved in ethyl acetate (20 ml) and subjected to catalytic hydrogenation using 10% palladium on carbon (300 mg) at 55 psi for 30 min. The catalyst was filtered and solvent removed to give 4-carbomethoxy-2,6-dimethylaniline as a solid (1.7 g, 100% yield).

C. N-(4-chloro-3-methyl-5-isoxazolyl)-2-(4-methoxycarbonyl-2,6-dimethyl) phenylaminocarbonyl-3-thiophenesulfonamide N-(4-chloro-3-methyl-5-isoxazolyl)-N-(methoxyethoxymethyl)-2-carboxylthiophene-3-sulfonamide (3.5 g, 8.5 mmol) (from step A) was dissolved in oxalyl chloride (5 ml) and a drop of DMF was added. This was stirred at room temperature for 6 hours. Excess oxalyl chloride was removed under reduced pressure and the mixture dried under high vacuum.

To a solution of 4-Carbomethoxy-2,6-dimethylaniline (0.9 g) (from step B) and triethyl amine (2 ml) in methylene chloride (20 ml) at 0° C. was added the acid chloride in 10 ml of methylene chloride (2.4 g, 4.98 mmol) prepared in the above step. The reaction mixture was permitted to warm to room temperature, was diluted with methylene chloride (50 ml) and was washed with 1 N HCl followed by saturated NaHCO$_3$ solution. The organic layer was dried over magnesium sulfate and the solvent removed giving the crude product. This was purified by column chromatography using 4:6 ethyl acetate and hexane as a eluent to give N-(4-chloro-3-methyl-5-isoxazolyl)-N-(methoxyethoxymethyl)2-(4-methoxycarbonyl-2,6-dimethyl)phenylaminocarbonyl-3-thiophenesulfonamide an oil (0.6 g, 20% yield).

N-(4-chloro-3-methyl-5-isoxazolyl)-N-(methoxyethoxymethyl)2-(4-methoxycarbonyl-2,6-dimethyl)phenylaminocarbonyl-3-thiophenesulfonamide (0.6 g) was dissolved in a mixture of methanol (8 ml) and concentrated HCl (1.5 ml) and the resultant reaction mixture was refluxed under stirring for 8 hours. Excess methanol was removed under reduced pressure and the residue dissolved in ethyl acetate (50 ml). This was washed with saturated sodium chloride solution. The organic layer was dried over magnesium sulfate and the solvent removed giving N-(4-chloro-3-methyl-5-isoxazolyl)-2-(4-methoxycarbonyl-2,6-dimethyl)phenylaminocarbonyl-3-thiophenesulfonamide which was crystallized using methylene chloride and hexane (0.23 g, 47% yield, m.p. 152–154° C.).

EXAMPLE 177

N-(4-chloro-3-methyl-5-isoxazolyl)-2-[3,4-(methylenedioxy)-6-methyl]phenylaminocarbonyl-3-thiophenesulfonamide

A. (3,4-methylenedioxy)-6-methylaniline

To a solution of (3,4-methylenedioxy)toluene (5 ml) in acetic acid (20 ml) cooled with a cold water bath was added, dropwise, nitric acid (70%, 5 ml). The mixture was stirred for 45 min. To work up, water (100 ml) was added and the resulting yellow precipitate was filtered and washed with water until the aqueous filtrate was colorless. The yellow solid was dissolved in EtOAc (250 ml) and dried (MgSO$_4$), and the solid was filtered off. The filtrate was subjected to catalytic hydrogenation (10% Pd/C, 1 atm) for 12 hours. The reaction mixture was then filtered off the catalyst and the filtrate was concentrated on a rotavap to give (3,4-methylenedioxy)-6-methylaniline as a brownish grey solid (5.49g, 87% yield).

B. N-(4-chloro-3-methyl-5-isoxazolyl)-2-[3,4-(methylenedioxy)-6-methyl]phenylaminocarbonyl-3-thiophenesulfonamide N-(4-chloro-3-methyl-5-isoxazolyl)-2-[3,4-(methylenedioxy)-6-methyl]phenylaminocarbonyl-3-thiophenesulfonamide was synthesized in the same manner as Example 94 using (3,4-methylenedioxy)-6-methylaniline. The crude product was purified by preparative HPLC to give N-(4-chloro-3-methyl-5-isoxazolyl)-2-[3,4-(methylenedioxy)-6-methyl]phenylaminocarbonyl-3-thiophenesulfonamide as a yellow solid (45% yield, m.p. 60–62° C.).

EXAMPLE 178

N-(4-chloro-3-methyl -5-isoxazolyl)-2-(3,4-dimethoxy-6-aminocarbonyl)phenylaminocarbonyl-3-thiophenesulfonamide N-(4-chloro-3-methyl-5-isoxazolyl)-2-(3,4-dimethoxy-6-aminocarbonyl)phenylaminocarbonyl-3-thiophenesulfonamide was synthesized in the same manner as for Example 94 using N-(4-chloro-3-methyl-5-isoxazolyl)2-{[2-carboxyl-4,5-(methylenedioxy)phenyl]aminocarbonyl}thiophene-3-sulfonamide (Example 151) and ammonium hydroxide. The crude product was purified by preparative HPLC to give N-(4-chloro-3-methyl-5-isoxazolyl)-2-(3,4-dimethoxy-6-aminocarbonyl) phenylaminocarbonyl-3-thiophenesulfonamide as yellow powder (66% yield, m.p. 189–192° C.).

EXAMPLE 179

N-(4-chloro-3-methyl-5-isoxazolyl)-2-[3,4-(methylenedioxy)-6-methyl]phenylacetyl-3-thiophenesulfonamide

A. (3,4-methylenedioxy)-6-methylbenzyl chloride

To a 1:1 mixture of ethyl ether (100 ml) and conc. HCl (100 ml) at 0° C. was added (3,4-methylenedioxy)toluene (10 ml). Formaldehyde (20 ml, 37% in water) was then added dropwise. The reaction was stirred at 0° C. for 2 hours and at room temperature for an additional 10 hours. The reaction mixture was then diluted with ethyl ether (100 ml) and the two layers were separated. The organic layer was dried (MgSO$_4$), the solid was filtered and the filtrate was concentrated. The residue was then heated with hexane (200 ml) and the insolubles were filtered off the hot solution. The filtrate was concentrated to give a mixture of (3,4-methylenedioxy)-6-methylbenzyl chloride (9.4 g, 63% yield) and bis[(3,4-methylenedioxy)-6-methyl] phenylmethane (3.6 g) as a white solid. This mixture was carried on to the next step without further purification.

B. N-(4-chloro-3-methyl-5-isoxazolyl)-2-[3,4-(methylenedioxy)-6-methyl]phenylacetyl-3-thiophenesulfonamide N-(4-chloro-3-methyl-5-isoxazolyl)-2-[3,4-(methylenedioxy)-6-methyl]phenylacetyl-3- thiophenesulfonamide was synthesized in the same manner as for Example 102 using (3,4-methylenedioxy)-6-methylbenzyl chloride instead of (3,4-methylenedioxy)benzyl chloride. The crude product was purified by preparative HPLC to give N-(4-chloro-3-methyl-5-isoxazolyl)-2-[3,4-(methylenedioxy)-6-methyl]phenylacetyl-3-thiophenesulfonamide as a yellow powder (71% yield, m.p. 42–45° C.)

EXAMPLE 180

N-(4-chloro-3-methyl-5-isoxazolyl)-2-[3,4-(methylenedioxy)-6-methanesulfonylaminomethyl]phenylaminocarbonyl-3-thiophenesulfonamide A. N-(3,4-methylenedioxy)benzyl-methanesulfonamide To a solution of piperonylamine (6.07 g, 38.95 mmol) and triethylamine (5.37 g, 53.12 mmol) in dichloromethane (100 ml) at 0° C. was added methanesulfonyl chloride (4.14 g, 35.41 mmol). The reaction was stirred at 0° C. for 1 hour. The mixture was then diluted with dichloromethane (100 ml) and washed with 1 N HCl (2×100 ml). The organic layer was dried ($MgSO_4$), the solid was filtered and the filtrate was concentrated to give N-(3,4-methylenedioxy)benzyl-methanesulfonamide as a grey solid (8.4 g, 92% yield).

B. N-[3,4-(methylenedioxy)-6-amino]benzyl-methanesulfonamide

N-[3,4-(methylenedioxy)-6-amino]benzyl-methanesulfonamide was synthesized in the same manner as for (3,4-methylenedioxy)-6-methylaniline (Example 177).

C. N-(4-chloro-3-methyl-5-isoxazolyl)-2-[3,4-(methylenedioxy)-6-methanesulfonylaminomethyl]phenylaminocarbonyl-3-thiophenesulfonamide N-(4-chloro-3-methyl-5-isoxazolyl)-2-[3,4-(methylenedioxy)-6-methanesulfonylaminomethyl]phenylaminocarbonyl-3-thiophenesulfonamide was synthesized in the same manner as Example 94. The crude product was recrystalized from acetonitrile and water to give N-(4-chloro-3-methyl-5-isoxazolyl)-2-[3,4-(methylenedioxy)-6-methanesulfonylaminomethyl]phenylaminocarbonyl-3-thiophenesulfonamide as an off-white solid (13% yield, m.p. 147–150° C.).

EXAMPLE 181

N-(4-chloro-3-methyl-5-isoxazolyl)-2-[3,4-(methylenedioxy)-6-cyanomethyl]phenylaminocarbonyl-3-thiophenesulfonamide A. [3,4-(methylenedioxy)-6-amino]phenylacetonitrile

[3,4-(methylenedioxy)-6-amino]phenylacetonitrile was synthesized in the same manner as for (3,4-methylenedioxy)-6-methylaniline (Example 177).

B. N-(4-chloro-3-methyl-5-isoxazolyl)-2-[3,4-(methylenedioxy)-6-cyanomethyl]phenylaminocarbonyl-3-thiophenesulfonamide N-(4-chloro-3-methyl-5-isoxazolyl)-2-[3,4-(methylenedioxy)-6-cyanomethyl]phenylaminocarbonyl-3-thiophenesulfonamide was synthesized in the same manner as in Example 94. The crude product was recrystalized from acetonitrile/water to give N-(4-chloro-3-methyl-5-isoxazolyl)-2-[3,4-(methylenedioxy)-6-cyanomethyl]phenylaminocarbonyl-3-thiophenesulfonamide as a red-brownish powder (15% yield, m.p. 190–193° C.).

EXAMPLE 182

N-(4-chloro-3-methyl-5-isoxazolyl)-2-[3,4-(methylenedioxy)-6-(3-hydroxypropyl)]phenylaminocarbonyl-3-thiophenesulfonamide A. 3-(3,4-methylenedioxy)phenyl-1-propanol To a solution of 3-(3,4-methylenedioxy)phenylpropanoic acid (5 g, 25.75 mmol) in anhydrous THF (20 ml) at 0° C. was added $BH_3$.THF (51.5 ml, 1.0 M in THF, 51.5 mmol). The mixture was refluxed for 1 hour. Then the THF was evaporated on a rotavap. The residue was treated with methanol (20 ml) and the solution was concentrated. This process was repeated 6 times to give 3-(3,4-methylenedioxy)phenyl-1-propanol as an oil (4.7 g, ~100 yield).

B. 3-[3,4-(methylenedioxy)-6-amino]phenyl-1-propanol

3-[3,4-(methylenedioxy)-6-amino]phenyl-1-propanol was synthesized in the same manner as for (3,4-methylenedioxy)-6-methylaniline (Example 177).

C. N-(4-chloro-3-methyl-5-isoxazolyl)-2-[3,4-(methylenedioxy)-6-(3-hydroxypropyl)]phenylaminocarbonyl-3-thiophenesulfonamide N-(4-chloro-3-methyl-5-isoxazolyl)-2-[3,4-(methylenedioxy)-6-(3-hydroxypropyl)]phenylaminocarbonyl-3-thiophenesulfonamide was synthesized in the same manner as Example 94. The crude product was purified by preparative HPLC to give N-(4-chloro-3-methyl-5-isoxazolyl)-2-[3,4-(methylenedioxy)-6-(3-hydroxypropyl)]phenylaminocarbonyl-3-thiophenesulfonamide as a dull yellow powder (18% yield, m.p. 66–69° C.).

EXAMPLE 183

N-(4-chloro-3-methyl-5-isoxazolyl)-2-[3,4-(methylenedioxy)-6-cyano]phenylacetyl-3-thiophenesulfonamide A. Methyl (3,4-methylenedioxy)phenylacetate Methyl (3,4-methylenedioxy)phenylacetate was prepared as described by known methods (see, Rachele (1963) *Journal of Organic Chemistry* 28:2898).

B. Methyl 6-bromo-(3,4-methylenedioxy)phenylacetate

To a solution of methyl (3,4-methylenedioxy)phenylacetate (5 g, 25.8 mmol) in acetic acid (15 ml) was added, dropwise, bromine until a red-brown color persisted. After stirring at RT for 30 minutes, the reaction mixture was partitioned between water (200 ml) and ether (200 ml). The organic layer was washed with water (3×200 ml), dried ($MgSO_4$), the solid was filtered off and the filtrate was concentrated to give methyl 6-bromo-(3,4-methylenedioxy)phenylacetate as an oil (5.9 g, 84% yield).

C. Methyl (3,4-methylenedioxy)-6-cyanophenylacetate

Methyl (3,4-methylenedioxy)-6-cyanophenylacetate was prepared as described by L. Friedman and H. Shechter in the Journal of Organic Chemistry 26:2522 (1961).

D. t-Butyl (3,4-methylenedioxy)-6-cyanophenylacetate

To a solution of methyl (3,4-methylenedioxy)-6-cyanophenylacetate (5 g, 18.32 mmol) in methanol (100 ml) was added 1 N NaOH (50 ml). The reaction was stirred at room temperature for 1.5 hours. Methanol was then stripped off on a rotavap. The aqueous residue was acidified with conc. HCl to pH~1 and extracted with ethyl acetate. The organic layer was dried (MgSO$_4$), the solid was filtered and the filtrate was concentrated to give a solid. The solid was treated with thionyl chloride (50 ml) and the mixture was refluxed for 10 min before the volatiles were stripped off on a rotavap. The residue was dissolved in dichloromethane (15 ml) and the solution was added dropwise to a solution of 2-methyl-2-propanol (6.8 g, 91.6 mmol) and triethylamine (9.3 g, 91.6 mmol) in dichloromethane (100 ml) at 0° C. The mixture was stirred at 0° C. for 1 hour and at room temperature for 2 hours. The mixture was then washed with water (3×150 ml). The organic layer was dried (MgSO$_4$), the solid was filtered and the filtrate was concentrated to give t-butyl (3,4-methylenedioxy)-6-cyanophenylacetate as a solid (335 mg, 7% yield).

E. N-(4-chloro-3-methyl-5-isoxazolyl)-2-[3,4-(methylenedioxy)-6-cyano]phenylacetyl-3-thiophenesulfonamide To a solution of N-(4-chloro-3-methyl-5-isoxazolyl)-2-carboxyl-3-thiophenesulfonamide (2.78 g, 8.63 mmol) in anhydrous DMF (30 ml) was added carbonyidiimidazole (1.40 g, 8.63 mmol). The mixture was stirred at room temperature for 20 min to give mixture I.

To a solution of t-butyl (3,4-methylenedioxy)-6-cyanophenylacetate (1.5 g, 5.75 mmol) in anhydrous DMF (15 ml) was added NaH (1.2 g, 60% dispersion in mineral oil, 29.9 mmol) at 0° C. The mixture was stirred at room temperature for 30 min to give mixture II. Mixture I was syringed to mixture II at 0° C. and the resulting mixture was stirred at 0° C. for 1 hour and at RT for 10 hours. The crude mixture was poured to a 2:2:1 mixture of acetonitrile/water/conc. HCl and the resulting mixture was heated at 40° C. for 12 hours. Acetonitrile was then removed on a rotavap and the aqueous residue was partitioned between ethyl acetate (200 ml) and 1 N HCl (150 ml). The organic layer was washed with 1 N HCl (3×150 ml) and dried (MgSO$_4$), the solid was filtered off and the filtrate was concentrated. The residue was purified by preparative HPLC to give N-(4-chloro-3-methyl-5-isoxazolyl)-2-[3,4-(methylenedioxy)-6-cyano]phenylacetyl-3-thiophenesulfonamide as a light dull yellow powder (450 mg, 17% yield, m.p. 105–108° C.).

EXAMPLE 184

N-(4-chloro-3-methyl-5-isoxazolyl)-2-[3,4-(methylenedioxy)-6-dimethylaminocarbonylmethyl]phenylaminocarbonyl-3-thiophenesulfonamide

A. N,N-dimethyl (3,4-methylenedioxy)phenylacetamide

N,N-dimethyl (3,4-methylenedioxy)phenylacetamide was synthesized in the same manner as described in Example 94.

B. N,N-dimethyl (3,4-methylenedioxy)-6-aminophenylacetamide

N,N-dimethyl (3,4-methylenedioxy)-6-aminophenylacetamide was synthesized in the same manner as (3,4-methylenedioxy)-6-methylaniline (see Example 177).

C. N-(4-chloro-3-methyl-5-isoxazolyl)-2-[3,4-(methylenedioxy)-6-dimethylaminocarbonylmethyl]phenylaminocarbonyl-3-thiophenesulfonamide N-(4-chloro-3-methyl-5-isoxazolyl)-2-[3,4-(methylenedioxy)-6-dimethylaminocarbonylmethyl]phenylaminocarbonyl-3-thiophenesulfonamide was synthesized in the same manner as Example 94. The crude product was recrystalized from acetonitrile/water to give N-(4-chloro-3-methyl-5-isoxazolyl)-2-[3,4-(methylenedioxy)-6-dimethylaminocarbonylmethyl]phenylaminocarbonyl-3-thiophenesulfonamide as a greyish powder (400 mg, 19% yield, m.p. 190–193° C.).

EXAMPLE 185

N-(4-chloro-3-methyl-5-isoxazolyl)-2-[3,4-(methylenedioxy)-6-methyl]phenylhydroxyimino-3-thiophenesulfonamide To N-(4-chloro-3-methyl-5-isoxazolyl)-2-[3,4-(methylenedioxy)-6-methyl]phenylacetyl-3-thiophenesulfonamide (100 mg) was added NH$_2$OH.HCl (300 mg) and water (15 ml). After stirring for 5 min, NaOH pellet (300 mg) and methanol (2 ml) were added. The warm mixture was heated at 80° C. for 20 min and was cooled to 0° C. It was then poured into a dilute HCl solution (~30 ml). The resulting white precipitate was filtered to give N-(4-chloro-3-methyl-5-isoxazolyl)-2-[3,4-(methylenedioxy)-6-methyl]phenylhydroxyimino-3-thiophenesulfonamide as a white solid (72 mg, 70% yield, m.p. 154–156° C.).

EXAMPLE 186

N-(4-chloro-3-methyl-5-isoxazolyl)-2-{1-acetoxy-2-cis-[3,4-(methylenedioxy)-6-methyl]phenyl}vinyl-3-thiophenesulfonamide To a solution of N-(4-chloro-3-methyl-5-isoxazolyl)-2-[3,4-(methylenedioxy)-6-methyl]phenylacetyl-3-thiophenesulfonamide (50 mg, 0.11 mmol) in anhydrous DMF (1 ml) was added NaH (11 mg, 60% dispersion in mineral oil, 0.275 mmol). After stirring at room temperature for 5 min, acetic anhydride (16.8 mg, 0.165 mmol) was added. After stirring at room temperature for an additional 10 min., the mixture was poured into dilute HCl solution and the resulting precipitate was filtered to give N-(4-chloro-3-methyl-5-isoxazolyl)-2-{1-acetoxy-2-cis-[3,4-(methylenedioxy)-6-methyl]phenyl}vinyl-3-thiophenesulfonamide as a yellowish powder (40 mg, 73%, m.p. 55–58° C.).

EXAMPLE 187

N-(4-chloro-3-methyl-5-isoxazolyl)-2-(1,2,3-trimethoxy-6-cyano)phenylaminocarbonyl-3-thiophenesulfonamide

A. 2-amino-3,4,5-trimethoxybenzonitrile 2-amino-3,4,5-trimethoxybenzonitrile was synthesized in the same manner as (3,4-methylenedioxy)-6-methylaniline (see Example 177), and the crude product was recrystalized from methanol/water to give a yellow powder (13% yield).

B. N-(4-chloro-3-methyl-5-isoxazolyl)-2-(1,2,3-trimethoxy-6-cyano)phenylaminocarbonyl-3-thiophenesulfonamide N-(4-chloro-3-methyl-5-isoxazolyl)-2-(1,2,3-trimethoxy-6-cyano)phenylaminocarbonyl-3-thiophenesulfonamide was synthesized in the same manner as Example 148. The crude product was purified via preparative HPLC to give N-(4-chloro-3-methyl-5-isoxazolyl)-2-(1,2,3-trimethoxy-6-cyano)phenylaminocarbonyl-3-thiophenesulfonamide as a yellow powder (180 mg, 10% yield, m.p. 88–90° C.).

EXAMPLE 188

N-(3,4-dimethyl-5-isoxazolyl)-2-[3,4-(methylenedioxy)-6-methyl]phenylacetyl-3-thiophenesulfonamide N-(3,4-dimethyl-5-isoxazolyl)-2-[3,4-(methylenedioxy)-6-methyl]phenylacetyl-3-thiophenesulfonamide was synthesized in the same manner as Example 179. The crude product was purified via preparative HPLC to give N-(3,4-dimethyl-5-isoxazolyl)-2-[3,4-(methylenedioxy)-6-methyl]phenylacetyl-3-thiophenesulfonamide as a yellow powder (417 mg, 14% yield, m.p. 45–50° C.).

EXAMPLE 189

N-(4-chloro-5-methyl-3-isoxazolyl)-2-[3,4-(methylenedioxy)-6-methyl]phenylacetyl-3-thiophenesulforiamide N-(4-chloro-5-methyl-3-isoxazolyl)-2-[3,4-(methylenedioxy)-6-methyl]phenylacetyl-3-thiophenesulfonamide was synthesized in the same manner as Example 179. The crude product was purified via preparative HPLC to give N-(4-chloro-5-methyl-3-isoxazolyl)-2-[3,4-(methylenedioxy)-6-methyl]phenylacetyl-3-thiophenesulfonamide as a yellowish powder (330 mg, 16% yield, m.p. 46–50° C.).

EXAMPLE 190

Other compounds that have been prepared by the above methods or routine modifications thereof, include, but are not limited to: N-(4-chloro-3-methyl-5-isoxazolyl)-2-[(4-methoxyphenoxy)carbonyl]thiophene-3-sulfonamide, N-(4-bromo-3-methyl-5-isoxazolyl)-2-[(4-methylphenoxy)carbonyl]thiophene-3-sulfonamide, N-(4-bromo-3-methyl-5-isoxazolyl)-3-[(4-methylphenoxy)methyl]thiophene-2-sulfonamide, N-(4-bromo-3-methyl-5-isoxazolyl)-2-[(4-methylphenoxy)methyl]thiophene-3-sulfonamide, N-(4-bromo-3-methyl-5-isoxazolyl)-3-(4-methyl-trans-styryl)thiophene-2-sulfonamide, N-(4-bromo-3-methyl-5-isoxazolyl)-3-(4-methylphenethyl)thiophene-2-sulfonamide, N-(4-bromo-3-methyl-5-isoxazolyl)-2-[(4-methylphenyl)acetyl]thiophene-3-sulfonamide, N-(4-bromo-3-methyl-5-isoxazolyl)-2-[(3-methoxyphenyl)acetyl]thiophene-3-sulfonamide, N-(4-bromo-3-methyl-5-isoxazolyl)-3-(4-methylphenethyl)-5-(4-tolyl)thiophene-2-sulfonamide, N-(4-bromo-3-methyl-5-isoxazolyl)-3-(4-methylbenzyl)-5-(4-tolyl)thiophene-2-sulfonamide, N-(4-bromo-3-methyl-5-isoxazolyl)-3-(4-methyl-trans-styryl)-5-(4-tolyl)thiophene-2-sulfonamide, N-(4-chloro-3-methyl-5-isoxazolyl)-2-[3,4-(methylenedioxy)benzyl]thiophene-3-sulfonamide, N-(4-chloro-3-methyl-5-isoxazolyl)-2-[(5-methyl-3-isoxazolyl)aminocarbonyl]thiophene-3-sulfonamide, N-(4-bromo-3-methyl-5-isoxazolyl)-2-[(3-hydroxyl-6-pyridazinyl)aminocarbonyl]thiophene-3-sulfonamide, N-(4-bromo-3-methyl-5-isoxazolyl)-3-{[3,4-(methylenedioxy)phenoxy]methyl}thiophene-2-sulfonamide, N-(4-bromo-3-methyl-5-isoxazolyl)-2-[(4-methyl)(cinnamyl)]thiophene-3-sulfonamide, N-(4-bromo-3-methyl-5-isoxazolyl)-3-[3,4-(methylenedioxy)phenethyl]thiophene-2-sulfonamide, N-(4-bromo-3-methyl-5-isoxazolyl)-3-[3,4-(methylenedioxy)-trans-styryl]thiophene-2-sulfonamide, N-(4-bromo-3-methyl-5-isoxazolyl)-2-[(4-methyl)phenethyl]thiophene-3-sulfonamide, N-(3,4-dimethyl-5-isoxazolyl)-2-(4-tolylacetylphenyl)thiophene-3-sulfonamide, N-(3,4-dimethyl-5-isoxazolyl)-2-3,4-(methylenedioxy)phenylacetyl]thiophene-3-sulfonamide, N-(4-chloro-3-methyl-5-isoxazolyl)-2-[2-hydroxy-4-methylphenyl)aminocarbonyl]thiophene-3-sulfonamide and others, including those set forth in TABLE 1 that are not specifically exemplified herein.

For example, N-(4-bromo-3-methyl-5-isoxazolyl)-3-[2-methyl-4,5-(methylenedioxy)cinnamyl]thiophene-2-sulfonamide, N-(4-bromo-3-methyl-5-isoxazolyl)-3-[2-(hydroxymethyl)-4,5-(methylenedioxy)cinnamyl]thiophene-2-sulfonamide, N-(4-bromo-3-methyl-5-isoxazolyl)-3-{2-[(tetrahydro-4H-pyran-2-ylxoy)methyl]-4,5-(methylenedioxy)cinnamyl}thiophene-2-sulfonamide and N-(4-bromo-3-methyl-5-isoxazolyl)-3-(2,4-dimethylcinnamyl)thiophene-2-sulfonamide have been prepared in the same manner as N-(4-bromo-3-methyl-5-isoxazolyl)-3-[3,4-(methylenedioxy)-trans-styryl]thiophene-2-sulfonamide. N-(4-bromo-3-methyl-5-isoxazolyl)-3-[2-methyl-4,5-(methylenedioxy)phenethyl]thiophene-2-sulfonamide and N-(4-bromo-3-methyl-5-isoxazolyl)-2-(2,4,6-trimethylphenethyl)thiophene-3-sulfonamide have been prepared in the same manner as N-(4-bromo-3-methyl-5-isoxazolyl)-2-[(4-methyl)phenethyl]thiophene-3-sulfonamide (see, Example 159). N-(4-bromo-3-methyl-5-isoxazolyl)-3-{[2-propyl-4,5-(methylenedioxy)phenoxy]methyl}thiophene-2-sulfonamide has been prepared in the same manner as N-(4-bromo-3-methyl-5-isoxazolyl)-3-[(4-methylphenoxy)methyl]thiophene-2-sulfonamide and N-(4-bromo-3-methyl-5-isoxazolyl)-3-{[3,4-(methylenedioxy)phenoxy]methyl}thiophene-2-sulfonamide. N-(4-bromo-3-methyl-5-isoxazolyl)-2-[2-methyl-4,5-(methylenedioxy)phenethyl]thiophene-3-sulfonamide has been prepared in the same manner as N-(4-bromo-3-methyl-5-isoxazolyl)-2-[(3,4-methylenedioxy)phenethyl]thiophene-3-sulfonamide. Compounds, such as N-(4-bromo-3-methyl-5-isoxazolyl)-3-(2-tolyl)thiophene-2-sulfonamide, N-(4-bromo-3-methyl-5-isoxazolyl)-3-(3-tolyl)thiophene-2-sulfonamide, N-(4-bromo-3-methyl-5-isoxazolyl)-3-(2-tolyl)thiophene-2-sulfonamide, N-(4-bromo-3-methyl-5-isoxazolyl)-3-(3-methoxyphenyl)thiophene-2-sulfonamide, N-(4-bromo-3-methyl-5-isoxazolyl)-3-(3-methoxyphenyl)thiophene-2-sulfonamide, N-(4-bromo-3-methyl-5-isoxazolyl)-3-(2-methoxyphenyl)thiophene-2-sulfonamide, N-(4-bromo-3-methyl-5-isoxazolyl)-3-(4-ethylphenyl)thiophene-2-sulfonamide, N-(4-bromo-3-methyl-5-isoxazolyl)-3-(4-propylphenyl)thiophene-2-sulfonamide, N-(4-bromo-3-methyl-5-isoxazolyl)-3-(4-iso-propylphenyl)thiophene-2-sulfonamide, N-(4-bromo-3-methyl-5-isoxazolyl)-3-(4-butylphenyl)thiophene-2-sulfonamide, N-(4-bromo-3-methyl-5-isoxazolyl)-3-(2,4-dimethylphenyl)thiophene-2-sulfonamide, N-(4-bromo-3-methyl-5-isoxazolyl)-3-(4-iso-butylphenyl)thiophene-2-sulfonamide, N-(4-bromo-3-methyl-5-isoxazolyl)-3-(4-iso-pentylphenyl)thiophene-2-sulfonamide, N-(4-bromo-3-methyl-5-isoxazolyl)-3-(2-methyl-4-propylphenyl)thiophene-2-sulfonamide, N-(4-bromo-3-methyl-5-isoxazolyl)-3-(4-iso-butyl-2-methylphenyl)thiophene-2-sulfonamide and N-(4-bromo-3-methyl-5-isoxazolyl)-3-(4-iso-pentyl-2-methylphenyl)thiophene-2-sulfonamide have been prepared in the same manner as N-(4-bromo-3-methyl-5-isoxazolyl)-3-[(3,4-methylenedioxy)phenyl]thiophene-2-sulfonamide (see, Example 125).

N-(4-bromo-3-methyl-5-isoxazolyl)-2-[2-methyl-4,5-(methylenedioxy)phenethyl]thiophene-3-sulfonamide has been prepared in the same manner as N-(4-Bromo-3-methyl-5-isoxazolyl)-2-[3,4-(methylenedioxy)phenethyl]thiophene-3-sulfonamide (Example 128). N-(4-bromo-3-methyl-5-isoxazolyl)-2-[2-methyl-4,5-(methylenedioxy)cinnamyl]thiophene-3-sulfonamide has been prepared in the same manner as N-(4-bromo-3-methyl-5-isoxazolyl)-2-[(4-methyl)(cinnamyl)]thiophene-3-sulfonamide (Example 158).

N-(4-bromo-3-methyl-5-isoxazolyl)-2-{[3,4-(methylenedioxy)phenoxy]methyl}thiophene-3-sulfonamide, N-(4-bromo-3-methyl-5-isoxazolyl)-2-[(2,4,6-trimethylphenoxy)methyl]thiophene-3-sulfonamide, N-(4-bromo-3-methyl-5-isoxazolyl)-2-{[4,5-(methylenedioxy)-2-propylphenoxy]methyl}thiophene-3-sulfonamide have been prepared in the same manner as N-(4-bromo-3-methyl-5-isoxazolyl)-2-[(4-methylphenoxy)methyl]thiophene-3-sulfonamide (Example 160).

Any corresponding N-(4-halo-3-methyl-5-isoxazolyl), N-(4-halo-5-methyl-3-isoxazolyl), N-(3,4-dimethyl-5-isoxazolyl), N-(4-halo-5-methyl-3-isoxazolyl), N-(4-halo-3-methyl-5-isoxazolyl), N-(4,5-dimethyl-3-isoxazolyl) derivative of any of these compounds or any compound disclosed herein may also be prepared and used as described herein.

EXAMPLE 191

Other compounds that can be prepared by the above methods or routine modifications thereof, include, but are not limited to:

N-(4-chloro-3-methyl-5-isoxazolyl)-2-(2,3,4-trimethoxy-6-methylphenylaminocarbonyl)thiophene-3-sulfonamide,
N-(4-chloro-3-methyl-5-isoxazolyl)-2-(2,3,4-trimethoxy-6-acetylphenylaminocarbonyl)thiophene-3-sulfonamide,
N-(4-chloro-3-methyl-5-isoxazolyl)-2-(2,3,4-trimethoxy-6-methoxycarbonylphenylaminocarbonyl)thiophene-3-sulfonamide,
N-(4-chloro-3-methyl-5-isoxazolyl)-2-(2,3,4-trimethoxy-6-carbonylphenylaminocarbonyl)thiophene-3-sulfonamide,
N-(4-chloro-3-methyl-5-isoxazolyl)-2-(2,3,4-trimethoxy-6-methanesulfonylphenylaminocarbonyl)thiophene-3-sulfonamide,
N-(4-chloro-3-methyl-5-isoxazolyl)-2-[2,3,4-trimethoxy-6-(cyanomethyl)phenylaminocarbonyl]thiophene-3-sulfonamide,
N-(4-chloro-3-methyl-5-isoxazolyl)-2-[2,3,4-trimethoxy-6-(2-hydroxyethyl)phenylaminocarbonyl]thiophene-3-sulfonamide,
N-(4-chloro-3-methyl-5-isoxazolyl)-2-[3,4-(methylenedioxy)-2-methoxy-6-methylphenylaminocarbonyl]thiophene-3-sulfonamide,
N-(4-chloro-3-methyl-5-isoxazolyl)-2-[3,4-(methylenedioxy)-2-methoxy-6-acetylphenylaminocarbonyl]thiophene-3-sulfonamide,
N-(4-chloro-3-methyl-5-isoxazolyl)-2-[3,4-(methylenedioxy)-2-methoxy-6-methoxycarbonlphenelaminocarbonyl]thiophene-3-sulfonamide,
N-(4-chloro-3-methyl-5-isoxazolyl)-2-[3,4-(methylenedioxy)-2-methoxy-6-carbonylphenylaminocarbonyl]thiophene-3-sulfonamide,
N-(4-chloro-3-methyl-5-isoxazolyl)-2-[3,4-(methylenedioxy)-2-methoxy-6-methanesulfonylphenylaminocarbonyl]thiophene-3-sulfonamide,
N-(4-chloro-3-methyl-5-isoxazolyl)-2-[3,4-(methylenedioxy)-2-methoxy-6-cyanophenylaminocarbonyl]thiophene-3-sulfonamide,
N-(4-chloro-3-methyl-5-isoxazolyl)-2-[3,4-(methylenedioxy)-2-methoxy-6-cyanomethylphenylaminocarbonyl]thiophene-3-sulfonamide,
N-(4-chloro-3-methyl-5-isoxazolyl)-2-[3,4-(methylenedioxy)-2-methoxy-6-(2-hydroxyethyl)phenylaminocarbonyl]thiophene-3-sulfonamide,
N-(4-chloro-3-methyl-5-isoxazolyl)-2-[3,4-(methylenedioxy)-2,6-dimethylphenylaminocarbonyl]thiophene-3-sulfonamide,
N-(4-chloro-3-methyl-5-isoxazolyl)-2-[3,4-(methylenedioxy)-6-acetyl-2-methylphenylaminocarbonyl]thiophene-3-sulfonamide,
N-(4-chloro-3-methyl-5-isoxazolyl)-2-[3,4-(methylenedioxy)-6-methoxycarbonyl-2-methylphenylaminocarbonyl]thiophene-3-sulfonamide,
N-(4-chloro-3-methyl-5-isoxazolyl)-2-[3,4-(methylenedioxy)-6-carboxyl-2-methylphenylaminocarbonyl]thiophene-3-sulfonamide,
N-(4-chloro-3-methyl-5-isoxazolyl)-2-[3,4-(methylenedioxy)-6-methoxy-2-methylphenylaminocarbonyl]thiophene-3-sulfonamide,
N-(4-chloro-3-methyl-5-isoxazolyl)-2-[3,4-(methylenedioxy)-6-methanesulfonyl-2-methylphenylaminocarbonyl]thiophene-3-sulfonamide,
N-(4-chloro-3-methyl-5-isoxazolyl)-2-[3,4-(methylenedioxy)-6-cyano-2-methylphenylaminocarbonyl]thiophene-3-sulfonamide,
N-(4-chloro-3-methyl-5-isoxazolyl)-2-[3,4-(methylenedioxy)-6-(cyanomethyl)-2-methylphenylaminocarbonyl]thiophene-3-sulfonamide,
N-(4-chloro-3-methyl-5-isoxazolyl)-2-[3,4-(methylenedioxy)-6-(2-hydroxyethyl)-2-methylphenylaminocarbonyl]thiophene-3-sulfonamide,
N-(4-chloro-3-methyl-5-isoxazolyl)-2-[3,4-(methylenedioxy)-2-cyano-6-methylphenylaminocarbonyl]thiophene-3-sulfonamide,
N-(4-chloro-3-methyl-5-isoxazolyl)-2-[3,4-(methylenedioxy)-6-methoxy-2-cyanophenylaminocarbonyl]thiophene-3-sulfonamide,
N-(4-chloro-3-methyl-5-isoxazolyl)-2-[3,4-(methylenedioxy)-2-acetyl-6-methylphenylaminocarbonyl]thiophene-3-sulfonamide,
N-(4-chloro-3-methyl-5-isoxazolyl)-2-[3,4-(methylenedioxy)-6-methoxy-2-acetylphenylaminocarbonyl]thiophene-3-sulfonamide,
N-(4-chloro-3-methyl-5-isoxazolyl)-2-(3-cyano-2,4,6-trimethylphenylaminocarbonyl)thiophene-3-sulfonamide,
N-(4-chloro-3-methyl-5-isoxazolyl)-2-(3-carboxyl-2,4,6-trimethylphenylaminocarbonyl)thiophene-3-sulfonamide,
N-(4-chloro-3-methyl-5-isoxazolyl)-2-(3-hydroxymethyl-2,4,6-trimethylphenylaminocarbonyl)thiophene-3-sulfonamide,
N-(4-chloro-3-methyl-5-isoxazolyl)-2-(3-methanesulfonyl-2,4,6-trimethylphenylaminocarbonyl)thiophene-3-sulfonamide,
N-(4-chloro-3-methyl-5-isoxazolyl)-2-(3-cyanomethyl-2,4,6-trimethylphenylaminocarbonyl)thiophene-3-sulfonamide,
N-(4-chloro-3-methyl-5-isoxazolyl)-2-[3-(2-hydroxyethyl)-2,4,6-trimethylphenylaminocarbonyl]thiophene-3-sulfonamide,
N-(4-chloro-3-methyl-5-isoxazolyl)-2-[3-(carboxylmethyl)-2,4,6-trimethylphenylaminocarbonyl]thiophene-3-sulfonamide, N-(4-chloro-3-methyl-5-isoxazolyl)-2-(4-cyano-2,6-dimethylphenylaminocarbonyl)thiophene-3-sulfonamide,
N-(4-chloro-3-methyl-5-isoxazolyl)-2-(4-cyano-2,6-dimethylphenylaminocarbonyl)thiophene-3-sulfonamide,
N-(4-chloro-3-methyl-5-isoxazolyl)-2-[4-(hydroxymethyl)-2,6-dimethylphenylaminocarbonyl]thiophene-3-sulfonamide,
N-(4-chloro-3-methyl-5-isoxazolyl)-2-[4-(2-hydroxyethyl)-2,6-dimethylphenylaminocarbonyl]thiophene-3-sulfonamide,
N-(4-chloro-3-methyl-5-isoxazolyl)-2-[4-(cyanomethyl)-2,6-dimethylphenylaminocarbonyl]thiophene-3-sulfonamide,
N-(4-chloro-3-methyl-5-isoxazolyl)-2-[4-(carboxylmethyl)-2,6-dimethylphenylaminocarbonyl]thiophene-3-sulfonamide,
N-(4-chloro-3-methyl-5-isoxazolyl)-2-(4-methanesulfonyl-2,6-dimethylphenylaminocarbonyl)thiophene-3-sulfonamide,
N-(4-chloro-3-methyl-5-isoxazolyl)-2-(2,3,4-trimethoxy-6-methylphenylacetyl)thiophene-3-sulfonamide,
N-(4-chloro-3-methyl-5-isoxazolyl)-2-(2,3,4-trimethoxy-6-acetylphenylacetyl)thiophene-3-sulfonamide,
N-(4-chloro-3-methyl-5-isoxazolyl)-2-(2,3,4-trimethoxy-6-methoxycarbonylphenylacetyl)thiophene-3-sulfonamide,
N-(4-chloro-3-methyl-5-isoxazolyl)-2-(2,3,4-trimethoxy-6-carboxylphenylacetyl)thiophene-3-sulfonamide,
N-(4-chloro-3-methyl-5-isoxazolyl)-2-(2,3,4-trimethoxy-6-methanesulfonylphenylacetyl)thiophene-3-sulfonamide,
N-(4-chloro-3-methyl-5-isoxazolyl)-2-[2,3,4-trimethoxy-6-(cyanomethyl)phenylacetyl]thiophene-3-sulfonamide,
N-(4-chloro-3-methyl-5-isoxazolyl)-2-[2,3,4-trimethoxy-6-(2-hydroxyethyl)phenylacetyl]thiophene-3-sulfonamide,
N-(4-chloro-3-methyl-5-isoxazolyl)-2-[3,4-(methylenedioxy)-2-methoxy-6-methylphenylacetyl]thiophene-3-sulfonamide,
N-(4-chloro-3-methyl-5-isoxazolyl)-2-[3,4-(methylenedioxy)-2-methoxy-6-acetylphenylacetyl]thiophene-3-sulfonamide,
N-(4-chloro-3-methyl-5-isoxazolyl)-2-[3,4-(methylenedioxy)-2-methoxy-6-methoxycarbonylphenylacetyl]thiophene-3-sulfonamide,
N-(4-chloro-3-methyl-5-isoxazolyl)-2-[3,4-(methylenedioxy)-2-methoxy-6-carboxylphenylacetyl]thiophene-3-sulfonamide,
N-(4-chloro-3-methyl-5-isoxazolyl)-2-[3,4-(methylenedioxy-2-methoxy-6-methanesulfonyl)phenylacetyl]thiophene-3-sulfonamide,
N-(4-chloro-3-methyl-5-isoxazolyl)-2-[3,4-(methylenedioxy)-2-methoxy-6-(cyano)phenylacetyl]thiophene-3-sulfonamide,
N-(4-chloro-3-methyl-5-isoxazolyl)-2-[3,4-(methylenedioxy)-2-methoxy-6-(cyanomethylphenylacetyl]thiophene-3-sulfonamide,
N-(4-chloro-3-methyl-5-isoxazolyl)-2-[3,4-(methylenedioxy)-2-methoxy-6-(2-hydroxyethyl)phenylacetyl]thiophene-3-sulfonamide,
N-(4-chloro-3-methyl-5-isoxazolyl)-2-[3,4-(methylenedioxy)-2,6-dimethylphenylacetyl]thiophene-3-sulfonamide,
N-(4-chloro-3-methyl-5-isoxazolyl)-2-[3,4-(methylenedioxy)-6-acetyl-2-methylphenylacetyl]thiophene-3-sulfonamide,
N-(4-chloro-3-methyl-5-isoxazolyl)-2-[3,4-(methylenedioxy)-6-methoxycarbonyl-2-methylphenylacetyl]thiophene-3-sulfonamide,
N-(4-chloro-3-methyl-5-isoxazolyl)-2-[3,4-(methylenedioxy)-6-carboxyl-2-methylphenylacetyl]thiophene-3-sulfonamide,
N-(4-chloro-3-methyl-5-isoxazolyl)-2-[3,4-(methylenedioxy)-6-methoxy-2-methylphenylacetyl]thiophene-3-sulfonamide,
N-(4-chloro-3-methyl-5-isoxazolyl)-2-[3,4-(methylenedioxy)-6-methanesulfonyl-2-methylphenylacetyl]thiophene-3-sulfonamide,
N-(4-chloro-3-methyl-5-isoxazolyl)-2-[3,4-(methylenedioxy)-6-cyano-2-methylphenylacetyl]thiophene-3-sulfonamide,
N-(4-chloro-3-methyl-5-isoxazolyl)-2-[3,4-(methylenedioxy)-6-(cyanomethyl)-2-methylphenylacetyl]thiophene-3-sulfonamide,
N-(4-chloro-3-methyl-5-isoxazolyl)-2-[3,4-(methylenedioxy)-6-(2-hydroxyethyl)-2-methylphenylacetyl]thiophene-3-sulfonamide,
N-(4-chloro-3-methyl-5-isoxazolyl)-2-[3,4-(methylenedioxy)-2-cyano-6-methylphenylacetyl]thiophene-3-sulfonamide,
N-(4-chloro-3-methyl-5-isoxazolyl)-2-[3,4-(methylenedioxy)-6-methoxy-2-cyanophenylacetyl]thiophene-3-sulfonamide,
N-(4-chloro-3-methyl-5-isoxazolyl)-2-[3,4-(methylenedioxy)-2-acetyl-6-methylphenylacetyl]thiophene-3-sulfonamide,
N-(4-chloro-3-methyl-5-isoxazolyl)-2-[3,4-(methylenedioxy)-6-methoxy-2-acetylphenylacetyl]thiophene-3-sulfonamide,
N-(4-chloro-3-methyl-5-isoxazolyl)-2-(3-cyano-2,4,6-trimethylphenylacetyl)thiophene-3-sulfonamide,
N-(4-chloro-3-methyl-5-isoxazolyl)-2-(3-carboxyl-2,4,6-trimethylphenylacetyl)thiophene-3-sulfonamide,
N-(4-chloro-3-methyl-5-isoxazolyl)-2-(3-hydroxymethyl-2,4,6-trimethylphenylacetyl)thiophene-3-sulfonamide,
N-(4-chloro-3-methyl-5-isoxazolyl)-2-(3-methanesulfonyl-2,4,6-trimethylphenylacetyl)thiophene-3-sulfonamide,
N-(4-chloro-3-methyl-5-isoxazolyl)-2-[3-(cyanomethyl)-2,4,6-trimethylphenylacetyl]thiophene-3-sulfonamide,
N-(4-chloro-3-methyl-5-isoxazolyl)-2-[3-(2-hydroxyethyl)-2,4,6-trimethylphenylacetyl]thiophene-3-sulfonamide,
N-(4-chloro-3-methyl-5-isoxazolyl)-2-[3-(carboxylmethyl)-2,4,6-trimethylphenylacetyl]thiophene-3-sulfonamide,
N-(4-chloro-3-methyl-5-isoxazolyl)-2-(4-cyano-2,6-dimethylphenylacetyl)thiophene-3-sulfonamide,
N-(4-chloro-3-methyl-5-isoxazolyl)-2-(4-carboxyl-2,6-dimethylpheneylacetyl)thiophene-3-sulfonamide,
N-(4-chloro-3-methyl-5-isoxazolyl)-2-(4-hydroxymethyl-2,6-dimethylphenylacetyl)thiophene-3-sulfonamide,
N-(4-chloro-3-methyl-5-isoxazolyl)-2-[4-(2-hydroxyethyl)-2,6-(dimethyl)phenylacetyl]thiophene-3-sulfonamide,
N-(4-chloro-3-methyl-5-isoxazolyl)-2-[4-cyanomethyl-2,6-(dimethyl)phenylacetyl]thiophene-3-sulfonamide,
N-(4-chloro-3-methyl-5-isoxazolyl)-2-[4-(carboxylmethyl)-2,6-dimethylphenylacetyl]thiophene-3-sulfonamide, and
N-(4-chloro-3-methyl-5-isoxazolyl)-2-(4-methanesulfonyl-2,6-dimethylphenylacetyl)thiophene-3-sulfonamide.

EXAMPLE 192

Other compounds, having activity generally at $IC_{50}$ concentrations of 10 μM or substantially less for $ET_A$ or $ET_B$ receptors, in which $Ar^2$ contains a heterocyclic ring, such as thienyl-, furyl- and pyrrole-sulfonamides of interest herein, can be or have been prepared (see, e.g., TABLE 1) by methods analogous to those set forth in the above Examples. Such compounds include, but are not limited to the following compounds: N-(4-bromo-3-methyl-5-isoxazolyl)-2-carboxyl -1-methylindole-3-sulfonamide, N-(4-chloro-3-methyl-5-isoxazolyl)-2-[(4-oxacyclohexyl)oxycarbonyl]

thiophene-3-sulfonamide, 2-[3,4-(methylenedioxy) phenylacetyl]thiophene-3-sulfonamide, N-(4-chloro-3-methyl-5-isoxazolyl)-{2-[3,4-(methylenedioxy)phenyl] acetyl}thiophene-3-sulfonamide oxime, N-(4-chloro-3-methyl-5-isoxazolyl)-2-phenylbenzo[b]thiophene sulfonamide, N-(4-chloro-3-methyl-5-isoxazolyl)-2-[(4-tolyl)aminocarbonyl]-1-methylindole-3-sulfonamide, N-(4-chloro-3-methyl-5-isoxazolyl)-2-[(4-methoxyphenoxy) carbonyl]thiophene-3-sulfonamide, N-(4-bromo-3-methyl-5-isoxazolyl)-1-[3,4-(methylenedioxy)benzyl]indole-2-sulfonamide, N-(4-bromo-3-methyl-5-isoxazolyl)-2-[(4-methylphenoxy)carbonyl]thiophene-3-sulfonamide, N-(4-chloro-3-methyl-5-isoxazolyl)-2-[(4-methoxyphenyl) acetyl]thiophene-3-sulfonamide, N-(4-chloro-3-methyl-5-isoxazolyl)-6-methoxy-2-[3,4-(methylenedioxy)benzyl] benzo[b]thiophene-3-sulfonamide, N-(4-bromo-3-methyl-5-isoxazolyl)-3-[(4-methylphenoxy)methyl]thiophene-2-sulfonamide, N-(4-bromo-3-methyl-5-isoxazolyl)-2-[(4-methylphenoxy)methyl]thiophene-3-sulfonamide, N-(4-bromo-3-methyl-5-isoxazolyl)-3-(4-methyl-trans-styryl) thiophene-2-sulfonamide, N-(4-bromo-3-methyl-5-isoxazolyl)-3-(4-methylphenethyl)thiophene-2-sulfonamide, N-(4-bromo-3-methyl-5-isoxazolyl)-2-[(4-methylphenyl)acetyl]thiophene-3-sulfonamide, N-(4-chloro-3-methyl-5-isoxazolyl)-2-[(3-methoxyphenyl) acetyl]thiophene-3-sulfonamide, N-(4-chloro-3-methyl-5-isoxazolyl)-2-{1-hydroxy-1-[3,4-(methylenedioxy)benzyl] ethyl}thiophene-3-sulfonamide, N-4-(bromo-3-methyl-5-isoxazolyl)-3-(4-methylphenethyl)(4-tolyl)thiophene-2-sulfonamide, N-(4-bromo-3-methyl-5-isoxazolyl)-3-(4-methylbenzyl)-5-(4-tolyl)thiophene-2-sulfonamide, N-(4-bromo-3-methyl-5-isoxazolyl)-3-(4-methyl-trans-styryl)-5-(4-tolyl)thiophene-2-sulfonamide, N-(4-chloro-3-methyl-5-isoxazolyl)-2-[β,β-(ethylenedioxy)3,4-(methylenedioxy) phenethyl]thiophene-3-sulfonamide, N-(4-chloro-3-methyl-5-isoxazolyl)-2-[β-(dimethylamino)-3,4-(methylenedioxy) phenethy]thiophene-3-sulfonamide, N-(4-chloro-3-methyl-5-isoxazolyl)-2-{α-hydroxy-[3,4-(methylenedioxy)phenyl] acetyl}thiophene-3-sulfonamide; N-(4-chloro-5-methyl-3-isoxazolyl)-2-[3,4-(methylenedioxy)benzyl]benzo[b] thiophene-3-sulfonamide; N-(4-bromo-3-methyl-5-isoxazolyl)-3-styrylthiophene-2-sulfonamide; N-(4-bromo-3-methyl-5-isoxazolyl)-2-styrylthiophene-3-sulfonamide; N-(4-bromo-3-methyl-5-isoxazolyl)-2-(benzoylamino) thiophene-3-sulfonamide; N-(4-bromo-3-methyl-5-isoxazolyl)-2-[(phenyl)methylaminocarbonyl]thiophene-3-sulfonamide; N-(4-bromo-3-methyl-5-isoxazolyl)-5-(phenylthio)furan-2-sulfonamide; N-(4-bromo-3-methyl-5-isoxazolyl)-5-(hydroxymethyl)furan-2-sulfonamide; N-(4-bromo-3-methyl-5-isoxazolyl)-5-(carbomethoxy)furan-2-sulfonamide; N-(4-bromo-3-methyl-5-isoxazolyl)-2,5-dimethylfuran-3-sulfonamide; N-(4-bromo-3-methyl-5-isoxazolyl)-2-(diisopropylaminocarbonyl)thiophene-3-sulfonamide; N-(4-bromo-3-methyl-5-isoxazolyl)-2-(diethylaminocarbonyl)thiophene-3-sulfonamide; N-(4-bromo-3-methyl-5-isoxazolyl)-5-styrylfuran-2-sulfonamide; N-(4-bromo-3-methyl-5-isoxazolyl)-5-styrylthiophene-2-sulfonamide; N-(4-chloro-3-methyl-5-isoxazolyl)-2-[3,4-(methylenedioxy)benzyl]-5-(dimethylamino)benzo[b]thiophene-3-sulfonamide; N-(4-chloro-3-methyl-5-isoxazolyl)-2-[3,4-(methylenedioxy) benzyl]-7-methoxybenzo[b]thiophene-3-sulfonamide; N-(4-chloro-3-methyl-5-isoxazolyl)-2-[3,4-(methylenedioxy) benzyl]-7-phenoxybenzo[b]thiophene-3-sulfonamide; N-(4-chloro-3-methyl-5-isoxazolyl)-2-[3,4-(methylenedioxy) benzyl]-5-methoxybenzo[b]thiophene-3-sulfonamide; N-(4-chloro-3-methyl-5-isoxazolyl)-2-[3,4-(methylenedioxy) benzyl]-5-isobutylaminobenzo[b]thiophene-3-sulfonamide; N-(4-chloro-3-methyl-5-isoxazolyl)-2-[3,4-(methylenedioxy)benzyl]-5-benzylaminobenzo[b] thiophene-3-sulfonamide; N-(4-chloro-3-methyl-5-isoxazolyl)-2-[3,4-(methylenedioxy)phenoxy]benzo[b] thiophene-3-sulfonamide; N-(4-chloro-3-methyl-5-isoxazolyl)-2-[3,4-(methylenedioxy)phenoxy]-5-dimethylaminobenzo[b]thiophene-3-sulfonamide; N-(4-chloro-3-methyl-5-isoxazolyl)-2-[(3,4-methylenedioxy) phenyl]acetyl-5-dimethylaminobenzo[b]thiophene-3-sulfonamide; N-(4-chloro-3-methyl-5-isoxazolyl)-2-[3,4-(methylenedioxy)benzylcarbonyl]-N-methylindole-3-sulfonamide; N-(4-chloro-3-methyl-5-isoxazolyl)-2-[3,4-(methylenedioxy)phenoxycarbonyl]indole-3-sulfonamide; N-(4-chloro-3-methyl-5-isoxazolyl)-2-[3,4-(methylenedioxy)phenoxycarbonyl]-N-methylindole-3-sulfonamide; N-(4-chloro-3-methyl-5-isoxazolyl)-2-[3,4-(methylenedioxy)phenoxycarbonyl]indole-3-sulfonamide; N-(4-chloro-3-methyl-5-isoxazolyl)-2-[3,4-(methylenedioxy)benzyl]-N-methylindole-3-sulfonamide; N-(4-chloro-3-methyl-5-isoxazolyl)-2-[3,4-(methylenedioxy)benzyl]indole-3-sulfonamide; N-(4-chloro-3-methyl-5-isoxazolyl)-2-[3,4-(methylenedioxy) benzyloxycarbonyl]-7-(N,N-dimethylamino)benzo[b] thiophene-3-sulfonamide; N-(4-chloro-3-methyl-5-isoxazolyl)-2-[3,4-(methylenedioxy)benzyl]-7-(N,N-dimethylamino)benzo[b]thiophene-3-sulfonamide; N-(4-chloro-3-methyl-5-isoxazolyl)-2-[3,4-(methylenedioxy) benzoyl]-7-(N,N-dimethyl)amino)benzo[b]thiophene-3-sulfonamide; N-(4-chloro-3-methyl-5-isoxazolyl)-7-(N,N-dimethylamino)benzo[b]thiophene-3-sulfonamide; N-(4-chloro-3-methyl-5-isoxazolyl)-7-(methoxycarbonyl)benzo [b]thiophene-3-sulfonamide; N-(4-chloro-3-methyl-5-isoxazolyl)-2-[3,4-(methylenedioxy)benzyl]-7-(methoxy) benzo[b]thiophene-3-sulfonamide; N-(4-chloro-3-methyl-5-isoxazolyl)-7-(methoxy)benzo[b]thiophene-3-sulfonamide; N-(4-bromo-3-methyl-5-isoxazolyl)-2-(4-methylphenethyl) thiophene-3-sulfonamide; N-(4-bromo-3-methyl-5-isoxazolyl)-2-(trans-4-methylcinnamyl)thiophene-3-sulfonamide; N-(4-bromo-3-methyl-5-isoxazolyl)-3-(4-methylphenethyl)thiophene-2-sulfonamide; N-(4-bromo-3-methyl-5-isoxazolyl)-3-(3-methylphenethyl)thiophene-2-sulfonamide; N-(4-bromo-3-methyl-5-isoxazolyl)-3-(2-methylphenethyl)thiophene-2-sulfonamide; N-(4-bromo-3-methyl-5-isoxazolyl)-3-(trans-4-methylcinnamyl) thiophene-2-sulfonamide; N-(4-bromo-3-methyl-5-isoxazolyl)-3-(trans-3-methylcinnamyl)thiophene-2-sulfonamide; N-(4-bromo-3-methyl-5-isoxazolyl)-3-(trans-2-methylcinnamyl)thiophene-2-sulfonamide; N-(4-bromo-3-methyl-5-isoxazolyl)-3-[(4-methylphenoxy)methyl] thiophene-2-sulfonamide; N-(4-bromo-3-methyl-5-isoxazolyl)-3-[3,4-(methylenedioxy)phenethyl]thiophene-2-sulfonamide; N-(4-chloro-3-methyl-5-isoxazolyl)-2-{(3,4-(dimethoxy)phenyl]acetyl)}thiophene-3-sulfonamide; N-(4-chloro-3-methyl-5-isoxazolyl)-2-[(3,5-dimethoxyphenyl)acetyl]thiophene-3-sulfonamide; N-(4-chloro-3-methyl-5-isoxazolyl)-2-[(3,4,5-trimethoxyphenyl) acetyl]thiophene-3-sulfonamide; N-(4-chloro-3-methyl-5-isoxazolyl)-2-[3,4-(methylenedioxy)benzylsulfonyl] thiophene-3-sulfonamide; N-(4-chloro-3-methyl-5-isoxazolyl)-2-[3,4-(methylenedioxy)benzylsulfinyl] thiophene-3-sulfonamide; N-(4-chloro-3-methyl-5-isoxazolyl)-2-[3,4-(methylenedioxy)benzylsulfenyl] thiophene-3-sulfonamide; N-(4-chloro-3-methyl-5-isoxazolyl)-2-{1-(dimethylamino)-2-[3,4-(methylenedioxy) phenyl}ethylthiophene-3-sulfonamide; N-(4-chloro-3-methyl-5-isoxazolyl)-2-{1-methylamino)-2-[3,4-

(methylenedioxy)phenyl]ethyl}thiophene-3-sulfonamide; N-(4-chloro-3-methyl-5-isoxazolyl)-2-{1-(methoxylimino)-2-[3,4-(methylenedioxy)phenyl]ethyl}thiophene-3-sulfonamide; N-(4-chloro-3-methyl-5-isoxazolyl)-2-{1-(carboxyl)-2-[3,4-(methylenedioxy)phenyl]-ethyl}thiophene-3-sulfonamide; N-(4-chloro-3-methyl-5-isoxazolyl)-2-{2-(carboxyl)-1-[3,4-(methylenedioxy)benzyl]vinyl}thiophene-3-sulfonamide; N-(4-chloro-3-methyl-5-isoxazolyl)-2-{3-[3,4-(methylenedioxy)phenyl]-1,2,4-oxadiazol-5-lyl}thiophene-3-sulfonamide; and N-(4-chloro-3-methyl-5-isoxazolyl-2-{3-[3,4-(methylenedioxy)benzyl]-1,2,4-oxadiazol-5-lyl}thiophene-3-sulfonamide.

Additional compounds include, but are not limited to: N-(4-chloro-3-methyl-5-isoxazolyl)-2-{[2-(methanesulfonyl)-4,5-(methylenedioxy)phenyl]aminocarbonyl}thiophene-3-sulfonamide; N-(4-chloro-3-methyl-5-isoxazolyl)-2-{[3,4-(methylenedioxy)-6-carboxylphenyl]aminocarbonyl}thiophene-3-sulfonamide; N-(4-chloro-3-methyl-5-isoxazolyl)-2-{[4,5-(methylenedioxy)-2-(methoxycarbonyl)phenyl}aminocarbonyl}thiophene-3-sulfonamide; N-(4-chloro-3-methyl-5-isoxazolyl)-2-{[2-cyano-4,5-(methylenedioxy)phenyl]aminocarbonyl}thiophene-3-sulfonamide; N-(4-chloro-3-methyl-5-isoxazolyl)-2-{[4,5-(methylenedioxy)-2-hydroxymethyl)phenyl]aminocarbonylthiophene-3-sulfonamide; N-(4-chloro-3-methyl-5-isoxazolyl)-2-[(2-acetyl-4-methylphenyl]aminocarbonyl]thiophene-3-sulfonamide; N-(4-chloro-3-methyl-5-isoxazolyl)-2-{[2-(methanesulfonyl)-4-methylphenyl]aminocarbonyl}thiophene-3-sulfonamide; N-(4-chloro-3-methyl-5-isoxazolyl)-2-[(2-carboxyl-4-methylphenyl)aminocarbonyl]thiophene-3-sulfonamide; N-(4-chloro-3-methyl-5-isoxazolyl)-2-[(2-methoxycarbonyl-4-methylphenyl)aminocarbonyl]thiophene-3-sulfonamide; N-(4-chloro-3-methyl-5-isoxazolyl)-2-[(2-cyano-4-methylphenyl)aminocarbonyl]thiophene-3-sulfonamide; N-(4-chloro-3-methyl-5-isoxazolyl)-2-{[2-(hydroxymethyl)-4-methylphenyl]aminocarbonyl}thiophene-3-sulfonamide; N-(4-chloro-3-methyl-5-isoxazolyl)-2-[(3,4-dimethoxy-6-acetylphenyl)aminocarbonyl]thiophene-3-sulfonamide; N-(4-chloro-3-methyl-5-isoxazolyl)-2-{[2-(methanesulfonyl)-4,5-dimethoxyphenyl]aminocarbonyl}thiophene-3-sulfonamide; N-(4-chloro-3-methyl-5-isoxazolyl)-2-[(4,5-dimethoxy-2-carboxylphenyl)aminocarbonyl]thiophene-3-sulfonamide; N-(4-chloro-3-methyl-5-isoxazolyl)-2-[(4,5-dimethoxy-2-methoxycarboxyl)phenyl)aminocarbonyl]thiophene-3-sulfonamide; N-(4-chloro-3-methyl-5-isoxazolyl)-2-[2-cyano(4,5-dimethoxyphenyl)aminocarbonyl]thiophene-3-sulfonamide; N-(4-chloro-3-methyl-5-isoxazolyl)-2-(4,5-dimethoxy-2-hydroxymethyl)phenylaminocarbonylthiophene-3-sulfonamide; N-(4-chloro-3-methyl-5-isoxazolyl)-2-{[2-acetyl-4,5-(methylenedioxy)phenyl]acetyl}thiophene-3-sulfonamide; N-(4-chloro-3-methyl-5-isoxazolyl)-2-{[2-(methanesulfonyl)-4,5-(methylenedioxy)phenyl]-acetyl}thiophene-3-sulfonamide; N-(4-chloro-3-methyl-5-isoxazolyl)-2-{[carboxyl 4,5-(methylenedioxy)-2-phenylacetylthiophene-3-sulfonamide; N-(4-chloro-3-methyl-5-isoxazolyl)-2-{[4,5-(methylenedioxy)-2-methoxycarbonylphenyl]acetylthiophene-3-sulfonamide; N-(4-chloro-3-methyl-5-isoxazolyl)-2-{2-cyano[4,5-(methylenedioxy)-phenyl]acetyl}thiophene-3-sulfonamide; N-(4-chloro-3-methyl-5-isoxazolyl)-2-{2-hydroxymethyl[4,5-(methylenedioxy)-phenyl]acetyl}thiophene-3-sulfonamide; N-(4-chloro-3-methyl-5-isoxazolyl)-2-[(2,4-dimethoxy)phenyl)aminocarbonyl]thiophene-3sulfonamide; N-(4-chloro-3-methyl-5-isoxazolyl)-2-[(4-methoxy-2-methylphenyl)aminocarbonyl]thiophene-3-sulfonamide; N-(4-chloro-3-methyl-5-isoxazolyl)-2-[(2,3-dimethylphenyl)aminocarbonyl]thiophene-3-sulfonamide; N-(4-chloro-3-methyl-5-isoxazolyl)-2-[(2,4-dimethylphenyl)aminocarbonyl]thiophene-3-sulfonamide; N-(4-chloro-3-methyl-5-isoxazolyl)-2-[(2,5-dimethylphenyl)aminocarbonyl]thiophene-3-sulfonamide; N-(4-chloro-3-methyl-5-isoxazolyl)-2-[(2,6-dimethylphenyl)aminocarbonyl]thiophene-3-sulfonamide; N-(4-chloro-3-methyl-5-isoxazolyl)-2-[(3,4-dimethylphenyl)aminocarbonyl]thiophene-3-sulfonamide; N-(4-chloro-3-methyl-5-isoxazolyl)-2-[(2,5-dimethylphenyl)aminocarbonyl]thiophene-3-sulfonamide; N-(4-chloro-3-methyl-5-isoxazolyl)-2-(3,5-dimethyl)phenylaminocarbonylthiophene-3-sulfonamide; N-(4-chloro-3-methyl-5-isoxazolyl)-2-[(2-methoxy-6-methylphenyl)aminocarbonyl]thiophene-3-sulfonamide; N-(4-chloro-3-methyl-5-isoxazolyl)-2-[(2,4,6-trimethylphenyl)aminocarbonyl]-thiophene-3-sulfonamide; N-(4-chloro-3-methyl-5-isoxazolyl)-2-[(4-methoxy-2-methylphenyl)aminocarbonyl]-thiophene-3-sulfonamide; N-(4-chloro-3-methyl-5-isoxazolyl)-2-[2-ethyl(4-methoxy-)phenyl)aminocarbonyl)thiophene-3-sulfonamide; N-(4-chloro-3-methyl-5-isoxazolyl)-2-[(2-isopropyl-4-methoxy-phenyl)aminocarbonyl]thiophene-3-sulfonamide; N-(4-chloro-3-methyl-5-isoxazolyl)-2-[(2-propyl-4-methoxy-phenyl)aminocarbonyl]-thiophene-3-sulfonamide; N-(4-chloro-3-methyl-5-isoxazolyl)-2-[(4-methoxy-2-biphenylaminocarbonyl]-thiophene-3-sulfonamide; N-(4-chloro-3-methyl-5-isoxazolyl)-2-{[3,4-(methylenedioxy)-6-methylphenyl)acetyl]-thiophene-3-sulfonamide; N-(4-chloro-3-methyl-5-isoxazolyl)-2-{[3,4-(methylenedioxy)-6-ethylphenyl)acetyl}thiophene-3-sulfonamide; N-(4-chloro-3-methyl-5-isoxazolyl)-2-{[3,4-(methylenedioxy)-6-methoxyphenyl]acetyl}thiophene-3-sulfonamide.

EXAMPLE 193

N-(3,4-Dimethyl-5-isoxazolyl)-4-biphenylsulfonamide (a) 4-Biphenylsulfonyl chloride 4-Biphenylsulfonic acid (3.0 g, 12.8 mmol) was heated at 70° C. with phosphorus oxychloride (1.30 ml, 14.0 mol) for 2 h. Excess phosphorus oxychloride was removed under reduced pressure. The residue was decomposed with ice water and extracted with ethyl acetate. The extract was washed with 5% sodium bicarbonate solution, dried over anhydrous magnesium sulfate and concentrated to yield 2.9 g of crude 4-biphenylsulfonyl chloride.

(b) N-(3,4-Dimethyl-5-isoxazolyl)-4-biphenylsulfonamide

The 4-biphenylsulfonyl chloride from step (a) was added to a solution of 5-amino-3,4-dimethylisoxazole (250 mg, 2.2 mmol) and 4-(dimethyl)aminopyridine (5 mg) in dry pyridine (2.0 ml). The reaction mixture was stirred at room temperature for 4 h. Pyridine was removed under reduced pressure and the residue was partitioned between water and ethyl acetate. The organic layer was washed with 1N HCl (2×25 ml), brine (25 ml) and dried over anhydrous magnesium sulfate. Evaporation of the solvents left an oily residue that, after purification by column chromatography over silica gel (1% methanol in chloroform as eluent), yielded 337 mg (45%) of a white solid. Recrystallization from ethyl acetate/hexanes gave white crystals, m.p. 154–155° C.

EXAMPLE 194

N-(4-Bromo-3-methyl-5-isoxazolyl)-4-biphenylsulfonamide (a) 5-Amino-4-bromo-3-methylisoxazole 5-Amino-3-methylisoxazole (0.98 g, 10 mmol) was dissolved in chloroform (15 ml) and cooled to 0° C. N-Bromosuccinimide (1.78 g, 10 mmoles) was added in small portions over a period of 10 min. The stirring was continued for another 10 minutes at 0° C. The reaction mixture was diluted with chloroform (50 ml), washed with water (2×50 ml) and the organic layer was dried over magnesium sulfate. Removal of the solvent under reduced pressure gave the crude product, which was purified by column chromatography using 9:1, hexanes/ethyl acetate as the eluent, to give 5-amino-4-bromo-3-methylisoxazole (1.55 g, 87% yield).

(b) N-(4-Biphenylsulfonyl)-N-(4-bromo-3-methyl-5-isoxazolyl)-4-biphenylsulfonamide 5-Amino-4-bromo-3-methylisoxazole (0.179 g, 1.0 mmol) was dissolved in dry pyridine (2 ml). 4-Biphenylsulfonyl chloride (0.509 g, 2.2 mmol) was added with stirring at ambient temperature. N,N-dimethylaminopyridine (5 mg) was added, and stirring was continued at 50° C. for 16 h. The reaction mixture was diluted with dichloromethane (75 ml), washed with 1N HCl (2×50 ml) and the organic phase was dried over magnesium sulfate. The solvent was removed under reduced pressure to yield a crude product, which was purified by column chromatography using 8:2, hexanes/ethyl acetate, to give 0.390 g (60% yield) of N-(4-biphenylsulfonyl)-N-(4-bromo-3-methyl-5-isoxazolyl)-4-biphenylsulfonamide.

(c) N-(4-Bromo-3-methyl-5-isoxazolyl)-4-biphenylsulfonamide

N-(4-biphenylsulfonyl)-N-(4-bromo-3-methyl-5-isoxazolyl)-4-biphenylsulfonamide (0.150 g, 0.233 mmol) was dissolved in tetrahydrofuran (THF). Sodium hydroxide (0.120 g, 3.0 mmol) was added and the solution was warmed to 45° C. to dissolve the sodium hydroxide. Stirring was continued for 20 min. Tetrahydrofuran was removed under reduced pressure. The residue was dissolved in water, cooled to 0° C. and acidified to pH 3–4 with concentrated HCl. The solid precipitate was filtered off and dried in vacuo to give N-(4-bromo-3-methyl-5-isoxazolyl)-4-biphenylsulfonamide (94% yield), which was further purified by recrystallization from chloroform/hexanes, m.p. 133–135° C.

EXAMPLE 195

N-(3,4-Dimethyl-5-isoxazolyl)-2-dibenzofuransulfonamide

N-(3,4-Dimethyl-5-isoxazolyl)-2-dibenzofuransulfonamide was prepared, using the method described in Example 193b, from 5-amino-3,4-dimethylisoxazole and 2-benzofuransulfonyl chloride in 32% yield. Purification was achieved by recrystallization from chloroform/hexanes to give a white "cotton-like" solid, m.p. 173–175° C. (dec.).

EXAMPLE 196

N-(4-Methyl-3-trifluoromethyl-5-isoxazolyl)-4-biphenylsulfonamide

N-(4-Methyl-3-trifluoromethyl-5-isoxazolyl)-4-biphenylsulfonamide was prepared in the same manner as described in Example 194b from 5-amino-4-methyl-3-trifluoromethyl-isoxazole and 4-biphenylsulfonyl chloride in 78% yield. Purification was achieved by recrystallization from methanol/water to give a white solid, m.p. 139–140° C.

EXAMPLE 197

N-(4-Tridecyl-3-trifluoromethyl-5-isoxazolyl)-4-biphenylsulfonamide

N-(4-Tridecyl-3-trifluoromethyl-5-isoxazolyl)-4-biphenylsulfonamide was prepared, in the same manner as described in Example 194b, from 5-amino-4-tridecyl-3-trifluoromethyl-isoxazole and 4-biphenylsulfonyl chloride in 81% yield. Purification was achieved by recrystallization from methanol/water to give an off white solid, m.p. 115–116° C.

EXAMPLE 198

N-(4-Methyl-3-trifluoromethyl-5-isoxazolyl)-4-biphenylsulfonamide

N-(4-Methyl-3-trifluoromethyl-5-isoxazolyl)-4-biphenylsulfonamide was prepared, as described in Example 194, from 5-amino-4-methyl-3-trifluoromethylisoxazole and 4-biphenyisulfonyl chloride in 78% yield. Purification was achieved by recrystallization from ethyl acetate/hexanes to give a white solid, m.p. 139–140° C.

EXAMPLE 199

N-(4-Bromo-5-methyl-3-isoxazolyl)-4-biphenylsulfonamide (a) 3-Amino-4-bromo-5-methylisoxazole 3-Amino-5-methylisoxazole (1.96 g, 20 mmol) was dissolved in chloroform (10 ml) and cooled to 0° C. N-Bromosuccinimide (3.56 g, 20 mmol) was added in small portions over a period of 10 min. The stirring was continued for another 15 minutes at 0° C. The reaction mixture was diluted with chloroform (100 ml), washed with water (2×50 ml) and the organic layer was dried over magnesium sulfate. Removal of the solvent under reduced pressure gave the crude product, which was purified by column chromatography, using 9:1 hexanes/ethyl acetate as the eluent, to give 3-amino-4-bromo-5-methylisoxazole (1.40 g, 40% yield).

(b) N-(4-bromo-5-methyl-3-isoxazolyl)-4-biphenylsulfonamide

N-(4-bromo-5-methyl-3-isoxazolyl)-4-biphenylsulfonamide was prepared, using the method in Example 193b, from 3-amino-4-bromo-5-methylisoxazole and 4-biphenylsulfonyl chloride in 5% yield. The crude product was purified by column chromatography. After recrystallization from ethyl acetate/hexanes, N-(4-bromo-5-methyl-3-isoxazolyl)-4-biphenylsulfonamide (m.p. 154–156° C.) was obtained in 51% yield.

EXAMPLE 200

N-(4-Chloro-3-methyl-5-isoxazolyl)-4-biphenylsulfonamide (a) 5-Amino-4-chloro-3-methylisoxazole Using the method in Example 194a, 5-amino-4-chloro-3-methylisoxazole was prepared from 5-amino-3-methylisoxazole and N-chloro-succinimide in 90% yield.

(b) N-(4-Chloro-3-methyl-5-isoxazolyl)-4-biphenylsulfonamide

Sodium hydride (188 mg, 4.4 mmol) was suspended in dry THF (1 ml) and cooled to 0° C. A solution of 5-amino-4-chloro-3-methylisoxazole (mg, mmol) in dry THF (1 ml) was added with stirring. Once the addition was complete, the reaction mixture was warmed to room temperature for 10 min. The solution was recooled to 0° C., and 4-biphenylsulfonyl chloride (0.283 ml, 2.2 mmol) was added. Stirring was continued at 25° C. for 2 h. Excess sodium hydride was decomposed by the addition of methanol (0.4 ml) followed by water (0.5 ml). The THF was removed under reduced pressure and the residue was dissolved in water (20 ml) and basified by addition of sodium hydroxide (pH 9–10). Neutral impurities were removed by extraction with ethyl acetate (2×10 ml). The aqueous layer was acidified to pH 2–3 using concentrated HCl and extracted with ethyl acetate (3×10 ml). The combined organic layer was dried over magnesium sulfate. Removal of the solvent gave N-(4-chloro-3-methyl-5-isoxazolyl)-4-biphenylsulfonamide in 83% yield. This product was purified by recrystallization from ethyl acetate/hexanes as a white solid, m.p. 129–132° C.

EXAMPLE 201

2,5-Dimethoxy-N-(4-bromo-3-methyl-5-isoxazolyl)benzenesulfonamide 2,5-Dimethoxy-N-(4-bromo-3-methyl-5-isoxazolyl)benzenesulfonamide was prepared from 5-amino-4-bromo-3-methylisoxazole and 2,5-dimethoxybenzenesulfonyl chloride according to the procedures described in Example 200. The crude product was purified by recrystallization from ethyl acetate/hexanes to give a crystalline solid, m.p. 118–120°, yield 58%.

EXAMPLE 202

N-(4-bromo-3-methyl-5-isoxazolyl)-2-biphenylsulfonamide

A. 2-Biphenylsulfonyl chloride

2-Bromobiphenyl (2.33 g, 10 mmol) was dissolved in ether (10 ml) and cooled to −78° C. n-Butyllithium (2.5 M solution in hexane, 4.8 ml, 12 mmol) was added dropwise under constant stirring and an argon atmosphere. The resultant reaction mixture was stirred at −70° C. to −60° C. for 1 h. The reaction mixture was cooled to −78° C. and sulfuryl chloride (0.88 ml, 11 mmol) was added dropwise. After addition, the reaction mixture was allowed to attain ambient temperature slowly and stirred for 1 h. The reaction mixture was diluted with ethyl acetate (50 ml), washed with water and the organic layer dried over anhydrous $MgSO_4$. Removal of the solvent under reduced pressure gave a crude product, which was purified by column chromatography, using hexane followed by 5% ethyl acetate in hexane as eluent, to give 2-biphenylsulfonyl chloride as a solid (1.3 g, 51% yield).

B. N-(4-bromo-3-methyl-5-isoxazolyl)-2-biphenylsulfonamide

N-(4-bromo-3-methyl-5-isoxazolyl)-2-biphenylsulfonamide was prepared in the same manner as described in Example 200b from 5-amino-4-bromo-3-methylisoxazole and 2-biphenylsulfonyl chloride in 71% yield. Purification was achieved by recrystallization from ethyl acetate/hexanes to give a crystalline solid, m.p. 145–147° C.

EXAMPLE 203

N-(4-Chloro-3-methyl-5-isoxazolyl)-2-biphenylsulfonamide

N-(4-Chloro-3-methyl-5-isoxazolyl)-2-biphenylsulfonamide was prepared in the same manner as described in Example 202 from 5-amino-4-chloro-3-methylisoxazole and 2-biphenylsulfonyl chloride in 74% yield. Purification was achieved by recrystallization from ethyl acetate/hexanes to give a crystalline solid, m.p. 132–134° C.

EXAMPLE 204

N-(4-Bromo-3-methyl-5-isoxazolyl)-3-biphenylsulfonamide

A. 3-Biphenylsulfonyl chloride

3-Bromobiphenyl (1.5 g, 6.4 mmol) was dissolved in ether (15 ml) and cooled to −78° C. t-Butyllithium (1.7 M solution in hexane, 3.8 ml, 6.4 mmol) was added dropwise under constant stirring and an argon atmosphere. The resultant reaction mixture was stirred at −10° C. to −5° C. for 6 h. The reaction mixture was cooled to −78° C. and sulfuryl chloride (0.64 ml, 6.4 mmol) was added dropwise. After completion of the addition, the reaction mixture was allowed to attain ambient temperature slowly and stirred for 1 h. The reaction mixture was diluted with ethyl acetate (50 ml), washed with water and the organic layer dried over anhydrous $MgSO_4$. Removal of the solvent under reduced pressure gave crude product, which was purified by column chromatography, using hexane followed by 5% ethyl acetate in hexane as eluent, to give 3-biphenylsulfonyl chloride as an oil (0.8 g, 49% yield).

B. N-(4-bromo-3-methyl-5-isoxazolyl)-3-biphenylsulfonamide

N-(4-bromo-3-methyl-5-isoxazolyl)-3-biphenylsulfonamide was prepared in the same manner as described in Example 200b from 5-amino-4-bromo-3-methylisoxazole and 3-biphenylsulfonyl chloride in 22% yield. This was purified by HPLC (5% $CH_3CN$ to 100% $CH_3CN$ over 30 min.) to give a solid., m.p. 78–82° C.

EXAMPLE 205

N-(4-chloro-3-methyl-5-isoxazolyl)-3-biphenylsulfonamide

N-(4-chloro-3-methyl-5-isoxazolyl)-3-biphenylsulfonamide was prepared in the same manner as described in Example 204 from 5-amino-4-chloro-3-methylisoxazole and 3-biphenylsulfonyl chloride in 63% yield. This was purified by HPLC (5% $CH_3CN$ to 100% $CH_3CN$ over 30 min.) to give a solid, m.p. 84–86° C.

EXAMPLE 206

N-(3-methyl-5-isoxazolyl)-4-(4-methylphenyl)benzenesulfonamide

(a) N-(3-methyl-5-isoxazolyl)-4-bromobenzenesulfonamide 4-brombenzenesulfonyl chloride (solid) was added, in five portions, to a solution of 3-methyl-5-aminoisoxazole (3.82 g, 40 mmol) in dry pyridine (30 ml). This was stirred at room temperature for 3 h and the pyridine was removed under reduced pressure. The residue was dissolved in THF (300 ml) and a 5% NaOH solution (100 ml) was added. Stirring continued for 1 h at room temperature. The THF was removed under reduced pressure and the resultant residue was neutralized to pH 2 using concentrated hydrochloric acid. This was extracted with ethyl acetate (3×200 ml) and the combined organic layer was dried over $MgSO_4$ and concentrated. The crude product was recrystallized using hexane/ethyl acetate giving N-(3-methyl-5-isoxazolyl)-4-bromobenzenesulfonamide (9.2 g, 72% yield).

(b) N-(3-methyl-5-isoxazolyl)-4-(4-methylphenyl) benzenesulfonamide

Nitrogen was bubbled through a biphasic mixture of ethanol (15 ml), toluene (15 ml) and 2M sodium carbonate solution (15 ml). N-(3-methyl-5-isoxazolyl)-4-bromobenzene sulfonamide (0.951 g, 3 mmol), 4-methylbenzeneboronic acid (0.56 g, 4 mmol) and tetrakistriphenylphosphine palladium (0) (300 mg) were added. The reaction mixture was kept at 80° C., under a $N_2$ atmosphere for 24 h, with stirring, and was then diluted with water (50 ml) and extracted with ether (50 ml) to remove neutral impurities and excess 4-methylbenzeneboronic acid. The aqueous phase was neutralized to pH 2 using concentrated hydrochloric acid and the resultant solid was filtered. This was dried under vacuum and recrystallized using hexane/ethyl acetate giving N-(3-methyl-5-isoxazolyl)-4-(4-methylphenyl)benzenesulfonamide (1.0 g, 100% yield, m.p. 194–198° C.).

EXAMPLE 207

N-(4-bromo-3-methyl-5-isoxazolyl)-4-(4-methylphenyl)benzenesulfonamide

N-bromosuccinimide (NBS) (0.178 g, 1 mmol), in one lot, was added to a stirred suspension of N-(3-methyl-5-isoxazolyl)-4-(4-methylphenyl)benzenesulfonamide (0.327 g, 1 mmol, Example 206b) in chloroform (12 ml). The reaction mixture was stirred for 10 min then diluted with dichloromethane (50 ml). This was washed with water (2×50 ml). The organic layer was dried over $MgSO_4$ and concentrated. The crude product was recrystallized using hexane/ethyl acetate giving N-(4-bromo-3-methyl-5-isoxazolyl)-4-(4-methylphenyl)benzenesulfonamide (350 mg, 86% yield, m.p. 153–156° C.).

EXAMPLE 208

N-(4-chloro-3-methyl-5-isoxazolyl)-4-(4-methylphenyl)benzenesulfonamide

N-chlorosuccinimide (0.266 g, 2 mmol) was added, in one lot, to a stirred suspension of N-(3-methyl-5-isoxazolyl)-4-(4-methylphenyl)benzenesulfonamide (0.327 g, 1 mmol, Example 206b) in chloroform (10 ml) and stirred at room temperature for 2 h The reaction mixture was diluted with dichloromethane (50 ml) and washed with water (2×50ml). The organic layer was dried over $MgSO_4$ and concentrated. The crude product was purified by column chromatography using ethyl acetate as eluent to give N-(4-chloro-3-methyl-5-isoxazolyl)-4-(4-methylphenyl)benzenesulfonamide [210 mg, 58% yield, m.p. 260° C. (de coup)].

EXAMPLE 209

N-(3-methyl-5-isoxazolyl)-4-[(4-trifluoromethyl) phenyl]benzenesulfonamide

N-(3-methyl-5-isoxazolyl)-4-(4-trifluoromethylphenyl) benzenesulfonamide was prepared in the same manner as described in Example 206B, using N-(3-methyl-5-isoxazolyl)-4-bromobenzenesulfonamide and 4-trifluoromethylbenzeneboronic acid resulting in the final product in a 78% yield, m.p. 150–153° C. The product was recrystallized using an acetonitrile and water mixture.

EXAMPLE 210

N-(4-bromo-3-methyl-5-isoxazolyl)-4-[(4-trifluoromethyl)phenyl]benzenesulfonamide N-(4-bromo-3-methyl-5-isoxazolyl)-4-[(4-trifluoromethyl)phenyl]benzenesulfonamide was prepared in the same manner as described in Example 207, using N-(3-methyl-5-isoxazolyl)-4-(4-trifluoromethylphenyl) benzenesulfonamide (Example 209) and NBS (reaction time 30 min at room temperature). The crude product was purified by column chromatography on silica gel using ethyl acetate as eluent resulting in the final product in 56% yield, m.p. 113–117° C.

EXAMPLE 211

N-(3-methyl-5-isoxazolyl)-4-(4-methoxyphenyl) benzenesulfonamide

N-(3-methyl-5-isoxazolyl)-4-(4-methoxyphenyl) benzenesulfonamide was prepared in the same manner as described in Example 206b, using N-(3-methyl-5-isoxazolyl)-4-bromobenzenesulfonamide (Example 206a) and 4-methoxybenzeneboronic acid resulting in an 82% yield of the final product, m.p. 1 94–1 96° C. The product was recrystallized using hexane/ethyl acetate.

EXAMPLE 212

N-(4-bromo-3-methyl-5-isoxazolyl)-4-(4-methoxyphenyl)benzenesulfonamide

N-(4-bromo-3-methyl-5-isoxazolyl)-4-(4-methoxyphenyl)benzenesulfonamide was prepared in the same manner as described in Example 207 using N-(3-methyl-5-isoxazolyl)-4-(4-methoxyphenyl) benzenesulfonamide (Example 211) and NBS (reaction time 30 min at room temperature). The crude product was purified by column chromatography on silica gel using ethyl acetate as eluent giving the final product in 78% yield, m.p. 208° C. (dec). The product was recrystallized using hexane/ethyl acetate.

EXAMPLE 213

N-(4-bromo-3-methyl-5-isoxazolyl)-4-(3-methoxyphenyl)benzenesulfonamide (a) N-(3-methyl-5-isoxazolyl)-4-(3-methoxyphenyl) benzenesulfonamide N-(3-methyl-5-isoxazolyl)-4-(3-methoxyphenyl) benzenesulfonamide was prepared in the same manner as described in Example 206b, using N-(3-methyl-5-isoxazolyl)-4-bromobenzenesulfonamide (Example 206a) and 3-methoxybenzeneboronic acid resulting in a 77% yield.

(b) N-(4-bromo-3-methyl-5-isoxazolyl)-4-(3-methoxyphenyl)benzenesulfonamide

N-(4-bromo-3-methyl-5-isoxazolyl)-4-(3-methoxyphenyl)benzenesulfonamide was prepared in the same manner as described in Example 207 using N-(3- methyl-5-isoxazolyl)-4-(3-methoxyphenyl)benzenesulfonamide and NBS (reaction time 30 min at room temperature). The crude product was purified by column chromatography on silica gel using ethyl acetate as eluent giving the final product, after recrystallization using hexane/ethyl acetate, in 75% yield, m.p. 140–144° C.

EXAMPLE 214

N-(4-bromo-3-methyl-5-isoxazolyl)-4-(2-methoxyphenyl)benzenesulfonamide (a) N-(3-methyl-5-isoxazolyl)-4-(2-methoxyphenyl)benzenesulfonamide N-(3-methyl-5-isoxazolyl)-4-(2-methoxyphenyl)benzenesulfonamide was prepared in the same manner as described in Example 206 using N-(3-methyl-5-isoxazolyl)-4-bromobenzenesulfonamide and 2-methoxybenzeneboronic acid resulting in an 81% yield of the final product.

(b) N-(4-bromo-3-methyl-5-isoxozolyl)-4-(2-methoxyphenyl)benzenesulfonamide

N-(4-bromo-3-methyl-5-isoxozolyl)-4-(2-methoxyphenyl)benzenesulfonamide was prepared in the same manner as described in Example 207, using N-(3-methyl-5-isoxazolyl)-4-(2-methoxyphenyl)benzenesulfonamide and NBS (reaction time 30 min at room temp.) The crude product was purified by column chromatography on silica gel using ethyl acetate as eluent to give the final product in 68% yield, m.p. 205–209° C.

EXAMPLE 215

N-(4-bromo-3-methyl-5-isoxazolyl)-4-(3,4-methylenedioxyphenyl)benzenesulfonamide (a) N-(3-methyl-5-isoxazolyl)-4-(3,4-methylenedioxyphenyl)benzenesulfonamide N-(3-methyl-5-isoxazolyl)-4-(3,4-methylenedioxyphenyl)benzenesulfonamide was prepared in the same manner as described in Example 206b, using N-(3-methyl-5-isoxazolyl)-4-bromobenzenesulfonamide and 3,4-methylenedioxyphenylboronic acid resulting in a 67% yield of final product.

(b) N-(4-bromo-3-methyl-5-isoxazolyl)-4-(3,4-methylenedioxyphenyl)benzenesulfonamide N-(4-bromo-3-methyl-5-isoxazolyl)-4-(3,4-methylenedioxyphenyl)benzenesulfonamide was prepared in the same manner as described in Example 207, using N-(3-methyl-5-isoxazolyl)-4-(3,4-methylenedioxyphenyl)benzenesulfonamide and NBS in THF as solvent resulting in a 35% yield. The crude product was purified by HPLC, m.p. 172–174° C.

EXAMPLE 216

N-(4-bromo-3-methyl-5-isoxazolyl)-4-(3-methylphenyl)benzenesulfonamide (a) N-(3-methyl-5-isoxazolyl)-4-(3-methylphenyl)benzenesulfonamide N-(3-methyl-5-isoxazolyl)-4-(3-methylphenyl)benzenesulfonamide was prepared in the same manner as described in Example 206b, using N-(3-methyl-5-isoxazolyl)-4-bromobenzenesulfonamide (Example 206a) and 3-methylbenzeneboronic acid resulting in an 82% yield.

(b) N-(4-bromo-3-methyl-5-isoxazolyl)-4-(3-methylphenyl)benzenesulfonamide

N-(4-bromo-3-methyl-5-isoxazolyl)-4-(3-methylphenyl)benzenesulfonamide was prepared in the same manner as described in Example 207, using N-(3-methyl-5-isoxazolyl)-4-(3-methylphenyl)benzenesulfonamide and NBS in THF as solvent (reaction time 30 min at room temperature). The crude product was purified by HPLC resulting in a 31% yield of the final product, m.p. 186–189° C.

EXAMPLE 217

Assays for Identifying Compounds that Exhibit Endothelin Antagonistic and/or Agonist Activity Compounds that are potential endothelin antagonists are identified by testing their ability to compete with $^{125}$I-labeled ET-1 for binding to human $ET_A$ receptors or $ET_B$ receptors present on isolated cell membranes. The effectiveness of the test compound as an antagonist or agonist of the biological tissue response of endothelin can also be assessed by measuring the effect on endothelin induced contraction of isolated rat thoracic aortic rings. The ability of the compounds to act as antagonists or agonists for $ET_B$ receptors can be assess by testing the ability of the compounds are to inhibit endothelin-1 induced prostacyclin release from cultured bovine aortic endothelial cells.

A. Endothelin Binding Inhibition—Binding Test #1: Inhibition of Binding to $ET_A$ Receptors TE 671 cells (ATCC Accession No. HTB 139) express $ET_A$ receptors. These cells were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 ml of buffer A (5 mM HEPES buffer, pH 7.4 containing aprotinin (100 KIU/ml)) and then frozen and thawed once. 5 ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml and stored at −70° C. until use.

The membrane suspension was diluted with binding buffer (30 mM HEPES buffer, pH 7.4 containing 150 mM NaCl, 5 mM $MgCl_2$, 0.5% Bacitracin) to a concentration of 8 μg/50 μl. $^{125}$I-endothelin-1 (3,000 cpm, 50 mL) was added to 50 μL of either: (A) endothelin-1 (for non specific binding) to give a final concentration 80 nM); (B) binding buffer (for total binding); or (C) a test compound (final concentration 1 nM to 100 μM). The membrane suspension (50 μL), containing up to 8 μg of membrane protein, was added to each of (A), (B), or (C). Mixtures were shaken, and incubated at 4° C. for 16–18 hours, and then centrifuged at 4° C. for 25 min at 2,500×g. Alternatively, the incubation was conducted at 24° C. When incubated at 24° C., the $IC_{50}$ concentrations are 2- to 10-fold higher than when the incubation is conducted at 4° C. This, must be kept in mind when comparing $IC_{50}$ concentrations among compounds provided herein.

The supernatant, containing unbound radioactivity, was decanted and the pellet counted on a Genesys multiwell gamma counter. The degree of inhibition of binding (D) was calculated according to the following equation:

$$\% D = 100 - \frac{(C) - (A)}{(B) - (A)} \times 100$$

Each test was generally performed in triplicate.

B. Endothelin Binding Inhibition—Binding Test #2: Inhibition of Binding to $ET_B$ Receptors COS7 cells were transfected with DNA encoding the $ET_B$ receptor. The resulting cells, which express the human $ET_B$ receptor, were grown to confluence in T-150 flasks. Membrane was prepared as described above. The binding assay was performed as described above using the membrane preparation diluted with binding buffer to a concentration of 1 µg/50 µl.

Briefly, the COS7 cells, described above, that had been transfected with DNA encoding the $ET_B$ receptor and express the human $ET_B$ receptor on their surfaces were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. 57,800×g for 15 min, the pellet was resuspended in 5 ml of buffer A (5 mM HEPES buffer, pH 7.4 containing aprotinin (100 KIU/ml)) and then frozen and thawed once. Five ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml.

The binding assay was performed as described above using the membrane preparation diluted to give 1 µg/50 µl of binding buffer.

C. Test for Activity Against Endothelin-induced Contraction of Isolated Rat Thoracic Aortic Rings The effectiveness of the test compound as an antagonist or agonist of the biological tissue response of endothelin also is assessed by measuring the effect on endothelin induced contraction of isolated rat thoracic aortic rings (see, eq., Borges et al. (1989) *Eur. J. Pharmacol.* 165:223–230) or by measuring the ability to contract the tissue when added alone.

Compounds to be tested are prepared as 100 µM stocks. If necessary to effect dissolution, the compounds are first dissolved in a minimum amount of DMSO and diluted with 150 mM NaCl. Because DMSO can cause relaxation of the aortic ring, control solutions containing varying concentrations of DMSO were tested.

The thoracic portion of the adult rat aorta is excised, the endothelium abraded by gentle rubbing and then cut into 3 mm ring segments. Segments are suspended under a 2 g preload in a 10 ml organ bath filled with Krebs'-Henseleit solution saturated with a gas mixture of 95% $O_2$ and 5% $CO_2$ (118 mM NaCl, 4.7 mM KCl, 1.2 mM $MgSO_4$, 1.2 mM $KH_2PO_4$, 25 mM $NaHCO_3$, 2.5 mM $CaCl_2$, 10 mM D-glucose).

There is a correlation between activity as an antagonist of endothelin-induced thoracic aortic ring contraction and activity as an inhibitor of binding of endothelin to endothelin receptors. The $pA_2$ is a linear function of the log of the $IC_{50}$.

D. Assay for Identifying Compounds that have Agonist and/or Antagonistic Activity Against $ET_B$ Receptors

1. Stimulation of Prostacyclin Release

Since endothelin-1 stimulates the release of prostacyclin from cultured bovine aortic endothelial cells, the compounds that have agonist or antagonist activity are identified by their ability to inhibit endothelin-1 induced prostacyclin release from such endothelial cells by measuring 6-keto $PGF_{1\alpha}$ substantially as described by (Filep et al. (1991) *Biochem. Biophys. Res. Commun.* 177 171–176. Bovine aortic cells are obtained from collagenase-treated bovine aorta, seeded into culture plates, grown in Medium 199 supplemented with heat inactivated 15% fetal calf serum, and L-glutamine (2 mM), penicillin, streptomycin and fungizone, and subcultured at least four times. The cells are then seeded in six-well plates in the same medium. Eight hours before the assay, after the cells reach confluence, the medium is replaced. The cells are then incubated with a) medium alone, b) medium containing endothelin-1 (10 nM), c) test compound alone, and d) test compound+endothelin-1 (10 nM).

After a 15 min incubation, the medium is removed from each well and the concentrations of 6-keto $PGF_{1\alpha}$ are measured by a direct immunoassay. Prostacyclin production is calculated as the difference between the amount of 6-keto $PGF_{1\alpha}$ released by the cells challenged with the endothelin-1 minus the amount released by identically treated unchallenged cells. Compounds that stimulate 6-keto $PGF_{1\alpha}$ release possess agonist activity and those which inhibit endothelin-1 6-keto $PGF_{1\alpha}$ release possess antagonist activity.

2. Inhibition of Sarafotoxin 6c Induced Contraction

Sarafotoxin 6c is a specific $ET_B$ antagonist that contracts rat fundal stomach strips. The effectiveness of tests compounds to inhibit this sarafotoxin 6c-induced contraction of rat fundal stomach strips is used as a measure $ET_B$ antagonist activity. Two isolated rat fundal stomach strips are suspended under a 1 g load in a 10 ml organ bath filled with Krebs'-Henseleit solution containing 10 µM cyclo(D-Asp-Pro-D-Val-Leu-D-Trp) (BQ-123; see, U.S. Pat. No. 5,114, 918 to Ishikawa et al.), 5 µM indomethacin, and saturated with a gas mixture of 95% $O_2$/5% $CO_2$. Changes in tension are measured isometrically and recorded using a Grass Polygraph coupled to a force transducer. Sarafotoxin 6c is added cumulatively to one strip while the second strip is preincubated for 15 min with a test compound prior to addition of cumulative doses of sarafotoxin 6C. The effects of the test compounds on the concentration-response curve for sarafotoxin 6c are examined.

E. Deoxycorticosterone Acetate (DOCA)-salt Hypertensive Rat Model for Assessing in vivo Activity of Selected Compounds Selected compounds disclosed herein have been tested for activity in the deoxycorticosterone acetate (DOCA)-salt hypertensive rat model. To perform these tests, silastic MDX4-4210 elastomer implants containing 47 mg (DOCA) were prepared according to the method of Ornmsbee et al. ((1973) the *J. Pharm. Sci.* 62:255–257). Briefly, DOCA is incorporated into silicon rubber implants for sustained release. To prepare the implants the DOCA is incorporated into unpolymerized silicone rubber, catalyst is added and the mixture is cast in a hemicylindrical shape.

Sprague Dawley rats (7–8 weeks old) were unilaterally nephrectomized under ketamine anesthesia and a DOCA-implant was placed on the left lateral dorsal abdomen of the animal. The rats were allowed to recover for three weeks. During recovery they were permitted free access to normal rat chow and 0.9% NaCl drinking solution in place of drinking water. The rats develop hypertension within 3 weeks.

All animals were used in the tests between 21 and 30 days post surgery. The mean arterial blood pressure in these animals ranged from 165–200 mm Hg.

On the day of experimentation, catheters were inserted under brevital anesthesia into the right femoral artery for measurement of blood pressure, and into the right femoral vein for administration of a selected compound. The animals were placed in a restrainer and allowed to recover for a minimum of 60 min or until a steady mean arterial blood pressure was recorded. At that time, the selected compound or control vehicle was administered either intravenously, as a 60 minute infusion, or orally by oral gavage. Blood pressure was recorded continuously for a further 10 hrs.

F. Effect of Intravenous Administration on ET-1-induced Pressor Responses in Conscious, Autonomically Blocked Rats; a Model for Assessing in vivo Activity of Selected Compounds Male Sprague Dawley rats (250–450 g) were anesthetized (Brevital 50 mg/kg, IP) and cannulae were placed in the femoral artery to measure mean arterial pressure (MAP) and in the femoral vein for intravenous drug administration. Animals were placed in a restrainer and allowed to regain consciousness. Thirty minutes later autonomic blockade was administered (atropine methyl nitrate, 3 mg/kg, IV, followed by propranolol, 2 mg/kg, IV). An hour later animals received a bolus injection of vehicle (0.5 ml) followed thirty minutes later by intravenous bolus administration of ET-1 (Control, 1 µg/kg). Following recovery from this challenge, test compounds were administered by intravenous bolus administration (0.5 ml) and then re-challenged with ET-1 thirty minutes later. Results are expressed as the percent inhibition of the ET-1-induced pressor response after administration of the test compound compared to the pressor response induced by the control ET-1 challenge. In some cases a third ET-1 challenge was administered ninety minutes after administration of the test compound.

G. Results

1. In vitro

The $IC_{50}$ for each of the compounds of the preceding Examples for $ET_A$ and $ET_B$ receptors has been measured. Almost all of the compounds have an $IC_{50}$ of less than 10 µM for either or both of the $ET_A$ and $ET_B$ receptors. Many of the compounds have an $IC_{50}$ less than about 10 µM, others have an $IC_{50}$ less than about 1 µM and some of the compounds have an $IC_{50}$ less than about 0.1 µM. A number of the compounds have an $IC_{50}$ for $ET_A$ receptors that is substantially less (10 to 100-fold or more) than for $ET_B$ receptors, and, thus are selective for $ET_A$ receptors. Others of the compounds are $ET_B$ selective.

2. In vivo a. Selected compounds, such as N-(4-chloro-3-methyl-5-isoxazolyl)-2-(N-(4-methyl-phenyl)aminocarbonyl) thiophene-3-sulfonamide, N-(4-bromo-3-methyl-5-isoxazolyl)-2-[3,4-(methylenedioxy)benzyl]benzo[b] thiophene-3-sulfonamide, N-(4-chloro-3-methyl-5-isoxazolyl)-2-(3,4,-methylenedioxy)benzyl)benzo[b] thiophene-3-sulfonamide, N-(4-chloro-3-methyl-5-isoxazolyl)-2-[β-hydroxy(3,4-methylenedioxy) phenylethyl]thiophene-3-sulfonamide, N-(4-chloro-3-methyl-5-isoxazolyl)-2-(3,4-methylenedioxybenzylcarbonyl)thiophene-3-sulfonamide, have been tested in the hypertensive rat model, and were effective in decreasing blood pressure.

b. Selected compounds, such as N-(4-chloro-3-methyl-5-isoxazolyl)-2-{[3,4-(methylenedioxy)phenyl] acetyl}thiophene-3-sulfonamide, N-(4-chloro-3-methyl-5-isoxazolyl)2-{[2-acetyl-4,5-(methylenedioxy)phenyl]aminocarbonyl}thiophene-3-sulfonamide, N-(4-chloro-3-methyl-5-isoxazolyl)-2-[(4-methoxy-2-methylphenyl)aminocarbonyl] thiophene-3-sulfonamide and N-(4-chloro-3-methyl-5-isoxazolyl)-2-[2-cyano-4,5-dimethoxyphenyl) aminocarbonyl]thiophene-3-sulfonamide, and -(4-chloro-3-methyl-5-isoxazolyl)-2-[2-methyl-4,5-(methylenedioxy)phenylacetyl]thiophene-3-sulfonamide have been tested in the autonomically blocked, normotensive rat model and shown to have substantial activity, reducing pressure about 30% in 30 min at dosages as low as 30 mg/kg, and more than 50% at dosages of 60 mg/kg. On the average dosages of 30–60 mg/kg of the test compound resulted in a 40–60% inhibition of pressor response.

Since modifications will be apparent to those of skill in this art, it is intended that this invention be limited only by the scope of the appended claims.

We claim:

1. A compound that has formula I:

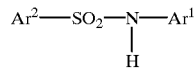

or a pharmaceutically acceptable salt, acid or ester thereof, wherein:

$Ar^1$ is a five or six membered aromatic ring;
$Ar^2$ has formula IV:

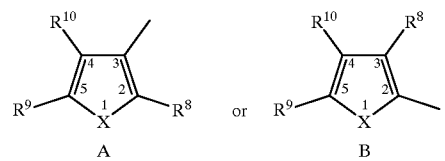

in which
X is S, O or $NR^{11}$ in which $R^{11}$ is hydrogen or has up to about 30 carbon atoms, and is selected from alkyl, alkenyl, alkynyl, aryl, alkylaryl, heterocyclyl, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocyclyl, aralkyl, aralkoxy, cycloalkyl, cycloalkenyl or cycloalkynyl; $R^{11}$ and $R^{15}$ are unsubstituted or are substituted with one or more substituents each selected independently from Z, which is hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, C(O)R$^{16}$, CO$_2$R$^{16}$, SH, S(O)$_n$R$^{16}$ in which n is 0–2, NHOH, NR$^{12}$R$^{16}$, NO$_2$, N$_3$, OR$^{16}$, R$^{12}$NCOR$^{16}$ or CONR$^{12}$R$^{16}$; R$^{16}$ is hydrogen, alkyl, alkenyl, alkynyl, aryl, alkylaryl, heterocyclyl, aralkyl, aralkoxy, cycloalkyl, cycloalkenyl or cycloalkynyl; R$^{12}$, which is selected independently from R$^{11}$ and Z, is selected from hydrogen, alkyl, alkenyl, alkynyl, aryl, alkylaryl, heterocyclyl, aralkyl, aralkoxy, cycloalkyl, cycloalkenyl, cycloalkynyl, C(O)R$^{17}$ and S(O)$_n$R$^{17}$ in which n is 0–2; and R$^{17}$ is hydrogen, alkyl, alkenyl, alkynyl, aryl, alkylaryl, heterocyclyl, aralkyl, aralkoxy, cycloalkyl, cycloalkenyl or cycloalkynyl; each of R$^{11}$, R$^{12}$, R$^{15}$ and R$^{16}$ is unsubstituted or substituted with any of the groups set forth for Z; and R$^8$, R$^9$ and R$^{10}$ are each independently selected as follows from (i) or (ii):

(i) R$^8$, R$^9$ and R$^{10}$, which each are hydrogen or have up to about 50 carbon atoms, and are each independently selected from halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, C(O)R$^{18}$, acetoxy-(CH=CH)—, CO$_2$R$^{18}$, SH, (CH$_2$)$_r$C(O)(CH$_2$)$_n$R$^{18}$, (CH$_2$)$_r$(CH=CH)$_s$(CH$_2$)$_n$R$^{18}$, (CH$_2$)$_r$C(O)(CH=CH)$_s$(CH$_2$)$_n$R$^{18}$, (CH$_2$)$_r$(CH=CH)$_s$C(O)(CH$_2$)$_n$R$^{18}$, (CH$_2$)$_r$NH(CH=CH)$_s$(CH$_2$)$_n$R$^{18}$, (CH$_2$)$_r$(CH=CH)$_s$NH(CH$_2$)$_n$R$^{18}$, (CH$_2$)$_r$C(O)NH(CH$_2$)$_n$R$^{18}$, C(O)(CH$_2$)$_r$NH(CH$_2$)$_n$R$^{18}$, (CH$_2$)$_r$NH(CH$_2$)$_n$R$^{18}$, (CH$_2$)$_r$R$^{18}$, S(O)$_m$R$^{18}$ in which m is 0–2, s, n and r are each independently 0 to 6, HNOH, NR$^{18}$R$^{19}$, NO$_2$, N$_3$, OR$^{18}$, R$^{19}$NCOR$^{18}$ and CONR$^{19}$R$^{18}$, in which R$^{19}$ is selected from hydrogen, alkyl, alkenyl, alkynyl, aryl, alkylaryl, alkoxy, aryloxy, heterocyclyl, aralkyl, aralkoxy, cycloalkyl, cycloalkenyl, cycloalkynyl, C(O)R$^{20}$ and S(O)$_n$R$^{20}$ in which n is 0–2; and R$^{18}$ and R$^{20}$ are independently selected from hydrogen, alkyl, alkenyl, alkynyl, aryl, heteroaryl, alkylaryl, heterocyclyl, alkoxy, aryloxy, aralkyl, aralkoxy, cycloalkyl, cycloalkenyl and cycloalkynyl; and any of the groups set forth for R$^8$, R$^9$ and R$^{10}$ are unsubstituted or substituted with any substituents set forth for Z, which is hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, C(O)R$^{21}$, CO$_2$R$^{21}$, SH, S(O)$_n$R$^{21}$ in which n is 0–2, NHOH, NR$^{22}$R$^{21}$, NO$_2$, N$_3$, OR$^{21}$, R$^{22}$NCOR$^{21}$ or CONR$^{22}$R$^{21}$; R$^{22}$ is selected from hydrogen, alkyl, alkenyl, alkynyl, aryl, alkylaryl, heterocyclyl, aralkyl, alkoxy, aralkoxy, cycloalkyl, cycloalkenyl, cycloalkynyl, C(O)R$^{23}$ and S(O)$_n$R$^{23}$ in which n is 0–2; and R$^{21}$ and R$^{23}$ are independently selected from hydrogen, alkyl, alkenyl, alkynyl, aryl, alkylaryl, heterocyclyl, aralkyl, aralkoxy, cycloalkyl, cycloalkenyl and cycloalkynyl, with the proviso that if R$^8$ is NR$^{18}$R$^{19}$, OR$^{18}$, R$^{19}$NCOR$^{18}$, CONR$^{19}$R$^{18}$, CO$_2$R$^{18}$, (CH$_2$)$_r$NH(CH=CH)$_s$(CH$_2$)$_n$R$^{18}$, (CH$_2$)$_r$(CH=CH)$_s$NH(CH$_2$)$_n$R$^{18}$, (CH$_2$)$_r$C(O)NH(CH$_2$)$_n$R$^{18}$, C(O)(CH$_2$)$_r$NH(CH$_2$)$_n$R$^{18}$, (CH$_2$)$_r$NH(CH$_2$)$_n$R$^{18}$ or (CH$_2$)$_r$R$^{18}$ and R$^{18}$ is an aryl group having 5 or 6 members, then the aryl group has at least two substituents, or (ii) any two of R$^8$, R$^9$ and R$^{10}$ with the carbon to which each is attached form an aryl, aromatic ring, heteroaromatic ring, carbocyclic or heterocyclic ring, which is saturated or unsaturated, having from about 3 to about 16 members, that is substituted with one or more substituents, each substituent is independently selected from Z; the other of R$^8$, R$^9$ and R$^{10}$ is selected as in (i); and the heteroatoms are NR$^{11}$, O, or S, with the proviso that Ar$^2$ is not 5-halo-3-loweralkylbenzo[b]thienyl, 5-halo-3-loweralkylbenzo[b]furyl or 5-halo-3-loweralkylbenzo[b]pyrrolyl.

2. A compound of claim 1 or a pharmaceutically acceptable salt, acid, or ester thereof, wherein R$^1$ is halide, methyl or (C$_9$–C$_{13}$) alkyl.

3. A compound of claim 1 or pharmaceutically acceptable salts, acids or esters thereof, wherein Ar$^1$ is a phenyl group.

4. A compound of claim 1 or pharmaceutically acceptable salts, acids or esters thereof, wherein R$^1$ is H, lower alkyl, halide or pseudohalide; and R$^2$ is lower alkyl, lower alkenyl, lower alkynyl, lower haloalkyl or hydrogen.

5. A compound of claim 1 or a pharmaceutically acceptable salt, acid, or ester thereof, wherein R$^1$ is selected from halide, CH$_3$, C$_2$H$_5$, CF$_3$, C$_2$F$_5$, n-C$_3$H$_7$ and cyclo-C$_3$H$_7$, and R$^2$ is selected from H, CH$_3$, C$_2$H$_5$, CF$_3$, C$_2$F$_5$, n-C$_3$H$_7$ and cyclo-C$_3$H$_7$.

6. A compound of claim 1 or pharmaceutically acceptable salts, acids or esters thereof in which Ar$^2$ formula IVA or IVB:

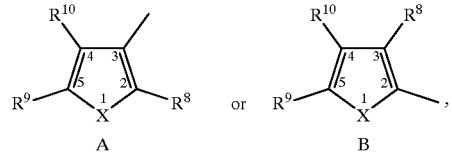

wherein:

X is NR$^{11}$, O, or S;

R$^8$ is selected from among (CH$_2$)$_r$C(O)(CH$_2$)$_n$R$^{18}$, (CH$_2$)$_r$NH(CH$_2$)$_n$R$^{18}$, (CH$_2$)$_r$NH(CH$_2$)$_n$R$^{18}$, (CH$_2$)$_r$(CH=CH)$_s$(CH$_2$)$_n$R$^{18}$, (CH$_2$)$_r$C(O)(CH=CH)$_s$(CH$_2$)$_n$R$^{18}$, (CH$_2$)$_r$(CH=CH)$_s$C(O)(CH$_2$)$_n$R$^{18}$, (CH$_2$)$_r$(CH=CH)$_s$NH(CH$_2$)$_n$R$^{18}$, C=N(OH)(CH$_2$)$_r$R$^{18}$, (CH$_2$)$_r$C(O)NH(CH$_2$)$_n$R$^{18}$, C(O)(CH$_2$)$_r$NH(CH$_2$)$_n$R$^{18}$, (CH$_2$)$_r$NH(CH=CH)$_s$(CH$_2$)$_n$R$^{18}$, (CH$_2$)$_r$C(O)NH(CH$_2$)$_n$R$^{18}$, (CH$_2$)$_r$NH(CH$_2$)$_n$R$^{18}$, (CH$_2$)$_r$R$^{18}$, with the proviso that if R$^8$ is (CH$_2$)$_r$C(O)NH(CH$_2$)$_n$R$^{18}$, (CH$_2$)$_r$C(O)NH(CH$_2$)$_n$R$^{18}$ or (CH$_2$)$_r$R$^{18}$, and R$^{18}$ is phenyl, the phenyl group is substituted at least two positions;

and R$^9$ and R$^{10}$ are independently selected from hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, C(O)R$^{18}$, (OAC)CH=CHR$^{18}$, CO$_2$R$^{18}$, SH, (CH$_2$)$_r$C(O)(CH$_2$)$_n$R$^{18}$, (CH$_2$)$_r$(CH=CH)$_s$(CH$_2$)$_n$R$^{18}$, (CH$_2$)$_r$C(O)(CH=CH)$_s$(CH$_2$)$_n$R$^{18}$, (CH$_2$)$_r$(CH=CH)$_s$C(O)(CH$_2$)$_n$R$^{18}$, (CH$_2$)$_r$NH(CH=CH)$_s$(CH$_2$)$_n$R$^{18}$, C=N(OH)(CH$_2$)$_r$R$^{18}$, (CH$_2$)$_r$(CH=CH)$_s$NH(CH$_2$)$_n$R$^{18}$, (CH$_2$)$_r$C(O)NH(CH$_2$)$_n$R$^{18}$, C(O)(CH$_2$)$_r$NH(CH$_2$)$_n$R$^{18}$, (CH$_2$)$_r$NH(CH$_2$)$_n$R$^{18}$, (CH$_2$)$_r$R$^{18}$, S(O)$_m$R$^{18}$ in which m is 0–2, s, n and r are each independently 0 to 6, HNOH, NR$^{18}$R$^{19}$, NO$_2$, N$_3$, OR$^{18}$, R$^{19}$NCOR$^{18}$ and CONR$^{19}$R$^{18}$, in which R$^{19}$ is selected from hydrogen, alkyl, alkenyl, alkynyl, aryl, alkylaryl, alkoxy, aryloxy, heterocyclyl, aralkyl, aralkoxy, cycloalkyl, cycloalkenyl, cycloalkynyl, C(O)R$^{20}$ and S(O)$_n$R$^{20}$ in which n is 0–2; and R$^{18}$ and R$^{20}$ are independently selected from hydrogen, alkyl, alkenyl, alkynyl, aryl, heteroaryl, alkylaryl, heterocyclyl, alkoxy, aryloxy, aralkyl, aralkoxy, cycloalkyl, cycloalkenyl and cycloalkynyl.

7. A compound of claim 1 or pharmaceutically acceptable salts, acids or esters thereof, wherein $R^{18}$ is aryl or heteroaryl.

8. A compound of claim 1 or pharmaceutically acceptable salts, acids or esters thereof, wherein $R^{18}$ is phenyl or pyrimidinyl.

9. A compound of claim 1 or pharmaceutically acceptable salts, acids or esters thereof wherein $R^9$ and $R^{10}$ are hydrogen, halide, loweralkyl, or halo loweralkyl.

10. A compound of claim 1 or pharmaceutically acceptable salts, acids or esters thereof, wherein $R^{19}$ is hydrogen or lower alkyl; and $R^{18}$ is aryl.

11. A compound of claim 1 or pharmaceutically acceptable salts, acids or esters thereof, wherein $Ar^2$ is phenylaminocarbonylthienyl, phenylaminocarbonylfuryl, phenylaminocarbonylpyrrolyl, phenylacetylthienyl, phenylacetylfuryl, phenylacetylpyrrolyl, acetoxystyrylthienyl, acetoxystyrylfuryl or acetoxystyrylpyrrolyl, with the proviso that, when $Ar^2$ is a phenylaminocarbonylthienyl, phenylaminocarbonylfuryl, phenylaminocarbonylpyrrolyl, the phenyl group is substituted with at least two substituents selected from Z, which is hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, C(O)$R^{21}$, CO$_2R^{21}$, SH, S(O)$_nR^{21}$ in which n is 0–2, NHOH, NR$^{22}R^{21}$, NO$_2$, N$_3$, OR$^{21}$, R$^{22}$NCOR$^{21}$ or CONR$^{22}R^{21}$; R$^{22}$ is selected from hydrogen, alkyl, alkenyl, alkynyl, aryl, alkylaryl, heterocyclyl, aralkyl, alkoxy, aralkoxy, cycloalkyl, cycloalkenyl, cycloalkynyl, C(O)$R^{23}$ and S(O)$_nR^{23}$ in which n is 0–2; and $R^{21}$ and $R^{23}$ are independently selected from hydrogen, alkyl, alkenyl, alkynyl, aryl, alkylaryl, heterocyclyl, aralkyl, aralkoxy, cycloalkyl, cycloalkenyl and cycloalkynyl.

12. A compound of claim 1 or pharmaceutically acceptable salts, acids or esters thereof, wherein X is S, O, NR$^{11}$ in which R$^{11}$ is hydrogen, or loweralkyl, or aryl, which is unsubstituted or substituted with loweralkyl, halogen, hydrogen or loweralkyl.

13. A compound of claim 1 or pharmaceutically acceptable salts, acids or esters thereof, wherein R$^{11}$ is phenyl.

14. A compound of claim 1 or pharmaceutically acceptable salts, acids or esters thereof, wherein Ar$^2$ has formula VI:

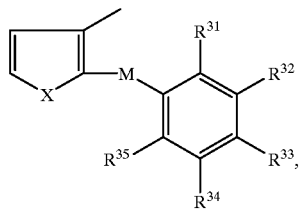

wherein:
M is (CH$_2$)$_m$C(O)(CH$_2$)$_r$, (CH$_2$)$_m$C(O)NH(CH$_2$)$_r$, CH(OH)(CH$_2$)$_r$, (CH$_2$)$_m$(CH=CH)(CH$_2$)$_r$, (CH$_2$)$_m$C(O)(CH$_2$)$_s$NH(CH$_2$)$_r$, (CH$_2$)$_m$(CH=CH)(CH$_2$)$_r$, C=N(OH)(CH$_2$)$_r$, (CH$_2$)$_m$C(O)(CH=CH)$_s$NH(CH$_2$)$_r$, CH(CH$_3$)C(O)(CH$_2$)$_r$, CH(CH$_3$)C(O)(CH$_2$)$_m$(CH=CH)(CH$_2$)$_r$, (CH$_2$)$_r$, (CH$_2$)$_r$O or C(O)O, in which m,s and r are each independently 0 to 6;

R$^{31}$, R$^{32}$, R$^{33}$, R$^{34}$ and R$^{35}$ are each independently selected from (i) or (ii) as follows:

(i) R$^{31}$, R$^{32}$, R$^{33}$, R$^{34}$ and R$^{35}$ are each independently selected from among H, OH, NHR$^{38}$, CONR$^{38}R^{39}$, NO$_2$, cyano, halide, pseudohalide, alkyl, alkenyl, alkynyl, aryl, arylalkyl, heteroaryl, alkoxy, alkylamino, alkylthio, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, alkoxycarbonyl, arylaminocarbonyl, alkylaminocarbonyl, aminocarbonyl, (alkylaminocarbonyl)alkyl, carboxyl, carboxyalkyl, carboxyalkenyl, alkylsulfonylaminoalkyl, cyanoalkyl, acetyl, acetoxyalkyl, hydroxyalkyl, alkyoxyalkoxy, hydroxyalkyl, (acetoxy)alkoxy, (hydroxy)alkoxy and formyl; or (ii) at least two of R$^{31}$, R$^{32}$, R$^{33}$, R$^{34}$ and R$^{35}$, which substitute adjacent carbons on the ring, together form alkylenedioxy, alkylenethioxyoxy or alkylenedithioxy, which is unsubstituted or substituted by replacing one or more hydrogens with halide, loweralkyl, loweralkoxy or halo loweralkyl, and the others of R$^{31}$, R$^{32}$, R$^{33}$, R$^{34}$ and R$^{35}$ are selected as in (i); and R$^{38}$ and R$^{39}$ are each independently selected from hydrogen, alkyl, alkenyl, alkynyl, aryl, haloalkyl, alkylaryl, heterocyclyl, arylalkyl, arylalkoxy, alkoxy, aryloxy, cycloalkyl, cycloalkenyl and cycloalkynyl, with the proviso that when M is (CH$_2$)$_m$C(O)NH(CH$_2$)$_r$, then at least two of R$^{31}$, R$^{32}$, R$^{33}$, R$^{34}$ and R$^{35}$ are not hydrogen.

15. A compound of claim 14, wherein M is (CH$_2$)$_m$C(O)(CH$_2$)$_r$, (CH$_2$)$_m$C(O)NH(CH$_2$)$_r$, (CH$_2$)$_m$(CH=CH)(CH$_2$)$_r$, (CH$_2$)$_m$C(O)(CH$_2$)$_s$NH(CH$_2$)$_r$, (CH$_2$)$_m$(CH=CH)(CH$_2$)$_r$, C=N(OH)(CH$_2$)$_r$, CH(OH)(CH$_2$)$_r$, (CH$_2$)$_r$, (CH$_2$)$_r$O or C(O)O.

16. A compound of claim 14 or a pharmaceutically acceptable salt, acid or ester thereof, wherein R$^{31}$, R$^{32}$, R$^{33}$, R$^{34}$ and R$^{35}$ are selected from (i) or (ii)

(i) R$^{31}$, R$^{32}$, R$^{33}$, R$^{34}$ and R$^{35}$ are each independently selected from among lowealkyl, halide, haloloweralkyl, and loweralkoxy; and (ii) at least two of R$^{31}$, R$^{32}$, R$^{33}$, R$^{34}$ and R$^{35}$ form ethylenedioxy or methylenedioxy and the others are selected as in (i).

17. A compound of claim 14 or pharmaceutically acceptable salts, acids or esters thereof, wherein M is

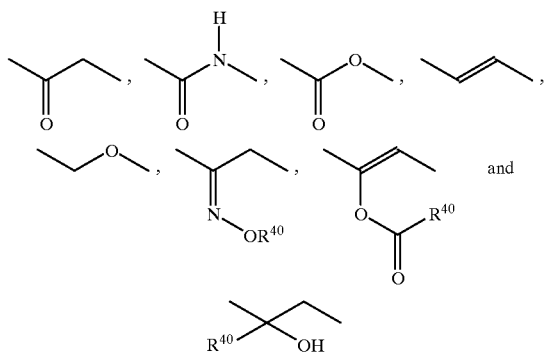

in which R$^{40}$ is hydrogen, alkyl, alkoxy, alkoxyalkyl or haloalkyl.

18. A compound of claim 14 or pharmaceutically acceptable salts, acids or esters thereof, wherein at least two of R$^{31}$, R$^{32}$, R$^{33}$, R$^{34}$ and R$^{35}$, which substitute adjacent carbons on the ring, together form alkylenedioxy, alkylenethioxyoxy or alkylenedithioxy, which is unsubstituted or substituted by replacing one or more hydrogens with halide, loweralkyl, loweralkoxy or halo loweralkyl.

19. A compound of claim 14 or pharmaceutically acceptable salts, acids or esters thereof, wherein at least one of $R^{31}$ and $R^{35}$ is other than hydrogen.

20. A compound of claim 14 or pharmaceutically acceptable salts, acids or esters thereof, wherein $Ar^2$ has formula VII:

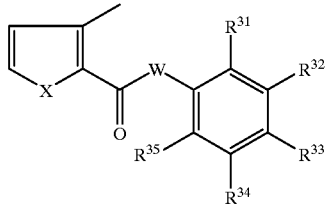

in which W is $CH_2$ or NH.

21. A compound of claim 14 or a pharmaceutically acceptable salt, acid or ester thereof, wherein M is selected from

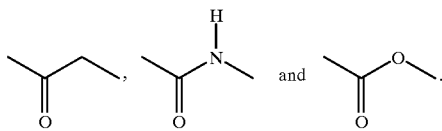

22. A compound of claim 17, wherein $R^{40}$ is methyl, ethyl or hydrogen.

23. A compound of claim 14 or a pharmaceutically acceptable salt, acid or ester thereof, wherein $R^{31}$, $R^{32}$, $R^{33}$, $R^{34}$ and $R^{35}$ are selected from (i) or (ii):
  (i) $R^{31}$, $R^{32}$, $R^{33}$, $R^{34}$ and $R^{35}$ are each independently selected from loweralkyl, haloloweralkyl, phenyl, alkoxy, loweralkylsulfonylaminoloweralkyl, cyanoloweralkyl, acetyl, loweralkoxycarbonyl, cyano, OH, acetoxyloweralkyl, hydroxy loweralkyl, acetoxy loweralkoxy or loweralkoxycarbonyl; or
  (ii) $R^{32}$ and $R^{33}$ or $R^{33}$ and $R^{34}$ form alkylene dioxy, and the others of $R^{31}$, $R^{32}$, $R^{33}$, $R^{34}$ and $R^{35}$ are selected as in (i).

24. A compound of claim 14 or a pharmaceutically acceptable salt, acid or ester thereof, wherein $R^{31}$, $R^{33}$ and $R^{35}$ are selected from (i) or (ii):
  (i) $R^{33}$ and $R^{35}$ are other than hydrogen and are selected from loweralkyl or lower alkoxy, or
  (ii) at least one of $R^{31}$ or $R^{35}$ is loweralkyl or lower alkoxy, and $R^{32}$ and $R^{33}$ or $R^{33}$ and $R^{34}$ form methylenedioxy or ethylenedioxy.

25. A compound of claim 1 or a pharmaceutically acceptable salt, acid, or ester thereof, wherein $R^9$ and $R^{10}$ form a ring so that $Ar^2$ is benzo[b]thienyl, benzo[b]furyl, or indolyl, with the proviso that there is one or more substituent and they are other than 5-halo and 3-loweralkyl, and the other of $R^8$, $R^9$ and $R^{10}$ is selected from aryl, $(CH_2)_rR^{18}$, $C(O)R^{18}$, $CO_2R^{18}$, $NR^{18}R^{19}$, SH, $S(O)_nR^{18}$ in which n is 0–2, HNOH, $NO_2$, $N_3$, $OR^{18}$, $R^{19}NCOR^{18}$ and $CONR^{19}R^{18}$.

26. A compound of claim 1 or a pharmaceutically acceptable salt, acid, or ester thereof, wherein $R^1$ is halide or $CH_3$, and $R^2$ is H, $CH_3$, $C_2H_5$, or $CF_3$.

27. A compound of claim 1 or a pharmaceutically acceptable salt, acid, or ester thereof, wherein $Ar^2$ is thienyl.

28. A compound of claim 1 or a pharmaceutically acceptable salt, acid, or ester thereof, wherein $Ar^2$ is furyl.

29. A compound of claim 1 or a pharmaceutically acceptable salt, acid, or ester thereof, wherein $Ar^2$ is pyrrolyl.

30. A compound of claim 1 or a pharmaceutically acceptable salt, acid, or ester thereof that is a (phenylacetyl)thiophenesulfonamide.

31. A compound of claim 1 or a pharmaceutically acceptable salt, acid, or ester thereof that is a (phenyoxy)thiophenesulfonamide.

32. A pharmaceutical composition, comprising a compound of claim 1 or a pharmaceutically acceptable salt, acid, or ester thereof in a pharmaceutically acceptable carrier.

33. A method for the treatment of endothelin-mediated diseases, comprising administering an effective amount of a compound of claim 1 or a pharmaceutically acceptable salt, ester or acid thereof, wherein the effective amount is sufficient to ameliorate one or more of the symptoms of the disease.

34. The method of claim 33, wherein the disease is selected from the group consisting of hypertension, cardiovascular disease, asthma, pulmonary hypertension, inflammatory diseases, ophthalmologic disease, menstrual disorders, obstetric conditions, wounds, gastroenteric disease, renal failure, immunosuppressant-mediated renal vasoconstriction, erythropoietin-mediated vasoconstriction, endotoxin shock, anaphylactic shock and hemorrhagic shock.

35. The method of claim 33, wherein the disease is selected from the group consisting of hypertension, cardiovascular disease, pulmonary hypertension, erythropoietin-mediated vasoconstriction, endotoxin shock, anaphylactic shock and hemorrhagic shock.

36. The method of claim 33, wherein the disease is selected from the group consisting of asthma and inflammatory diseases.

37. A method for inhibiting the binding of an endothelin peptide to endothelin$_A$ ($ET_A$) or endothelin$_B$ ($ET_B$) receptors, comprising contacting the receptors an endothelin peptide and with a compound of claim 1 or a pharmaceutically acceptable salt, ester or acid thereof, wherein:
  the contacting is effected prior to, simultaneously with or subsequent to contacting the receptors with the endothelin peptide.

38. A method for altering endothelin receptor-mediated activity, comprising contacting endothelin receptors with a compound of claim 1 or a pharmaceutically acceptable salt, ester or acid thereof.

39. A pharmaceutical composition formulated for single dosage administration, comprising an effective amount of a compound of claim 1 or a pharmaceutically acceptable salt, ester or acid thereof, wherein the amount is effective for ameliorating the symptoms of an endothelin-mediated disease.

40. An article of manufacture, comprising packaging material and a compound of claim 1 or a pharmaceutically acceptable salt, ester or acid thereof within the packaging material, wherein the compound is effective for antagonizing the effects of endothelin, ameliorating the symptoms of an endothelin-mediated disorder, or inhibiting the binding of an endothelin peptide to an ET receptor with an $IC_{50}$ of less than about 10 μM, and the packaging material includes a label that indicates that the sulfonamide or salt thereof is used for antagonizing the effects of endothelin, inhibiting the binding of endothelin to an endothelin receptor or treating an endothelin-mediated disorder.

41. A compound or a pharmaceutically acceptable salt, acid or ester of a compound of claim 15, wherein $R^{31}$, $R^{32}$, $R^{33}$, $R^{34}$ and $R^{35}$ are selected from (i) or (ii)

(i) $R^{31}$, $R^{32}$, $R^{33}$, $R^{34}$ and $R^{35}$ are each independently selected from among loweralkyl, halide, haloloweralkyl, and loweraloxy; and (ii) at least two of $R^{31}$, $R^{32}$, $R^{33}$, $R^{34}$ and $R^{35}$ form ethylenedioxy or methylenedioxy and the others are selected as in (i).

42. A compound or a pharmaceutically acceptable salt, acid or ester of a compound claim 41, wherein M is

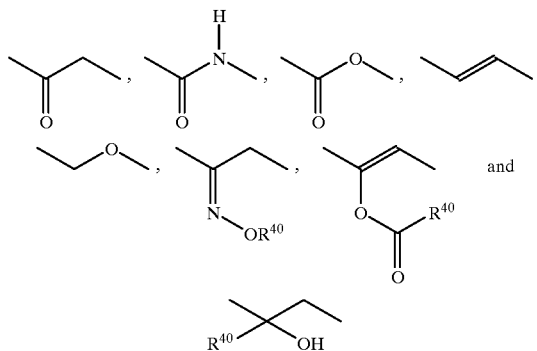

in which $R^{40}$ is hydrogen, alkyl, alkoxy, alkoxyalkyl or haloalkyl.

43. A compound or a pharmaceutically acceptable salt, acid or ester of a compound claim 42, wherein at least two of $R^{31}$, $R^{32}$, $R^{33}$, $R^{34}$ and $R^{35}$, which substitute adjacent carbons on the ring, together form alkylenedioxy, alkylenethioxyoxy or alkylenedithioxy, which is unsubstituted or substituted by replacing one or more hydrogens with halide, loweralkyl, loweralkoxy or halo loweralkyl.

44. A compound or a pharmaceutically acceptable salt, acid or ester of a compound claim 42, wherein at least one of $R^{31}$ and $R^{35}$ is other than hydrogen.

45. A compound or a pharmaceutically acceptable salt, acid or ester of a compound claim 44, wherein $Ar^2$ has formula VII:

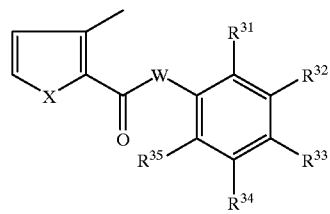

in which W is $CH_2$ or NH.

46. A compound of claim 42 or a pharmaceutically acceptable salt, acid or ester thereof, wherein M is selected from

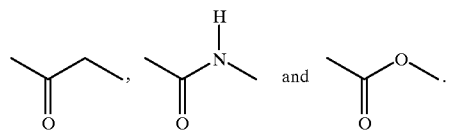

47. A compound of claim 42 or a pharmaceutically acceptable salt, acid or ester thereof, wherein $R^{40}$ is methyl, ethyl or hydrogen.

48. A compound of claim 47 or a pharmaceutically acceptable salt, acid or ester thereof, wherein $R^{31}$, $R^{33}$, and $R^{35}$ are selected from (i) or (ii):
   (i) $R^{33}$ and $R^{35}$ are other than hydrogen and are selected from loweralkyl or lower alkoxy, or
   (ii) at least one of $R^{31}$ or $R^{35}$ is loweralkyl or lower alkoxy, and $R^{32}$ and $R^{33}$ or $R^{33}$ and $R^{34}$ form methylenedioxy or ethylenedioxy.

49. A compound of claim 48 or a pharmaceutically acceptable salt, acid or ester thereof, wherein $R^9$ and $R^{10}$ form a ring so that $Ar^2$ is benzo[b]thienyl, benzo[b]furyl, or indolyl, with the proviso that there is one or more substituent and they are other than 5-halo and 3-loweralkyl, and the other of $R^8$, $R^9$ and $R^{10}$ is selected from aryl, $(CH_2)_nR^{18}$, $C(O)R^{18}$, $CO_2R^{18}$, $NR^{18}R^{19}$, SH, $S(O)_nR^{18}$ in which n is 0–2, HNOH, $NO_2$, $N_3$, $OR^{18}$, $R^{19}NCOR^{18}$ and $CONR^{19}R^{18}$.

50. A compound of claim 48 or a pharmaceutically acceptable salt, acid or ester thereof, wherein $Ar^2$ is thienyl.

51. A compound of claim 41 or a pharmaceutically acceptable salt, acid or ester thereof, wherein $Ar^2$ is thienyl.

52. The method of claim 33, wherein the disease is glaucoma.

* * * * *

UNITED STATES PATENT AND TRADEMARK OFFICE
CERTIFICATE OF CORRECTION

PATENT NO. : 6,342,610 B2
DATED : January 29, 2002
INVENTOR(S) : Chan et al.

It is certified that error appears in the above-identified patent and that said Letters Patent is hereby corrected as shown below:

<u>Title page,</u>
Item [52], please replace "548/543" with -- 540/543 --

<u>Column 25,</u>
Line 67, please replace "$CH_2CH_2C(O)(CH)_2$" with -- $CH_2CH_2C(O)(CH = CH)$ --; and please replace "$CH_2CHC(O)CH_2$" with -- $CH = CHC(O)CH_2$ --;

<u>Column 37,</u>
Lines 23-24, Table 1, please replace "2-tolyl" with -- 4-tolyl --;

<u>Column 39,</u>
Line 67, please replace "VII" with -- VIII --;

<u>Column 42,</u>
Lines 31-32, please replace "4´-trifluorophenyl" with -- 4´-trifluoromethylphenyl --;

<u>Column 43,</u>
Line 17, Table 2, please replace "4´-trifluorophenyl" with
-- 4´-trifluoromethylphenyl --;

<u>Column 54,</u>
Line 30, please replace "carbomethoxy" with -- carboxyl --;

<u>Column 57,</u>
Line 58, please replace "mg" with -- g --;

<u>Column 58,</u>
Line 15, please delete "ethyl";

<u>Column 61,</u>
Line 15, please replace "258" with -- 0.258 --;
Line 32, please replace "11.16" with -- 0.16 --;

<u>Column 67,</u>
Line 47, please replace "9.7" with -- 97 --;

<u>Column 69,</u>
Lines 28-29, please replace "2-methyl" with -- 1-methyl --;
Line 54, please replace "mol" with -- mmol --;

UNITED STATES PATENT AND TRADEMARK OFFICE
CERTIFICATE OF CORRECTION

PATENT NO.    : 6,342,610 B2
DATED         : January 29, 2002
INVENTOR(S)   : Chan et al.

It is certified that error appears in the above-identified patent and that said Letters Patent is hereby corrected as shown below:

Column 78,
Line 26, please replace "64E" with -- 65E --;
Line 27, please replace "4-methoxyphenyl" with -- 3-thienyl --;
Line 56, please replace "1.7" with -- 17 --;

Column 79,
Line 55, please replace "4-ethylbenzene" with -- 4-isopropylbenzene --;

Column 80,
Lines 1-2, please replace "4-ethyl" with -- 4-isopropyl --;
Lines 6 and 18, please replace "4-isopropyl" with -- 4-isopropylphenyl --;

Column 81,
Line 32, please replace "4-isopropyl" to -- 4-propylphenyl --;

Column 83,
Lines 57 and 58, please replace "3,4-methylenedioxy" with
-- 3,4-methylenedioxybenzyl --;

Column 88,
Line 30, please replace both "ml" with -- $\mu$l --;

Column 93,
Line 33, please replace "warm" with -- cool --;
Line 44, please replace "142-142" with -- 142 --;

Column 94,
Line 29, please replace "9.39" with -- 939 --;
Line 63, please replace "mg" with -- g --;
Line 64, please replace "0.18" with -- 18 --;

Column 96,
Line 25, please replace "-3-sulfonyl" with -- thiophene-3-sulfonyl --;

Column 98,
Lines 9, 16 and 24, please replace "117" with -- 116 --;

UNITED STATES PATENT AND TRADEMARK OFFICE
CERTIFICATE OF CORRECTION

PATENT NO.    : 6,342,610 B2
DATED         : January 29, 2002
INVENTOR(S)   : Chan et al.

It is certified that error appears in the above-identified patent and that said Letters Patent is hereby corrected as shown below:

Column 99,
Line 57, please insert -- 4-Methylaniline (6.6 mmol) was added. -- between "hours." and "The";

Column 100,
Line 25, please delete "(Example 123)";
Line 46, please replace "N-methyl-4-methylaniline" with -- N-methylaniline --;

Column 104,
Lines 16 and 19, please replace "6" with -- 5 --;
Lines 60 and 63, please replace "ml" with -- $\mu$l --;

Column 106,
Line 48, please replace "5-methyl-3-isoxazolyl" with -- 3-methyl-5-isoxazolyl --;

Column 107,
Lines 15, 18, 20, 27, 28, 34, 37, 40 and 43, please replace "4-phenyl" with -- phenyl --;

Column 109,
Line 44, please replace "sulfonamide" with -- sulfonyl]pyrrole --;

Column 111,
Line 25, please replace "140A" with -- 139A --;
Line 39, please replace "6.30" with -- 630 --;

Column 112,
Line 2, please replace "141C" with -- 140C --

Column 114,
Line 64, please replace "147" with -- 146C --;

Column 115,
Lines 37-42, please replace "N-(4-chloro-3-methyl-5-isoxazolyl)2-{[4,5-dimethoxy-2] 4,5-dimethoxy-2-methoxycarbonyl)phenyl]phenylaminocarbonyl}thiophene-3-sulfonamide" with -- N-(4-chloro-3-methyl-5-isoxazolyl)-2-{{2-[(4,5-dimethoxy-2-methoxycarbonyl)phenylaminocarbonyl]-4,5-dimethoxy}phenylaminocarbonyl} thiophene-3-sulfonamide --;
Line 65, please replace "10" with -- 1.0 --;

UNITED STATES PATENT AND TRADEMARK OFFICE
CERTIFICATE OF CORRECTION

PATENT NO. : 6,342,610 B2
DATED : January 29, 2002
INVENTOR(S) : Chan et al.

It is certified that error appears in the above-identified patent and that said Letters Patent is hereby corrected as shown below:

Column 116,
Lines 14 and 26, please replace "methylenedioxy" with -- dimethoxy --;
Lines 17-20, please replace "N-(4-chloro-3-methyl-5-isoxazolyl)2-{[4,5-dimethoxy-2] 4,5-dimethoxy-2-methoxycarbonyl)phenyl]phenylaminocarbonyl}thiophene-3-sulfonamide" with -- N-(4-chloro-3-methyl-5-isoxazolyl)-2-{{2-[(4,5-dimethoxy-2-methoxycarbonyl)phenylaminocarbonyl]-4,5-dimethoxy}phenylaminocarbonyl}thiophene-3-sulfonamide --;

Column 119,
Line 16, please delete "phenyl";
Line 34, please replace "4-tolylmagnesium" with -- 4-methylbenzylmagnesium --;

Column 130,
Lines 17 and 29, please replace "phenyl" with -- benzyl --;
Lines 53, 63 and 66, please replace "1,2,3" with -- 2,3,4 --.

Column 131,
Line 3, please replace "1,2,3" with -- 2,3,4 --.

Column 154,
Lines 11-13, 16-24, cancel claims 2, 4 and 5.

Column 157,
Lines 63-65, cancel claim 26.

Signed and Sealed this

Eighth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,342,610 B2
DATED : January 29, 2002
INVENTOR(S) : Chan et al.

It is certified that error appears in the above-identified patent and that said Letters Patent is hereby corrected as shown below:

Title page,
Item [63], Related U.S. Application Data, please delete "which is a continuation-in-part of application No. 08/247,072, filed on May 20, 1994, now Pat. No. 5,571,821, which is a continuation-in-part of application No. 08/222,287, filed on Apr. 5, 1994, now Pat. No. 5,591,761, which is a continuation-in-part of application No. 08/142,552, filed on Oct. 21, 1993, now Pat. No. 5,514,691, which is a continuation-in-part of application No. 08/142,159, filed on Oct. 21, 1993, now Pat. No. 5,464,853, which is a continuation-in-part of application No. 08/142,631, filed on Oct. 21, 1993, now abandoned, which is a continuation-in-part of application No. 08/100,565, filed on Jul. 30, 1993, now abandoned, which is a continuation-in-part of application No. 08/100,125, filed on Jul. 30, 1993, now abandoned, which is a continuation-in-part of application No. 08/065,202, filed on May 20, 1993, now abandoned."

Signed and Sealed this

Twentieth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO.  : 6,342,610 B2
DATED       : January 29, 2002
INVENTOR(S) : Chan et al.

It is certified that error appears in the above-identified patent and that said Letters Patent is hereby corrected as shown below:

<u>Column 83,</u>
Lines 13 and 15, please replace "dimethyl" with -- dimethoxy --.

Signed and Sealed this

Fifth Day of August, 2003

JAMES E. ROGAN
*Director of the United States Patent and Trademark Office*